United States Patent
Martinez et al.

(10) Patent No.: US 7,320,972 B2
(45) Date of Patent: Jan. 22, 2008

(54) 4-BIARYLYL-1-PHENYLAZETIDIN-2-ONES

(75) Inventors: Eduardo Martinez, New York, NY (US); John J. Talley, Somerville, MA (US); Stephen Antonelli, Lynn, MA (US); Timothy C. Barden, Salem, MA (US); Regina Lundrigan-Soucy, Charlestown, MA (US); Wayne C. Schairer, Westboro, MA (US); Jing-Jing Yang, Boxborough, MA (US); Daniel P. Zimmer, Somerville, MA (US); Brian Cali, Arlington, MA (US); Mark G. Currie, Sterling, MA (US); Peter S. Yorgey, Cambridge, MA (US)

(73) Assignee: Microbia, Inc., Cambridge, MA (US)

( * ) Notice: Subject to any disclaimer, the term of this patent is extended or adjusted under 35 U.S.C. 154(b) by 512 days.

(21) Appl. No.: 10/986,570

(22) Filed: Nov. 10, 2004

(65) Prior Publication Data

US 2005/0209165 A1    Sep. 22, 2005

Related U.S. Application Data

(60) Provisional application No. 60/614,005, filed on Sep. 28, 2004, provisional application No. 60/592,529, filed on Jul. 30, 2004, provisional application No. 60/549,577, filed on Mar. 3, 2004, provisional application No. 60/518,698, filed on Nov. 10, 2003.

(51) Int. Cl.
C07D 205/08 (2006.01)
A61K 31/397 (2006.01)
A61K 31/7052 (2006.01)
A61P 3/06 (2006.01)
A61P 9/10 (2006.01)

(52) U.S. Cl. ............................. 514/210.02; 540/200

(58) Field of Classification Search ................ 540/200; 514/210.02
See application file for complete search history.

(56) References Cited

U.S. PATENT DOCUMENTS 5,561,227 A    10/1996  Thiruvengadam et al. .. 540/200
6,093,812 A    7/2000   Thiruvengadam et al. .. 540/200
2002/0137689 A1  9/2002  Glombik et al.
2004/0126423 A1  7/2004  Moore et al.
2007/0135357 A1*  6/2007  Sings et al. ................... 514/25

FOREIGN PATENT DOCUMENTS

WO    WO 93/02048    2/1993

OTHER PUBLICATIONS

Agarwal, Rajesh et al., Indian Journal of Chemistry, Section B: Organic Chemistry Including Medicinal Chemistry (1989), 28B(10), 893-6.*
Huang et al., Fenxi Ceshi Tongbao 10, 39-43 (1991) (abstract only).
Search Report for PCT/US04/037715.

* cited by examiner

*Primary Examiner*—Mark L. Berch
(74) *Attorney, Agent, or Firm*—Heslin Rothenberg Farley & Mesiti, P.C.; Philip E. Hansen

(57) ABSTRACT

4-Biarylyl-1-phenylazetidin-2-ones useful for the treatment of hypercholesterolemia are disclosed. The compounds are of the general formula

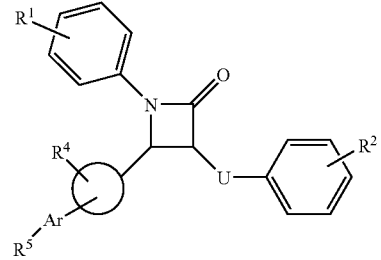

in which

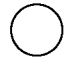

represents an aryl or heteroaryl residue; Ar represents an aryl residue; U is a two to six atom chain; and the R's represent substituents.

71 Claims, No Drawings

4-BIARYLYL-1-PHENYLAZETIDIN-2-ONES

CROSS REFERENCE TO RELATED APPLICATIONS

This application claims priority from U.S. provisional applications Ser. Nos. 60/518,698; 60/549,577; 60/592,529; and 60/614,005, filed Nov. 10, 2003; Mar. 3, 2004; Jul. 30, 2004; and Sep. 28, 2004, respectively. The entire disclosures of all are incorporated herein by reference.

FIELD OF THE INVENTION

The invention relates to a chemical genus of 4-biarylyl-1-phenylazetidin-2-ones useful for the treatment of hypercholesterolemia and cholesterol-associated benign and malignant tumors.

BACKGROUND OF THE INVENTION 1,4-Diphenylazetidin-2-ones and their utility for treating disorders of lipid metabolism are described in U.S. Pat. No. 6,498,156, USRE37,721 and PCT application WO02/50027, the disclosures of which are incorporated herein by reference as they relate to utility.

SUMMARY OF THE INVENTION

In one aspect the invention relates to compounds of formula:

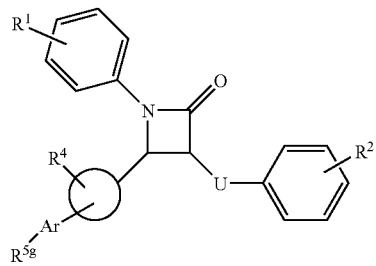

which comprises compounds of two closely related genera, Φ and Ψ:

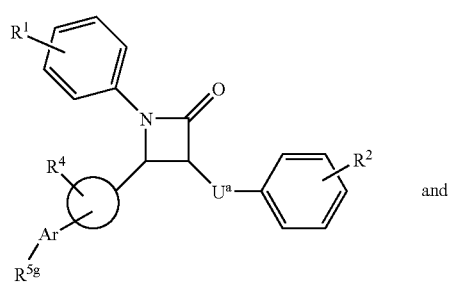

and

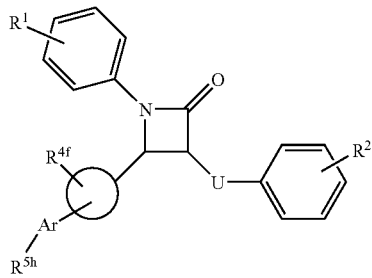

wherein

represents an aryl or heteroaryl residue; Ar represents an aryl residue; $R^1$ represents one, two, three, four or five residues chosen independently from H, halogen, —OH, loweralkyl, $OCH_3$, $OCF_2H$, $OCF_3$, $CH_3$, $CF_2H$, $CH_2F$, —O-loweralkyl, methylenedioxy, ethylenedioxy, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, phenyl, benzyl, phenoxy, benzyloxy, —$PO_3H_2$, —$SO_3H$, —$B(OH)_2$, a sugar, a polyol, a glucuronide and a sugar carbamate; $R^2$ represents one, two, three, four or five residues chosen independently from H, halogen, —OH, loweralkyl, $OCH_3$, $OCF_2H$, $OCF_3$, $CH_3$, $CF_2H$, $CH_2F$, —O-loweralkyl, methylenedioxy, ethylenedioxy, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, —$PO_3H_2$, —$SO_3H$, —$B(OH)_2$, a sugar, a polyol, a glucuronide and a sugar carbamate; $R^4$ represents one, two, three or four residues chosen independently from H, halogen, —OH, loweralkyl, —O-loweralkyl, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, —$PO_3H_2$, —$SO_3H$, —$B(OH)_2$, a sugar, a polyol, a glucuronide and a sugar carbamate; $R^{4f}$ is —OH, —SH or —$B(OH)_2$; $R^{5g}$ represents one, two, three, four or five residues on Ar chosen independently from halogen, —OH, loweralkyl, —O-loweralkyl, methylenedioxy, ethylenedioxy, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, —$PO_3H_2$, —$SO_3H$, —$B(OH)_2$, a sugar, a polyol, a glucuronide and a sugar carbamate; $R^{5h}$ represents one, two, three, four or five residues on Ar chosen independently from hydrogen, halogen, —OH, loweralkyl, —O-loweralkyl, methylenedioxy, ethylenedioxy, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, —$PO_3H_2$, —$SO_3H$, —$B(OH)_2$, a sugar, a polyol, a glucuronide and a sugar carbamate; U is ($C_2$-$C_6$)-alkylene in which one or more —$CH_2$— may be replaced by a radical chosen from —S—, —S(O)—, —$SO_2$—, —O—, —C(=O)—, —CHOH—, —NH—, CHF, $CF_2$, —CH(O-loweralkyl)-, —CH(O-loweracyl)-, —CH($OSO_3H$)—, —CH($OPO_3H_2$)—, —CH($OB(OH)_2$)—, or —NOH—, with the provisos that (1) adjacent —$CH_2$— residues are not replaced by —S—, —S(O)—, —$SO_2$— or —O—; and (2) —S—, —S(O)—, —$SO_2$—, —O— and —NH— residues are not separated only by a single carbon; $U^a$ is the same as U except that $U^a$ excludes —$CH_2CH_2CH(OH)$—.

The genera Φ and Ψ exclude compounds in which $R^{5g}$ is —CN; 2,5-dimethoxy; 2,6-dimethoxy or halogen when neither ring of the biphenyl residue is further substituted.

The genera Φ and Ψ also exclude compounds in which $R^{5g}$ is 2-hydroxy when

represents a 2,5-thienyl residue.

Subgenera include biphenyl compounds of general formulae I-VII:

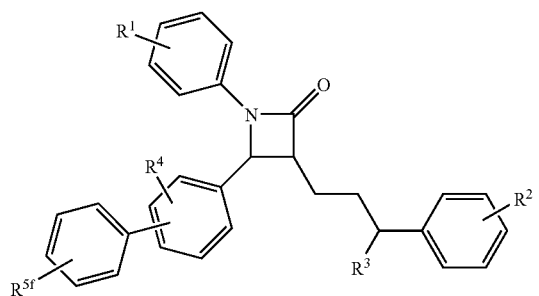

I

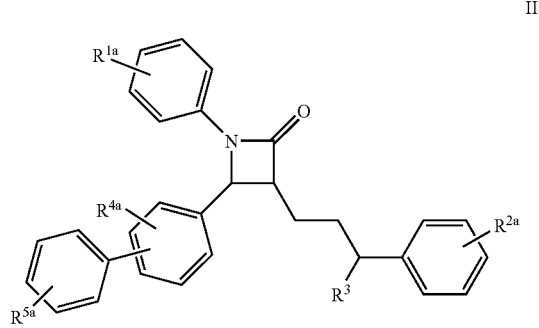

II

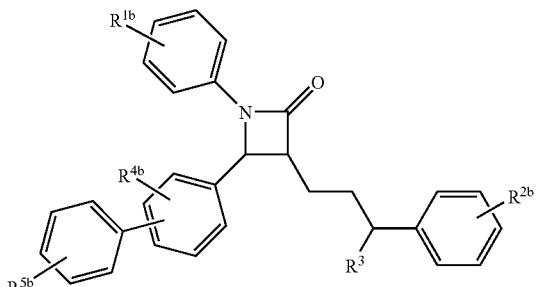

III

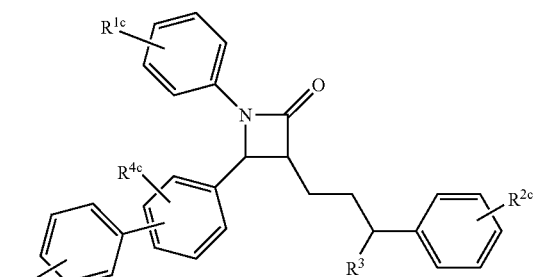

IV

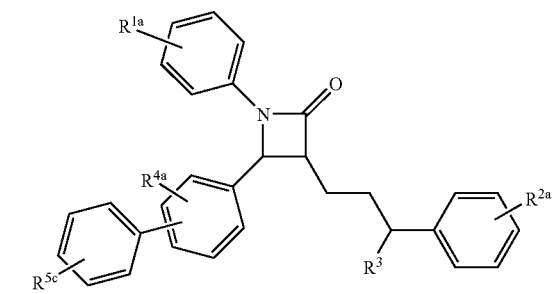

V

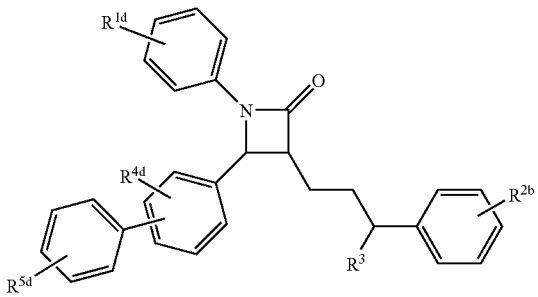

VI

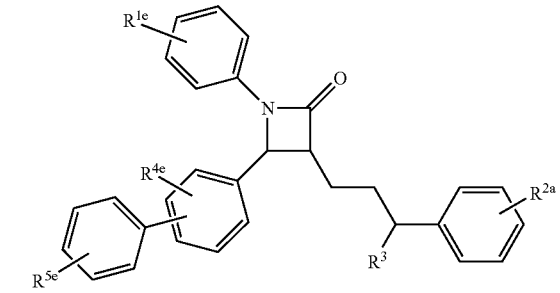

VII

In formula I, $R^1$ and $R^2$ represent one or two residues chosen independently from H, halogen, —OH, loweralkyl, $OCH_3$, $OCF_2H$, $OCF_3$, $CH_3$, $CF_2H$, $CH_2F$, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy, a sugar, a glucuronide and a sugar carbamate; $R^3$ is chosen from H, —OH, fluoro, —O-loweralkyl and —O-acyl; $R^4$ represents one, two, three or four residues chosen independently from H, halogen, —OH, loweralkyl, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy, a sugar, a glucuronide and a sugar carbamate; $R^{5f}$ represents one, two, three, four or five residues chosen independently from halogen, —OH, loweralkyl, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy, a sugar, a glucuronide a sugar carbamate and —$N^+R^6R^7R^8X^-$; $R^6$ is $C_1$ to $C_{20}$ hydrocarbon or forms a five- to seven-membered ring with $R^7$; $R^7$ is alkyl or forms a five- to seven-membered ring with $R^6$; $R^8$ is alkyl or together with $R^6$ or $R^7$ forms a second five- to seven-membered ring; and X is an anion.

In formula II one of $R^{1a}$, $R^{4a}$ and $R^{5a}$ is -Q-A-$N^+R^9R^{10}R^{11}X^-$ and the other two of $R^{1a}$, $R^{4a}$ and $R^{5a}$ are chosen independently from hydrogen, halogen, —OH, loweralkyl, $OCH_3$, $OCF_2H$, $OCF_3$, $CH_3$, $CF_2H$, $CH_2F$, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy. $R^{2a}$ represents one or two residues chosen independently from H, halogen, —OH, loweralkyl, $OCH_3$, $OCF_2H$, $OCF_3$, $CH_3$, $CF_2H$, $CH_2F$, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy and benzyloxy. $R^3$ is chosen from H, —OH, fluoro, —O-loweralkyl and —O-acyl. Q is chosen from a direct bond, —O—, —S—, —NH—, —$CH_2O$—, —$CH_2NH$—, —C(=O)—, —CONH—, —NHCO—, —O(C=O)—, —(C=O)O—, —NHCONH—, —OCONH— and —NHCOO—. A is chosen from $C_2$ to $C_{20}$ hydrocarbon, substituted alkyl of 2 to 20 carbons, substituted aryl, substituted arylalkyl, and oxaalkyl of four to fifty carbons; and, when Q is a direct bond, —C(=O) or —O(C=O)—, A may additionally be methylene. $R^9$ is $C_1$ to $C_{20}$ hydrocarbon or forms a five- to seven-membered ring with A or $R^{10}$; $R^{10}$ is alkyl, forms a double bond with A or forms a five- to seven-membered ring with $R^9$; $R^{11}$ is alkyl or together with $R^{10}$ or $R^9$ forms a second five- to seven-membered ring; and X is an anion.

In formula III, $R^{2b}$ represents one or two residues chosen independently from H, halogen, —OH, loweralkyl, $OCH_3$, $OCF_2H$, $OCF_3$, $CH_3$, $CF_2H$, $CH_2F$, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy. $R^3$ is chosen from H, —OH, fluoro, —O-loweralkyl and —O-acyl. One of $R^{1b}$, $R^{4b}$ and $R^{5b}$ is $R^{12}$ and the other two of $R^{1b}$, $R^{4b}$ and $R^{5b}$ are chosen independently from hydrogen, halogen, —OH, loweralkyl, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy, a sugar, a glucuronide, and a sugar carbamate; $R^{12}$ is ($C_0$ to $C_{30}$)alkylene-$G_n$ in which one or more —$CH_2$— residues in said alkylene may be replaced by —S—, —SO—, $SO_2$—, —O—, —NH—, —N(alkyl)-, —N(phenyl)-, —N(alkylphenyl)-, —$N^+$(alkyl)$_2$—, —$N^+$(phenyl)$_2$—, —$N^+$(alkylphenyl)$_2$—, —C(=O)—, —C(=S), CH=CH—, —C=C—, phenylene or —N[(C=O)alkyleneCOOH]—; G is chosen from —$SO_3H$, —$PO_3H_2$, —O—$PO_3H_2$, —COOH, —C(N=H)$NH_2$, a polyol, a sugar, a glucuronide, a sugar carbamate, —$N^+R^{6a}R^{7a}R^{8a}X^-$, and a mono or bicyclic trialkylammoniumalkyl residue; $R^{6a}$ is $C_1$ to $C_{20}$ hydrocarbon; $R^{7a}$ is alkyl; $R^{8a}$ is alkyl; n is one, two, three, four or five and X is an anion.

In compounds of formula IV, $R^{1c}$ and $R^{2c}$ represent one or two residues chosen independently from H, halogen, —OH, loweralkyl, $OCH_3$, $OCF_2H$, $OCF_3$, $CH_3$, $CF_2H$, $CH_2F$, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, hydroxyamidino, guanidino, dialkylguanidino, phenyl, benzyl, phenoxy, benzyloxy, a glucuronide, and a sugar carbamate. $R^3$ is chosen from H, —OH, fluoro, —O-loweralkyl and —O-acyl. $R^{4c}$ represents one, two, three or four residues chosen independently from H, halogen, —OH, loweralkyl, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy, a glucuronide and a sugar carbamate; and $R^{5f}$ represents one, two, three, four or five residues chosen independently from halogen, —OH, loweralkyl, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy, a sugar, a glucuronide a sugar carbamate and —$N^+R^6R^7R^8X^-$.

In compounds of formula V, $R^{1a}$, $R^{2a}$ and $R^{4a}$ each represents one or two residues chosen independently from H, halogen, —OH, loweralkyl, $OCH_3$, $OCF_2H$, $OCF_3$, $CH_3$, $CF_2H$, $CH_2F$, —O-loweralkyl, methylenedioxy, hydroxyloweralkyl, —CN, $CF_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy. $R^3$ is chosen from H, —OH, fluoro, —O-loweralkyl and —O-acyl. $R^{5c}$ is -Q-A-N$^+$R$^9$R$^{10}$R$^{11}$R$^{11}$X$^-$; Q is chosen from a direct bond, —O—, —S—, —NH—, —CH$_2$O—, —CH$_2$NH—, —C(=O)—, —CONH—, —NHCO—, —CH$_2$NH (C=O)—, —O(C=O)—, —(C=O)O—, —NHCONH—, —OCONH— and —NHCOO—; and A is chosen from C$_2$ to C$_{20}$ hydrocarbon, substituted alkyl of 2 to 20 carbons, substituted aryl, substituted arylalkyl, and oxaalkyl of four to fifty carbons; and, when Q is a direct bond, —C(=O) or —O(C=O)—, A may additionally be methylene.

In compounds of formula V$^1$, R$^{2b}$ represents one or two residues chosen independently from H, halogen, —OH, loweralkyl, OCH$_3$, OCF$_2$H, OCF$_3$, CH$_3$, CF$_2$H, CH$_2$F, —O-loweralkyl, methylenedioxy, hydroxyloweralkyl, —CN, CF$_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy. R$^3$ is chosen from H, —OH, fluoro, —O-loweralkyl and —O-acyl. One of R$^d$, R$^{4d}$ and R$^{5d}$ is R$^{12a}$ and the other two of R$^{1d}$, R$^{4d}$ and R$^{5d}$ are chosen independently from hydrogen, halogen, —OH, loweralkyl, —O-loweralkyl, methylenedioxy, hydroxyloweralkyl, —CN, CF$_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy and R$^{12a}$;

R$^{12a}$ is

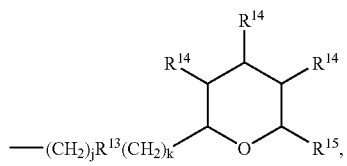

or, when R$^{5d}$ is R$^{12a}$, R$^{12a}$ may additionally be (C$_0$ to C$_{30}$)alkylene-G$_n$ in which one or more —CH$_2$— residues in said alkylene may be replaced by —S—, —SO—, SO$_2$—, —O—, —NH—, —N(alkyl)-, —N(phenyl)-, —N(alkylphenyl)-, —N$^+$(alkyl)$_2$—, —N$^+$(phenyl)$_2$—, —N$^+$(alkylphenyl)$_2$—, —C(=O)—, —C(=S), CH=CH—, —C=C—, phenylene or —N[(C=O)alkyleneCOOH]—; G is chosen from —SO$_3$H, —PO$_3$H$_2$, —O—PO$_3$H$_2$, —COOH, —C(N=H)NH$_2$, a polyol, a sugar, a glucuronide, a sugar carbamate, —N$^+$R$^{6a}$R$^{7a}$R$^{8a}$X$^-$, and a mono or bicyclic trialkylammoniumalkyl residue; R$^{13}$ is chosen from a direct bond, —C=C—, —OCH$_2$, —C(=O)— and —CHOH—; R$^{14}$ is chosen from —OH and —OC(=O)alkyl; R$^{15}$ is chosen from —CH$_2$OH, —CH$_2$C(=O)alkyl and —COOalkyl; j is 1-5; k is zero or 1-5; and n is 1-5.

In compounds of formula VII, R$^{1e}$, R$^{2a}$ and R$^{4e}$ each represents one or two residues chosen independently from H, halogen, —OH, loweralkyl, OCH$_3$, OCF$_2$H, OCF$_3$, CH$_3$, CF$_2$H, CH$_2$F, —O-loweralkyl, methylenedioxy, hydroxyloweralkyl, —CN, CF$_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy. R$^3$ is chosen from H, —OH, fluoro, —O-loweralkyl and —O-acyl. R$^{5e}$ is chosen from

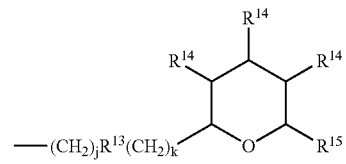

and (C$_0$ to C$_{30}$)alkylene-G$_n$ in which one or more —CH$_2$— residues in said alkylene may be replaced by —S—, —SO—, SO$_2$—, —O—, —NH—, —N(alkyl)-, —N(phenyl)-, —N(alkylphenyl)-, —N$^+$(alkyl)$_2$-, —N$^+$(phenyl)$_2$-, —N$^+$(alkylphenyl)$_2$—, —C(=O)—, —C(=S), CH=CH—, —C=C—, phenylene or —N[(C=O)alkyleneCOOH]—.

In a second aspect the invention relates to pharmaceutical formulations comprising a pharmaceutically acceptable carrier and a compound of the invention having a pharmaceutically acceptable counter anion and, optionally additionally comprising one or more of (1) an inhibitor of cholesterol biosynthesis; (2) a cholesterol ester transfer protein (CETP) inhibitor; (3) a bile acid sequestrant; (4) a nicotinic acid or derivative thereof; (5) a peroxisome proliferator-activator receptor alpha agonist; (6) an acylcoenzyme A:cholesterol acyltransferase (ACAT) inhibitor; (7) an obesity control medication; (8) a hypoglycemic agent; (9) an antioxidant and (10) an antihypertensive compound.

In a third aspect, the invention relates to methods for preventing and/or treating a disorder of lipid metabolism, including hyperlipidemia, sitosterolemia and arteriosclerotic symptoms; inhibiting the absorption of cholesterol from the intestine; reducing the blood plasma or serum concentrations of LDL cholesterol; reducing the concentrations of cholesterol and cholesterol ester in the blood plasma or serum; reducing blood plasma or serum concentrations of C-reactive protein (CRP), reducing blood plasma or serum concentrations of triglycerides; reducing blood plasma or serum concentrations of apolipoprotein B; increasing blood plasma or serum concentrations of high density lipoprotein (HDL) cholesterol; increasing the fecal excretion of cholesterol; treating a clinical condition for which a cholesterol absorption inhibitor is indicated; reducing the incidence of cardiovascular disease-related events; reducing plasma or tissue concentration of at least one non-cholesterol sterol or 5α-stanol; treating or preventing vascular inflammation; preventing, treating, or ameliorating symptoms of Alzheimer's Disease; regulating the production or level of at least one amyloid β peptide in the bloodstream and/or brain of a subject; regulating the amount of ApoE isoform 4 in the bloodstream and/or brain; preventing and/or treating obesity; and preventing or decreasing the incidence of xanthomas. The methods comprise administering a compound described herein.

In a fourth aspect, the invention relates to methods and compositions for prevention or treatment of a cholesterol-associated tumor. The methods comprise administering a therapeutically effective amount of a compound of the invention to a patient at risk of developing a cholesterol-associated tumor or already exhibiting a cholesterol-associated tumor. The method also includes coadministering a therapeutically effective amount of a compound of the invention and at least one other anticancer agent.

In a fifth aspect, the invention relates to an article of manufacture comprising a container, instructions, and a pharmaceutical formulation as described above. The instructions are for the administration of the pharmaceutical formulation for a purpose chosen from: the prevention or treatment of a disorder of lipid metabolism; inhibiting the absorption of cholesterol from the intestine; reducing the plasma or tissue concentration of at least one non-cholesterol sterol or 5α-stanol; reducing the blood plasma or serum concentrations of LDL cholesterol; reducing the concentrations of cholesterol and cholesterol ester in the blood plasma or serum; increasing the fecal excretion of cholesterol; reducing the incidence of cardiovascular disease-related events; reducing blood plasma or serum concentrations of C-reactive protein (CRP); treating or preventing vascular inflammation; reducing blood plasma or serum concentrations of triglycerides; increasing blood plasma or serum concentrations of HDL cholesterol; reducing blood plasma or serum concentrations of apolipoprotein B; preventing, treating, or ameliorating symptoms of Alzheimer's Disease; regulating the production of amyloid β peptide; regulating the amount of ApoE isoform 4 in the bloodstream and/or brain; preventing and/or treating obesity; preventing or decreasing the incidence of xanthomas; and preventing or treating a cholesterol-associated tumor.

DETAILED DESCRIPTION OF THE INVENTION

Compounds of the genus represented by formulae Φ, Ψ, and I-VII above are inhibitors of cholesterol absorption from the intestine. As such they have utility in treating and preventing lipid disorders, such as hypercholesterolemia and hyperlipidemia. Because of their effect in lowering serum lipids, the compounds are useful in the treatment and prevention of atherosclerosis. The compounds can be used advantageously in combination with other hypolipidemic agents, including inhibitors of cholesterol biosynthesis, such as HMG-CoA reductase inhibitors. HMG-CoA reductase inhibitors include the "statins": lovastatin, simvastatin, pravastatin, rosuvastatin, mevastatin, atorvastatin, cerivastatin, pitavastatin, fluvastatin, bervastatin, crilvastatin, carvastatin, rivastatin, sirrivastatin, glenvastatin and dalvastatin. A further listing of non-limiting examples of antihyperlipidemic agents that may be used in combination with the compounds of the present invention may be found in columns 5-6 of U.S. Pat. No. 6,498,156, and in PCT WO 04/004778, the disclosures of which are incorporated herein by reference. As described above, the formulation may additionally contain at least one bile acid sequestrant. Sequestrants include cholestyramine, colestipol and colesevelam hydrochloride. The formulation may also contain a nicotinic acid or derivative thereof. Nicotinic acid derivatives include niceritrol, nicofuranose and acipimox. The formulation may also contain a peroxisome proliferator-activator receptor alpha agonist, which may be a fibric acid derivative. Fibric acids include fenofibrate, clofibrate, gemfibrozil, ciprofibrate, bezafibrate, clinofibrate, binifibrate and lifibrol. The formulation may also contain a CETP inhibitor. Examples of such are the compounds identified as JTT-705 in *Nature.* 406, (6792):203-7 (2000) and CP-529,414 (torcetrapib), described in US20030186952 and WO2000017164. Examples of CETP inhibitors are also found in *Current Opinion in Investigational Drugs.* 4(3):291-297 (2003). The formulation may also contain an ACAT inhibitor. Examples of such are the compounds identified as avasimibe in *Current Opinion in Investigational Drugs.* 3(9):291-297 (2003), and CL-277,082 in *Clin Pharmacol Ther.* 48(2):189-94 (1990). The formulation may also contain an obesity control medication. Examples of obesity control medications include gut hormone fragment peptide $YY_{3-36}$ ($PYY_{3-36}$)(*N. Engl. J. Med.* 349:941, 2003; IKPEAPGE DASPEELNRY YASLRHYLNL VTRQRY) or a variant thereof, glp-1 (glucagon-like peptide-1), exendin-4 (an inhibitor of glp-1), sibutramine, phentermine, phendimetrazine, benzphetamine hydrochloride (Didrex), orlistat (Xenical), diethylpropion hydrochloride (Tenuate), fluoxetine (Prozac), bupropion, ephedra, chromium, garcinia cambogia, benzocaine, bladderwrack (focus vesiculosus), chitosan, nomame herba, galega (Goat's Rue, French Lilac), conjugated linoleic acid, L-carnitine, fiber (psyllium, plantago, guar fiber), caffeine, dehydroepiandrosterone, germander (teucrium chamaedrys), B-hydroxy-β-methylbutyrate, ATL-962 (Alizyme PLC), T71 (Tularik, Inc.; Boulder Colo.), a ghrelin antagonist, Acomplia (rimonabant), AOD9604, alpha-lipoic acid (alpha-LA), and pyruvate. The formulation may also contain a hypoglycemic agent. Examples of of classes of hypoglycemic agents include the peroxisome proliferator-activator receptor gamma agonists (including, e.g. rosiglitazone, pioglitazone, ciglitazone; and metformin, phenformin, carbutamide, tolbutamide, acetohexamide, tolazamide, chlorpropamide, glyburide [glibenclamide], glipizide, and gliclazide). The formulation may also contain an antioxidant. Examples of antioxidants include probucol and AGI-1067.

The formulation may also contain an antihypertensive compound. Examples of classes of antihypertensive compounds include thiazide derivatives, β-adrenergic blockers, calcium-channel blockers, angiotensin-converting-enzyme (ACE) inhibitor, and angiotensin II receptor antagonists. Examples of thiazide derivatives include hydrochlorothiazide, chlorothiazide, and polythiazide. Examples of β-adrenergic blockers include atenolol, metoprolol, propranolol, timolol, carvedilol, nadolol, and bisoprolol. Examples of calcium-channel blockers include isradipine, verapamil, nitrendipine, amlodipine,nifedipine, nicardipine, isradipine, felodipine, nisoldipine, and diltiazem. Examples of angiotensin-converting-enzyme (ACE) inhibitors include delapril, captopril, enalopril, lisinopril, quinapril, perindopril, benazepril, trandolapril, fosinopril, ramipril, and ceranapril. Examples of angiotensin II receptor antagonists include candesartan, irbesartan, olmesartan, telmisartan, and aprosartan.

In one embodiment, the invention comprises a compound of the invention together with a statin. In another embodiment, the invention further comprises an agent chosen from niacin, a sequestrant and a fibrate. In another embodiment, the invention comprises a compound of the invention together with a statin, niacin, a sequestrant and a fibrate.

The present invention is also directed to methods of prevention or treatment of a cholesterol-associated tumor in patients who are either at risk of developing a cholesterol-associated tumor or already exhibit a cholesterol-associated tumor. The tumor may be either a benign or a malignant tumor of the prostate, breast, endometrium or colon. The compounds of the invention may be co-administered with at least one other anticancer agent, which may be a steroidal antiandrogen, a non-steroidal antiandrogen, an estrogen, diethylstilbestrol, a conjugated estrogen, a selective estrogen receptor modulator (SERM), a taxane, or an LHRH analog. Tests showing the efficacy of the therapy and the rationale for combination therapy are presented in PCT application WO 2004/010948, the disclosure of which is incorporated herein by reference.

The compounds of the invention may reduce both cholesterol levels in vivo and epoxycholesterol formation and thereby inhibit initiation and progression of benign and malignant cholesterol-associated tumors or cholesterol-associated cell growth or cell-masses. Compositions disclosed herein, for example, are useful for the treatment and/or prevention of benign prostatic hypertrophy, as well as tumors associated with prostate, colon, endometrial, or breast tissues.

Compositions of the invention comprise an effective dose or a pharmaceutically effective amount or a therapeutically effective amount of a compound described above and may additionally comprise at least one other anticancer agent, for the treatment or prevention of benign prostatic hypertrophy or other cholesterol-related benign or malignant tumors, particularly those associated with prostate, breast, endometrial or colon tissues. Examples of agents for use in compositions and methods of the invention include steroidal or non steroidal antiandrogens such as finasteride (PROSCAR®), cyproterone acetate (CPA), flutamide (4'-nitro-3'-trifluorormethyl isobutyranilide), bicalutamide (CASODEX®), and nilutamide; estrogens, diethylstilbestrol (DES); conjugated estrogens (e.g., PREMARIN®); selective estrogen receptor modulator (SERM) compounds such as tamoxifen, raloxifene, droloxifene, idoxifene; taxanes such as paclitaxel (TAXOL®) and docetaxel (TAXOTERE®); and LHRH analogs such as goserelin acetate (ZOLADEX®), and leuprolide acetate (LUPRON®).

Methods of the invention parallel the compositions and formulations. The methods comprise co-administering to a patient in need of treatment a therapeutically effective amount of an azetidinone according to the invention and one or more of: (a) a steroidal or non steroidal antiandrogen; (b) an estrogen; (c) diethylstilbestrol (DES); (d) a conjugated estrogen; (e) a selective estrogen receptor modulator (SERM); (f) a taxane; and (g) an LHRH analog. The term "selective estrogen receptor modulator" includes both estrogen agonist and estrogen antagonists and refers to compounds that bind with the estrogen receptor, inhibit bone turnover and prevent bone loss. In particular, estrogen agonists are compounds capable of binding to the estrogen receptor sites in mammalian tissue and mimicking the actions of estrogen in that tissue. Estrogen antagonists are compounds capable of binding to the estrogen receptor sites in mammalian tissue and blocking the actions of estrogen in that tissue. Exemplary SERMs are: tamoxifen (U.S. Pat. No. 4,536,516); 4-hydroxytamoxifen (U.S. Pat. No. 4,623,660); raloxifene (U.S. Pat. No. 4,418,068); idoxifene (U.S. Pat. No. 4,839,155; and droloxifene. For the taxanes see U.S. Pat. Nos. 6,395,770; 6,380,405; and 6,239,167. Azetidinones of the invention may also be combined with a steroidal or non steroidal antiandrogen, as described above.

Certain compounds of the invention may have the additional advantage that they suppress serum cholesterol and/or LDL levels while themselves not being appreciably absorbed into the mammalian circulation upon oral administration. As a result of the low-to-insignificant serum levels, fewer side-effects, such as drug-drug interactions, are observed.

Subgenera according to the invention include compounds of formulae Φ and Ψ in which U is chosen from —CH$_2$CH$_2$CH(OH)—, —SCH$_2$CH$_2$—, —S(O)CH$_2$CH$_2$—, —SCH$_2$C(=O)—, —SCH$_2$CH(OH)—, —CH(OH)CH$_2$CH$_2$— and —(CH$_2$)$_4$—, wherein the left end of the string is the point of attachment to the azetidinone ring and the right end of the string is the point of attachment to the phenyl ring. Other subgenera of compounds of formulae Φ and Ψ include ΦA and ΨA

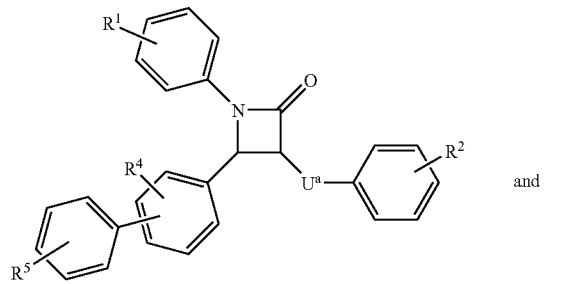

ΦA and

ΨA

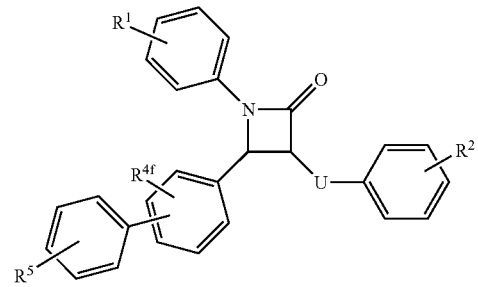

Futher subgenera include compounds of formulae ΦA and ΨA in which the ring bearing $R^5$ is in the para position, e.g.:

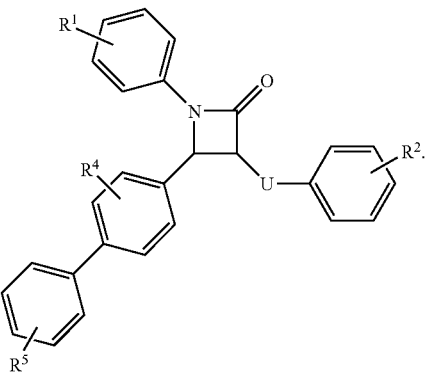

In another subgenus $R^1$ may be H or 4-fluoro; $R^2$ may be 4-fluoro; and $R^4$ may be H or hydroxy. In another subgenus, $R^4$ and $R^5$ are both hydroxy.

Other subgenera according to the invention include compounds in which $R^1$, $R^{1a}$, $R^2$, $R^{2a}$, $R^4$ and $R^{4a}$ are chosen independently from H, halogen, —OH, and methoxy; compounds in which $R^1$, $R^2$, $R^4$ and $R^5$ are chosen from H, a sugar, a glucuronide and a sugar carbamate; compounds in which $R^3$ is chosen from hydrogen and hydroxy; compounds in which $R^4$ or $R^{4a}$ is hydrogen; compounds in which $R^5$ or $R^{5a}$ is chosen from halogen, hydroxy, loweralkyl, —O-loweralkyl, $CF_3$, alkylsulfonyl and arylsulfonyl. Examples of compounds of formula II include those in which one of $R^{1a}$, $R^{1a}$ and $R^{5a}$ is -Q-A-N$^+$R$^9$R$^{10}$R$^{11}$X$^-$ and -Q-A- is chosen from (C$_2$ to C$_{20}$ hydrocarbon), —O—(C$_2$ to C$_{20}$ hydrocarbon), —NH(C$_2$ to C$_{20}$ hydrocarbon), —NHCO(C$_2$ to C$_{20}$ hydrocarbon) and oxaalkyl of four to twenty carbons. In this series of compounds, $R^9$, $R^{10}$ and $R^{11}$ are (1) loweralkyl or benzyl, or (2) $R^9$, $R^{10}$ and $R^{11}$ taken together form a diazabicyclooctane quat:

or (3) $R^9$, $R^{10}$ and $R^{11}$ taken together form a quinuclidinium quat:

Some of the compounds of the invention are quaternary salts, i.e. cationic species. Therefore they will always be presented as salts. Other compounds of formula I may contain basic or acidic residues, allowing them to be presented as salts. In the claims, reference to the acid includes its salts. Thus, for example, a claim to 4'-{(2S,3R)-3-[(3S)-3-(4-fluorophenyl)-3-hydroxypropyl]-4-oxo-1-phenylazetidin-2-yl}-3'-hydroxybiphenyl-4-sulfonic acid is intended to encompass as well sodium 4'-{(2S,3R)-3-[(3S)-3-(4-fluorophenyl)-3-hydroxypropyl]-4-oxo-1-phenylazetidin-2-yl}-3'-hydroxybiphenyl-4-sulfonate. The term "pharmaceutically acceptable salt" refers to salts whose counter ion derives from pharmaceutically acceptable non-toxic acids and bases. When the compounds contain a quat or a basic residue, suitable pharmaceutically acceptable base addition salts for the compounds of the present invention include inorganic acids, organic acids and, in the case of quats, water (which formally furnishes the hydroxide anion). Examples include hydroxide, acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodamide, salicylate, sebacate, stearate, tannate, theoclate, tosylate, and the like. When the compounds contain an acidic residue, suitable pharmaceutically acceptable base addition salts for the compounds of the present invention include ammonium, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Other base addition salts includes those made from: arecoline, arginine, barium, benethamine, benzathine, betaine, bismuth, clemizole, copper, deanol, diethylamine, diethylaminoethanol, epolamine, ethylenediamine, ferric, ferrous, glucamine, glucosamine, histidine, hydrabamine, imidazole, isopropylamine, manganic, manganous, methylglucamine, morpholine, morpholineethanol, n-ethylmorpholine, n-ethylpiperidine, piperazine, piperidine, polyamine resins, purines, theobromine, triethylamine, trimethylamine, tripropylamine, trolamine, and tromethamine.

In certain subgenera of compounds of formulae III, VI and VII, $R^{1b}$ is $R^{12}$; $R^{2b}$ and $R^{4b}$ are chosen from H, halogen, —OH, and methoxy; $R^{12}$ is ($C_6$ to $C_{20}$)alkylene-G in which one or more —$CH_2$— residues in said alkylene may be replaced by —O—, —NH—, —N(alkyl)-, —C(=O)— or —CH=CH—; and G is chosen from —$SO_3H$, a polyol, and a sugar. In a further embodiment, $R^5$ is $R^{12}$; $R^1$, $R^2$ and $R^4$ are chosen from H, halogen, —OH, and methoxy; $R^{12}$ is ($C_6$ to $C_{20}$)alkylene-G in which one or more —$CH_2$— residues in said alkylene may be replaced by —O—, —NH—, —N(alkyl)-, —C(=O)— or —CH=CH—; and G is chosen from —$SO_3H$, a polyol, and a sugar.

Definitions

Throughout this specification the terms and substituents retain their definitions.

Alkyl is intended to include linear, branched, or cyclic hydrocarbon structures and combinations thereof. When not otherwise restricted, the term refers to alkyl of 20 or fewer carbons. Lower alkyl refers to alkyl groups of 1, 2, 3, 4, 5 and 6 carbon atoms. Examples of lower alkyl groups include methyl, ethyl, propyl, isopropyl, butyl, s- and t-butyl and the like. Methyl is preferred. Preferred alkyl and alkylene groups are those of $C_{20}$ or below (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$). Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like.

$C_1$ to $C_{20}$ Hydrocarbon (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) includes alkyl, cycloalkyl, alkenyl, alkynyl, aryl and combinations thereof. Examples include benzyl, phenethyl, cyclohexylmethyl, camphoryl and naphthylethyl. The term "phenylene" refers to ortho, meta or para residues of the formulae:

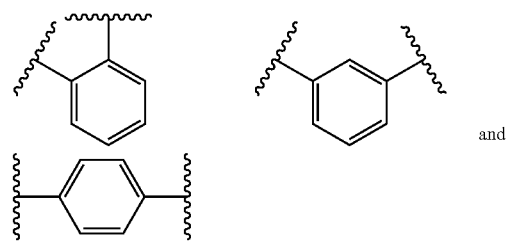

and

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. Methoxy is preferred.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl.

Polyol refers to a compound or residue having a plurality of —OH groups. Polyols may be thought of as alkyls in which a plurality of C—H bonds have been replaced by C—OH bonds. Common polyol compounds include for example glycerol, erythritol, sorbitol, xylitol, mannitol and inositol. Linear polyol residues will generally be of the empirical formula —$C_yH_{2y+1}O_y$, and cyclic polyol residues will generally be of the formula —$C_yH_{2y+1}O_y$. Those in which y is 3, 4, 5 and 6 are preferred. Cyclic polyols also include reduced sugars, such as glucitol.

Acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include, acetyl, propionyl, isobutyryl, t-butoxycarbonyl, benzoyl, benzyloxycarbonyl and the like. Lower-acyl refers to groups containing one to four carbons.

Aryl and heteroaryl refer to aromatic or heteroaromatic rings, respectively, as substituents. Heteroaryl contains one, two or three heteroatoms selected from O, N, or S. Both refer to monocyclic 5- or 6-membered aromatic or heteroaromatic rings, bicyclic 9- or 10-membered aromatic or heteroaromatic rings and tricyclic 13- or 14-membered aromatic or heteroaromatic rings. Aromatic 6, 7, 8, 9, 10, 11, 12, 13 and 14-membered carbocyclic rings include, e.g., benzene, naphthalene, indane, tetralin, and fluorene and the 5, 6, 7, 8, 9 and 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The term "sugar" is used in its normal sense, as defined in *Hawley's Condensed Chemical Dictionary* 12th Edition, Richard J. Lewis, Sr.; Van Nostrand Reinhold Co. New York. It encompasses any carbohydrate comprised of one or two saccharose groups. The monosaccharide sugars (often called simple sugars) are composed of chains of 2-7 carbon atoms. One of the carbons carries aldehydic or ketonic oxygen, which may be combined in acetal or ketal forms. The remaining carbons usually have hydrogen atoms and hydroxyl groups (or protecting groups for hydroxyl, such as acetate). Among monosaccharides which would be considered within the term "sugars" as intended in this application, are arabinose, ribose, xylose, ribulose, xylulose, deoxyribose, galactose, glucose, mannose, fructose, sorbose, tagatose, fucose, quinovose, rhamnose, manno-heptulose and sedoheptulose. Among the disaccharides are sucrose, lactose, maltose, and cellobiose. Unless specifically modified, the general term "sugar" refers to both D-sugars and L-sugars. The sugar may also be protected. The sugar may be attached through oxygen (as in U.S. Pat. No. 5,756,470) or through carbon (as in PCT WO 2002066464), the disclosures of both of which are incorporated herein by reference.

Reduced C-attached sugars or C-glycosyl compounds are also encompassed by the invention. The reduced sugars (e.g. glucitol), which could be classed either as polyols or as sugars, are also known as alditols. Alditols are polyols having the general formula HOCH2[CH(OH)]nCH2OH (formally derivable from an aldose by reduction of the carbonyl group.

The term "glucuronide" is also used in its normal sense to refer to a glycoside of glucuronic acid.

The term "sugar carbamate" refers to mono-, di- and oligosaccharides in which one or more hydroxyls have been derivatized as carbamates, particularly as phenyl carbamates and substituted phenyl carbamates. [See Detmers et al. *Biochim Biophys. Acta* 1486, 243-252 (2000), which is incorporated herein by reference.] A preferred sugar carbamate is:

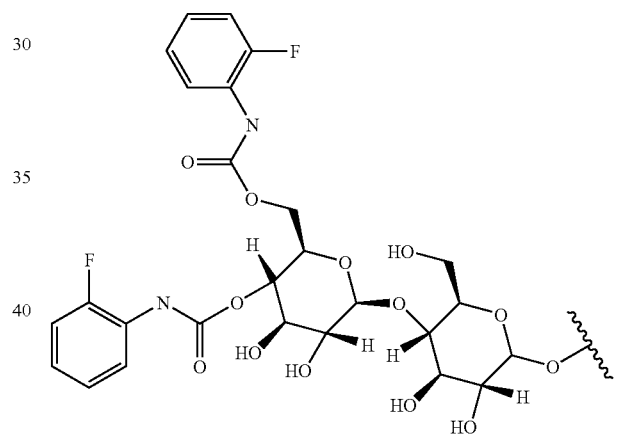

Examples of quats that fall within the definition of monocyclic and bicyclic trialkylammoniumalkyl residues include:

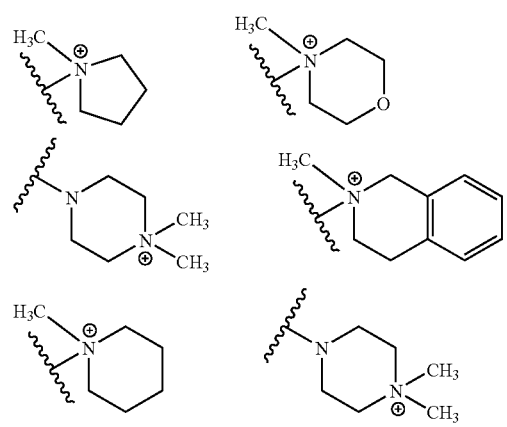

-continued

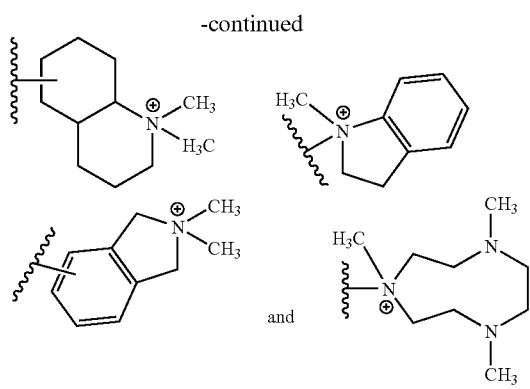

and

The term "prodrug" refers to a compound that is made more active in vivo. Commonly the conversion of prodrug to drug occurs by enzymatic processes in the liver or blood of the mammal. Many of the compounds of the invention may be chemically modified without absorption into the systemic circulation, and in those cases, activation in vivo may come about by chemical action (as in the acid-catalyzed cleavage in the stomach) or through the intermediacy of enzymes and microflora in the gastrointestinal GI tract.

In the characterization of the variables, it is recited that $R^9$ may form a five- to seven-membered ring with A or $R^{10}$; that $R^{10}$ may form a double bond with A or may form a five- to seven-membered ring with $R^9$; and that $R^{11}$ may form a second five- to seven-membered ring. It is intended that these rings may exhibit various degrees of unsaturation (from fully saturated to aromatic), may include heteroatoms and may be substituted with lower alkyl or alkoxy.

In the characterization of the variables, it is recited that R-groups, such as $R^5$, represent one, two, three, four or five residues chosen independently from a list of variable definitions. The structure below illustrates the intent of that language. In this example, $R^5$ represents three residues: —$CH_3$, —OH and —$OCH_3$.

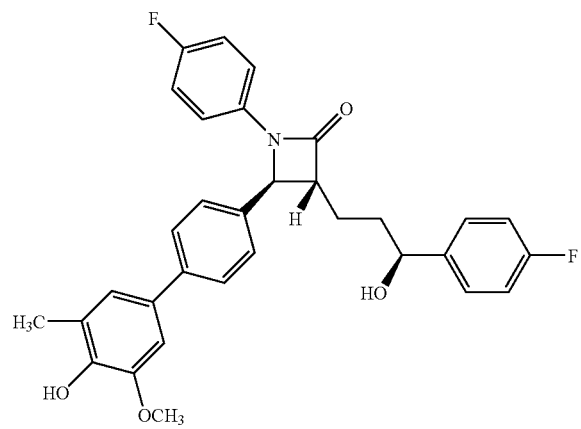

The variables are defined when introduced and retain that definition throughout. Thus, for example, $R^3$ is always chosen from H, —OH, fluoro, —O-loweralkyl and —O-acyl, although, according to standard patent practice, in dependent claims it may be restricted to a subset of these values. Superscripts are added to distinguish among residues that are attached similarly and that have overlapping Markush groups. For example, the substituent attached to the phenyl ring at the 1-position (i.e. on the nitrogen) of the azetidinone is always labeled $R^1$, but can be $R^1$, $R^{1a}$, $R^{1b}$ or $R^{1c}$ depending on the members of the Markush group defining it. For simplicity, the dependent claims, when multiply dependent, may refer to $R^1$ etc. This is intended to modify the appropriate value of the corresponding variable $R^1$, $R^{1a}$, $R^{1b}$, $R^{1c}$ etc. in each claim from which it depends. Thus a claim that recites "a compound according to any of claims 1 to 8 wherein $R^1$ is chosen from H, halogen, —OH and methoxy" intends to further limit, for example, the corresponding $R^{1a}$ substituent in claim 6, the $R^{1b}$ substituent in claim 7 and the $R^{1c}$ substituent in claim 8.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^3H$, $^{14}C$, $^{35}S$, 18F, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Radiolabeled compounds of Formulas I-VIII of this invention and pro-drugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The terms "methods of treating or preventing" mean amelioration, prevention or relief from the symptoms and/or effects associated with lipid disorders. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis. Throughout this application, various references are referred to. The disclosures of these publications in their entireties are hereby incorporated by reference as if written herein.

The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans.

The compounds may be use to treat or prevent vascular inflammation, as described in US published application 20030119757; to prevent, treat, or ameliorate symptoms of Alzheimer's Disease and to regulate the production or level of amyloid β peptide and ApoE isoform 4, as described in U.S. Pat. No. 6,080,778 and US published application 20030013699; and to prevent or decrease the incidence of xanthomas, as described in US published application 20030119809. The disclosures of all are incorporated herein by reference.

The compounds described herein contain two or more asymmetric centers and may thus give rise to enantiomers, diastereomers, and other stereoisomeric forms. Each chiral center may be defined, in terms of absolute stereochemistry, as ®- or (S)—. The present invention is meant to include all such possible isomers, as well as, their racemic and optically pure forms. Optically active ®- and (S)—, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formula XI is intended to encompass both of the pure enantiomers of that pair:

XI

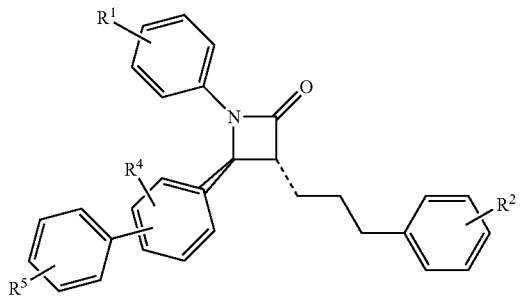

Means either pure R,S:

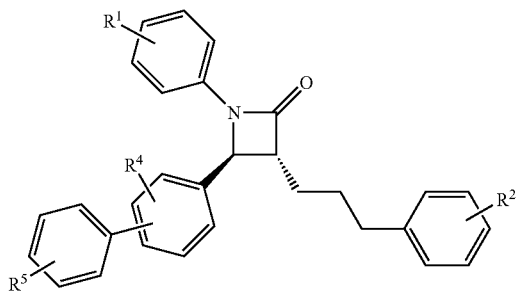

or pure S,R:

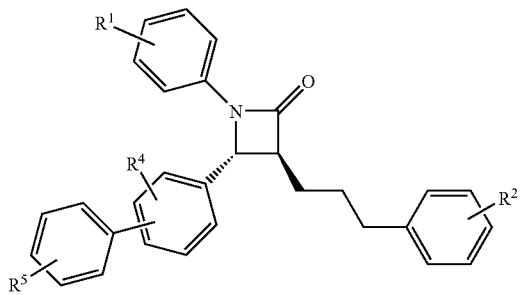

whereas

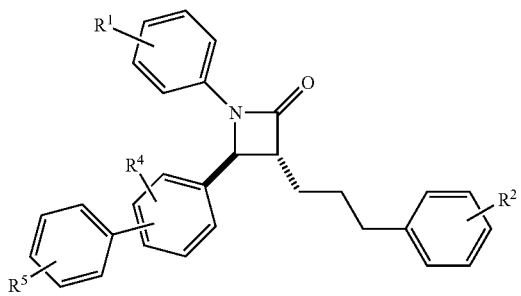

refers to a racemic mixture of R,S and S,R, i.e. having a trans relative configuration on the beta lactam ring.

The term "enantiomeric excess" is well known in the art and is defined for a resolution of ab into a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee; in other words, a 90% ee reflects the presence of 95% of one enantiomer and 5% of the other in the material in question.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

The abbreviations Me, Et, Ph, Tf, Ts and Ms represent methyl, ethyl, phenyl, trifluoromethanesulfonyl, toluenesulfonyl and methanesulfonyl respectively. A comprehensive list of abbreviations utilized by organic chemists (i.e.

persons of ordinary skill in the art) appears in the first issue of each volume of the *Journal of Organic Chemistry*. The list, which is typically presented in a table entitled "Standard List of Abbreviations" is incorporated herein by reference.

While it may be possible for the compounds of formulae Φ, Ψ and I-VIII to be administered as the raw chemical, it is preferable to present them as a pharmaceutical composition. According to a further aspect, the present invention provides a pharmaceutical composition comprising a compound of formula Φ, Ψ or I-VIII or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula Φ, Ψ and I-VIII or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or nonaqueous techniques. "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation.

Examples of excipients for use as the pharmaceutically acceptable carriers and the pharmaceutically acceptable inert carriers and the aforementioned additional ingredients include, but are not limited to:

BINDERS: corn starch, potato starch, other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch (e.g., STARCH 1500® and STARCH 1500 LM®, sold by Colorcon, Ltd.), hydroxypropyl methyl cellulose, microcrystalline cellulose (e.g. AVICEL™, such as, AVICEL-PH-101™, -103™ and -105™, sold by FMC Corporation, Marcus Hook, Pa., USA), or mixtures thereof;

FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, or mixtures thereof;

DISINTEGRANTS: agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, or mixtures thereof;

LUBRICANTS: calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g. peanut oil, cottonseed oil, sunflower oil, sesame oil, olive oil, corn oil and soybean oil), zinc stearate, ethyl oleate, ethyl laurate, agar, syloid silica gel (AEROSIL 200, W. R. Grace Co., Baltimore, Md. USA), a coagulated aerosol of synthetic silica (Degussa Co., Plano, Tex. USA), a pyrogenic silicon dioxide (CAB-O-SIL, Cabot Co., Boston, Mass. USA), or mixtures thereof;

ANTI-CAKING AGENTS: calcium silicate, magnesium silicate, silicon dioxide, colloidal silicon dioxide, talc, or mixtures thereof;

ANTIMICROBIAL AGENTS: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenyl, phenylethyl alcohol, phenylmercuric acetate, phenylmercuric nitrate, potassium sorbate, propylparaben, sodium benzoate, sodium dehydroacetate, sodium propionate, sorbic acid, thimersol, thymo, or mixtures thereof; and COATING AGENTS: sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnuba wax, microcrystalline wax, or mixtures thereof.

The dose range for adult humans is generally from 0.005 mg to 10 g/day orally. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

In Vivo Assay of Hypolipidemic Agents using the Rat Cholesterol Absorption Model. This model is based on models described by Burnett et al (2002), *Bioorg. Med. Chem. Lett.* 2002 Feb. 11;12(3):315-8 and *J. Lipid Res.* 1999 October;40(10):1747-57. Female Sprague-Dawley rats weighing 150-250 g are separated into groups of 3 and fasted overnight. The animals (4-6/group) are dosed perorally with 300 µL test compounds in olive oil or suitable vehicle. Thirty minutes later, 3-5 microCuries $^3$H-cholesterol per rat are delivered perorally in 300 µL olive oil. After three hours, 200 µL serum is collected, vortexed with scintillation fluid, and measured for radioactivity in a scintillation counter. Percent inhibition is defined as $100*(1-C_{test}/C_{ctrl})$, where $C_{test}$ and $C_{ctl}$ refer to $^3$H levels in serum for the test compound and for the vehicle only control, respectively. Percent inhibition values are reported for a fixed dose. The $ED_{50}$ is the dose at which the half-maximal effect on serum $^3$H levels is observed for a given test compound.

In Vivo Assay of Hypolipidemic Agents using the Mouse Cholesterol Absorption Model. Female CD-1 mice weighing 20-30 g are separated into groups of 3-8 and fasted overnight. The animals (3-8/group) are dosed perorally with 200 µL test compound in olive oil or suitable vehicle. Thirty minutes later, 3-5 microCuries $^3$H-cholesterol per mouse are delivered perorally in 200 µL olive oil. After three hours, 100 µL serum is collected, vortexed with scintillation fluid, and measured for radioactivity in a scintillation counter. Percent inhibition and $ED_{50}$ are defined as in the Rat Cholesterol Absorption Model above.

In Vivo Assay of Hypolipidemic Agents Using the Hyperlipidemic Hamster: Hamsters are separated into groups of six and given a controlled cholesterol diet (Purina Chow #5001 containing 0.5% cholesterol) for seven days. Diet consumption is monitored to determine dietary cholesterol exposure in the face of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by intramuscular (IM) injection of ketamine and sacrificed by decapitation. Blood is collected into vacutainer tubes containing EDTA for plasma lipid analysis and the liver excised for tissue lipid analysis. Lipid analysis is conducted as per published procedures [Schnitzer-Polokoff, R., et al, *Comp. Biochem. Physiol.*, 99A, 4, 665-670 (1991)] and data are reported as percent reduction of lipid versus control.

In Vivo Assay of Hypolipidemic Agents using the Hamster Acute Cholesterol Absorption Model. Male Syrian Hamsters weighing 120 g are separated into groups of 3-6 and fasted overnight. The animals (3-6/group) are dosed perorally with 200 µL test compound in olive oil or suitable vehicle. Thirty minutes later, 3-5 microCuries $^3$H-cholesterol per hamster are delivered perorally in 200 µL olive oil. After three hours, 100-200 µL serum is collected, vortexed with scintillation fluid, and measured for radioactivity in a scintillation counter. Percent inhibition and $ED_{50}$ are defined as in the Rat Cholesterol Absorption Model above.

The bioabsorption of the compounds herein described may be examined using the Caco-2 cell monolayer model of Hilgers et al. [*Pharm. Res.* 7, 902 (1990)].

Pharmacokinetics. To study the pharmacokinetics of compounds, bioavailability studies are carried out in rats. Compounds are prepared in suitable formulations: 5% ethanol in olive oil for oral administration and 2% DMSO: 20% cyclodextrins in $H_2O$ for intravenous administration. Compounds are administered intravenously via tail vein injection and orally by gavage to independent groups of CD rats (200-250 g). Serum is collected at various time points and assayed for the presence of compounds using an LC/MS/MS detection method. Samples are diluted 15-fold in 30% acetonitrile in water, then injected (35 mL) into a 3.2 ml/min flow of 5% methanol in water onto a sample extraction cartridge (Waters Oasis HLB Direct Connect), washed for 30 seconds, then loaded onto a reverse phase HPLC column (Thermo Electron Betasil C18 Pioneer 50×2.1 mm, 5 um particle size). Samples are eluted from the reverse phase HPLC column with a gradient: (Mobile Phase A: 5 mM ammonium acetate in $dH_2O$, Mobile Phase B: 20% methanol in acetonitrile; 40% B ramping to 95% B over 4 minutes, and holding for 3 minutes, then returning to initial conditions to re-equilibrate the column for 1 min, all at a flow rate of 0.3 ml/min.). A Micromass Quattro Micro (Waters Corp.; Milford, Mass.) triple quadrupole mass spectrometer operated in MRM mode is used for detection. Concentrations are calculated based on standard concentration curves of compounds. MassLynx software (Waters, Corp.; Milford, Mass.) is used to calculate the absolute concentration of test compound in each serum sample. A concentration versus time plot is generated from the data in Microsoft Excel, Summit Software PK Solutions 2.0 or GraphPad Prism (GraphPad Software, Inc., San Diego, Calif.) to generate pharmacokinetic curves. An area under the curve ($AUC_n$, n=length of experiment in minutes or hours) is calculated from the concentration vs. time data by the software using the trapezoid method for both the orally and intravenously dosed animals. Oral Bioavailability (F) over the length of the experiment is calculated using the equation:

$$F=(AUC_{oral}*Dose_{i.v.})/(AUC_{i.v.}*Dose_{oral})$$

Representative compounds of the invention were tested in the Rat Cholesterol Absorption model above. The compounds of the invention exhibited inhibition as shown below in Tables 1 and 2

TABLE 1

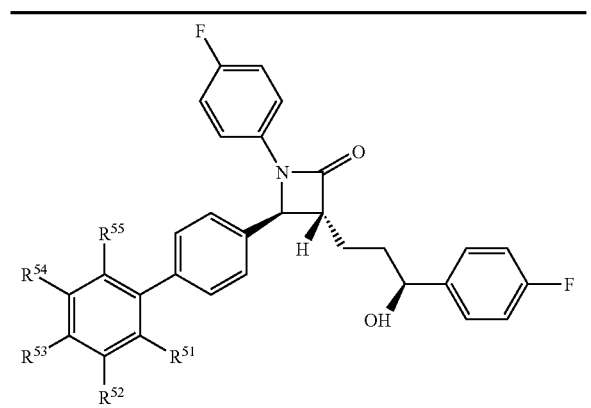

| Example # | $R^{51}$ | $R^{52}$ | $R^{53}$ | $R^{54}$ | $R^{55}$ | % inhibition at 1 mg/kg |
|---|---|---|---|---|---|---|
| 2 | | | OH | | | 54[1] |
| 3 | | | | | | 15[1] |
| 4 | | OH | | | | 72 |
| 5 | | | OMe | | | 26[1] |
| 7 | OH | | | | | 30 |
| 8 | | | SO$_2$Me | | | 53 |
| 9 | | OMe | OMe | OMe | | 40 |
| 10 | | SO$_2$Me | | | | 54[2] |
| 11 | OMe | OMe | | | | 28 |
| 12 | | OMe | | | | 70 |
| 13 | | CHO | | | | 70 |
| 14 | | CN | | | | 32[3] |
| 15 | | | SO$_2$NMe$_2$ | | | 8 |
| 16 | | CH$_2$OH | | | | 72 |
| 17 | | | NMe$_2$ | | | 43 |
| 18 | | | CH$_2$OH | | | 48 |
| 19 | | OH | | Br | | 66 |
| 20 | | O-glucuronide | | | | 59 |
| 21 | | CO$_2$H | | | | 68 |
| 22 | | | CO$_2$H | | | 52 |
| 23 | | NO$_2$ | | | | 54[1] |
| 26 | | NHAc | | | | 76[1] |
| 28 | | | NH$_2$ | | | 56 |
| 56 | | P=O(OH)$_2$ | | | | 59 |
| 76 | | O—C6-glucopyranose | | | | 56 |
| 77 | | O—C6-methyl glucopyranoside | | | | 70 |
| 78 | | O—C6-glucitol | | | | 51 |
| 81 | | OMe | OMe | | | 17 |
| 82 | | SMe | | | | 28 |
| 83 | | NMe2 | | | | 38 |
| 84 | | | CH=CH$_2$ | | | 51 |
| 85 | | OMe | | | CHO | 15 |
| 86 | | NH$_2$ | | | | 35 |
| 87 | | O—CH$_2$—CH$_2$—O | | | | 59 |
| 88 | | | CH$_2$CO$_2$H | | | 30 |
| 89 | | | CO$_2$Me | | | 45 |
| 90 | Me | | | | Me | 27 |
| 91 | | β-naphthyl | | | | 56 |
| 92 | CF$_3$ | | | | | 17 |
| 93 | Me | | | | | 28 |

TABLE 1-continued

| Example # | $R^{51}$ | $R^{52}$ | $R^{53}$ | $R^{54}$ | $R^{55}$ | % inhibition at 1 mg/kg |
|---|---|---|---|---|---|---|
| 94 | | Me | F | | | 30 |
| 95 | | O-glucopyranose | | | | 57 |
| 96 | OMe | OMe | OMe | | | 69 |
| 97 | OMe | | OMe | | | 40 |
| 98 | Me | | | | | 7 |
| 99 | | | CHO | | | 38 |
| 100 | | OEt | | | | 54 |
| 101 | | | OEt | | | 41 |
| 102 | | OMe | OH | | | 56 |
| 103 | | O—nPr | | | | 21 |
| 104 | | OH | | | CHO | 52 |
| 105 | | O—iPr | | | | 15 |
| 106 | | CO$_2$H | OH | | | 66 |
| 107 | | OMe | | OMe | | 49 |
| 108 | OH | | OH | | | 69 |
| 109 | | O—nBu | | | | 52 |
| 110 | | OH | CO$_2$H | | | 72 |
| 111 | | OMe | | F | | 72 |
| 112 | | OH | | F | | 75 |
| 113 | | C1-glucitol | | | | 67 |
| 114 | | OH | | OH | | 72 |
| 115 | | B(OH)$_2$ | | | | 70 |
| 116 | | | C1-glucopyranose | | | 81 |
| 117 | | C1-CH$_2$-glucopyranose | | | | 26 |
| 118 | | SO$_3$H | | | | 61 |
| 119 | | SH | | | | 56 |
| 120 | | NMe$_3^+$ | | | | 23 |

[1]% inhibition at 10 mg/kg
[2]% inhibition at 3 mg/kg
[3]% inhibition at 5 mg/kg

TABLE 2

| Example # | R51 | R52 | R53 | R1 | R4 ring | % inhibition at 1 mg/kg |
|---|---|---|---|---|---|---|
| 42 |  | OH |  | H | 2-hydroxy-5-methylphenyl | 87 |
| 44 |  | OH |  | F | 3-methylphenyl | 24 |
| 46 |  |  | OH | F | 3-methylphenyl | 30 |
| 49 |  | OH |  | H | 5-methylpyridin-2-yl | 30 |
| 50 |  | OH |  | H | 5-methylthien-2-yl | 27 |
| 51 |  |  | OH | H | 5-methylthien-2-yl | 39 |
| 53 |  | SO3H |  | H | 2-hydroxy-5-methylphenyl | 78 |
| 57 |  | OH |  | H | 4-methylphenyl | 73 |
| 59 |  | B(OH)2 |  | H | 4-methylphenyl | 70 |

TABLE 2-continued
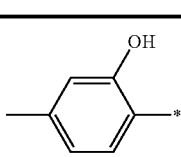
| Example # | R51 | R52 | R53 | R1 |  | % inhibition at 1 mg/kg |
|---|---|---|---|---|---|---|
| 61 | | P=O(OH)$_2$ | | H | 2-OH,5-* phenyl | 58[3] |
| 64 | | C1-glucitol | | H | 1,4-phenyl | 67 |
| 65 | | C1-glucitol | | H | 2-OH,5-* phenyl | 60[5] |
| 66 | | | C1-glucitol | H | 2-OH,5-* phenyl | 71[6] |
| 71 | | C6-S-glucopyranose | | H | 1,4-phenyl | 65 |
| 72 | | C6-R-glucopyranose | | H | 1,4-phenyl | 27[6] |
| 73 | | C6-S-glucopyranose | | H | 2-OH,5-* phenyl | 59 |
| 74 | | C6-R-glucopyranose | | H | 2-OH,5-* phenyl | 67 |

TABLE 2-continued
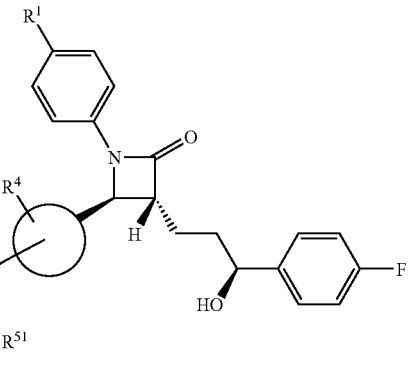
| Example # | R⁵¹ | R⁵² | R⁵³ | R¹ | R⁴ / ring | % inhibition at 1 mg/kg |
|---|---|---|---|---|---|---|
| 75 | | C6-S-glucitol | | H | 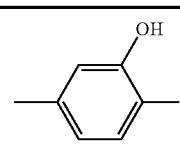 | 68 |
| 121 | | OH | F | | 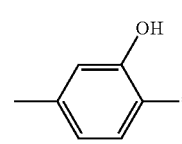 | 72⁷ |
| 122 | | P=O(OH)₂ | | H | 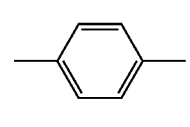 | 67 |
| 123 | | SO₂Me | | H | 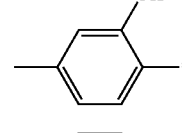 | 72 |
| 124 | | OH | | Ph | 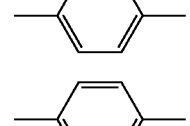 | 48 |
| 125 | | | OH | H | 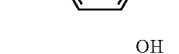 | 64 |
| 127 | | | P=O(OH)₂ | H | 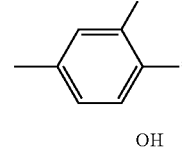 | 58 |
| 128 | | SO₃⁻Na⁺ | | | 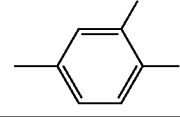 | 60 |
⁴The asterisk indicates the point of attachment to the azetidine ring.
⁵% inhibition at 0.1 mg/kg
⁶% inhibition at 0.3 mg/kg
⁷the asterisk indicates the point of attachment to the azetidine ring In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

The starting materials, in the case of suitably substituted azetidinones, may be obtained by the methods described in WO 02/50027, WO 97/16424, WO 95/26334, WO 95/08532 and WO 93/02048, the disclosures of which are incorporated herein by reference.

Processes for obtaining the compounds of the invention are presented below. Although detailed syntheses are not presented for every example in Tables 1 and 2, the procedures below illustrate the methods. The other compounds were made in analogous fashion to those whose synthesis is exemplified.

EXAMPLE 1

Preparation of the Intermediate 4-{(2S,3R)-1-(4-fluorophenyl)-3-[(3S)-3-(4-fluorophenyl)-3-hydroxypropyl]-4-oxoazetidin-2-yl}phenyl trifluoromethanesulfonate

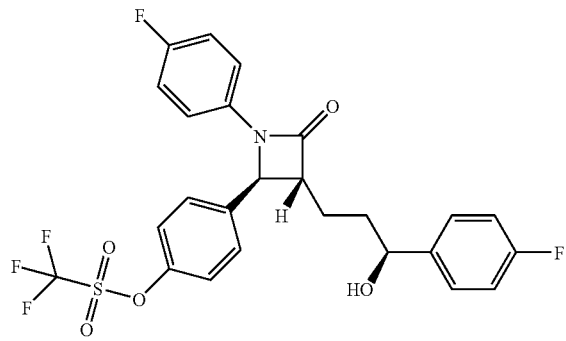

(3R,4S)-1-(4-Fluorophenyl)-3-[(3S)-3-(4-fluorophenyl)-3-hydroxypropyl]-4-(4-hydroxyphenyl)azetidin-2-one (150.4 mg, 0.367 mmol) and 4-dimethylaminopyridine (9.4 mg, 0.077 mmol) were dissolved in methylene chloride (10.0 mL). Triethylamine (100 μL, 72.6 mg, 0.717 mmol) was added via syringe followed by N-phenyltrifluoromethanesulfonimide (143.6 mg, 0.402 mmol) added as a solid. The reaction was stirred for 3.5 h at room temperature and then poured into water (40 mL) and extracted with 1:1 ethyl acetate-hexane (75 mL). The organic layer was washed with water (40 mL) and brine (40 mL), then dried over sodium sulfate, filtered, concentrated and purified by chromatography (12 g silica gel, 10% to 90% ethyl acetate-hexane) to afford 4-{(2S,3R)-1-(4-fluorophenyl)-3-[(3S)-3-(4-fluorophenyl)-3-hydroxypropyl]-4-oxoazetidin-2-yl}phenyl trifluoromethanesulfonate (190.8 mg, 96% yield) as a clear film (eventually becomes a while solid); mp 121.6° C.; $R_f$ 0.38 (2:3 ethyl acetate-hexane); $^1$H NMR (300 MHz, CDCl$_3$) δ 7.41 (d, J=8.7 Hz, 2H), 7.31-7.26 (m, 4H), 7.19 (dd, J=9.0, 4.6 Hz, 2H), 7.01 (t, J=8.7 Hz, 2H), 6.95 (t, J=8.7 Hz, 2H), 4.71 (t, J=6.0 Hz, 1H), 4.67 (d, J=2.3 Hz, 1H), 3.10-3.04 (m, 1H), 2.08-1.86 (m, 4H) ppm; MS [M−OH] 524.5.

EXAMPLE 2

Preparation of (3R,4S)-1-(4-fluorophenyl)-3-[(3S)-3-(4-fluorophenyl)-3-hydroxypropyl]-4-(4'-hydroxybiphenyl-4yl)azetidin-2-one

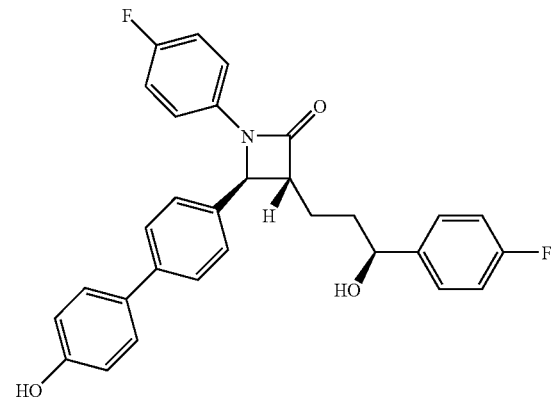

4-{(2S,3R)-1-(4-Fluorophenyl)-3-[(3S)-3-(4-fluorophenyl)-3-hydroxypropyl]-4-oxoazetidin-2-yl}phenyl trifluoromethanesulfonate (162.5 mg, 0.30 mmol) and tetrakis(triphenylphosphine)palladium(0) (17.3 mg, 0.015 mmol) were dissolved in toluene (2.5 mL). 2.0 M aqueous potassium carbonate (0.3 mL) and a solution of 4-hydroxyphenylboronic acid (57.9 mg, 0.42 mmol) in ethanol (1.0 mL) were added. The reaction was stirred vigorously for 5 h at refluxing temperature under a nitrogen atmosphere and then diluted with water (2.5 mL), extracted with ethyl acetate (3×10 mL), washed with brine (10 mL), dried over sodium sulfate, filtered, concentrated and purified by chromatography (12 g silica gel, 10% to 100% ethyl acetate-hexane) to afford (3R,4S)-1-(4-fluorophenyl)-3-[(3S)-3-(4-fluorophenyl)-3-hydroxypropyl]-4-(4'-hydroxybiphenyl-4-yl)azetidin-2-one (112 mg, 77% yield) as a clear film; mp 110° C.; $R_f$ 0.5 (1:1 ethyl acetate-hexane); $^1$H NMR (300 MHz, CDCl$_3$) δ 7.5 (d, J=9.0 Hz, 2H) 7.4 (d, J=9.0 Hz, 2H) 7.3 (m, 6H), 6.9 (m, 6H), 4.7 (m, 1H), 4.6 (s, 1H), 3.15 (m, 1H), 2.1-1.9 (m, 4H) ppm; MS [M+H] 486.5.

In the same manner was obtained:

EXAMPLE 3

(3R,4S)-4-Biphenyl-4-yl-1-(4-fluorophenyl)-3-[(3S)-3-(4-fluorophenyl)-3-hydroxypropyl]azetidin-2-one

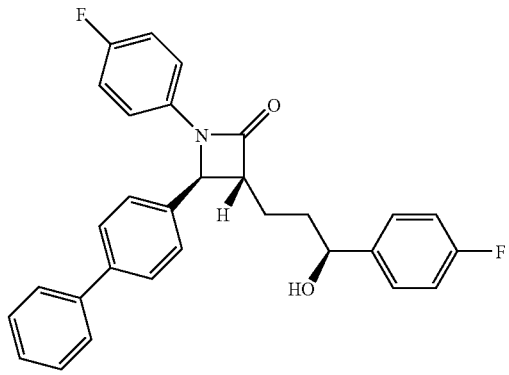

(3R,4S)-4-Biphenyl-4-yl-1-(4-fluorophenyl)-3-[(3S)-3-(4-fluorophenyl)-3-hydroxypropyl]azetidin-2-one (11.8 mg, 54% yield) as a clear film; purification by chromatography (4 g silica gel, 10% to 100% ethyl acetate-hexane) and then by reverse-phase HPLC (21 mm column, 50% to 100% acetonitrile-0.1% trifluoroacetic acid in water); R$_f$ 0.47 (3:2 ethyl acetate-hexane); $^1$H NMR (300 MHz, CD$_3$OD) δ 7.63 (d, J=8.3 Hz, 2H), 7.61-7.58 (m, 2H), 7.45-7.39 (m, 4H), 7.35-7.28 (m, 5H), 7.02 (t, J=8.8 Hz, 2H), 7.00 (t, J=8.8 Hz, 2H), 4.63 (t, J=5.7 Hz, 1H), 3.15-3.00 (m, 1H), 2.05-1.84 (m, 5H) ppm; MS [M−OH] 452.5.

EXAMPLE 4

(3R,4S)-1-(4-Fluorophenyl)-3-[(3S)-3-(4-fluorophenyl)-3-hydroxypropyl]-4-(3'-hydroxybiphenyl-4-yl)azetidin-2-one

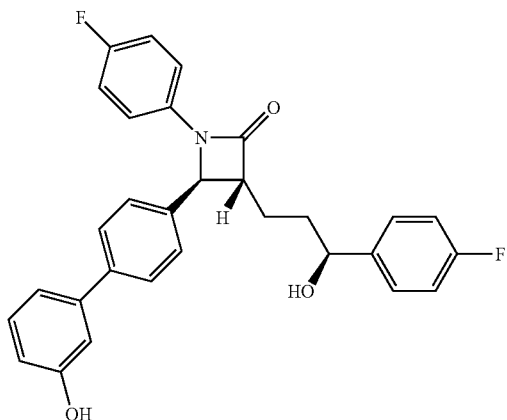

(3R,4S)-1-(4-Fluorophenyl)-3-[(3S)-3-(4-fluorophenyl)-3-hydroxypropyl]-4-(3'-hydroxybiphenyl-4-yl)azetidin-2-one (110 mg, 76% yield using a reaction time of 4 h) as an off white solid; purification by chromatography (12 g silica gel, 10% to 100% ethyl acetate-hexane); mp 107° C.; R$_f$ 0.50 (1:1 ethyl acetate-hexane); $^1$H NMR (300 MHz, CDCl$_3$) δ 7.6 (d, J=8.9 Hz, 2H), 7.3 (d, J=8.9 Hz, 2H), 7.2 (m, 6H), 6.9 (m, 6H), 4.7(m, 1H), 4.6(s, 1H), 3.15 (m, 1H), 2.1-1.9 (m, 4H) ppm; MS [M+H] 486.5.

EXAMPLE 5

(3R,4S)-1-(4-fluorophenyl)-3-[(3S)-3-(4-fluorophenyl)-3-hydroxypropyl]-4-(4'-methoxybiphenyl-4-yl)azetidin-2-one

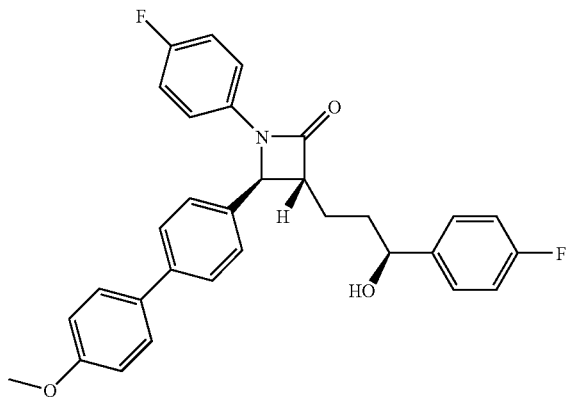

(3R,4S)-1-(4-fluorophenyl)-3-[(3S)-3-(4-fluorophenyl)-3-hydroxypropyl]-4-(4'-methoxybiphenyl-4-yl)azetidin-2-one (86 mg, 67% yield using a reaction time of 16 h) as a white solid; purification by chromatography (12 g silica gel, 10% to 100% ethyl acetate-hexane); mp 103° C.; R$_f$ 0.75 (1:1 ethyl acetate-hexane); $^1$H NMR (300 MHz, CDCl$_3$) δ 7.4 (m, 4H), 7.3 (m, 6H), 6.9 (m, 6H), 4.75 (m, 1H), 4.65 (s, 1H), 3.85 (s, 3H), 3.2 (m, 1H), 2.1-1.9 (m, 4H) ppm; MS [M−OH] 482.5.

EXAMPLE 6

(3R,4S)-1-(4-fluorophenyl)-3-[(3S)-3-(4-fluorophenyl)-3-hydroxypropyl]-4-(6-hydroxybiphenyl-3-yl)azetidin-2-one

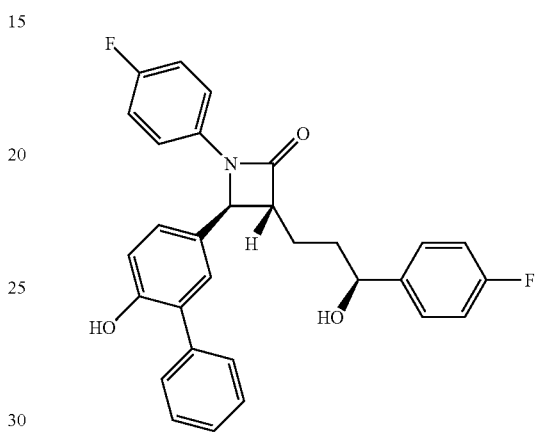

(3R,4S)-1-(4-fluorophenyl)-3-[(3S)-3-(4-fluorophenyl)-3-hydroxypropyl]-4-(6-hydroxybiphenyl-3-yl)azetidin-2-one (36 mg, 40% yield using a reaction time of 16 h) as a white solid; purification by chromatography (12 g silica gel, 10% to 100% ethyl acetate-hexane); mp 113° C.; R$_f$ 0.70 (1:1 ethyl acetate-hexane); $^1$H NMR (300 MHz, CDCl$_3$) δ 7.5-6.9 (m, 16H), 4.75 (m, 1H), 4.65 (s, 1H), 3.2 (m, 1H), 2.1-1.9 (m, 4H) ppm; MS [M+H] 486.5.

EXAMPLE 7

(3R,4S)-1-(4-fluorophenyl)-3-[(3S)-3-(4-fluorophenyl)-3-hydroxypropyl]-4-(2'-hydroxybiphenyl-4-yl)azetidin-2-one

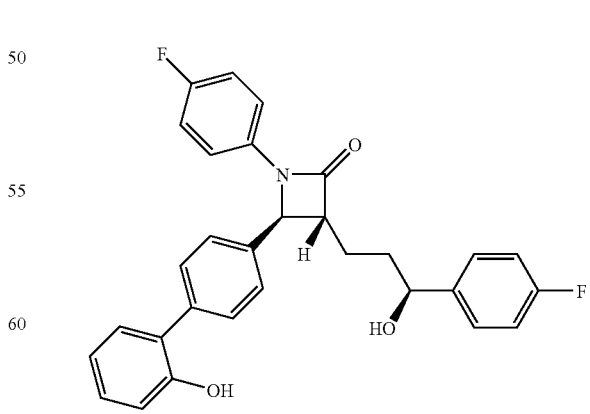

(3R,4S)-1-(4-fluorophenyl)-3-[(3S)-3-(4-fluorophenyl)-3-hydroxypropyl]-4-(2'-hydroxybiphenyl-4-yl)azetidin-2-one (74 mg, 51% yield using a reaction time of 2 h) as a white solid; purification by chromatography (12 g silica gel, 10% to 100% ethyl acetate-hexane); mp 101° C.; $R_f$ 0.50 (1:1 ethyl acetate-hexane); $^1$H NMR (300 MHz, CDCl$_3$) δ 7.6 (d, J=9.0 Hz, 2H), 7.4 (d, J=9.0 Hz, 2H), 7.25 (m, 6H), 6.9 (m, 6H), 6.3 (s, 1H), 4.65 (m, 2H), 3.1 (m, 1H), 2.1-1.9 (m, 4H) ppm; MS [M+H] 486.5.

EXAMPLE 8

(3R,4S)-1-(4-fluorophenyl)-3-[(3S)-3-(4-fluorophenyl)-3-hydroxypropyl]-4-[4'-(methylsulfonyl)biphenyl-4-yl]azetidin-2-one

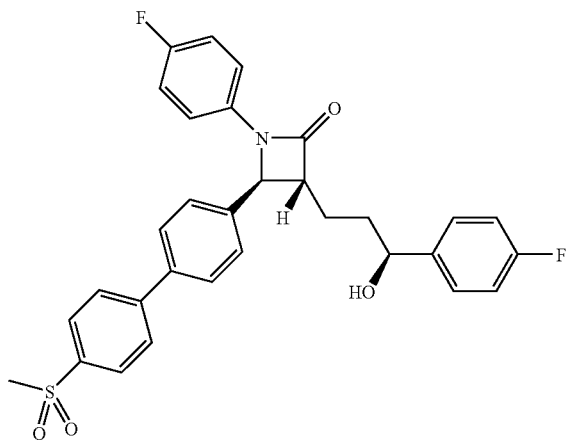

(3R,4S)-1-(4-fluorophenyl)-3-[(3S)-3-(4-fluorophenyl)-3-hydroxypropyl]-4-[4'-(methylsulfonyl)biphenyl-4-yl]azetidin-2-one (80 mg, 79% yield using a reaction time of 4 h) as a white solid; purification by chromatography (12 g silica gel, 10% to 100% ethyl acetate-hexane); mp 111° C.; $R_f$ 0.40 (1:1 ethyl acetate-hexane); $^1$H NMR (300 MHz, CDCl$_3$) δ 8.1 (d, J=9.3 Hz, 2H), 7.8 (d, J=9.3 Hz, 2H), 7.6 (d, J=8.1 Hz, 2H), 7.5 (d, J=8.1 Hz, 2H), 7.3 (m, 5H), 6.9 (m, 3H), 6.3 (s, 1H), 4.7 (m, 1H), 4.6 (s, 1H), 3.1 (s, 4H), 2.1-1.9 (m, 4H) ppm; MS [M–OH] 530.6.

EXAMPLE 9

(3R,4S)-1-(4-fluorophenyl)-3-[(3S)-3-(4-fluorophenyl)-3-hydroxypropyl]-4-(3',4',5'-trimethoxybiphenyl-4-yl)azetidin-2-one

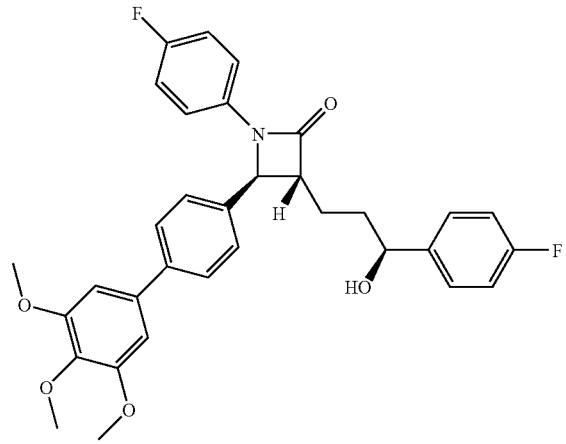

(3R,4S)-1-(4-fluorophenyl)-3-[(3S)-3-(4-fluorophenyl)-3-hydroxypropyl]-4-(3',4',5'-trimethoxybiphenyl-4-yl)azetidin-2-one (93 mg, 90% yield using a reaction time of 2 h) as a white solid; purification by chromatography (12 g silica gel, 10% to 100% ethyl acetate-hexane); mp 103° C.; $R_f$ 0.4 (1:1 ethyl acetate-hexane); $^1$H NMR (300 MHz, CDCl$_3$) δ 7.6 (d, J=9.0 Hz, 2H), 7.5 (d, J=9.0 Hz, 2H), 7.3 (m, 4H), 7.0 (m, 4H), 6.8 (s, 2H), 4.7 (m, 1H), 4.6 (s, 1H), 3.9 (s, 9H), 3.1 (s, 1H), 2.1-1.9 (m, 4H) ppm; MS [M–OH] 542.6.

EXAMPLE 10

(3R,4S)-1-(4-fluorophenyl)-3-[(3S)-3-(4-fluorophenyl)-3-hydroxypropyl]-4-[3'-(methylsulfonyl)biphenyl-4-yl]azetidin-2-one

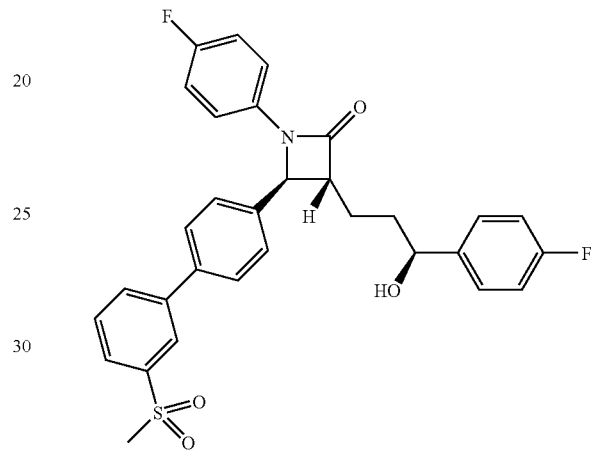

(3R,4S)-1-(4-fluorophenyl)-3-[(3S)-3-(4-fluorophenyl)-3-hydroxypropyl]-4-[3'-(methylsulfonyl)biphenyl-4-yl]azetidin-2-one (92 mg, 90% yield using a reaction time of 2 h) as a white solid; purification by chromatography (12 g silica gel, 10% to 100% ethyl acetate-hexane); mp 104° C.; $R_f$ 0.45 (1:1 ethyl acetate-hexane); $^1$H NMR (300 MHz, CDCl$_3$) δ 8.2-6.8 (m, 15H), 4.7 (m, 1H), 4.65 (s, 1H), 3.2 (m, 1H), 3.1 (s, 3H), 2.1-1.9 (m, 4H) ppm; MS [M–OH] 530.6.

EXAMPLE 11

(3R,4S)-4-(2',3'-dimethoxybiphenyl-4-yl)-1-(4-fluorophenyl)-3-[(3S)-3-(4-fluorophenyl)-3-hydroxypropyl]azetidin-2-one

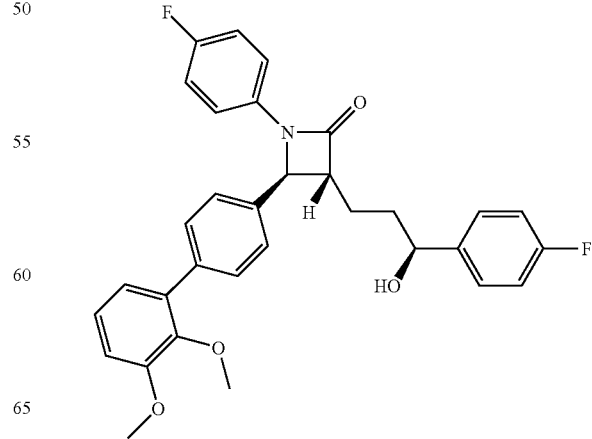

(3R,4S)-4-(2',3'-dimethoxybiphenyl-4-yl)-1-(4-fluorophenyl)-3-[(3S)-3-(4-fluorophenyl)-3-hydroxypropyl]azetidin-2-one (132.0 mg, 90% yield using a reaction time of 2 h) as a white solid; purification by chromatography (12 g silica gel, 10% to 100% ethyl acetate-hexane); mp 101° C.; R$_f$ 0.70 (1:1 ethyl acetate-hexane); $^1$H NMR (300 MHz, CDCl$_3$) δ 7.6 (d, J=8.5 Hz, 2H), 7.4 (d, J=8.5 Hz, 2H), 7.3 (m, 5H), 7.0 (m, 6H), 4.7 (m, 1H), 4.6 (s, 1H), 3.9 (s, 3H), 3.7 (s, 3H), 3.3 (m, 1H), 2.1-1.9 (m, 4H) ppm; MS [M−OH] 512.6.

EXAMPLE 12

(3R,4S)-1-(4-fluorophenyl)-3-[(3S)-3-(4-fluorophenyl)-3-hydroxypropyl]-4-(3'-methoxybiphenyl-4-yl)azetidin-2-one

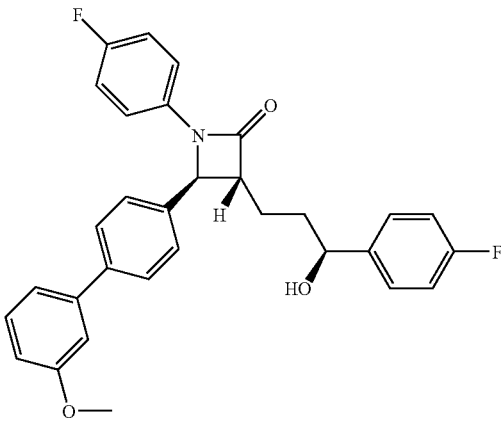

(3R,4S)-1-(4-fluorophenyl)-3-[(3S)-3-(4-fluorophenyl)-3-hydroxypropyl]-4-(3'-methoxybiphenyl-4-yl)azetidin-2-one (36.1 mg, 77% yield) as a clear foam; purification by chromatography (12 g silica gel, 5% to 95% ethyl acetate-hexane); R$_f$ 0.52 (40% ethyl acetate-hexane); $^1$H NMR (300 MHz, CDCl$_3$) δ 7.58 (d, J=8.7 Hz, 2H), 7.30 (m, 7H), 7.15 (dt, J=13.5, 1.5 Hz, 1H), 7.09 (t, J=2.4 Hz, 1H), 7.00 (t, J=10.4 Hz, 2H), 6.92 (m, 3H), 4.73 (t, J=6.2 Hz, 1H), 4.67 (d, J=2.1 Hz, 1H), 3.86 (s, 3H), 1.95 (m, 4H); MS [M−OH] 482.5.

EXAMPLE 13

4'-{(2S,3R)-1-(4-fluorophenyl)-3-[(3S)-3-(4-fluorophenyl)-3-hydroxypropyl]-4-oxoazetidin-2-yl}biphenyl-3-carbaldehyde

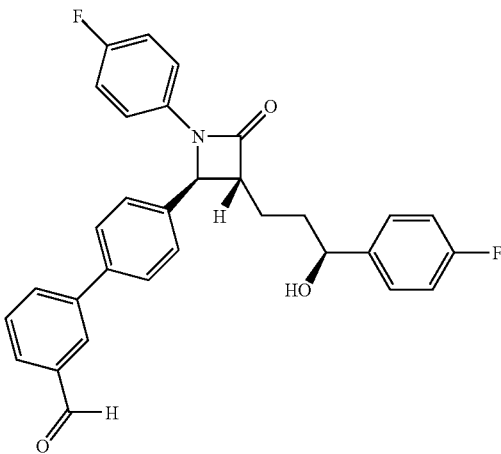

4'-{(2S,3R)-1-(4-fluorophenyl)-3-[(3S)-3-(4-fluorophenyl)-3-hydroxypropyl]-4-oxoazetidin-2-yl}biphenyl-3-carbaldehyde (32.7 mg, 67% yield) as a clear foam; purification by chromatography (12 g silica gel, 5% to 95% ethyl acetate-hexane); R$_f$ 0.72 (50% ethyl acetate-hexane); $^1$H NMR (300 MHz, CDCl$_3$) δ 10.09 (s, 1H), 8.09 (d, J=1.8 Hz, 1H), 7.85 (m, 2H), 7.62 (m, 3H), 7.44 (d, J=7.8 Hz, 2H), 7.27 (m, 4H), 7.03 (t, J=8.6 Hz, 2H), 6.95 (t, J=8.8 Hz, 2H), 4.74 (m, 1H), 4.70 (d, J=2.4 Hz, 1H), 3.14 (m, 1H), 1.97 (m, 4H) ppm; MS [M−OH] 480.5.

EXAMPLE 14

4'-{(2S,3R)-1-(4-fluorophenyl)-3-[(3S)-3-(4-fluorophenyl)-3-hydroxypropyl]-4-oxoazetidin-2-yl}biphenyl-3-carbonitrile

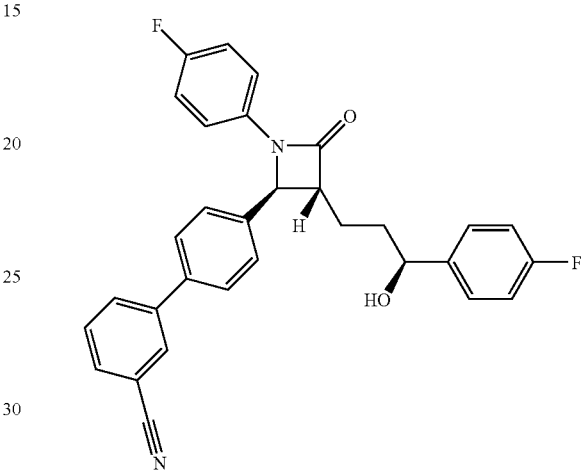

4'-{(2S,3R)-1-(4-fluorophenyl)-3-[(3S)-3-(4-fluorophenyl)-3-hydroxypropyl]-4-oxoazetidin-2-yl}biphenyl-3-carbonitrile (32.5 mg, 57% yield) as a clear foam; purification by chromatography (12 g silica gel, 5% to 95% ethyl acetate-hexane); R$_f$ 0.69 (50% ethyl acetate-hexane); $^1$H NMR (300 MHz, CDCl$_3$) δ 7.84 (m, 1H), 7.79 (m, 1H), 7.64 (m, 1H), 7.55 (m, 3H), 7.44 (d, J=6.6 Hz, 2H), 7.28 (m, 4H), 7.02 (t, J=8.9 Hz, 2H), 6.95 (t, J=8.9 Hz, 2H), 4.75 (t, J=6.2 Hz, 1H), 4.68 (d, J=2.1 Hz, 1H), 3.13 (m, 1H), 2.01 (m, 4H) ppm; MS [M−OH] 477.5.

EXAMPLE 15

4'-{(2S,3R)-1-(4-fluorophenyl)-3-[(3S)-3-(4-fluorophenyl)-3-hydroxypropyl]-4-oxoazetidin-2-yl}biphenyl-N,N-dimethylbiphenyl-4-sulfonamide

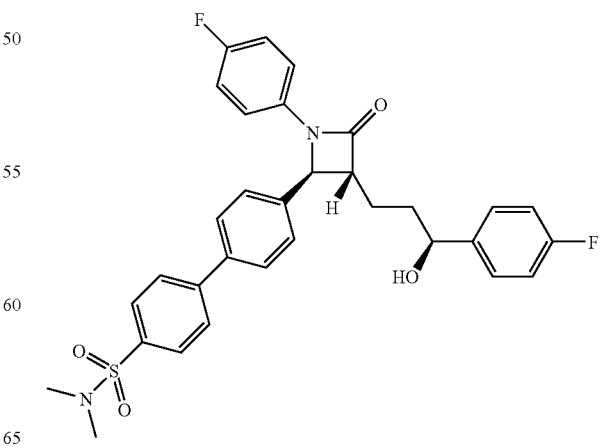

4'-{(2S,3R)-1-(4-fluorophenyl)-3-[(3S)-3-(4-fluorophenyl)-3-hydroxypropyl]-4-oxoazetidin-2-yl}biphenyl-N,N-dimethylbiphenyl-4-sulfonamide (39.6 mg, 73% yield) as a faint yellow foam; purification by chromatography (12 g silica gel, 5% to 95% ethyl acetate-hexane); R*f* 0.50 (50% ethyl acetate-hexane); ¹H NMR (300 MHz, CDCl₃) δ 7.83 (d, J=5.4 Hz, 2H), 7.72 (d, J=8.1 Hz, 2H), 7.61 (d, J=8.1 Hz, 2H), 7.44 (d, J=8.4 Hz, 2H), 7.25 (m, 4H), 7.02 (t, J=8.4, 9.0 Hz, 2H), 6.95 (t, J=8.7 Hz, 2H), 4.74 (t, J=5.5 Hz, 1H), 4.69 (d, J=1.8 Hz, 1H), 3.13 (m, 1H), 2.75 (s, 6H), 2.01 (m, 4H) ppm; MS [M−OH] 559.7.

EXAMPLE 16

(3R,4S)-1-(4-Fluorophenyl)-3-[(3S)-3-(4-fluorophenyl)-3-hydroxypropyl]-4-(3'-(hydroxymethyl)biphenyl-4-yl)azetidin-2-one

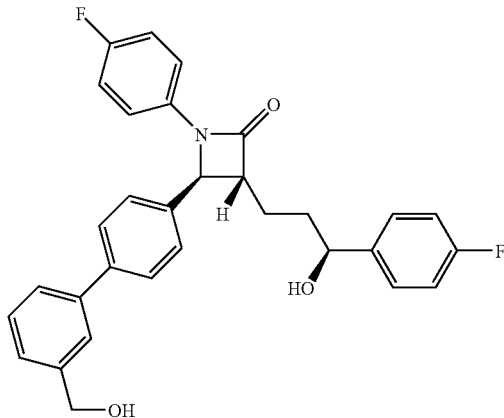

(3R,4S)-1-(4-Fluorophenyl)-3-[(3S)-3-(4-fluorophenyl)-3-hydroxypropyl]-4-(3'-(hydroxymethyl)biphenyl-4-yl)azetidin-2-one (37.3 mg, 80% yield) as a clear foam; purification by chromatography (12 g silica gel, 5% to 95% ethyl acetate-hexane); R*f* 0.43 (50% ethyl acetate-hexane); ¹H NMR (300 MHz, CDCl₃) δ 7.59 (m, 3H), 7.49 (m, 2H), 7.37 (m, 3H), 7.27 (m, 4H), 7.02 (t, J=8.7 Hz, 2H), 6.95 (t, J=8.7 Hz, 2H), 4.74 (m, 1H), 4.67 (d, J=2.4 Hz, 1H), 3.14 (m, 1H), 1.99 (m, 4H) ppm; MS [M−OH] 482.5.

EXAMPLE 17

(3R,4S)-4-[4'(dimethylamino)biphenyl-4-yl]-1-(4-fluorophenyl)-3-[(3S)-3-(4-fluorophenyl)-3-hydroxypropyl]azetidin-2-one

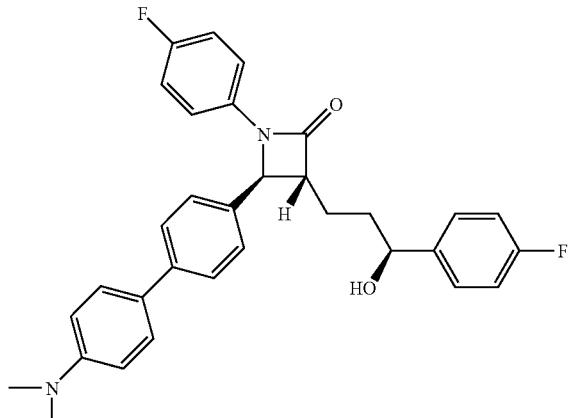

(3R,4S)-4-[4'(dimethylamino)biphenyl-4-yl]-1-(4-fluorophenyl)-3-[(3S)-3-(4-fluorophenyl)-3-hydroxypropyl] azetidin-2-one (35.4 mg, 79% yield) as a white foam; purification by chromatography (12 g silica gel, 5% to 95% ethyl acetate-hexane); R*f* 0.78 (50% ethyl acetate-hexane); ¹H NMR (300 MHz, CDCl₃) δ 7.53 (m, 4H), 7.31 (m, 8H), 7.02 (t, J=8.7 Hz, 2H), 6.94 (t, J=8.7 Hz, 2H), 4.73 (m, 1H), 4.64 (d, J=2.1 Hz, 1H), 3.14 (m, 1H), 3.10 (s, 6H) 1.97 (m, 4H) ppm; MS [M+H] 513.6.

EXAMPLE 18

(3R,4S)-1-(4-fluorophenyl)-3-[(3S)-3-(4-fluorophenyl)-3-hydroxypropyl]-4-[4-(hydroxymethyl)phenyl] azetidin-2-one

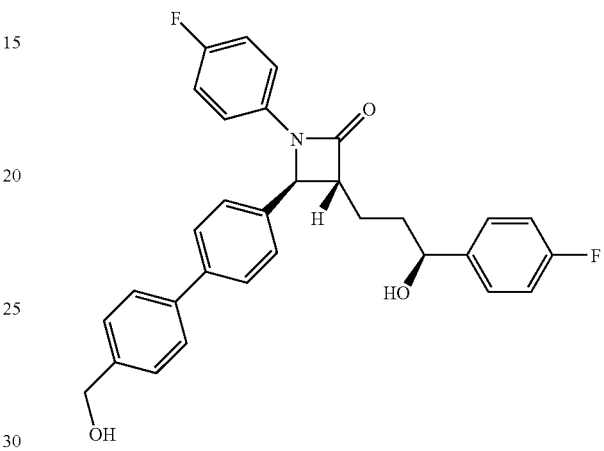

(3R,4S)-1-(4-fluorophenyl)-3-[(3S)-3-(4-fluorophenyl)-3-hydroxypropyl]-4-[4-(hydroxymethyl)phenyl]azetidin-2-one (37.2 mg, 75% yield with a 7% impurity) as a clear film; purification by chromatography (12 g silica gel, 5% to 95% ethyl acetate-hexane); R*f* 0.43 (50% ethyl acetate-hexane); ¹H NMR (300 MHz, CDCl₃) δ 7.57 (m, 4H), 7.44 (d, J=8.4, 2H), 7.38 (d, J=8.4, 2H), 7.27 (m, 4H), 7.02 (t, J=8.9 Hz, 2H), 6.95 (t, J=8.7 Hz, 2H), 4.73 (m, 3H), 4.66 (d, J=2.4 Hz, 1H), 3.12 (m, 1H), 1.97 (m, 4H) ppm; MS [M−OH] 482.5.

EXAMPLE 19

Preparation of (3R,4S)-4-(2'-bromo-5'-hydroxybiphenyl-4-yl)-1-(4-fluorophenyl)-3-[(3S)-3-(4-fluorophenyl)-3-hydroxypropyl]azetidin-2-one

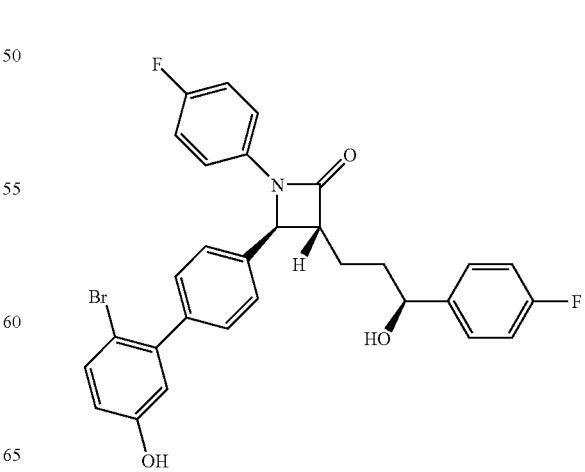

(3R,4S)-1-(4-Fluorophenyl)-3-[(3S)-3-(4-fluorophenyl)-3-hydroxypropyl]-4-(3'-hydroxybiphenyl-4-yl)azetidin-2-one (19.2 mg, 0.04 mmol) was dissolved in chloroform (0.4 mL) and tetrabutylammonium tribromide (18.8 mg, 0.04 mmol) was added at room temperature. After 10 minutes, saturated aqueous sodium thiosulfate (2 mL) was added to quench the reaction. The mixture was poured into a seperatory funnel, extracted with dichloromethane (4×10 mL), dried over sodium sulfate, filtered and concentrated. (3R,4S)-4-(2'-bromo-5'-hydroxybiphenyl-4-yl)-1-(4-fluorophenyl)-3-[(3S)-3-(4-fluorophenyl)-3-hydroxypropyl]azetidin-2-one was purified by chromatography (12 g silica gel, 5% to 95% ethyl acetate-hexane) and then by reverse-phase HPLC (21 mm column, 50% to 100% acetonitrile-0.1% trifluoroacetic acid in water) to afford (3R,4S)-4-(2'-bromo-5'-hydroxybiphenyl-4-yl)-1-(4-fluorophenyl)-3-[(3S)-3-(4-fluorophenyl)-3-hydroxypropyl]azetidin-2-one (8.0 mg, 34% yield) as a clear foam; $R_f$ 0.51 (50% ethyl acetate-hexane); $^1$H NMR (300 MHz, CDCl$_3$) δ 7.49 (d, J=8.7 Hz, 1H), 7.40 (m, 4H), 7.29 (m, 4H), 7.02 (t, J=8.7 Hz, 2H), 6.95 (t, J=8.7 Hz, 2H), 6.80 (d, J=3.3, 1H), 6.73 (dd, J=3.0, 3.0 Hz, 1H), 4.74 (t, J=6.2 Hz, 2H), 4.67 (d, J=2.1 Hz, 1H), 3.14 (m, 1H) 1.99 (m, 4H) ppm; MS [M−OH] 547.4.

EXAMPLE 20

Preparation of 4'-{(2S,3R)-1-(4-fluorophenyl)-3-[(3S)-3-(4-fluorophenyl)-3-hydroxypropyl]-4-oxoazetidin-2-yl}biphenyl-3-yl β-L-glucopyranosiduronic Acid

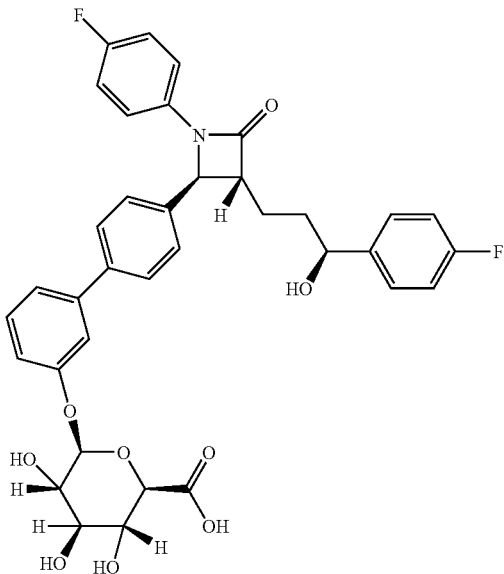

Step 1: Preparation of (1S)-1-(4-fluorophenyl)-3-[(3R,4S)-1-(4-fluorophenyl)-2-oxo-4-(4-{[(trifluoromethyl)sulfonyl]oxy}-phenyl)azetidin-3-yl]propyl acetate 4-{(2S,3R)-1-(4-fluorophenyl)-3-[(3S)-3-(4-fluorophenyl)-3-hydroxypropyl]-4-oxoazetidin-2-yl}phenyl trifluoromethanesulfonate (0.16 g, 0.35 mmol) was dissolved in dichloromethane (2 mL). To this was added acetic anhydride (0.04 mL, 0.45 mmol), triethylamine (0.08 mL, 0.60 mmol) and 4-dimethylaminopyridine (18.3 mg, 0.15 mmol). The reaction was stirred at room temperature for 18 h after which time it was diluted with water (5 mL) and extracted with dichloromethane (10 mL). The aqueous layer was re-extracted with dichloromethane (3×10 mL) and the organic fractions were combined, dried over sodium sulfate, filtered and concentrated. The residue was purified by chromatography (12 g silica gel, 5% to 95% ethyl acetate-hexane) to afford (1S)-1-(4-fluorophenyl)-3-[(3R,4S)-1-(4-fluorophenyl)-2-oxo-4-(4-{[(trifluoromethyl)sulfonyl]oxy}-phenyl)azetidin-3-yl]propyl acetate (0.20 g, 0.35 mmol, 100%) as a clear film.

Step 2: Preparation of (1S)-1-(4-fluorophenyl)-3-[(2S,3R)-1-(4-fluorophenyl)-2-(3'-hydroxybiphenyl-4-yl)-4-oxoazetidin-3-yl]propyl acetate The product of step 1 (0.20 g, 0.35 mmol) and tetrakis(triphenylphosphine)palladium(0) (20.3 mg, 0.018 mmol) were dissolved in toluene (10 mL). 2.0 M aqueous potassium carbonate (0.35 mL) and a solution of 4-hydroxyphenylboronic acid (67.8 mg, 0.49 mmol) in ethanol (2.5 mL) was added. The reaction was stirred vigorously for 4 h at refluxing temperature under a nitrogen atmosphere and then diluted with water (2.5 mL), extracted with ethyl acetate (3×10 mL), washed with brine (10 mL), dried over sodium sulfate, filtered, concentrated and purified by chromatography (12 g silica gel, 5% to 95% ethyl acetate-hexane) to afford (1S)-1-(4-fluorophenyl)-3-[(2S,3R)-1-(4-fluorophenyl)-2-(3'-hydroxybiphenyl-4-yl)-4-oxoazetidin-3-yl]propyl acetate (157 mg, 85% yield) as a clear film.

Step 3: Preparation of (1S)-1-(4-fluorophenyl)-3-((3R,4S)-1-(4-fluorophenyl)-2-oxo-4-{3'-[(2,3,4-tri-O-acetyl-6-hydroperoxy-β-L-gluco-hexodialdo-1,5-pyranosyl)oxy]biphenyl-4-yl}azetidin-3-yl)propyl acetate The product of step 2 (69.4 mg, 0.132 mmol) and methyl 2,3,4-tri-O-acetyl-1-O-(2,2,2-trifluoroethanimidoyl)-D-glucopyranuronate (49.0 mg, 0.110 mmol) were azeotroped with toluene (3×15 mL) and dried in vacuo for 18 h. The dried syrup was suspended in dichloromethane (1.1 mL) and the reaction was cooled to −25° C. Freshly distilled (over calcium hydride) boron trifluoride diethyl etherate was added and the reaction was maintained at −25° C. for 2 h and warmed to 10° C. over about 3.5 h. The mixture was diluted with saturated aqueous ammonium chloride (2 mL), extracted with ethyl acetate (3×10 mL), washed with brine (10 mL), dried over sodium sulfate, filtered, concentrated and purified by chromatography (12 g silica gel, 5% to 95% ethyl acetate-hexane) to afford (1S)-1-(4-fluorophenyl)-3-((3R,4S)-1-(4-fluorophenyl)-2-oxo-4-{3'-[(2,3,4-tri-O-acetyl-6-hydroperoxy-β-L-gluco-hexodialdo-1,5-pyranosyl)oxy]biphenyl-4-yl}azetidin-3-yl)propyl acetate (57.2 mg, 87% based on recovered starting material) as a white foam.

Step 4: Preparation of 4'-{(2S,3R)-1-(4-fluorophenyl)-3-[(3S)-3-(4-fluorophenyl)-3-hydroxypropyl]-4-oxoazetidin-2-yl}biphenyl-3-yl β-L-glucopyranosiduronic acid The product of step 3 (57.2 mg, 0.068 mmol) was dissolved in 1:1 methanol-triethylamine (2.8 mL). To this solution was added water (4.25 mL). The reaction progress was monitored by TLC (5% acetic acid and 15% methanol in dichloromethane) and was complete after 19 hours. The methanol and triethylamine were evaporated in vacuo, the residue was acidified with 1 N aqueous hydrochloric acid (1.4 mL), extracted with ethyl acetate (20 mL), washed with brine (5 mL), dried over sodium sulfate, filtered, concentrated and purified by chromatography (10 g silica gel, 5% acetic acid and 15% methanol in dichloromethane) to afford 4'-{(2S,3R)-1-(4-fluorophenyl)-3-[(3S)-3-(4-fluorophenyl)-3-hydroxypropyl]-4-oxoazetidin-2-yl}biphenyl-3-yl β-L-glucopyranosiduronic acid (32.6 mg, 73%) as an off-white foam; $R_f$ 0.37 (5% acetic acid and 15% methanol in dichloromethane); $^1$H NMR (300 MHz, CD$_3$OD) δ 7.63 (d, J=7.8 Hz, 2H), 7.43 (d, J=8.1 Hz, 2H), 7.33 (m, 7H), 7.06 (m, 5H), 5.03 (m, 1H), 4.63 (t, J=5.1, 5.1 Hz, 2H), 3.94 (m, 3H), 3.13 (m, 1H) 1.91 (m, 4H) ppm; MS [M−H] 660.6.

EXAMPLE 21

Preparation of 4'-{(2S,3R)-1-(4-fluorophenyl)-3-[(3S)-3-(4-fluorophenyl)-3-hydroxypropyl]-4-oxoazetidin-2-yl]biphenyl-3-carboxylic acid

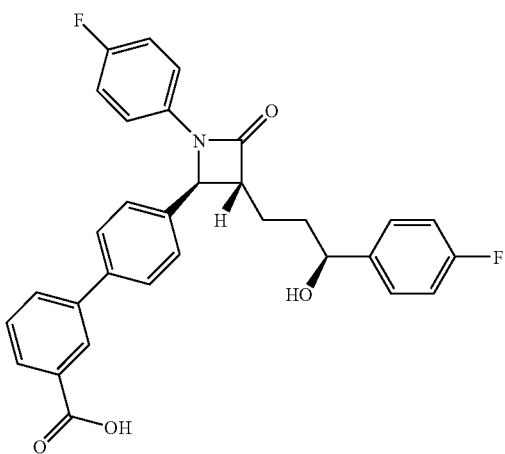

4-{(2S,3R)-1-(4-fluorophenyl)-3-[(3S)-3-(4-fluorophenyl)-3-hydroxypropyl]-4-oxoazetidin-2-yl}phenyl trifluoromethanesulfonate (51.1 mg, 0.094 mmol) and 3-carboxyphenylboronic acid (21.9 mg, 0.132 mmol) were dissolved in 1:1 toluene:ethanol (2 mL). 2.0 M aqueous potassium carbonate (0.14 mL) was added and the solution degassed. Tetrakis(triphenylphosphine)palladium(0) (5.1 mg, 0.005 mmol) was added and the reaction stirred vigorously for 2 h at refluxing temperature under a nitrogen atmosphere. The cooled reaction was diluted into dichloromethane (15 mL), water (3 mL) was added and the pH was adjusted to 3 with 5% aqueous sodium bisulfate. The layers were separated and the aqueous layer extracted with dichloromethane (2×5 mL). The combined organic extracts were dried over sodium sulfate, filtered, concentrated and purified by chromatography (12 g silica gel, 5% methanol in dichloromethane) to afford 4'-{(2S,3R)-1-(4-fluorophenyl)-3-[(3S)-3-(4-fluorophenyl)-3-hydroxypropyl]-4-oxoazetidin-2-yl]biphenyl-3-carboxylic acid (41.9 mg, 86% yield) as a colorless foam; $R_f$ 0.15 (5% methanol in dichloromethane); $^1$H NMR (300 MHz, CDCl$_3$) δ?8.31 (m, 1H), 8.09 (dt, J=7.8, 1.5 Hz, 1H), 7.79-7.39 (m, 6H), 7.23-7.32 (m, 4H), 6.90-7.02 (m, 4H), 4.75 (t, J=5.7 Hz, 1H), 4.69 (d, J=2.1 Hz), 3.12 (m, 1H), 2.10-1.90 (m, 4H) ppm; MS [M−H] 512.5.

In the same manner was obtained:

EXAMPLE 22

4'-{(2S,3R)-1-(4-fluorophenyl)3-[(3S)-3-(4-fluorophenyl)-3-hydroxypropyl]-4-oxoazetidin-2-yl] biphenyl-4-carboxylic acid

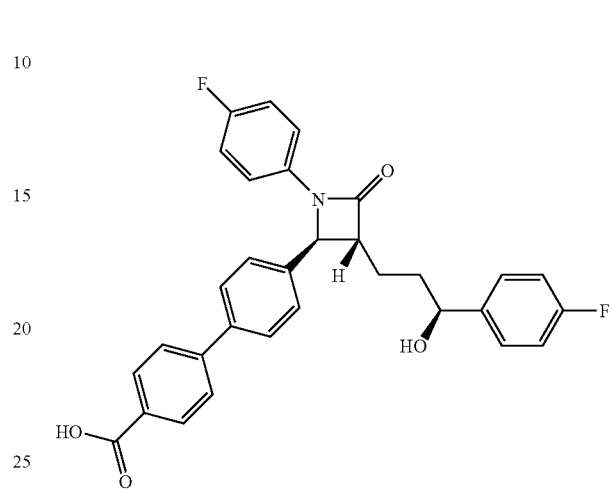

4'-{(2S,3R)-1-(4-fluorophenyl)3-[(3S)-3-(4-fluorophenyl)-3-hydroxypropyl]-4-oxoazetidin-2-yl]biphenyl-4-carboxylic acid (21.0 mg, 67% yield) as a white foam; purification by chromatography (12 g silica gel, 5% methanol in dichloromethane); $R_f$ 0.14 (5% methanol in dichloromethane); $^1$H NMR (300 MHz, CDCl$_3$) δ ?8.17 (d, J=8.4 Hz, 2H), 7.65 (t, J=8.1 Hz, 4H), 7.43 (d, J=8.4 Hz, 2H), 7.33-7.24 (m, 4H), 7.04-6.92 (m, 4H), 4.77 (t, J=5.7 Hz, 1H), 4.70 (d, J=2.1 Hz, 1H), 3.15 (m, 1H), 1.92-2.09 (m, 4H) ppm; MS [M−H] 512.5.

EXAMPLE 23

Preparation of (3R,4S)-1-(4-fluorophenyl)-3-[(3S)-3-(4-fluorophenyl)-3-hydroxypropyl]-4-(3'-nitrobiphenyl-4-yl)azetidin-2-one

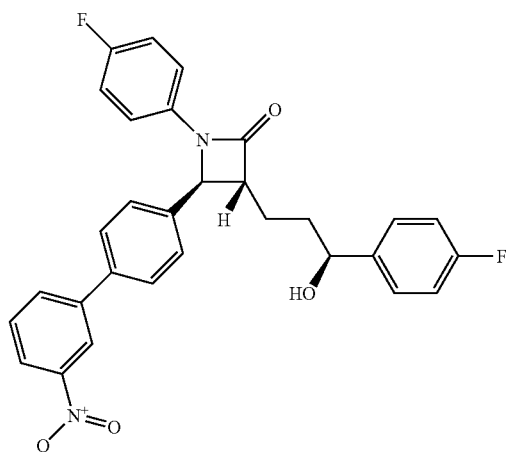

4-{(2S,3R)-1-(4-fluorophenyl)-3-[(3S)-3-(4-fluorophenyl)-3-hydroxypropyl]-4-oxoazetidin-2-yl}phenyl trifluoromethanesulfonate (50.0 mg, 0.092 mmol) and 3-nitrophenylboronic acid (21.6 mg, 0.129 mmol) were dissolved in 1:1 toluene:ethanol (2 mL). 2.0 M aqueous potassium carbonate (0.092 mL) was added and the solution degassed. Tetrakis(triphenylphosphine)palladium(0) (5.7 mg, 0.005 mmol) was added and the reaction stirred vigorously for 2 h at refluxing temperature under a nitrogen atmosphere. The cooled reaction was diluted into dichloromethane (15 mL). The layers were separated and the aqueous layer further extracted with dichloromethane (2×5 mL). The combined extracts were dried over sodium sulfate, filtered, concentrated and purified by chromatography (12 g silica gel, 5% to 50% ethyl acetate-hexane) to afford (3R,4S)-1-(4-fluorophenyl)-3-[(3S)-3-(4-fluorophenyl)-3-hydroxypropyl]-4-(3'-nitrobiphenyl-4-yl)azetidin-2-one (45.0 mg, 95% yield) as a clear film; $R_f$ 0.33 (50% ethyl acetate-hexane); $^1$H NMR (300 MHz, CDCl$_3$) δ ?8.42 (m, 1H), 8.21 (ddd, J=8.1, 2.4, 1.2 Hz, 1H), 7.89 (ddd, J=7.9, 1.5, 1.2 Hz, 1H), 7.63 (d, J=8.1 Hz, 2H), 7.45 (d, J=8.1 Hz, 2H), 7.33-7.22 (m, 4H), 7.04-6.92 (m, 4H), 4.76 (t, J=6.0 Hz, 1H), 4.71 (d, J=2.1 Hz, 1H), 3.14 (m, 1H), 1.91-2.11 (m, 4H) ppm; MS [M−OH] 497.5.

In the same manner was obtained:

EXAMPLE 26

N-(4'-{(2S,3R)-1-(4-fluorophenyl)-3-[(3S)-3-(4-fluorophenyl)-3-hydroxypropyl]-4-oxoazetidin-2-yl}biphenyl-3-yl)acetamide

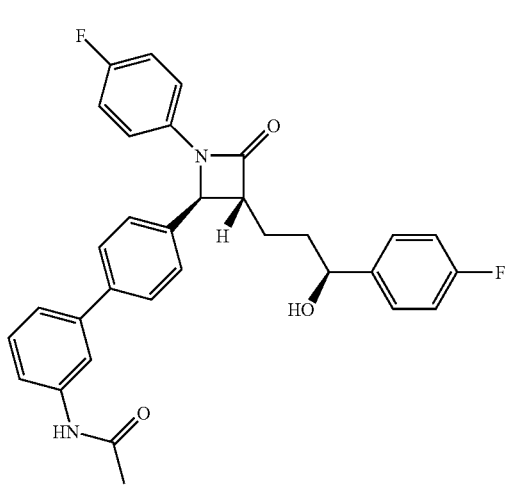

N-(4'-{(2S,3R)-1-(4-fluorophenyl)-3-[(3S)-3-(4-fluorophenyl)-3-hydroxypropyl]-4-oxoazetidin-2-yl}biphenyl-3-yl)acetamide (18.8 mg, 44% yield) as a white foam; purification by chromatography (12 g silica gel, 50% ethyl acetate-hexane); $R_f$ 0.07 (50% ethyl acetate-hexane); $^1$H NMR (300 MHz, CDCl$_3$) δ 7.81 (b, 1H), 7.72-7.19 (m, 12H), 6.99 (t, J=8.7 Hz, 2H), 6.93 (t, J=9.0 Hz, 2H), 4.72 (t, J=5.7 Hz, 1H), 4.65 (d, J=2.1 Hz, 1H), 3.13 (m, 1H), 2.17 (s, 3H), 2.04-1.88 (m, 4H) ppm; MS [M−OH] 509.6.

EXAMPLE 28

(3R,4S)-4-(4'-aminobiphenyl-4-yl)-1-(4-fluorophenyl)-3-[(3S)-3-(4-fluorophenyl)-3-hydroxypropyl]azetidin-2-one

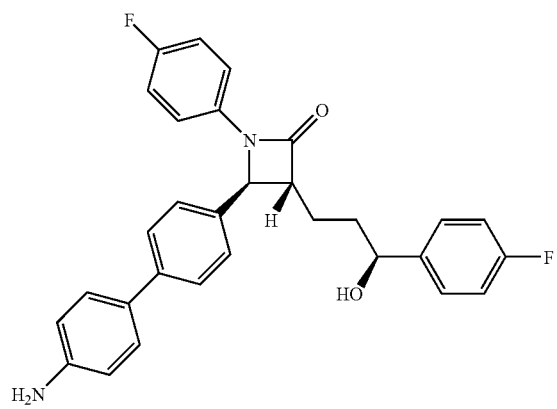

(3R,4S)-1-(4-fluorophenyl)-3-[(3S)-3-(4-fluorophenyl)-3-hydroxypropyl]-4-(4'-aminobiphenyl-4-yl)azetidin-2-one (42.0 mg, 95% yield) as a brown film; purification by chromatography (12 g silica gel, 50% ethyl acetate-hexane); $R_f$ 0.32 (50% ethyl acetate-hexane); $^1$H NMR (300 MHz, CDCl$_3$) δ 7.52 (d, J=8.1 Hz, 2H), 7.39-7.23 (m, 8H), 7.00 (t, J=8.7 Hz, 2H), 6.92 (t, J=8.7 Hz, 2H), 6.74 (d, J=8.4 Hz, 2H), 4.72 (t, J=5.7 Hz, 1H), 4.63 (d, J=2.4 Hz, 1H), 3.14 (m, 1H), 2.11-1.91 (m, 4H) ppm; MS [M+H] 485.5.

EXAMPLE 29

(3R,4S)-1-(2',3'-difluorophenyl)-3-[(3S)-3-(4-fluorophenyl)-3-hydroxypropyl]-4-(3',4'-difluorobiphenyl-4-yl)azetidin-2-one

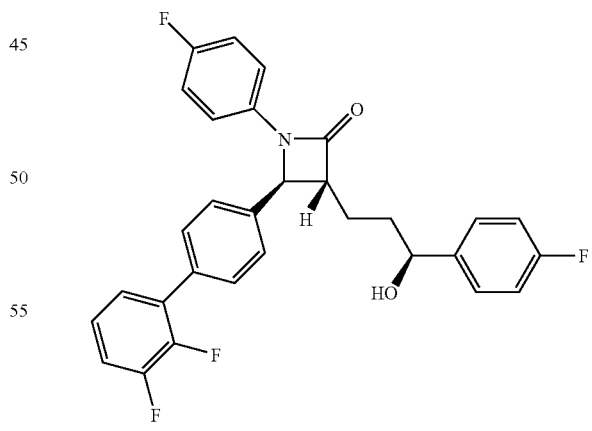

(3R,4S)-1-(2',3'-difluorophenyl)-3-[(3S)-3-(4-fluorophenyl)-3-hydroxypropyl]-4-(3',4'-difluorobiphenyl-4-yl)azetidin-2-one (36.9 mg, 86% yield) as a clear film; purification by chromatography (12 g silica gel, 5% to 50% ethyl acetate-hexane); $R_f$ 0.51 (50% ethyl acetate-hexane); $^1$H NMR (300 MHz, CDCl$_3$) δ 7.55 (dd, J=8.3, 1.5 Hz, 2H), 7.41 (d, J=6.9 Hz, 2H), 7.32-7.22 (m, 4H), 7.19-7.12 (m, 3H), 7.01 (t, J=8.7 Hz, 2H), 6.95 (t, J=9.0 Hz, 2H), 4.74 (t, J=6.0 Hz, 1H), 4.68 (d, J=2.7 Hz, 1H), 3.14 (m, 1H), 2.07-1.90 (m, 4H) ppm; MS [M−OH] 488.5.

EXAMPLE 31

1-[4-(4-{(2S,3R)-2-(3'-hydroxybiphenyl-4-yl)-3-[(3S)-3-hydroxy-3-phenylpropyl]-4-oxoazetidin-1-yl}phenyl)butyl]-1-azoniabicyclo[2.2.2]octane chloride.

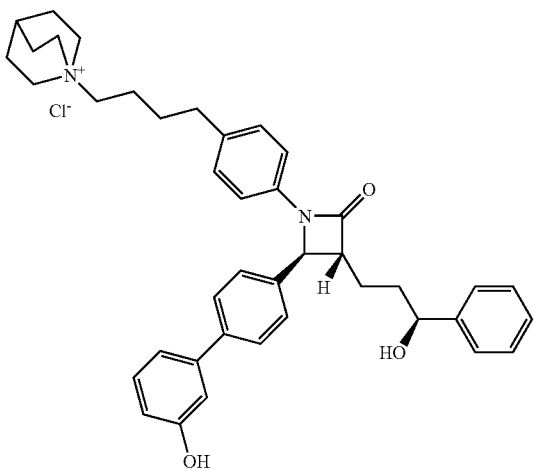

A quaternary salt is made in the following manner. (3-{[tert-butyl(dimethyl)silyl]oxy}phenyl)boronic acid and 4-bromostyrene are coupled under Suzuki conditions with tetrakis(triphenylphosphine)palladium(0) and 2.0 M aqueous potassium carbonate in toluene-ethanol solvent. The product is reacted with chlorosulfonyl isocyanate in ethereal solvent followed by alkali aqueous work-up to generate a β-lactam. The amide proton is exchanged for an aryl group by reaction with 4-iodophenylcarbonylallyl (generated from the commercially available acid by borane reduction and protected with allyl chloroformate) using trans-1,2-cyclohexanediamine and copper (I) iodide in decane-dioxane as solvent. Deprotonation of the 3-position of the β-lactam with a suitable base, such as lithium diisopropylamide, and subsequent quenching with tert-butyl {[(1S)-4-iodo-1-phenylbutyl]oxy}dimethylsilane (generated from the commercially available (S)-(−)-3-chloro-1-phenyl-1-propanol by protection with tert-butyldimethylchlorosilane and Finkelstein reaction with sodium iodide) provide the 3-substituted intermediate. The allyloxycarbonate protecting group is removed with ammonium formate and tetrakis(triphenylphosphine)palladium(0) in tetrahydrofuran and the resulting alcohol converted into the bromide using carbon tetrabromide and triphenylphosphine in dichloromethane. The silyl protecting groups are removed from the benzyl alcohol and the phenyl using 48% hydrofluoric acid in acetonitrile. The resulting compound is reacted with a tertiary amine, such as quinuclidine, purified by HPLC and passed through a chloride ion-exchange column to afford 1-[4-(4-{(2S,3R)-2-(3'-hydroxybiphenyl-4-yl)-3-[(3S)-3-hydroxy-3-phenylpropyl]-4-oxoazetidin-1-yl}phenyl)butyl]-1-azoniabicyclo[2.2.2]octane chloride.

EXAMPLE 32

Illustrated in Scheme I below is the general method for the preparation of cholesterol absorption inhibitors of general formula 32. Imines 2 are made by refluxing 4-cyanoaniline with the appropriate aldehyde in isopropanol. Condensation of imine 2 with the benzyloxazolidinone compound 3 using titanium tetrachloride, and subsequent cyclization using N,O-bistrimethylacetamide and catalytic tetra-n-butylammonium fluoride, affords the azetidinone 4. Reduction of the cyano group in 4 to the amine 5 is accomplished under hydrogen atmosphere over excess Raney-Nickel in ethanol and ammonium hydroxide. Acylation with the appropriate acid chloride [Br(CH2)$_n$COCl], followed by reaction with hydrofluoric acid in acetonitrile to remove the silyl protecting groups, and subsequent reaction with taurine provides the finally product 32. It is noted that in this scheme the taurine is for illustration and that a large variety of functional groups can be substituted in its place.

Scheme I

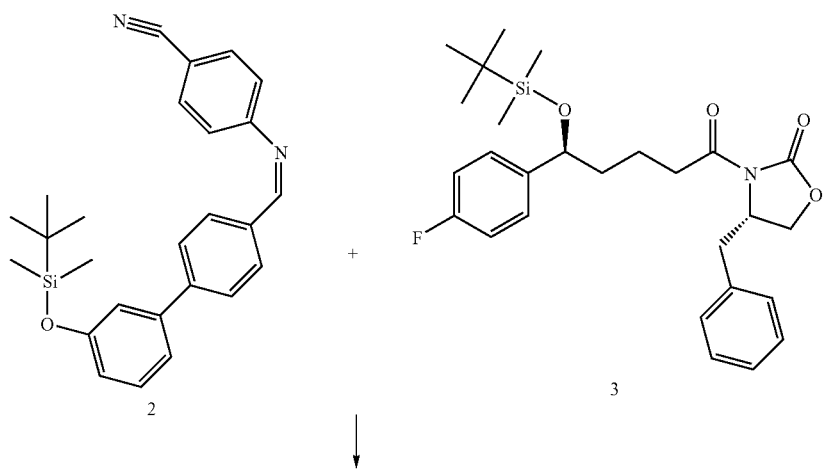

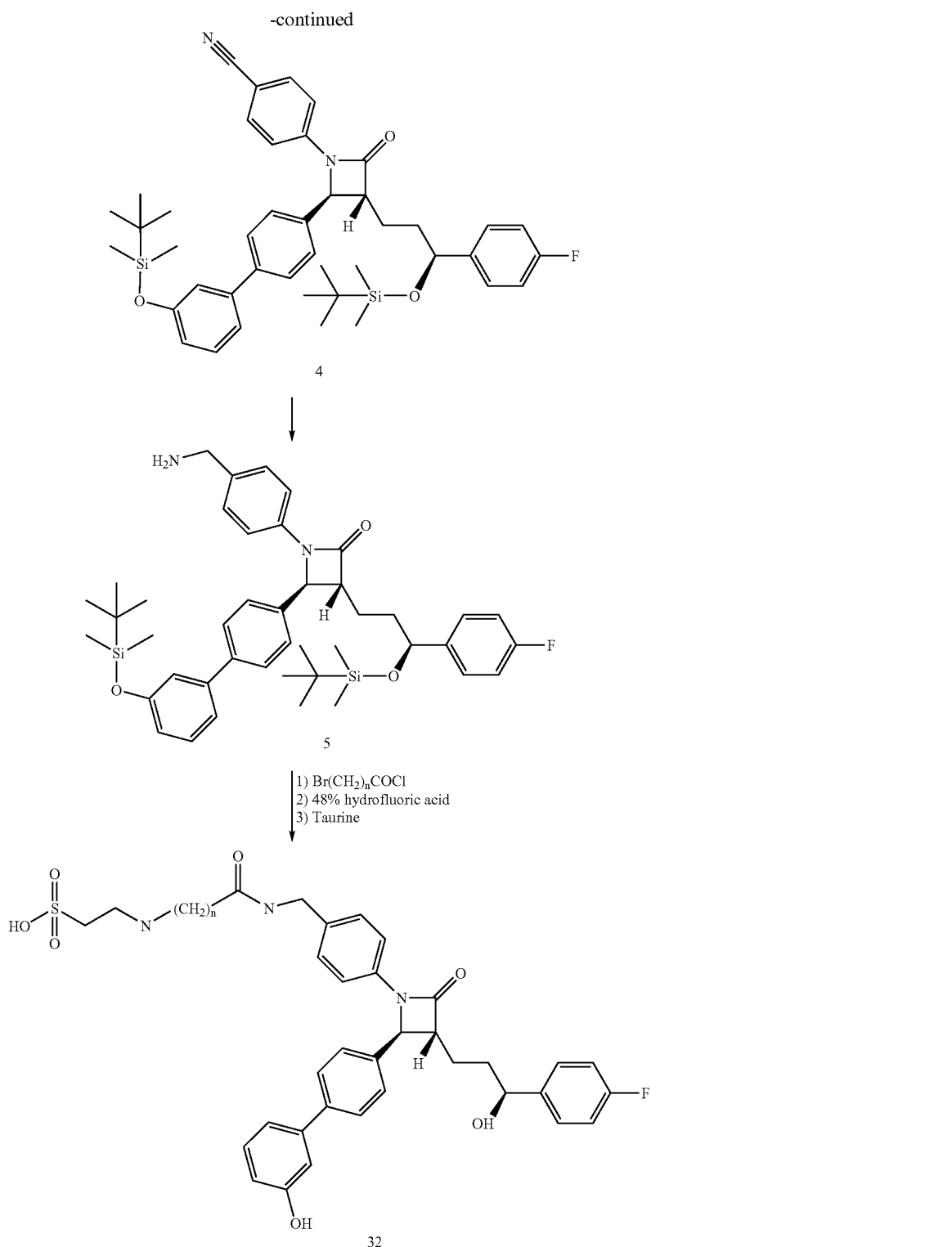

EXAMPLE 33

Illustrated in Scheme II below is the general method for the preparation of cholesterol absorption inhibitors of general formula 33. The aldehyde 7 is made by Suzuki coupling of 4-bromobenzaldehyde with 3-cyanophenylboronic acid. Refluxing 4-fluoroaniline with the aldehyde 7 in isopropanol makes the imine 8. Condensation of imine 8 with benzyloxazolidinone compound 3 using titanium tetrachloride and subsequent cyclization, using N,O-bistrimethylacetamide and catalytic tetra-n-butylammonium fluoride, affords the azetidinone 9. Reduction of the cyano group in 9 to the amine 10 is accomplished under hydrogen atmosphere over excess Raney-Nickel in ethanol and ammonium hydroxide. Acylation with the appropriate acid chloride [Br(CH2)$_n$COCl], followed by reaction with hydrofluoric acid in acetonitrile to remove the silyl protecting groups, and reaction with taurine provides the final product 11. It is noted that in this scheme the taurine is for illustration and that a large variety of functional groups can be substituted in its place.

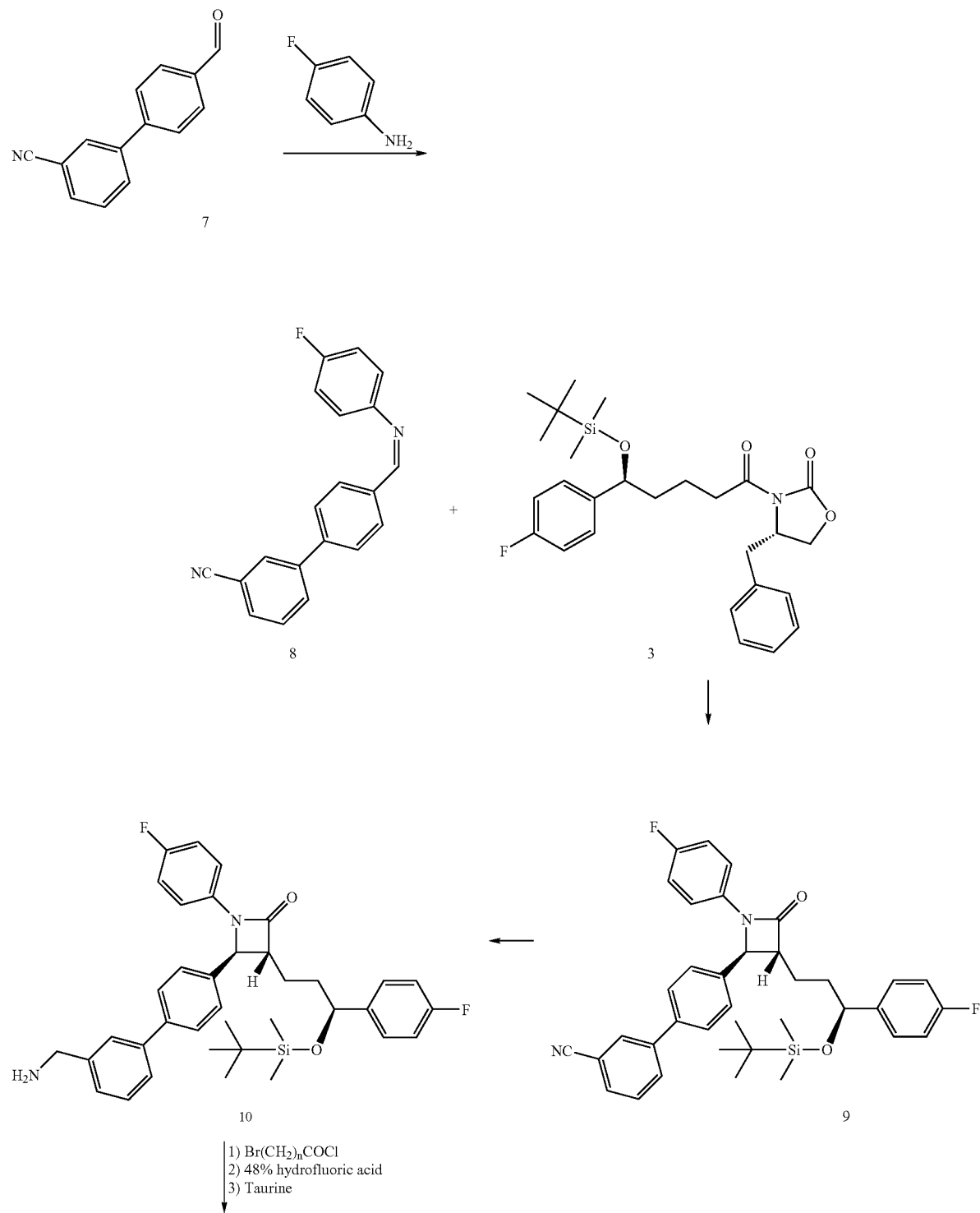

Scheme II

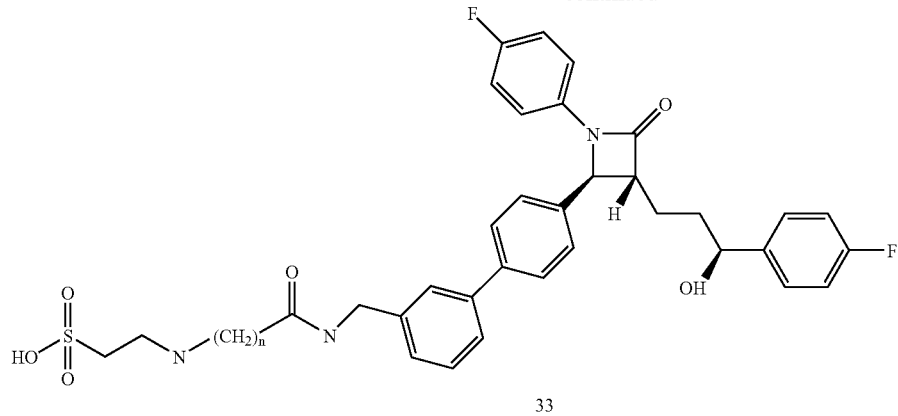

33

EXAMPLE 34

Illustrated in Scheme III below is the general method for the preparation of cholesterol absorption inhibitors of general formula 34. An imine is made by condensing 4-bromobenzaldehyde with 4-cyanoaniline, followed by condensation with the benzyloxazolidinone compound 3 using titanium tetrachloride, and subsequent cyclization, using N,O-bistrimethylacetamide and catalytic tetra-n-butylammonium fluoride, to afford the azetidinone 12. Hydrofluoric acid in acetonitrile is used to remove the silyl protecting group, and coupling to bis(pinacolato)diboron using catalytic palladium affords compound 13. Suzuki coupling with intermediate 20 affords compound 14. Reduction of the cyano group is accomplished under hydrogen atmosphere over excess Raney-Nickel in ethanol and ammonium hydroxide, and acetate groups are removed with triethylamine-methanol-water to provide 15. Acylation with the appropriate acid chloride [Br(CH2)$_n$COCl] followed by reaction with taurine provides the final product 16. It is noted that in this scheme the taurine is for illustration and that a large variety of functional groups can be substituted in its place.

Scheme III

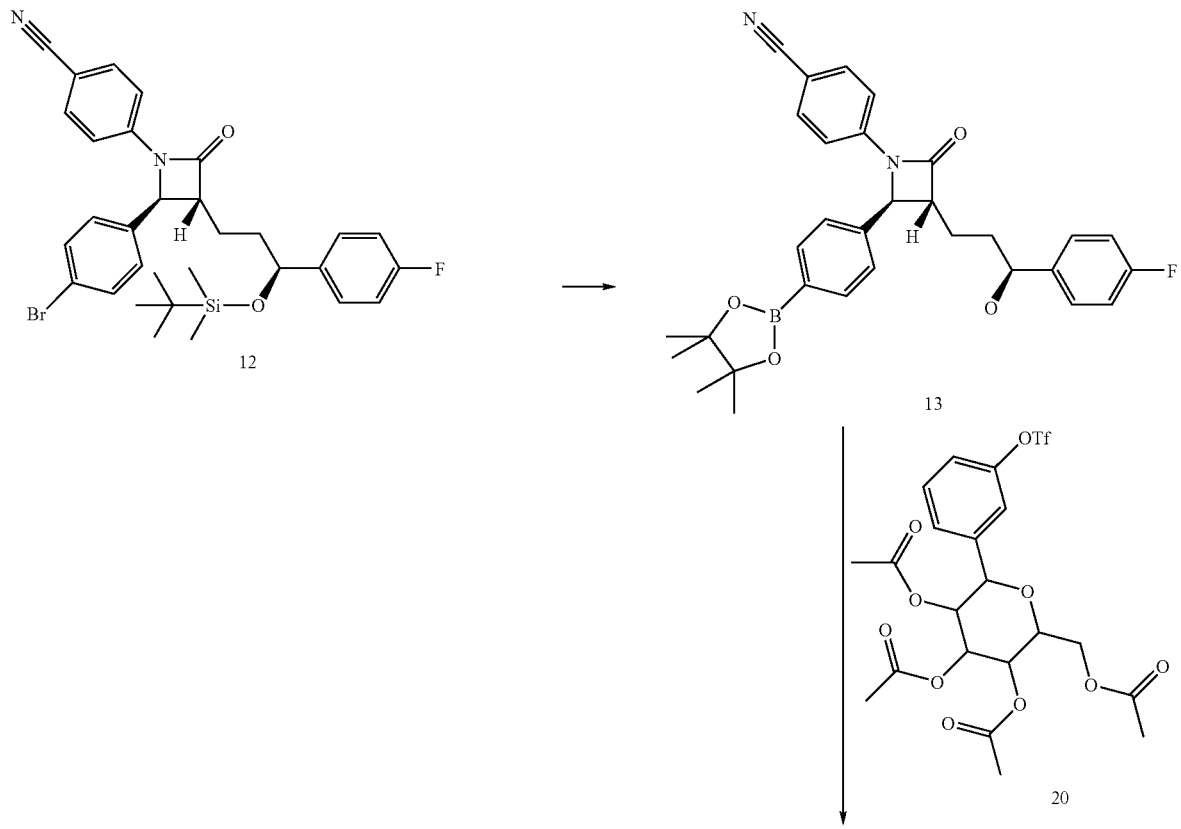

-continued

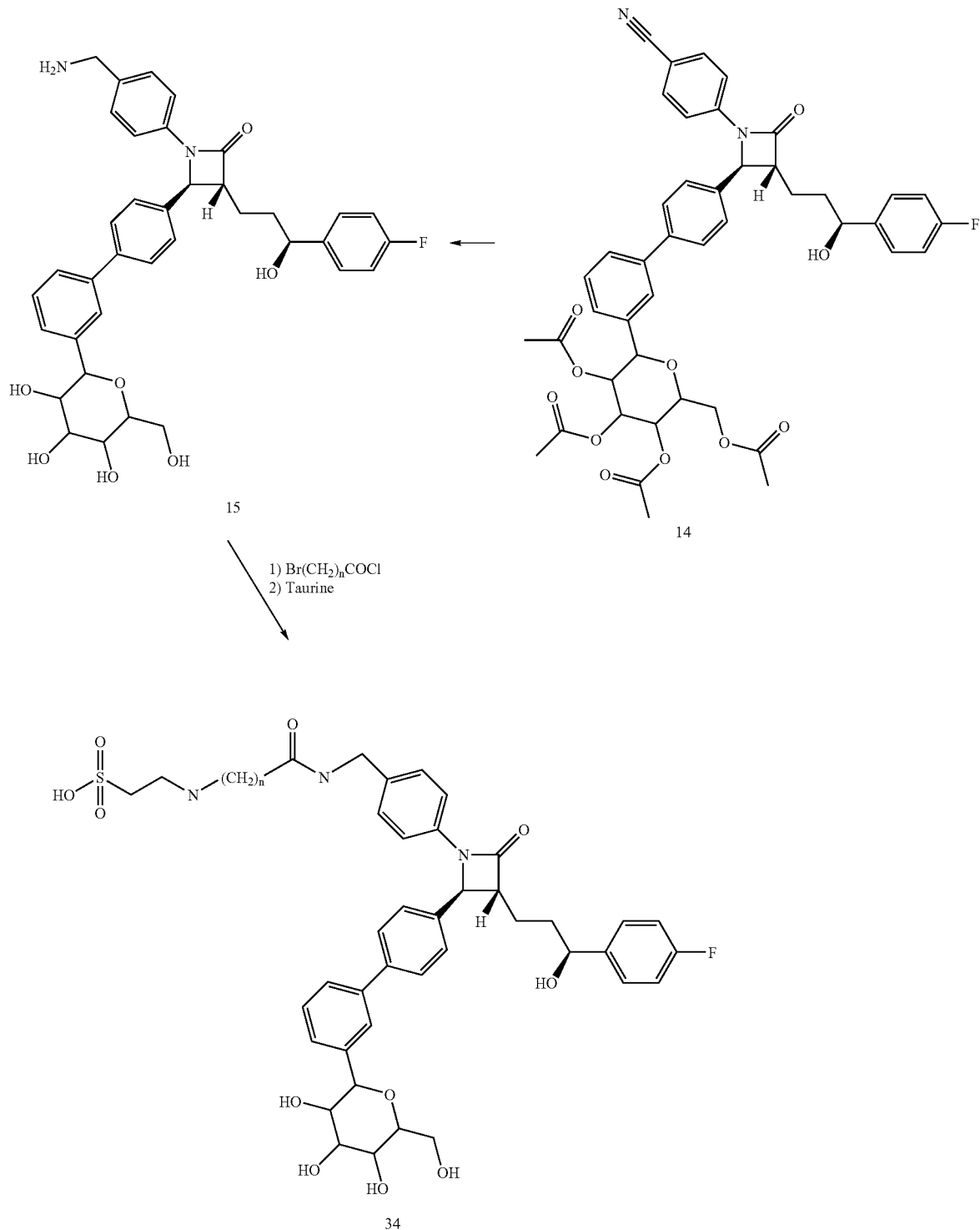

Synthesis of Intermediate 20: 3-Allyloxyphenyl lithium is reacted with glucopyranolactone 17, followed by reductive cleavage of the hemiketal with triethylsilane and boron trifluoride diethyl etherate to provide benzyl-protected glycoside 18. Removal of the allyl group with palladium catalyst and tri-n-butyltin hydride followed by hydrogenation using palladium on carbon under a hydrogen atmosphere provides phenyl glycoside 19. Reaction with N-phenyltrifluoromethanesulfonimide provides the triflate and peracetylation using acetic anhyride in pyridine afford intermediate 20.

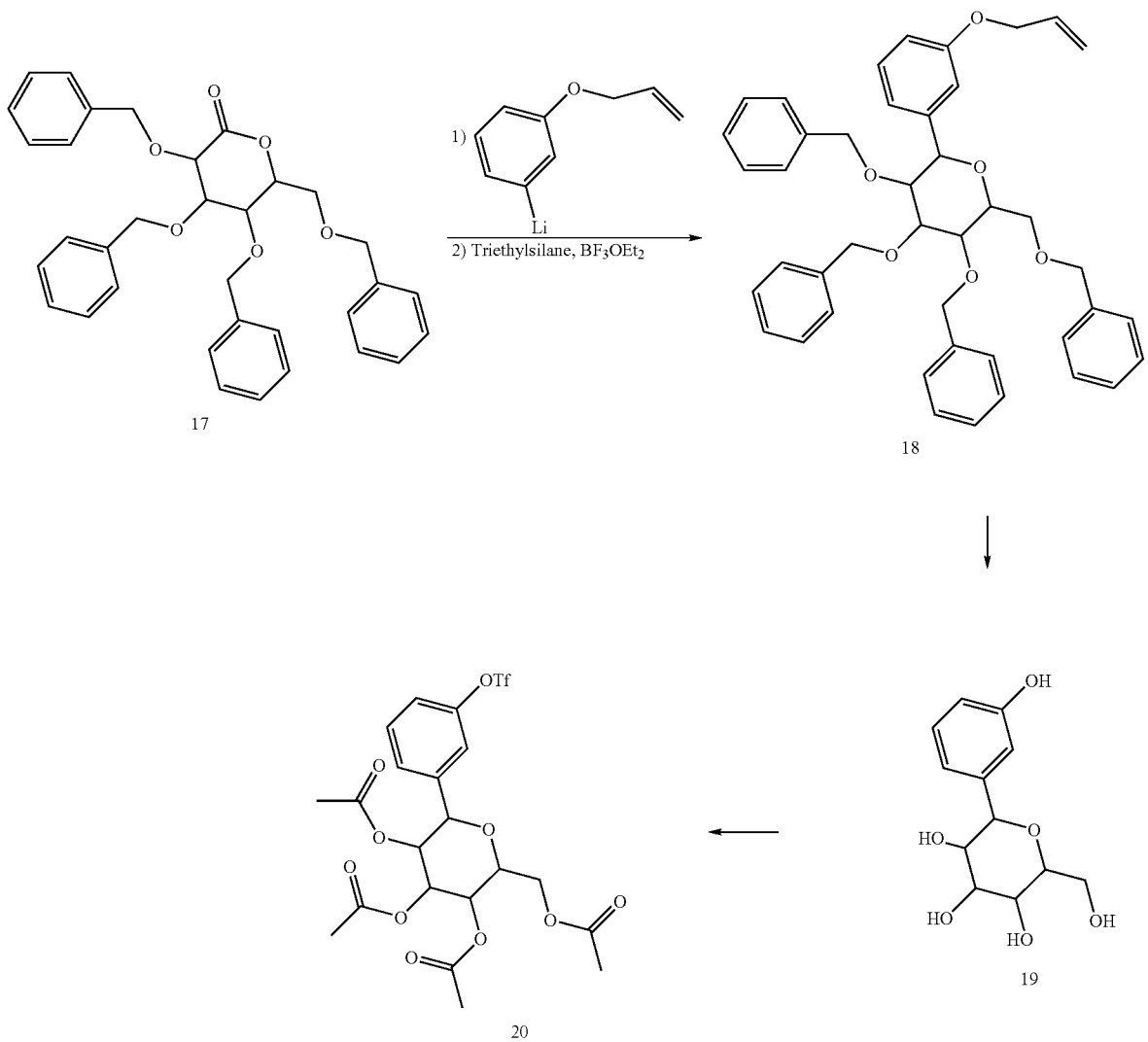

EXAMPLE 35

(4S)-4-Benzyl-3-[5-(4-fluorophenyl)-5-oxopentanoyl]-1,3-oxazolidin-2-one

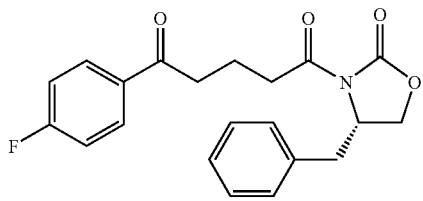

5-(4-Fluorophenyl)-5-oxopentanoic acid (10.08 g, 47.9 mmol) and triethylamine (6.8 mL, 4.94 g, 48.8 mmol) were dissolved in tetrahydrofuran (50 mL). The reaction was cooled to −5° C. (ice/brine bath), trimethylacetyl chloride (6.0 mL, 5.87 g, 48.7 mmol) was added quickly drop-wise and the mixture was warmed to room temperature and stirred for 1.5 h. The reaction was cooled to −5° C. (ice/brine bath) again for 30 min, filtered through Celite®, washed with cold 1:1 hexane-tetrahydrofuran (60 mL) and hexane (120 mL). The filtrate was concentrated, dissolved in N,N-dimethylformamide (16 mL) and to this mixture was added (S)-benzyl-2-oxazolidinone (8.47 g, 47.8 mmol) and 4-dimethylaminopyridine (8.57 g, 70.2 mmol) as solids. The reaction was stirred at room temperature for 20 h, poured into 1.0 N hydrochloric acid (400 mL) and extracted with ethyl acetate (2×300 mL). The organic layer was washed with water (400 mL), quarter saturated sodium bicarbonate solution (400 mL), brine (200 mL), dried over sodium sulfate, filtered, and concentrated. The residue was purified by crystallization from hot isopropyl alcohol (75 mL) with slow cooling to room temperature over 16 h. The crystals were filtered cold and washed with cold isopropyl alcohol (50 mL) to afford (4S)-4-benzyl-3-[5-(4-fluorophenyl)-5-oxopentanoyl]-1,3-oxazolidin-2-one (13.87 g, 78% yield) as a white crystalline solid; mp 114.5° C.; $R_f$ 0.29 (1:2 ethyl acetate-hexane); $^1$H NMR (300 MHz, CDCl$_3$) δ 8.03-7.98 (m, 2H), 7.37-7.19 (m, 5H), 7.14 (t, J=8.7 Hz, 2H), 4.72-4.64 (m, 1H), 4.25-4.15 (m, 2H), 3.32 (dd, J=13.3, 3.4 Hz, 1H), 3.12-3.01 (m, 4H), 2.78 (dd, J=13.3, 9.6 Hz, 1H), 2.15 (quint., J=7.2 Hz, 2H) ppm.

EXAMPLE 36

(4S)-4-Benzyl-3-[(5S)-5-(4-fluorophenyl)-5-hydroxypentanoyl]-1,3-oxazolidin-2-one

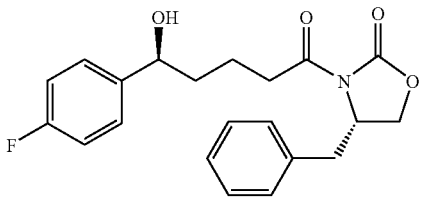

(4S)-4-Benzyl-3-[5-(4-fluorophenyl)-5-oxopentanoyl]-1,3-oxazolidin-2-one (13.87 g, 37.54 mmol) was dissolved in dichloromethane (40 mL). Into a separate flask were added borane-methyl sulfide complex (3.6 mL, ~38 mmol), 1.0 M®-1-methyl-3,3-diphenyltetrahydro-3H-pyrrolo[1,2-c][1,3,2]oxazaborole in toluene (1.9 mL, 1.9 mmol) and dichloromethane (20 mL). This mixture was cooled to −5° C. (ice/methanol bath) and the ketone solution was added drop-wise via cannula over 5 min. The reaction was stirred at −5° C. for 5.5 h and then quenched by slow addition of methanol (9 mL), 5% hydrogen peroxide solution (30 mL) and 1 M aqueous sulfuric acid (20 mL) respectively. The reaction was poured into water (500 mL) and extracted with ethyl acetate (500 mL). The organic layer was washed with water (500 mL), 0.1 N hydrochloric acid (300 mL) and brine (300 mL), dried over sodium sulfate, filtered, and concentrated to afford (4S)-4-benzyl-3-[(5S)-5-(4-fluorophenyl)-5-hydroxypentanoyl]-1,3-oxazolidin-2-one, which was used in subsequent reactions without further purification; $R_f$ 0.14 (1:2 ethyl acetate-hexane); $^1$H NMR (300 MHz, CDCl$_3$) δ 7.37-7.24 (m, 5H), 7.19 (d, J=7.3 Hz, 2H), 7.02 (t, J=8.9 Hz, 2H), 4.72-4.61 (m, 2H), 4.21-4.13 (m, 2H), 3.27 (dd, J=13.2, 3.0 Hz, 1H), 2.99-2.94 (m, 2H), 2.74 (dd, J=13.2, 9.6 Hz, 1H), 2.27 (br s, 1H), 1.88-1.66 (m, 4H) ppm; MS [M−OH]$^+$ 354.0.

EXAMPLE 37

(4S)-4-Benzyl-3-[(5S)-5-{[tert-butyl(dimethyl)silyl]oxy}-5-(4-fluorophenyl)pentanoyl]-1,3-oxazolidin-2-one

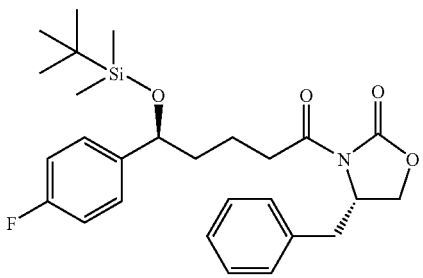

(4S)-4-Benzyl-3-[(5S)-5-(4-fluorophenyl)-5-hydroxypentanoyl]-1,3-oxazolidin-2-one (37.54 mmol) was dissolved in N,N-dimethylformamide (40 mL) and then imidazole (2.97 g, 43.6 mmol) and tert-butyldimethylsilyl chloride (6.12 g, 40.6 mmol) were added. The reaction was stirred at room temperature for 19 h, poured into 0.1 N hydrochloric acid (500 mL) and extracted with 1:1 ethyl acetate-hexane (500 mL). The organic layer was washed with water (2×500 mL), brine (300 mL), dried over sodium sulfate, filtered, and concentrated. The residue was purified by crystallization from methanol (55 mL) by heating to a light boil and cooling slowly to room temperature over 18 h. The crystals were filtered cold and washed with cold methanol (45 mL) to afford (4S)-4-benzyl-3-[(5S)-5-{[tert-butyl(dimethyl)silyl]oxy}-5-(4-fluorophenyl)pentanoyl]-1,3-oxazolidin-2-one (16.04 g, 88% yield) as a white crystalline solid; mp 87.6° C.; $R_f$ 0.66 (1:2 ethyl acetate-hexane); $^1$H NMR (300 MHz, CDCl$_3$) δ 7.36-7.18 (m, 7H), 6.99 (t, J=8.7 Hz, 2H), 4.69-4.61 (m, 2H), 4.18-4.13 (m, 2H), 3.27 (dd, J=13.5, 3.2 Hz, 1H), 2.96-2.89 (m, 2H), 2.73 (dd, J=13.5, 9.7 Hz, 1H), 1.82-1.63 (m, 4H), 0.88 (s, 9H), 0.04 (s, 3H), −0.15 (s, 3H) ppm; MS [M−OSi(CH$_3$)$_2$C(CH$_3$)$_3$]$^+$354.0.

EXAMPLE 38

N-{(1E)-[2-(Allyloxy)-4-bromophenyl]methylene}aniline

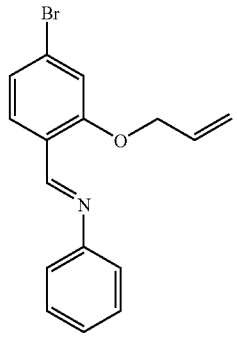

4-Bromosalicylaldehyde (4.02 g, 20.0 mmol) [prepared from 3-bromophenyl analogous to the procedure of Casiraghi, et. al. *Journal of the Chemical Society, Perkin Transactions 1: Organic and Bio-Organic Chemistry* (1978), 318-21] was dissolved in anhydrous N,N-dimethylformamide (13 mL). Potassium carbonate (3.9 g, 28.0 mmol) was added as a solid to give a yellow suspension. Allyl bromide (2.6 mL, 3.63 g, 30.0 mmol) was added via syringe. The reaction stirred for 17 h at room temperature and was then diluted with water and extracted three times with 1:1 ethyl acetate-hexane. The combined organic layers were washed with water (5×), brine, dried over sodium sulfate, filtered and concentrated to afford 2-(allyloxy)-4-bromobenzaldehyde (4.83 g, 100% yield) as a yellow solid which was used without further purification in the next step; $R_f$ 0.38 (1:9 ethyl acetate-hexane); MS [M+H]$^+$241.0.

2-(Allyloxy)-4-bromobenzaldehyde (5.05 g, 20.9 mmol) was dissolved with warming in isopropanol (18 mL). Freshly distilled aniline (1.99 g, 21.3 mmol) was added with isopropanol (4 mL) and the reaction was heated to 50° C. A yellow precipitate formed within 30 min and isopropanol (5 mL) was added to aid stirring. The reaction was stirred at 50° C. for 16 h, by which time proton NMR showed no aldehyde present. The reaction was cooled with stirring. The mixture was diluted with hexane (20 mL), the solid was filtered and washed with the mother liquor, washed with hexane and air dried to afford N-{(1E)-[2-(allyloxy)-4-bromophenyl]methylene}aniline (5.69 g, 86% yield) as a light yellow powder; $^1$H NMR (300 MHz, CDCl$_3$) δ 8.87 (s, 1H), 8.03 (d, J=8.4 Hz, 1H), 7.43-7.36 (m, 2H), 7.27-7.17 (m, 4H), 7.099 (d, J=1.8 Hz, 1H), 6.06 (ddt, J=17.2, 10.5, 5.3 Hz, 1H), 5.43 (AB q, J=17.3, 3.0 Hz, 1H), 5.33 (AB q, J=10.5, 2.8 Hz, 1H), 4.62 (ddd, J=5.2, 1.5, 1.5 Hz, 2H) ppm.

EXAMPLE 39

(3R,4S)-4-(4-Bromo-2-hydroxyphenyl)-3-[(3S)-3-{[tert-butyl(dimethyl)silyl]oxy}-3-(4-fluorophenyl)propyl]-1-phenylazetidin-2-one

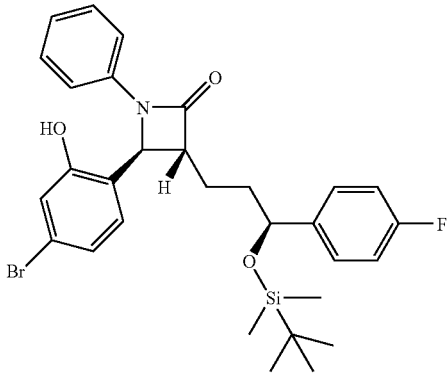

2-(Allyloxy)-4-bromobenzaldehyde (2.79 g, 8.83 mmol) and (4S)-4-Benzyl-3-[(5S)-5-{[tert-butyl(dimethyl)silyl]oxy}-5-(4-fluorophenyl)pentanoyl]-1,3-oxazolidin-2-one (3.3 g, 6.8 mmol) were combined in a 100-mL 3-neck round bottom flask fitted with a thermometer and nitrogen inlet. Anhydrous dichloromethane (60 mL) was added to give a light yellow solution which was cooled to –30° C. Diisopropylethylamine (2.3 mL, 1.71 g, 13.2 mmol) was added via syringe. Titanium tetrachloride (0.86 mL, 1.48 g, 7.82 mmol) was added dropwise over 6 min at an internal temperature between –28° to –26° C. to give a reddish brown solution. The reaction stirred under nitrogen for 3 h between –30 to –25° C. and was then cooled to –35° C. and quenched slowly with glacial acetic acid (6 mL) over 6 min. The reaction was poured into a cold (0° C.) 7% tartaric acid solution (125 mL). Ethyl acetate (200 mL) was added and the mixture was warmed to room temperature with stirring. A 5% sodium sulfite solution (60 mL) was added and the layers were separated. The aqueous layer was extracted with ethyl acetate (2×200 mL). The combined organic layers were washed with a saturated sodium bicarbonate solution, water and brine, dried over sodium sulfate, filtered and concentrated. The residue was purified by chromatography (120 g silica gel, 1% to 90% ethyl acetate-hexane) to afford (4S)-3-[(2R,5S)-2-[(S)-[2-(allyloxy)-4-bromophenyl](anilino)methyl]-5-{[tert-butyl(dimethyl)silyl]oxy}-5-(4-fluorophenyl)pentanoyl]-4-benzyl-1,3-oxazolidin-2-one (4.54 g, 83% yield); R$_f$ 0.38 (1:4 ethyl acetate-hexane); MS [M+H]$^+$ 801.0.

(4S)-3-[(2R,5S)-2-[(S)-[2-(Allyloxy)-4-bromophenyl](anilino)methyl]-5-{[tert-butyl(dimethyl)silyl]oxy}-5-(4-fluorophenyl)pentanoyl]-4-benzyl-1,3-oxazolidin-2-one (1.2 g, 1.5 mmol) was dissolved in anhydrous methyl tert-butyl ether (10 mL) and stirred at room temperature under nitrogen. N,O-bistrimethylsilylacetamide (1.1 mL, 4.5 mmol) was added followed by a catalytic amount (~5 mg) of tetrabutylammonium fluoride trihydrate. The reaction was stirred at room temperature for 19 h, quenched at room temperature with glacial acetic acid (160 μL) and partitioned between ethyl acetate and water and separated. The aqueous layer was extracted with ethyl acetate. The combined organic layers were washed with a saturated sodium bicarbonate solution, water, brine, dried over sodium sulfate, filtered and concentrated. The residue was purified by chromatography (120 g silica gel, 1% to 85% ethyl acetate-hexane) to afford (3R,4S)-4-[2-(allyloxy)-4-bromophenyl]-3-[(3S)-3-{[tert-butyl(dimethyl)silyl]oxy}-3-(4-fluorophenyl)propyl]-1-phenylazetidin-2-one (816 mg, 87% yield); R$_f$ 0.56 (1:4 ethyl acetate-hexane).

(3R,4S)-4-[2-(Allyloxy)-4-bromophenyl]-3-[(3S)-3-{[tert-butyl(dimethyl)silyl]oxy}-3-(4-fluorophenyl)propyl]-1-phenylazetidin-2-one (1.34 g, 2.15 mmol) was dissolved in deoxygenated tetrahydrofuran (20 mL). Morpholine (1.8 mL, 1.8 g, 20.6 mmol) was added with additional deoxygenated tetrahydrofuran (5 mL). The reaction was purged with nitrogen and tetrakis(triphenylphosphine)palladium(0) (220 mg, 0.19 mmol) was added. The reaction was purged with nitrogen again. After 1.5 h at room temperature the reaction was diluted with ethyl acetate, washed twice with 1 N hydrochloric acid, saturated sodium bicarbonate solution, water and brine, dried over sodium sulfate and filtered. The solution was treated with activated charcoal, filtered, concentrated and purified by chromatography (40 g silica gel, 6% to 80% ethyl acetate-hexane) to afford (3R,4S)-4-(4-bromo-2-hydroxyphenyl)-3-[(3S)-3-{[tert-butyl(dimethyl)silyl]oxy}-3-(4-fluorophenyl)propyl]-1-phenylazetidin-2-one (1.04 g, 83% yield); R$_f$ 0.38 (1:4 ethyl acetate-hexane); $^1$H NMR (300 MHz, CDCl$_3$) δ 7.28-7.18 (m, 6H), 7.09-6.92 (m, 6H), 5.91 (s, 1H), 4.93 (d, J=2.3 Hz, 1H), 4.65 (t, J=5.4 Hz, 1H), 3.06 (ddd, J=4.8, 2.3, 2.3 Hz, 1H), 1.98-1.77 (m, 4H), 0.86 (s, 9H), 0.006 (s, 3H), –0.16 (s, 3H) ppm; MS [M–H]+581.7.

EXAMPLE 40

(3R,4S)-4-(4-Bromo-2-{[tert-butyl(dimethyl)silyl]oxy}phenyl)-3-[(3S)-3-{[tert-butyl(dimethyl)silyl]oxy}-3-(4-fluorophenyl)propyl]-1-phenylazetidin-2-one

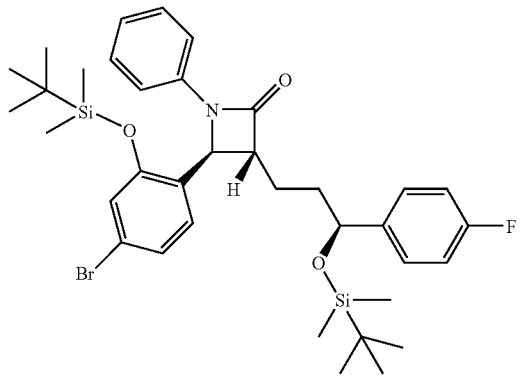

(3R,4S)-4-(4-Bromo-2-hydroxyphenyl)-3-[(3S)-3-{[tert-butyl(dimethyl)silyl]oxy}-3-(4-fluorophenyl)propyl]-1-phenylazetidin-2-one (1.04 g, 1.79 mmol) was dissolved in anhydrous dichloromethane (5 mL), anhydrous N,N-dimethylformamide (5 mL) and stirred under nitrogen at room temperature. 2,6-Lutidine (1.0 mL, 920 mg, 8.6 mmol) was added followed by drop-wise addition of tert-butyldimethylsilyl trifluromethane sulfonate (1.2 mL, 1.38 g, 5.22 mmol). The reaction was stirred under nitrogen at room temperature for 2.25 h. 2,6-Lutidine (0.25 mL, 230 mg, 2.15 mmol) was added followed by addition of tert-butyldimethylsilyl trifluromethane sulfonate (0.4 mL, 460 mg, 1.74 mmol) and after a total of 4.5 h at room temperature the reaction was diluted with ethyl acetate and water and the layers were separated. The aqueous layer was extracted with ethyl acetate and the combined organic layers were washed with 0.5 N hydrochloric acid, saturated sodium bicarbonate solution, water (4 times) and brine, dried over sodium sulfate, filtered, concentrated and purified by chromatography (40 g silica gel, 1% to 85% ethyl acetate-hexane) to afford (3R,4S)-4-(4-bromo-2-{[tert-butyl(dimethyl)silyl]oxy}phenyl)-3-[(3S)-3-{[tert-butyl(dimethyl)silyl]oxy}-3-(4-fluorophenyl)propyl]-1-phenylazetidin-2-one (1.23 g, 99% yield); $R_f$ 0.57 (1:4 ethyl acetate-hexane); $^1$H NMR (300 MHz, CDCl$_3$) δ 7.33-7.14 (m, 6H), 7.09-6.91 (m, 6H), 4.99 (d, J=2.3 Hz, 1H), 4.62 (t, J=5.6 Hz, 1H), 3.06 (ddd, J=4.9, 2.5, 2.3 Hz, 1H), 1.97-1.69 (m, 4H), 1.03 (s, 9H), 0.84 (s, 9H), 0.33 (s, 3H), 0.29 (s, 3H), −0.01 (s, 3H), −0.20 (s, 3H) ppm.

EXAMPLE 41

5-Bromo-2-{(2S,3R)-3-[(3S)-3-{[tert-butyl(dimethyl)silyl]oxy}-3-(4-fluorophenyl)propyl]-4-oxo-1-phenylazetidin-2-yl}phenyl acetate

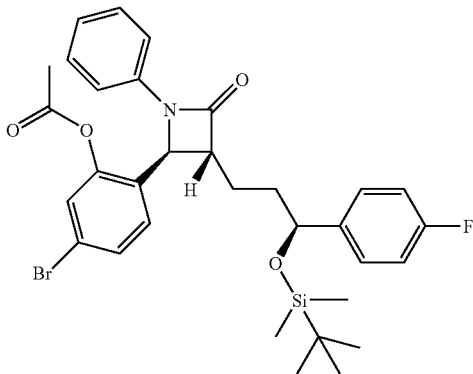

(3R,4S)-4-(4-Bromo-2-hydroxyphenyl)-3-[(3S)-3-{[tert-butyl(dimethyl)silyl]oxy}-3-(4-fluorophenyl)propyl]-1-phenylazetidin-2-one (293 mg, 0.50 mmol) was dissolved in anhydrous dichloromethane (3 mL). 4-Dimethylaminopyridine (183 mg, 1.5 mmol) was added followed by acetic anhydride (280 μL, 302 mg, 3.0 mmol). After 1 h the reaction was filtered through a plug of silica gel and eluted with dichloromethane. The solvent was concentrated, azeotroped with toluene and purified by chromatography (40 g silica gel, 1% to 85% ethyl acetate-hexane) to afford 5-bromo-2-{(2S,3R)-3-[(3S)-3-{[tert-butyl(dimethyl)silyl]oxy}-3-(4-fluorophenyl)propyl]-4-oxo-1-phenylazetidin-2-yl}phenyl acetate (245 mg, 78% yield); $R_f$ 0.47 (1:4 ethyl acetate-hexane); $^1$H NMR (300 MHz, CDCl$_3$) δ 7.38-7.16 (m, 9H), 7.14-6.94 (m, 3H), 4.69 (t, J=5.4 Hz, 1H), 4.64 (d, J=2.3 Hz, 1H), 3.06 (ddd, J=4.7, 2.3, 2.2 Hz, 1H), 2.30 (s, 3H), 1.97-1.78 (m, 4H), 0.89 (s, 9H), 0.032 (s, 3H), −0.14 (s, 3H) ppm; MS [M−OSi(CH$_3$)$_2$C(CH$_3$)$_3$]$^+$ 493.8.

EXAMPLE 42

(3R,4S)-4-(3,3'-Dihydroxybiphenyl-4-yl)-3-[(3S)-3-(4-fluorophenyl)-3-hydroxypropyl]-1-phenylazetidin-2-one

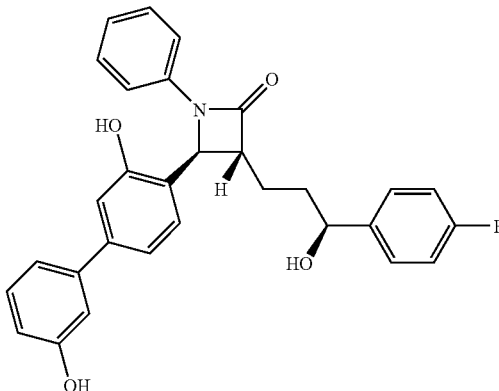

Using Suzuki coupling methodology, 5-Bromo-2-{(2S,3R)-3-[(3S)-3-{[tert-butyl(dimethyl)silyl]oxy}-3-(4-fluorophenyl)propyl]-4-oxo-1-phenylazetidin-2-yl}phenyl acetate (100 mg, 0.16 mmol) was combined with 3-hydroxyphenyl boronic acid (29 mg, 0.21 mmol) with deoxygenated toluene (3 mL) and deoxygenated ethanol (1 mL). 2.0 M aqueous potassium carbonate (0.31 mL, 0.31 mmol) was added and the vessel was purged with nitrogen. Tetrakis(triphenylphosphine)palladium(0) (9 mg, 0.008 mmol) was added and the vessel purged again. The reaction was heated to 70° C. for 1.5 h, cooled, diluted with water and extracted with ethyl acetate (2×). The combined organic layers were washed with water, brine, dried over sodium sulfate, filtered, concentrated and purified by chromatography (40 g silica gel, 20% to 90% ethyl acetate-hexane) to afford 4-{(2S,3R)-3-[(3S)-3-{[tert-butyl(dimethyl)silyl]oxy}-3-(4-fluorophenyl)propyl]-4-oxo-1-phenylazetidin-2-yl}-3'-hydroxybiphenyl-3-yl acetate (70 mg, 69% yield)); $R_f$ 0.34 (1:2 ethyl acetate-hexane); $^1$H NMR (300 MHz, CDCl$_3$) δ 7.34-7.17 (m, 10H), 7.06-6.90 (m, 5H), 6.79 (ddd, J=8.1, 2.5, 0.8 Hz, 1H), 6.03 (br s, 1H), 4.67 (d, J=2.3 Hz, 1H), 4.64 (t, J=5.6 Hz, 1H), 3.26 (ddd, J=4.8, 2.5, 2.4 Hz, 1H), 2.27 (s, 3H), 1.94-1.73 (m, 4H), 0.84 (s, 9H), −0.02 (s, 3H), −0.19 (s, 3H) ppm; MS [M−OSi(CH$_3$)$_2$C(CH$_3$)$_3$]$^+$ 508.0.

4-{(2S,3R)-3-[(3S)-3-{[tert-Butyl(dimethyl)silyl]oxy}-3-(4-fluorophenyl)propyl]-4-oxo-1-phenylazetidin-2-yl}-3'-hydroxybiphenyl-3-yl acetate (70 mg, 0.11 mmol) was dissolved in methanol (2.45 mL). Water (0.73 mL) was added dropwise followed by triethylamine (2.2 mL) and the reaction stirred at room temperature for 1 h. Toluene (3 mL) and methanol (5 mL) were added and the reaction was concentrated to give 69 mg of crude (3R,4S)-3-[(3S)-3-{[tert-butyl(dimethyl)silyl]oxy}-3-(4-fluorophenyl)propyl]-4-(3,3'-dihydroxybiphenyl-4-yl)-1-phenylazetidin-2-one which was used without further purification.

(3R,4S)-3-[(3S)-3-{[tert-Butyl(dimethyl)silyl]oxy}-3-(4-fluorophenyl)propyl]-4-(3,3'-dihydroxybiphenyl-4-yl)-1-phenylazetidin-2-one (73 mg, 0.122 mmol) was dissolved in acetonitrile (5 mL) and transferred to a polypropylene conical vial. 48% Hydrofluoric acid (1 mL) was added dropwise and the reaction stirred at room temperature for 1 h. The reaction was quenched with 1 N sodium hydroxide (24 mL) and transferred to a flask containing pH 7.4 phosphate buffer (24 mL). The pH of the solution was adjusted to 7.5-8.0 with saturated sodium bicarbonate solution then extracted with ethyl acetate (3×). The combined organic layers were washed with saturated sodium bicarbonate solution (2×), water, brine, dried over sodium sulfate, filtered, concentrated and purified by chromatography (12 g silica gel, 40% to 100% ethyl acetate-hexane) to afford (3R,4S)-4-(3,3'-dihydroxybiphenyl-4-yl)-3-[(3S)-3-(4-fluorophenyl)-3-hydroxypropyl]-1-phenylazetidin-2-one (53 mg, 69% yield)); $^1$H NMR (300 MHz, CDCl$_3$) δ 7.30-7.13 (m, 7H), 7.08-6.85 (m, 8H), 6.78 (ddd, J=8.1, 2.3, 0.9 Hz, 1H), 5.04 (d, J=2.3 Hz, 1H), 4.61 (t, J=5.9 Hz, 1H), 3.07 (ddd, J=5.7, 1.8, 1.5 Hz, 1H), 2.08-1.80 (m, 4H) ppm; MS [M+H]$^+$ 584.0 [M–H]$^-$ 582.0.

EXAMPLE 43

(3R,4S)-4-(3-bromophenyl)-1-(4-fluorophenyl)-3-[(3S)-3-(4-fluorophenyl)-3-hydroxypropyl]azetidin-2-one

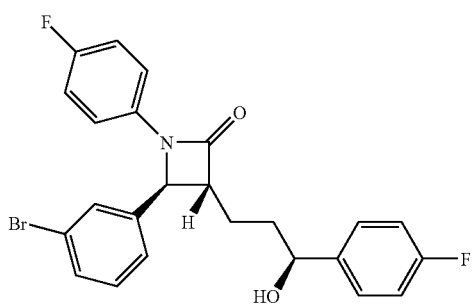

Synthesized using a similar procedure as Example 39 starting from 4-fluoroaniline and 3-bromobenzaldehyde. The benzylic TBDMS protecting group was removed using 48% hydrofluoric acid as described in Example 42. Purified by chromatography (silica gel, 10% to 60% ethyl acetate-hexane) to afford (3R,4S)-4-(3-bromophenyl)-1-(4-fluorophenyl)-3-[(3S)-3-(4-fluorophenyl)-3-hydroxypropyl]azetidin-2-one (86 mg); $^1$H NMR (300 MHz, CDCl$_3$) δ 7.50-7.45 (m, 2H), 7.33-7.18 (m, 6H), 7.07-6.91 (m, 4H), 4.72 (t, J=5.8 Hz, 1H), 4.57 (d, J=2.4 Hz, 1H), 3.10 (ddd, J=4.8, 2.4, 2.4 Hz, 1H), 2.12 (br s, 1H), 2.06-1.86 (m, 4H) ppm; MS [M+HCO$_2^-$]$^-$ 516.0.

EXAMPLE 44

(3R,4S)-1-(4-fluorophenyl)-3-[(3S)-3-(4-fluorophenyl)-3-hydroxypropyl]-4-(3'-hydroxybiphenyl-3-yl)azetidin-2-one

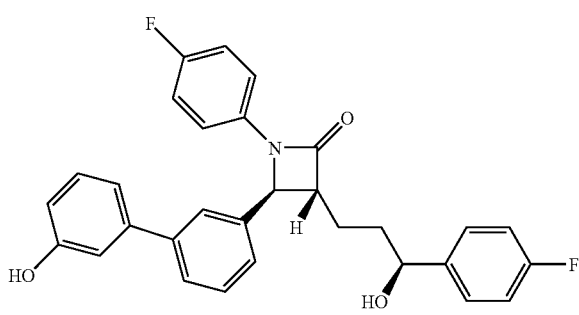

(3R,4S)-4-(3-Bromophenyl)-1-(4-fluorophenyl)-3-[(3S)-3-(4-fluorophenyl)-3-hydroxypropyl]azetidin-2-one (43 mg, 0.091 mmol) was coupled with 3-hydroxyphenyl boronic acid (18 mg, 0.13 mmol) under standard Suzuki conditions illustrated by Example 42. Purified by chromatography (silica gel, 10% to 90% ethyl acetate-hexane) to afford (3R,4S)-1-(4-fluorophenyl)-3-[(3S)-3-(4-fluorophenyl)-3-hydroxypropyl]-4-(3'-hydroxybiphenyl-3-yl)azetidin-2-one (19.7 mg, 45% yield); R$_f$ 0.30 (1:1 ethyl acetate-hexane); $^1$H NMR (300 MHz, CDCl$_3$) δ 7.57-7.40 (m, 3H), 7.34-7.22 (m, 6H), 7.10 (ddd, 7.7, 1.6, 0.9 Hz 1H), 7.04-6.90 (m, 5H), 6.84 (ddd, J=8.2, 2.6, 0.9 Hz, 1H), 5.10 (br s, 1H), 4.72 (t, J=5.9 Hz, 1H), 4.67 (d, J=2.4 Hz, 1H), 3.16 (ddd, J=5.0, 2.6, 2.4 Hz, 1H), 2.26 (br s, 1H), 2.08-1.88 (m, 4H) ppm.

EXAMPLE 45

(3R,4S)-1-(4-fluorophenyl)-3-[(3S)-3-(4-fluorophenyl)-3-hydroxypropyl]-4-(4'-hydroxybiphenyl-3-yl)azetidin-2-one

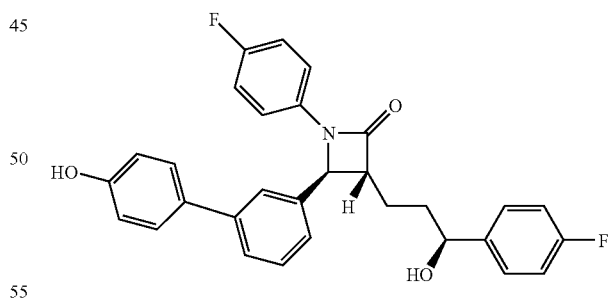

(3R,4S)-4-(3-Bromophenyl)-1-(4-fluorophenyl)-3-[(3S)-3-(4-fluorophenyl)-3-hydroxypropyl]azetidin-2-one (42 mg, 0.089 mmol) was coupled with 4-hydroxyphenyl boronic acid (18 mg, 0.13 mmol) under standard Suzuki conditions illustrated by Example 42. Purified by chromatography (silica gel, 10% to 90% ethyl acetate-hexane) to afford (3R,4S)-1-(4-fluorophenyl)-3-[(3S)-3-(4-fluorophenyl)-3-hydroxypropyl]-4-(4'-hydroxybiphenyl-3-yl)azetidin-2-one (27 mg, 63% yield); R$_f$ 0.31 (1:1 ethyl acetate-hexane); $^1$H NMR (300 MHz, CDCl$_3$) δ 7.54-7.37 (m, 6H), 7.32-7.22 (m, 4H), 7.04-6.87 (m, 6H), 5.24 (br s, 1H), 4.72 (t, J=6.0 Hz, 1H), 4.67 (d, J=2.4 Hz, 1H), 3.17 (ddd, J=5.3, 2.5, 2.4 Hz, 1H), 2.26 (br s, 1H), 2.09-1.88 (m, 4H) ppm.

EXAMPLE 46

(3R,4S)-4-(4-Bromophenyl)-3-[(3S)-3-(4-fluorophenyl)-3-hydroxypropyl]-1-phenylazetidin-2-one

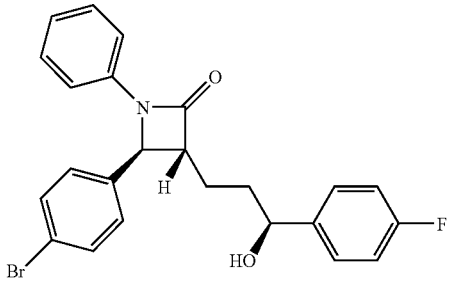

Synthesized using a similar procedure as Example 39 starting from aniline and 4-bromobenzaldehyde. The benzylic TBDMS protecting group was removed using 48% hydrofluoric acid as described in Example 42. Purification by chromatography (40 g silica gel, 10% to 90% ethyl acetate-hexane) afforded (3R,4S)-4-(4-bromophenyl)-3-[(3S)-3-(4-fluorophenyl)-3-hydroxypropyl]-1-phenylazetidin-2-one (982.6 mg, 75% overall yield) as a clear film; $R_f$ 0.45 (2:3 ethyl acetate-hexane); $^1$H NMR (300 MHz, CDCl$_3$) δ 7.49 (d, J=8.3 Hz, 2H), 7.31-7.19 (m, 8H), 7.07-6.98 (m, 3H), 4.70 (t, J=6.1 Hz, 1H), 4.61 (d, J=2.5 Hz, 1H), 3.04 (dt, J=7.4, 2.3 Hz, 1H), 2.24 (br s, 1H), 2.03-1.86 (m, 4H) ppm.

EXAMPLE 47

(3R,4S)-4-(5-Bromopyridin-2-yl)-3-[(3S)-3-(4-fluorophenyl)-3-hydroxypropyl]-1-phenylazetidin-2-one

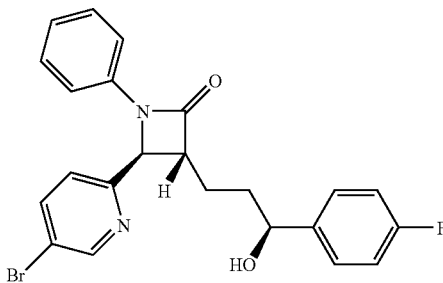

Synthesized using the same procedure as Example 39 starting from aniline and 5-bromo-2-pyridinecarboxaldehyde (prepared using a procedure described by Wang et. al., *Tetrahedron Letters* 41 (2000), 4335-4338). The benzylic TBDMS protecting group was removed using 48% hydrofluoric acid as described in Example 42. Purification by chromatography (12 g silica gel, 15% to 90% ethyl acetate-hexane) afforded (3R,4S)-4-(5-bromopyridin-2-yl)-3-[(3S)-3-(4-fluorophenyl)-3-hydroxypropyl]-1-phenylazetidin-2-one (23.3 mg, 3% overall yield) as a clear film; $R_f$ 0.07 (1:4 ethyl acetate-hexane); $^1$H NMR 300 MHz, CDCl$_3$) δ 8.66 (d, J=2.3 Hz, 1H), 7.80 (dd, J=8.3, 2.3 Hz, 1H), 7.34-7.29 (m, 3H), 7.24-7.17 (m, 4H), 7.09-6.99 (m, 3H), 4.82 (d, J=2.5 Hz, 1H), 4.75-4.71 (m, 1H), 3.21 (dt, J=7.0, 2.3 Hz, 1H), 2.31-1.89 (m, 5H) ppm.

EXAMPLE 48

(3R,4S)-4-(5-Bromo-2-thienyl)-3-[(3S)-3-(4-fluorophenyl)-3-hydroxypropyl]-1-phenylazetidin-2-one

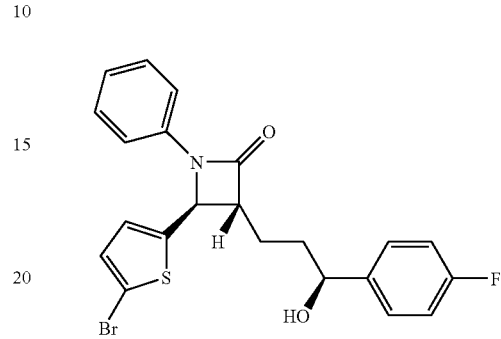

Synthesized using the same procedure as Example 39 starting from aniline and 5-bromo-2-thiophenecarboxaldehyde. The benzylic TBDMS protecting group was removed using 48% hydrofluoric acid as described in Example 42. Purification by chromatography (40 g silica gel, 15% to 90% ethyl acetate-hexane) afforded (3R,4S)-4-(5-bromo-2-thienyl)-3-[(3S)-3-(4-fluorophenyl)-3-hydroxypropyl]-1-phenylazetidin-2-one (212.4 mg, 23% overall yield) as a white solid; $R_f$ 0.13 (1:4 ethyl acetate-hexane); $^1$H NMR (300 MHz, CDCl$_3$) δ 7.36-7.21 (m, 6H), 7.10-7.06 (m, 1H), 7.02 (t, J=8.7 Hz, 2H), 6.89 (dd, J=19.7, 3.8 Hz, 2H), 4.83 (d, J=2.4 Hz, 1H), 4.71 (t, J=5.7 Hz, 1H), 3.25-3.19 (m, 1H), 2.20 (br s, 1H), 2.01-1.83 (m, 4H) ppm.

EXAMPLE 49

(3R,4S)-3-[(3S)-3-(4-Fluorophenyl)-3-hydroxypropyl]-4-[5-(3-hydroxyphenyl)pyridin-2-yl]-1-phenylazetidin-2-one

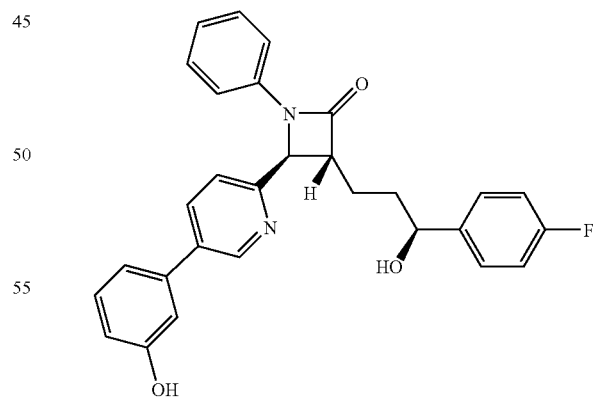

(3R,4S)-4-(5-Bromopyridin-2-yl)-3-[(3S)-3-(4-fluorophenyl)-3-hydroxypropyl]-1-phenylazetidin-2-one (23 mg, 0.051 mmol) was coupled with 3-hydroxyphenyl boronic acid (9.2 mg, 0.067 mmol) under standard Suzuki conditions illustrated by Example 42. Purification by chromatography (4 g silica gel, 15% to 100% ethyl acetate-hexane) afforded (3R,4S)-3-[(3S)-3-(4-fluorophenyl)-3-hydroxypropyl]-4-[5-

(3-hydroxyphenyl)pyridin-2-yl]-1-phenylazetidin-2-one (20.7 mg, 87% yield) as a clear film; $R_f$ 0.14 (1:1 ethyl acetate-hexane); $^1$H NMR (300 MHz, CDCl$_3$) δ 8.88 (d, J=2.2 Hz, 1H), 7.88 (dd, J=8.2, 2.3 Hz, 1H), 7.86-7.80 (m, 1H), 7.39-7.22 (m, 7H), 7.12-7.02 (m, 3H), 6.96 (t, J=8.7 Hz, 2H), 6.96-6.91 (m, 1H), 4.97 (d, J=2.3 Hz, 1H), 4.76-4.72 (m, 1H), 3.28-3.22 (m, 1H), 3.20 (br s, 1H), 2.17-1.90 (m, 4H), 1.80 (br s, 1H) ppm; MS [M+H]$^+$ 469.0.

EXAMPLE 50

(3R,4S)-3-[(3S)-3-(4-Fluorophenyl)-3-hydroxypropyl]-4-[5-(3-hydroxyphenyl)-2-thienyl]-1-phenylazetidin-2-one

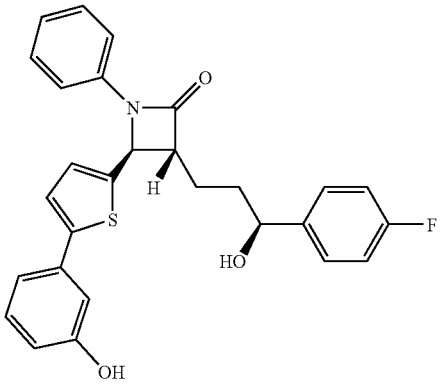

(3R,4S)-4-(5-Bromo-2-thienyl)-3-[(3S)-3-(4-fluorophenyl)-3-hydroxypropyl]-1-phenylazetidin-2-one (90.2 mg, 0.196 mmol) was coupled with 3-hydroxyphenyl boronic acid (32.2 mg, 0.233 mmol) under standard Suzuki conditions illustrated by Example 42. Purification by chromatography (12 g silica gel, 15% to 100% ethyl acetate-hexane) afforded (3R,4S)-3-[(3S)-3-(4-fluorophenyl)-3-hydroxypropyl]-4-[5-(3-hydroxyphenyl)-2-thienyl]-1-phenylazetidin-2-one (77.6 mg, 84% yield) as a clear foam; $R_f$ 0.36 (1:1 ethyl acetate-hexane); $^1$H NMR (300 MHz, CD$_3$OD) δ 7.31-6.93 (m, 14H), 6.70 (ddd, J=8.0, 2.3, 1.0 Hz, 1H), 4.89-4.88 (m, 1H), 4.64-4.59 (m, 1H), 3.77 (br s, 2H), 3.25-3.21 (m, 1H), 1.97-1.83 (m, 4H) ppm; MS [M−OH]$^+$ 456.0.

EXAMPLE 51

(3R,4S)-3-[(3S)-3-(4-Fluorophenyl)-3-hydroxypropyl]-4-[5-(4-hydroxyphenyl)-2-thienyl]-1-phenylazetidin-2-one

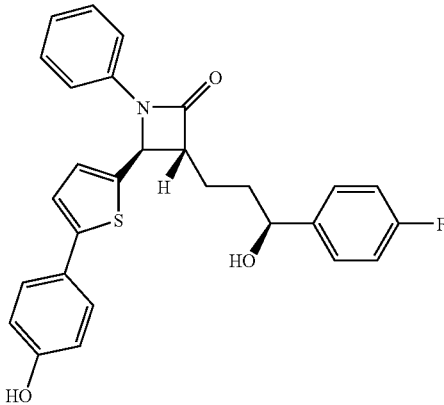

(3R,4S)-4-(5-Bromo-2-thienyl)-3-[(3S)-3-(4-fluorophenyl)-3-hydroxypropyl]-1-phenylazetidin-2-one (69.8 mg, 0.152 mmol) was coupled with 4-hydroxyphenyl boronic acid (25.2 mg, 0.183 mmol) under standard Suzuki conditions illustrated by Example 42. Purification by chromatography (12 g silica gel, 15% to 100% ethyl acetate-hexane) afforded (3R,4S)-3-[(3S)-3-(4-fluorophenyl)-3-hydroxypropyl]-4-[5-(4-hydroxyphenyl)-2-thienyl]-1-phenylazetidin-2-one (40.7 mg, 56% yield) as a clear foam; $R_f$ 0.39 (1:1 ethyl acetate-hexane); $^1$H NMR (300 MHz, CDCl$_3$) δ 7.64-7.60 (m, 4H), 7.56-7.48 (m, 5H), 7.33-7.27 (m, 2H), 7.25-7.20 (m, 2H), 7.07 (d, J=8.6 Hz, 2H), 6.81 (br s, 1H), 5.14 (d, J=2.3 Hz, 1H), 5.00-4.95 (m, 1H), 3.57-3.50 (m, 1H), 2.29-2.11 (m, 4H) ppm; MS [M+H]$^+$ 474.0.

EXAMPLE 53

Sodium 4'-{(2S,3R)-3-[(3S/R)-3-(4-fluorophenyl)-3-hydroxypropyl]-4-oxo-1-phenylazetidin-2-yl}-3'-hydroxybiphenyl-3-sulfonate

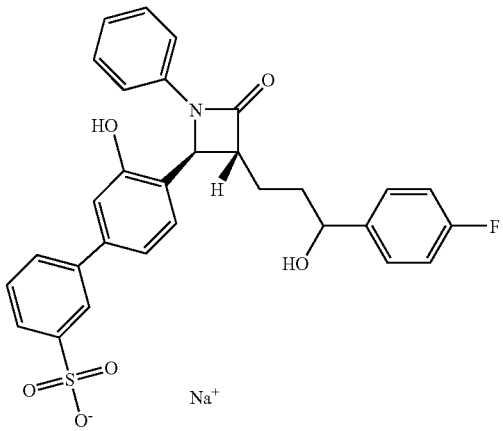

5-Bromo-2-{(2S,3R)-3-[(3S)-3-{[tert-butyl(dimethyl)silyl]oxy}-3-(4-fluorophenyl)propyl]-4-oxo-1-phenylazetidin-2-yl}phenyl acetate (140.0 mg, 0.223 mmol) was dissolved in acetonitrile (8.0 mL) and 48% hydrofluoric acid (0.8 mL) into a polypropylene Falcon® tube. The reaction was stirred for 4 h at room temperature and then poured into 0.5 M potassium phosphate (50 mL), extracted with 1:1 ethyl acetate-hexane (50 mL), washed with saturated sodium bicarbonate solution (50 mL) and brine (50 mL), dried over sodium sulfate, filtered, concentrated and purified by chromatography (12 g silica gel, 15% to 90% ethyl acetate-hexane) to afford 5-bromo-2-{(2S,3R)-3-[(3S)-3-(4-fluorophenyl)-3-hydroxypropyl]-4-oxo-1-phenylazetidin-2-yl}phenyl acetate (114.5 mg, 100% yield) as a clear foam; $R_f$ 0.11 (1:4 ethyl acetate-hexane).

5-Bromo-2-{(2S,3R)-3-[(3S)-3-(4-fluorophenyl)-3-hydroxypropyl]-4-oxo-1-phenylazetidin-2-yl}phenyl acetate (114.5 mg, 0.223 mmol) and 3-thioanisoleboronic acid (48.3 mg, 0.287 mol) were dissolved in toluene (3.0 mL) and ethanol (1.5 mL). A solution of 2.0 M aqueous sodium carbonate (0.215 mL, 0.43 mmol) and solid tetrakis(triphenylphosphine)palladium(0) (14.4 mg, 0.0125 mmol) were added and the vessel was vacuum/nitrogen purged (3×). The reaction was stirred vigorously for 4 h at 60° C. under a nitrogen atmosphere and then poured into 0.2 N hydrochloric acid (50 mL), extracted with 1:1 ethyl acetate-hexane (75 mL), washed with brine (50 mL), dried over sodium sulfate, filtered and concentrated to afford a mixture of products which was used directly in the next step; $R_f$ 0.79 (2:1 ethyl acetate-hexane) for (3R,4S)-3-[(3S)-3-(4-fluorophenyl)-3- hydroxypropyl]-4-[3-hydroxy-3'-(methylthio)biphenyl-4-yl]-1-phenylazetidin-2-one and 0.84 (2:1 ethyl acetate-hexane) for 4-{(2S,3R)-3-[(3S)-3-(4-fluorophenyl)-3-hydroxypropyl]-4-oxo-1-phenylazetidin-2-yl}-3'-(methylthio)biphenyl-3-yl acetate.

A 1:1 mixture of (3R,4S)-3-[(3S)-3-(4-fluorophenyl)-3-hydroxypropyl]-4-[3-hydroxy-3'-(methylthio)biphenyl-4-yl]-1-phenylazetidin-2-one and 4-{(2S,3R)-3-[(3S)-3-(4-fluorophenyl)-3-hydroxypropyl]-4-oxo-1-phenylazetidin-2-yl}-3'-(methylthio)biphenyl-3-yl acetate (0.223 mmol) was dissolved in dichloromethane (10 mL) and cooled to 0° C. 3-Chloroperoxybenzoic acid (64.3 mg, 0.373 mmol) was added in portions while monitoring by LCMS to make the arylsulfoxide. Once addition was complete the reaction was poured into quarter saturated sodium bicarbonate solution (50 mL), extracted with 1:1 ethyl acetate-hexane (75 mL), washed brine (50 mL), dried over sodium sulfate, filtered and concentrated. The residue was dissolved in dichloromethane (10 mL) and the Pummerer rearrangement was effected by the addition of trifluoroacetic anhydride (100 μL, 148.7 mg, 0.708 mmol). The reaction was stirred at room temperature for 4 h and then 3-chloroperoxybenzoic acid (121.7 mg, 0.705 mmol) was added to convert to the sulfone. The mixture was stirred for 15 min at room temperature, concentrated and dissolved in 3:3:1 methanol-triethylamine-water (7 mL) to hydrolyze the acetate and trifluoroacetate groups. The reaction was stirred for 2 h at room temperature, concentrated and dissolved in dichloromethane (10 mL). 3-Chloroperoxybenzoic acid (49.2 mg, 0.285 mmol) was added to oxidize the compound to the sulfonic acid. The reaction was stirred for 10 min at room temperature, diluted with 1:1 ethyl acetate-hexane (50 mL) and extracted with 1% saturated sodium bicarbonate solution (3×50 mL). The aqueous layer was acidified with 1.0 N hydrochloric acid (~10 mL), extracted with ethyl acetate (2×75 mL), diluted with triethylamine (1.0 mL), concentrated, purified by reverse-phase HPLC (Polaris C18-A 10 μ 250×21.2 mm column, 25% to 100% acetonitrile-0.1% trifluoroacetic acid in water) and passed through Dowex® sodium ion exchange resin to afford sodium 4'-{(2S,3R)-3-[(3S/R)-3-(4-fluorophenyl)-3-hydroxypropyl]-4-oxo-1-phenylazetidin-2-yl}-3'-hydroxybiphenyl-3-sulfonate (45.3 mg, 36% yield) as an off-white solid; ¹H NMR (300 MHz, CD₃OD) δ 8.04-6.98 (m, 16H), 5.17 (d, J=2.2 Hz, 0.66H), 5.14 (d, J=2.2 Hz, 0.33H), 4.70-4.60 (m, 1H), 3.21-3.14 (m, 1H), 2.09-1.89 (m, 4H) ppm; MS [M−Na]⁻ 546.0.

EXAMPLE 54

(3R,4S)-3-[(3S)-3-{[tert-Butyl(dimethyl)silyl]oxy}-3-(4-fluorophenyl)propyl]-4-(3'-hydroxybiphenyl-4-yl)-1-phenylazetidin-2-one

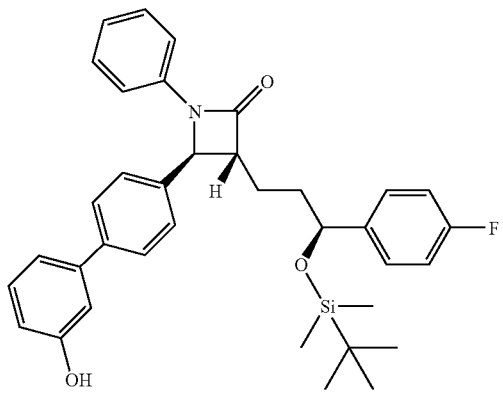

(3R,4S)-4-(3'-{[tert-Butyl(dimethyl)silyl]oxy}biphenyl-4-yl)-3-[(3S)-3-{[tert-butyl(dimethyl)silyl]oxy}-3-(4-fluorophenyl)propyl]-1-phenylazetidin-2-one (0.60 g, 0.86 mmol) was stirred at room temperature in dry methanol (20 mL) under a nitrogen atmosphere. Potassium fluoride (0.10 g, 1.72 mmol) was added and the reaction mixture was stirred 1.5 h at room temperature. The solution was poured into ethyl acetate and washed successively with water (2×), 10% aqueous sodium bicarbonate, water and brine. The organic solution was dried over sodium sulfate, filtered, concentrated and purified by chromatography over silica gel using ethyl acetate-hexane (gradient: 5% ethyl acetate to 50%) to afford (3R,4S)-3-[(3S)-3-{[tert-butyl(dimethyl)silyl]oxy}-3-(4-fluorophenyl)propyl]-4-(3'-hydroxybiphenyl-4-yl)-1-phenylazetidin-2-one (0.46 g, 92%) as a white foam; ¹H NMR (300 MHz, CDCl₃) δ 7.57 (d, J=8.2, Hz, 2H,) 7.37 (d, J=8.2 Hz, 2H), 6.9-7.4 (m, 12H), 6.8 (m, 1H), 4.9 (br s, 1H), 4.67 (t, J=6.0 Hz, 1H), 4.63 (d, J=2.5 Hz, 1H), 3.0-3.1 (m, 1H), 1.8-2.0 (m, 4H), 0.87 (s, 9H), 0.02 (s, 3H), −0.16 (s, 3H).

EXAMPLE 55

4'-{(2S,3R)-3-[(3S)-3-{[tert-Butyl(dimethyl)silyl]oxy}-3-(4-fluorophenyl)propyl]-4-oxo-1-phenylazetidin-2-yl}biphenyl-3-yl trifluoromethanesulfonate

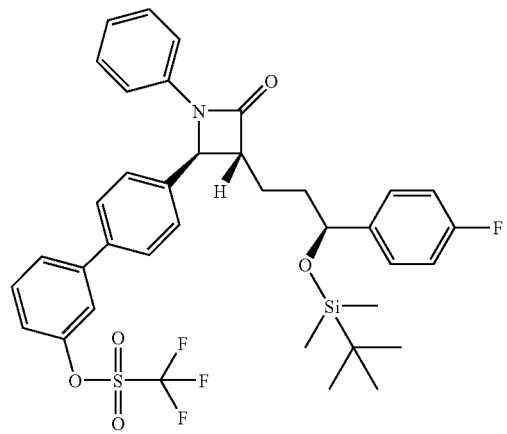

(3R,4S)-3-[(3S)-3-{[tert-Butyl(dimethyl)silyl]oxy}-3-(4-fluorophenyl)propyl]-4-(3'-hydroxybiphenyl-4-yl)-1-phenylazetidin-2-one (0.46 g, 0.79 mmol) was stirred at room temperature in dry dichloromethane (15 mL) under a nitrogen atmosphere. N-Phenyltrifluoromethanesulfonimide (0.39 g, 1.09 mmol), triethylamine (0.23 mL, 1.65 mmol) and 4-(dimethylamino)pyridine (0.02 g, 0.2 mmol) were added in succession and the reaction mixture was stirred 2 h at room temperature. The solution was poured into 0.5N aqueous hydrochloric acid (20 mL) and extracted with ethyl acetate. The organic phase was washed successively with water, 10% aqueous sodium bicarbonate, water and brine. The organic solution was dried over sodium sulfate, filtered and the solvent was removed in vacuo to afford 4'-{(2S,3R)-3-[(3S)-3-{[tert-butyl(dimethyl)silyl]oxy}-3-(4-fluorophenyl)propyl]-4-oxo-1-phenylazetidin-2-yl}biphenyl-3-yl trifluoromethanesulfonate as a white foam (0.56 g, 100%) by chromatography over silica gel using ethyl acetate-hexane (gradient: 5% ethyl acetate to 50%) ¹H NMR (300 MHz, CDCl₃) δ 6.9-7.3 (m, 17H), 4.68 (t, J=5.7 Hz, 1H), 4.65 (d, J=2.5 Hz, 1H), 3.0-3.1 (m, 1H), 1.8-2.0 (m, 6H), 0.88 (s, 9H), 0.02 (s, 3H), −0.16 (s, 3H).

EXAMPLE 56

(4'-{(2S,3R)-3-[(3S)-3-(4-Fluorophenyl)-3-hydroxypropyl]-4-oxo-1-phenylazetidin-2-yl}biphenyl-3-yl)phosphonic acid

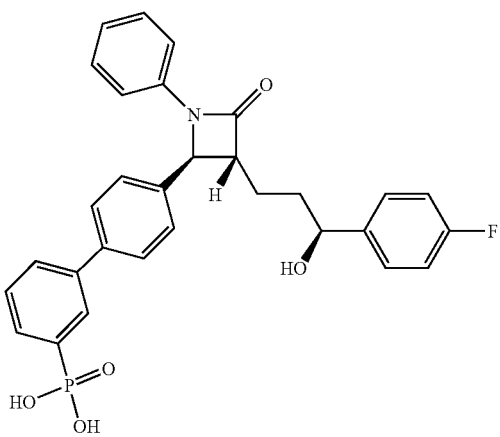

This reaction was performed using a PersonalChemistry™ microwave instrument set at normal absorbance, fixed hold time and 30 sec pre-stirring. A 10-mL reaction vial was charged with 4'-{(2S,3R)-3-[(3S)-3-{[tert-butyl(dimethyl)silyl]oxy}-3-(4-fluorophenyl)propyl]-4-oxo-1-phenylazetidin-2-yl}biphenyl-3-yl trifluoromethanesulfonate (0.27 g, 0.38 mmol), dimethyl phosphite (0.070 mL, 0.76 mmol) and triethylamine (0.15 mL, 1.08 mmol) in toluene (4 mL). Nitrogen was bubbled through the stirred solution for 5 min, tetrakis(triphenylphosphine)palladium(0) (0.1 g) was added, and the solution was covered with a blanket of nitrogen and sealed. The reaction mixture was heated for 11 min at 160° C., then cooled to room temperature and diluted with ethyl acetate. The yellow solution was washed successively with 0.5 M hydrochloric acid (20 mL) water (3×) and brine. The organic solution was dried over sodium sulfate, filtered and the solvent was removed by rotary evaporation under reduced pressure. Pure dimethyl (4'-{(2S,3R)-3-[(3S)-3-{[tert-butyl(dimethyl)silyl]oxy}-3-(4-fluorophenyl)propyl]-4-oxo-1-phenylazetidin-2-yl}biphenyl-3-yl)phosphonate was obtained as a white foam (0.26 g, 65%) by chromatography over silica gel using ethyl acetate-hexane (gradient: 5% ethyl acetate to 100%). $^1$H NMR (300 MHz, CDCl$_3$) δ 8.00 (dt, J=14.2, 1.5 Hz, 1H), 7.60 (d, J=8.5 Hz, 2H), 7.40(d, J=8.5 Hz, 2H), 6.9-7.8 (m, 12H), 4.68 (t, J=5.7 Hz, 1H), 4.64 (d, J=2.4 Hz, 1H), 3.81 (d, J=0.9 Hz, 1H), 3.77 (d, J=0.9 Hz, 1H), 3.0-3.1 (m, 1H), 1.8-2.2 (m, 4H), 0.88 (s, 9H), 0.02 (s, 3H), −0.16 (s, 3H) ppm A solution of dimethyl (4'-{(2S,3R)-3-[(3S)-3-{[tert-butyl(dimethyl)silyl]oxy}-3-(4-fluorophenyl)propyl]-4-oxo-1-phenylazetidin-2-yl}biphenyl-3-yl)phosphonate (0.32 g, 0.47 mmol) in dry dichloromethane (15 mL) under nitrogen was cooled in an ice bath and bromotrimethylsilane (0.30 mL, 2.27 mmol) was dripped in over 5 min. The reaction mixture was stirred at room temperature for 3 h, then poured into ice water (20 m]L) and extracted with ethyl acetate. The organic solution was washed successively with water (2×) and brine. The organic solution was dried over sodium sulfate, filtered and the solvent was removed by rotary evaporation under reduced pressure. The residue was purified by reverse-phase HPLC (Polaris C18-A 10 μ 250×21.2 mm column, 20% to 70% acetonitrile-0.1% trifluoroacetic acid in water) to afford (4'-{(2S,3R)-3-[(3S)-3-(4-fluorophenyl)-3-hydroxypropyl]-4-oxo-1-phenylazetidin-2-yl}biphenyl-3-yl)phosphonic acid (0.25 g, 99%) as a white powder; $^1$H NMR (300 MHz, CD$_3$OD) δ 8.04 (br d, J=14.2 Hz, 1H) 7.68 (d, J=8.5 Hz, 2H), 7.50(d, J=8.5 Hz, 2H), 7.0-7.8 (m, 12H), 4.93 (d, J=2.2 Hz, 1H), 4.63 (t, J=5.2 Hz, 1H), 3.1-3.2 (m, 1H), 1.8-2.1 (m, 4H) ppm; MS [M−H]$^-$ 531, [2M-H]$^-$ 1061.

EXAMPLE 57

(3R,4S)-3-[(3S)-3-(4-Fluorophenyl)-3-hydroxypropyl]-4-(3'-hydroxybiphenyl-4-yl)-1-phenylazetidin-2-one

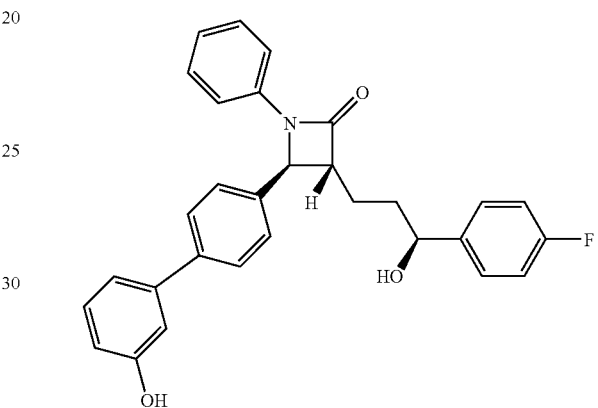

(3R,4S)-3-[(3S)-3-(4-Fluorophenyl)-3-hydroxypropyl]-4-(3'-hydroxybiphenyl-4-yl)-1-phenylazetidin-2-one was synthesized in a manner similar to that described in Example 42. (3R,4S)-4-(3'-{[tert-Butyl(dimethyl)silyl]oxy}biphenyl-4-yl)-3-[(3S)-3-{[tert-butyl(dimethyl)silyl]oxy}-3-(4-fluorophenyl)propyl]-1-phenylazetidin-2-one (0.60 g, 0.86 mmol) was stirred at room temperature in acetonitrile (18 mL) in a 40 ml polypropylene vial fitted with a screw cap. Hydrogen fluoride (48% aqueous, 2.0 mL, 48 mmol) was dripped in and stirring was continued at room temperature overnight. The reaction mixture was poured into an aqueous solution of 1 N sodium hydroxide (45 mL) buffered with 1 M sodium phosphate (45 mL, pH 7.4), then the pH of the solution was brought to pH 8 with the addition of aqueous 10% sodium bicarbonate solution. The mixture was extracted with ethyl acetate and the organic solution was washed successively with 10% sodium bicarbonate solution (2×), water (2×) and brine. The organic solution was dried over sodium sulfate, filtered and the solvent was removed by rotary evaporation under reduced pressure. Pure (3R,4S)-3-[(3S)-3-(4-fluorophenyl)-3-hydroxypropyl]-4-(3'-hydroxybiphenyl-4-yl)-1-phenylazetidin-2-one was obtained as a white foam (0.35 g, 87%) by chromatography over silica gel using ethyl acetate-hexane (gradient: 10% ethyl acetate to 60%) $^1$H NMR (300 MHz, CDCl$_3$) δ 7.56 (d, J=8.2, Hz, 2H), 7.39 (d, J=8.2 Hz, 2H), 7.0-7.3 (m, 12H), 6.80-6.86 (m, 1H), 5.00 (br s, 1H), 4.74 (t, J=6.2 Hz, 1H), 4.69 (d, J=2.2 Hz, 1H), 3.1-3.2 (m, 1H), 2.20 (br s, 1H), 1.8-2.1 (m, 4H) ppm; MS [M+HCO$_2$$^-$]$^-$ 512.

EXAMPLE 58

4'-{(2S,3R)-3-[(3S)-3-(4-Fluorophenyl)-3-hydroxypropyl]-4-oxo-1-phenylazetidin-2-yl}biphenyl-3-yl trifluoromethanesulfonate

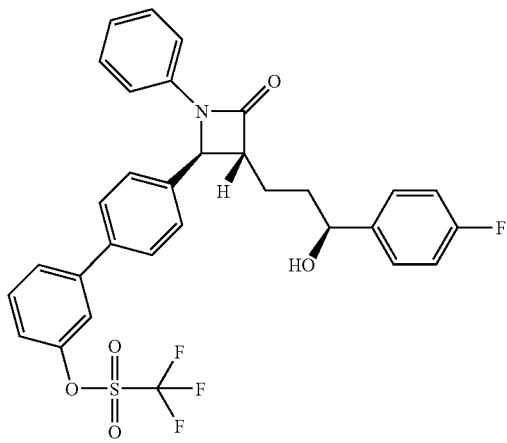

(3R,4S)-3-[(3S)-3-(4-Fluorophenyl)-3-hydroxypropyl]-4-(3'-hydroxybiphenyl-4-yl)-1-phenylazetidin-2-one (0.353 g, 0.77 mmol) was stirred at room temperature in dry dichloromethane (15 mL) under a nitrogen atmosphere.

Phenyltrifluoromethanesulfonimide (0.38 g, 1.69 mmol), triethylamine (0.23 mL, 1.65 mmol) and 4-dimethylaminopyridine (0.02 g, 0.2 mmol) were added in succession and the reaction mixture was stirred 1 h at room temperature. The solution was poured into 0.5 N hydrochloric acid (20 mL) and extracted with ethyl acetate. The organic phase was washed successively with water, 10% aqueous sodium bicarbonate, water and brine. The organic solution was dried over sodium sulfate, filtered and the solvent was removed by rotary evaporation under reduced pressure. Pure 4'-{(2S,3R)-3-[(3S)-3-(4-fluorophenyl)-3-hydroxypropyl]-4-oxo-1-phenylazetidin-2-yl}biphenyl-3-yl trifluoromethanesulfonate was obtained as a white foam (0.35 g, 76%) by chromatography over silica gel using ethyl acetate-hexane (gradient: 5% ethyl acetate to 50%); $^1$H NMR (300 MHz, CDCl$_3$) δ 7.0-7.6 (m, 17H), 4.74 (t, J=6.4 Hz, 1H), 4.72 (d, J=2.2 Hz, 1H), 3.1-3.2 (m, 1H), 2.16 (br s, 1H), 1.9-2.1 (m, 4H) ppm; MS [M+HCO$_2^-$]$^-$ 644.

EXAMPLE 59

(4'-{(2S,3R)-3-[(3S)-3-(4-Fluorophenyl)-3-hydroxypropyl]-4-oxo-1-phenylazetidin-2-yl}biphenyl-3-yl)boronic acid

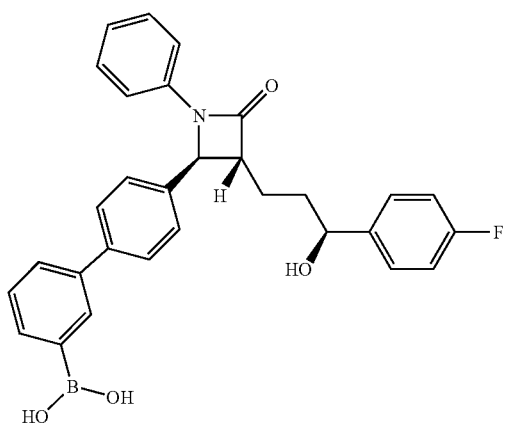

4'-{(2S,3R)-3-[(3S)-3-(4-Fluorophenyl)-3-hydroxypropyl]-4-oxo-1-phenylazetidin-2-yl}biphenyl-3-yl trifluoromethanesulfonate (0.15 g, 0.25 mmol), bis(pinacolato)diboron (0.70 g, 0.27 mmol), potassium acetate (0.80 g, 0.81 mmol) and dichloro[1,1'-bis(diphenylphosphino) ferrocene] palladium(II) (0.020 g, 0.03 mmol) were combined in dimethylsulfoxide (7 mL) in a 40-mL screw-cap vial at room temperature. The mixture was covered with a nitrogen atmosphere, the vial was sealed and the reaction was heated overnight at 80° C. The reaction mixture was cooled to room temperature, poured into water and extracted with ethyl acetate. The organic phase was washed successively with water (2×) and brine, dried over sodium sulfate, filtered and the solvent was removed by rotary evaporation under reduced pressure. Pure (3R,4S)-3-[(3S)-3-(4-fluorophenyl)-3-hydroxypropyl]-1-phenyl-4-[3'-(4,4,5,5-tetramethyl-1,3,2-dioxaborolan-2-yl)biphenyl-4-yl]azetidin-2-one was obtained as a white foam (0.097 g, 67%) by chromatography over silica gel using ethyl acetate-hexane (gradient: 5% ethyl acetate to 70%) $^1$H NMR (300 MHz, CDCl$_3$) δ 8.01(br s, 1H), 7.75-7.85 (m, 1H), 7.0-7.7 (m, 15H), 4.74 (t, J=6.2 Hz, 1H), 4.69 (d, J=2.2 Hz, 1H), 3.0-3.2 (m, 1H), 1.50 (br s, 1H), 1.8-2.1 (m, 4H), 1.35 (s, 6H), 1.24 (s, 6H) ppm; MS [M+HCO$_2^-$]$^-$ 577

(3R,4S)-3-[(3S)-3-(4-Fluorophenyl)-3-hydroxypropyl]-1-phenyl-4-[3'-(4,4,5,5-tetramethyl-1,3,2-dioxaborolan-2-yl)biphenyl-4-yl]azetidin-2-one (0.020 g, 0.034 mmol) was dissolved in ethanol (3 mL) and water (1 mL) at room temperature. Solid sodium carbonate (0.10 g, 1.2 mmol) was added and the mixture was rapidly stirred 2 h at room temperature. The solution was poured into 0.5 N hydrochloric acid (4 mL) and extracted with ethyl acetate. The organic phase was washed successively with water (2×) and brine, then dried over sodium sulfate, filtered and the solvent was removed by rotary evaporation under reduced pressure. The residue was purified by reverse-phase HPLC (Polaris C18-A 10 μ 250×21.2 mm column, 40% to 75% acetonitrile-0.1% trifluoroacetic acid in water) to afford (4'-{(2S,3R)-3-[(3S)-3-(4-fluorophenyl)-3-hydroxypropyl]-4-oxo-1-phenylazetidin-2-yl}biphenyl-3-yl)boronic acid as a white powder (0.012 g, 70%); $^1$H NMR (300 MHz, CD$_3$OD) δ 7.83 (br s, 1H), 7.0-7.7 (m, 16H), 4.92 (d, J=2.7 Hz, 1H), 4.63 (t, J=6.2 Hz, 1H), 3.1-3.2 (m, 1H), 1.8-2.1 (m, 4H) ppm; MS [M+HCO$^{2-}$]$^-$ 540.

EXAMPLE 60

Dimethyl [3-(4,4,5,5-tetramethyl-1,3,2-dioxaborolan-2-yl)phenyl]phosphonate

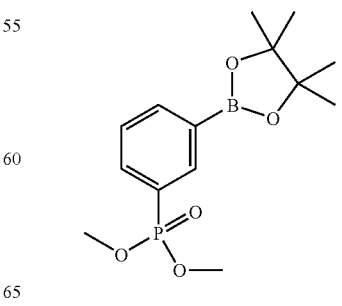

3-Chlorophenyl (0.50 g, 3.89 mmol) was stirred at room temperature in dry dichloromethane (20 mL) under a nitrogen atmosphere.

Phenyltrifluoromethanesulfonimide (1.80 g, 5.0 mmol), triethylamine (0.90 mL, 6.4 mmol) and 4-dimethylaminopyridine (0.10 g, 0.8 mmol) were added in succession and the reaction mixture was stirred 2 h at room temperature. The solution was poured into 0.5 N hydrochloric acid (20 mL) and extracted with ethyl acetate. The organic phase was washed successively with water, 10% aqueous sodium bicarbonate and brine. The organic solution was dried over sodium sulfate, filtered and the solvent was removed by rotary evaporation under reduced pressure. Pure 3-chlorophenyl trifluoromethanesulfonate was obtained as a colorless oil (0.92 g, 91%) by chromatography over silica gel using ethyl acetate-hexane (gradient: 5% to 50% ethyl acetate-hexane); $^1$H NMR (300 MHz, CDCl$_3$) δ 7.16-7.50 (m) ppm This reaction was performed using a PersonalChemistry™ microwave instrument set at normal absorbance, fixed hold time and 30 sec pre-stirring. A 10-mL reaction vial was charged with 3-chlorophenyl trifluoromethanesulfonate (0.60 g, 2.30 mmol), dimethyl phosphite (0.42 mL, 4.58 mmol) and triethylamine (0.64 mL, 4.59 mmol) in toluene (4 mL). Nitrogen was bubbled through the stirred solution for 5 min, the tetrakis(triphenylphosphine)palladium(0) (0.1 g) was added, the solution was covered with a blanket of nitrogen and sealed. The reaction mixture was heated 11 min at 160° C., then cooled to room temperature and diluted with ethyl acetate. The yellow solution washed successively with water (3×) and brine. The organic solution was dried over sodium sulfate, filtered and the solvent was removed by rotary evaporation under reduced pressure. Pure dimethyl (3-chlorophenyl)phosphonate was obtained as a colorless oil (0.27 g, 57%) by chromatography over silica gel using ethyl acetate-hexane (gradient: 5% ethyl acetate to 100%). $^1$H NMR (300 MHz, CDCl$_3$) δ 7.77 (br d, J=13.7 Hz, 1H), 7.68 (ddt, J=13.0, 7.5, 1.4 Hz, 1H), 7.53 (dquint., J=8.0, 1.1 Hz, 1H), 7.38-7.45 (m, 1H), 3.79 (s, 3H), 3.75 (s, 3H) ppm; MS [M+H]$^+$ 221, [2M+H]$^+$ 441

Bis(dibenzylideneacetone)palladium(0) (0.10 g, 0.17 mmol) and tricyclohexylphosphine (0.12 g, 0.43 mmol) were stirred 30 min in dry dioxane (1.0 mL) under an atmosphere of nitrogen at room temperature. Dimethyl (3-chlorophenyl) phosphonate (0.50 g, 2.26 mmol), bis(pinacolato)diboron (0.70 g, 0.27 mmol) and potassium acetate (0.30 g, 0.30 mmol) were mixed in dry dioxane (3.0 mL) at room temperature under a nitrogen atmosphere in a separate flask. A portion of the palladium catalyst solution (0.20 mL) was syringed into the flask containing the chlorophosphonate and this mixture was heated at 80° C. Additional 0.2 mL portions of the catalyst solution were syringed into the reaction mixture after 4 h and 8 h of heating at 80° C., then heating was continued overnight at 80° C. The reaction mixture was filtered through Celite® and the solvent was removed by rotary evaporation under reduced pressure. Chromatography over silica gel using ethyl acetate-hexane (gradient: 0% ethyl acetate to 80%) dimethyl [3-(4,4,5,5-tetramethyl-1,3,2-dioxaborolan-2-yl)phenyl]phosphonate as a colorless oil (0.41 g). $^1$H NMR showed a 60:40 mixture of product plus recovered starting material. This mixture was used as is in the next reaction without further purification. $^1$H NMR (300 MHz, CDCl$_3$) δ 8.22 (d, J=13.2 Hz, 1H), 7.95-8.00 (m, 1H), 7.88 (ddt, J=13.0, 7.5, 1.4 Hz, 1H), 7.43-7.50 (m, 1H), 3.76 (s, 3H), 3.73 (s, 3H) ppm; MS [M+H]$^+$ 312, [2M+H]$^+$ 625.

EXAMPLE 61

(4'-{(2S,3R)-3-[(3S)-3-(4-Fluorophenyl)-3-hydroxypropyl]-4-oxo-1-phenylazetidin-2-yl}-3'-hydroxybiphenyl-3-yl)phosphonic Acid

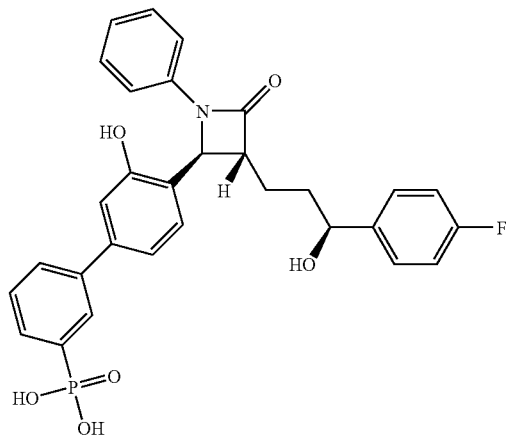

(3R,4S)-4-(4-Bromo-2-{[tert-butyl(dimethyl)silyl] oxy}phenyl)-3-[(3S)-3-{[tert-butyl(dimethyl)silyl]oxy}-3-(4-fluorophenyl)propyl]-1-phenylazetidin-2-one (0.080 g, 0.11 mmol), crude dimethyl [3-(4,4,5,5-tetramethyl-1,3,2-dioxaborolan-2-yl)phenyl]phosphonate (0.054 g total, 0.030 g calculated, 0.096 mmol) and aqueous 2 M potassium carbonate (0.12 mL, 0.24 mmol) were mixed in ethanol (1.0 mL) and toluene (3.0 mL). The solution was deoxygenated by bubbling nitrogen through the mixture for 5 min while stirring. Tetrakis(triphenylphosphine)palladium(0) (0.05 g) was added and the reaction was heated for 3 h at 70° C. under an atmosphere of nitrogen. The reaction was cooled to room temperature, diluted with ethyl acetate, washed with water and brine, dried over sodium sulfate and concentrated by rotary evaporation under reduced pressure. The product was purified by chromatography over silica gel using ethyl acetate-hexane (gradient: 10% ethyl acetate to 80%) to afford dimethyl (3'-{[tert-butyl(dimethyl)silyl]oxy}-4'-{(2S,3R)-3-[(3S)-3-{[tert-butyl(dimethyl)silyl]oxy}-3-(4-fluorophenyl)propyl]-4-oxo-1-phenylazetidin-2-yl}biphenyl-3-yl)phosphonate as a colorless syrup (0.065 g, 84%). $^1$H NMR (300 MHz, CDCl$_3$) δ 6.9-8.0 (m, 16H), 5.09 (d, J=2.2 Hz, 1H), 4.64 (d, J=6.1 Hz, 1H), 3.79 (d, J=2.4 Hz, 3H), 3.76 (d, J=2.4 Hz, 3H), 3.05-3.15 (m, 1H), 1.8-2.0 (m, 4H), 1.06 (s, 9H), 0.85 (s, 9H), 0.36 (s, 3H), 0.33 (s, 3H), 0.00 (s, 3H), −0.20 (s, 3H) ppm Dimethyl(3'-{[tert-butyl(dimethyl)silyl]oxy}-4'-{(2S,3R)-3-[(3S)-3-{[tert-butyl(dimethyl)silyl]oxy}-3-(4-fluorophenyl)propyl]-4-oxo-1-phenylazetidin-2-yl}biphenyl-3-yl)phosphonate (0.047 g, 0.058 mmol) was stirred at room temperature in dry methanol (2 mL) under a nitrogen atmosphere. Potassium fluoride (0.02 g, 0.34 mmol) was added and the reaction mixture was stirred for 30 min at room temperature. The solution was poured into ethyl acetate and washed successively with water (2×), and brine. The organic solution was dried over sodium sulfate, filtered and the solvent was removed by rotary evaporation under reduced pressure. Dimethyl(4'-{(2S,3R)-3-[(3S)-3-{[tert-butyl(dimethyl)silyl]oxy}-3-(4-fluorophenyl)propyl]-4-oxo-1-phenylazetidin-2-yl}-3'-hydroxybiphenyl-3-yl)phosphonate was obtained as a colorless glass (0.041 g, 100%) was used directly in the next reaction without further purification; MS [M–H]⁺ 688

A solution of dimethyl(4'-{(2S,3R)-3-[(3S)-3-{[tert-butyl (dimethyl)silyl]oxy}-3-(4-fluorophenyl)propyl]-4-oxo-1-phenylazetidin-2-yl}-3'-hydroxybiphenyl-3-yl)phosphonate (0.041 g, 0.059 mmol) in dry dichloromethane (5 mL) under nitrogen was cooled in ice and bromotrimethylsilane (0.030 mL, 0.30 mmol) was dripped in over 5 min. The reaction mixture was stirred at room temperature for 3 h, then methanol (1 mL) was added and the reaction was partitioned between water and ethyl acetate. The organic solution was washed successively with water (2×) and brine. The organic solution was dried over sodium sulfate, filtered and the solvent was removed by rotary evaporation under reduced pressure. The residue was purified by reverse-phase HPLC (Polaris C18-A 10 µ 250×21.2 mm column, 30% to 59% acetonitrile-0.1% trifluoroacetic acid in water) to afford (4'-{(2S,3R)-3-[(3S)-3-(4-fluorophenyl)-3-hydroxypropyl]-4-oxo-1-phenylazetidin-2-yl}-3'-hydroxybiphenyl-3-yl) phosphonic acid as a white powder (0.014 g, 44%); ¹H NMR (300 MHz, CD₃OD) δ 8.0 (d, J=13.6 Hz, 1H), 6.9-7.8 (m, 15H), 5.17 (d, J=2.1 Hz, 1H), 4.63 (d, J=5.2 Hz, 1H), 3.15-3.25 (m, 1H), 1.8-2.1 (m, 4H) ppm; MS [M–H]⁺ 546, [2M–H]⁺ 1093.

EXAMPLE 62

(1S)-2,3,4,6-Tetra-O-acetyl-1,5-anhydro-1-(3-bromophenyl)-D-glucitol

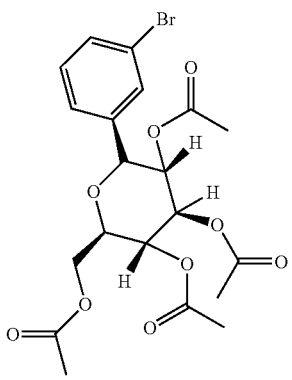

D-Glucopyranose (1.0 g, 5.55 mmol) was dissolved in 5 mL of acetic anhydride and 7 mL of pyridine at 0° C. To this mixture was added 4-dimethylaminopyridine (200 mg, 1.63 mmol), and the reaction was stirred while warming to room temperature. TLC (40% ethyl acetate-hexane) after 18 h showed complete consumption of the starting material and formation of a higher running spot. The reaction was poured into 50 mL of water and extracted into dichloromethane (3×50 mL). The organic layers were combine, washed with 1 N hydrochloric acid (3×20 mL), dried over sodium sulfate, filtered, concentrated and purified by column chromatography (50 g silica gel, 40% ethyl acetate-hexane) to afford 1,2,3,4,6-penta-O-acetyl-α-D-glucopyranose (2.10 g, 5.37 mmol).

1,2,3,4,6-penta-O-acetyl-α-D-glucopyranose (1.0 g, 2.60 mmol) was dissolved in 20 mL of dichloromethane and 1.90 mL of hydrobromic acid (33% in acetic acid) at 0° C., and the reaction was stirred while warming to room temperature. TLC (40% ethyl acetate-hexane) after 18 h showed complete consumption of the starting material and formation of a higher running spot. The reaction was slowly diluted with saturated sodium bicarbonate (25 mL), extracted into dichloromethane (2×100 mL), dried over sodium sulfate, filtered and concentrated to afford 2,3,4,6-tetra-O-acetyl-α-D-glucopyranosyl bromide which was used without purification.

Magnesium (0) (400 mg) was suspended in 17 mL of anhydrous diethyl ether, and to the suspension was added 100 µL of 1,2-dibromoethane. 1,3-dibromobenzene (3.8 g, 16.08 mmol) was added at a rate to keep a moderate reflux. After Grignard formation was complete (magnesium consumed and the reaction cooled), 2,3,4,6-tetra-O-acetyl-α-D-glucopyranosyl bromide (0.34 g, 0.80 mmol in 8 mL of anhydrous diethyl ether) was added drop-wise. The reaction was refluxed for 5 h, cooled to room temperature and poured into a separatory funnel with 20 mL of water. The flask was rinsed with 50 mL of diethyl ether and 3 mL of acetic acid (to dissolve the magnesium salts) and added to the seperatory funnel. The layers were separated and the aqueous layer was collected and concentrated in vacuo. The white pasty solid was dissolved in 15 mL of pyridine and 10 mL of acetic anhydride. After 20 h at room temperate the reaction was poured into 150 mL of water and extracted into dichloromethane (3×150 mL). The organic layers were combine, washed with 1 N hydrochloric acid (3×50 mL), dried over sodium sulfate, filtered, concentrated and purified by column chromatography (12 g silica gel, 5% to 95% ethyl acetate-hexane) to afford (1S)-2,3,4,6-tetra-O-acetyl-1,5-anhydro-1-(3-bromophenyl)-D-glucitol (0.178 g, 0.36 mmol, 45% yield) as a white foam; R$_f$ 0.4 (40% ethyl acetate-hexane); ¹H NMR (300 MHz, CDCl₃) δ 7.44 (m, 2H) 7.25 (m, 2H), 5.27-5.35 (m, 1H), 5.21 (t, J=9.6 Hz, 1H), 5.03 (t, J=9.7 Hz, 1H), 4.36 (d, J=9.9 Hz, 1H), 4.23-4.32 (m, 1H) 4.08-4.18 (m, 1H) 3.80-3.85 (m, 1H) 2.09 (s, 3H), 2.06 (s, 3H), 1.99 (s, 3H), 1.84 (s, 3H) ppm; MS [M+H]⁺ 488.4.

EXAMPLE 63

Synthesized in the Same Manner as Example 62, but Replacing 1,3 Dibromobenzene with 1,4 Dibromobenzene

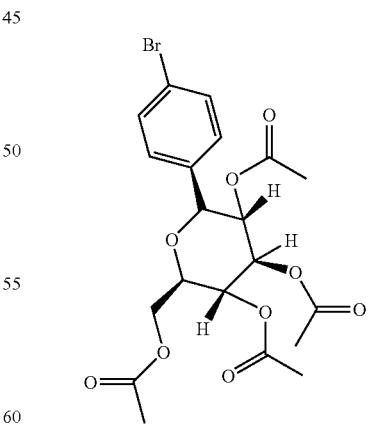

(1S)-2,3,4,6-Tetra-O-acetyl-1,5-anhydro-1-(4-bromophenyl)-D-glucitol was obtained (45% yield, white wax). R$_f$ 0.3 (40% ethyl acetate-hexane); ¹H NMR (300 MHz, CDCl₃) δ 7.47 (d, J=8.4 Hz, 2H), 7.31 (d, J=8.7 Hz, 2H), 5.31 (d, J=9.3 Hz, 1H), 5.21 (t, J=9.9 Hz, 1H), 5.09 (t, J=9.6 Hz, 1H), 4.37

(d, J=9.9 Hz, 1H), 4.12-4.33 (m, 2H), 3.83 (m, 1H), 2.09 (s, 3H), 2.06 (s, 3H), 2.00 (s, 3H), 1.83 (s, 3H) ppm; MS [M+H]+ 488.4.

EXAMPLE 64

(1S)-1,5-Anhydro-1-(4'-{(2S,3R)-3-[(3S)-3-(4-fluorophenyl)-3-hydroxypropyl]-4-oxo-1-phenylazetidin-2-yl}biphenyl-3-yl)-D-glucitol

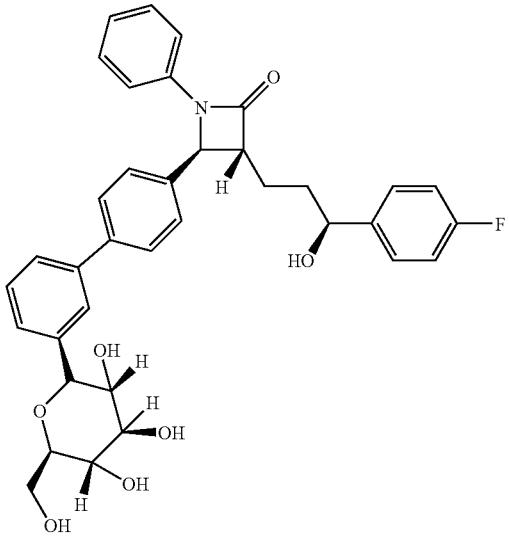

(3R,4S)-3-[(3S)-3-(4-Fluorophenyl)-3-hydroxypropyl]-1-phenyl-4-[4-(4,4,5,5-tetramethyl-1,3,2-dioxaborolan-2-yl)phenyl]azetidin-2-one (51.3 mg, 0.102 mmol) and (1S)-2,3,4,6-tetra-O-acetyl-1,5-anhydro-1-(3-bromophenyl)-D-glucitol (35.5 mg, 0.073 mmol) were dissolved in 2.0 mL of toluene and 0.25 mL of ethanol. 0.075 mL of 4 N potassium carbonate was added to the mixture followed by 5.0 mg of tetrakis(triphenylphosphine)palladium(0). The entire reaction was degassed three times with argon then heated to reflux for 4 h. The reaction was cooled to room temperature, diluted with 5 mL of water, and extracted with ethyl acetate (3×25 mL). The organic layers were combine, dried over sodium sulfate, filtered, concentrated and purified by column chromatography (12 g silica gel, 5% to 95% ethyl acetate-hexane) to afford 10.5 mg (13%) of (1S)-2,3,4,6-tetra-O-acetyl-1,5-anhydro-1-(4'-{(2S,3R)-3-[(3S)-3-(4-fluorophenyl)-3-hydroxypropyl]-4-oxo-1-phenylazetidin-2-yl}biphenyl-3-yl)-D-glucitol as a clear oil.

(1S)-2,3,4,6-Tetra-O-acetyl-1,5-anhydro-1-(4'-{(2S,3R)-3-[(3S)-3-(4-fluorophenyl)-3-hydroxypropyl]-4-oxo-1-phenylazetidin-2-yl}biphenyl-3-yl)-D-glucitol (10.5 mg, 0.013 mmol) was dissolved in 0.30 mL of methanol and 0.30 mL of triethylamine followed by drop-wise addition of water (0.80 mL). The yellowish mixture stirred at room temperature overnight. LCMS of the solution confirmed complete consumption of the starting material and formation of the fully deprotected material. The mixture was concentrated in vacuo, and purified by reverse-phase HPLC (Polaris C18-A 10 μ 250×21.2 mm column, 30% to 95% acetonitrile-0.1% trifluoroacetic acid in water) to afford 2.8 mg (35%) of the desired (1S)-1,5-anhydro-1-(4'-{(2S,3R)-3-[(3S)-3-(4-fluorophenyl)-3-hydroxypropyl]-4-oxo-1-phenylazetidin-2-yl}biphenyl-3-yl)-D-glucitol as a white powder; $^1$H NMR (300 MHz, CD$_3$OD) δ 7.65 (d, J=11.1 Hz, 2H), 7.54-7.23 (m, 10H), 7.05-6.89 (m, 3H), 4.61 (t, J=6.3 Hz, 1H), 4.19 (d, J=9.0 Hz, 1H), 3.87 (d, J=10.7 Hz, 1H), 3.73-3.63 (m, 1H), 3.49-3.36 (m, 3H) 3.22-3.18 (m, 2H), 1.89 (m, 4H) ppm; MS [M−OH]+ 596.5.

EXAMPLE 65

(1S)-1,5-Anhydro-1-(4'-{(2S,3R)-3-[(3S)-3-(4-fluorophenyl)-3-hydroxypropyl]-4-oxo-1-phenylazetidin-2-yl}-3'-hydroxybiphenyl-3-yl)-D-glucitol

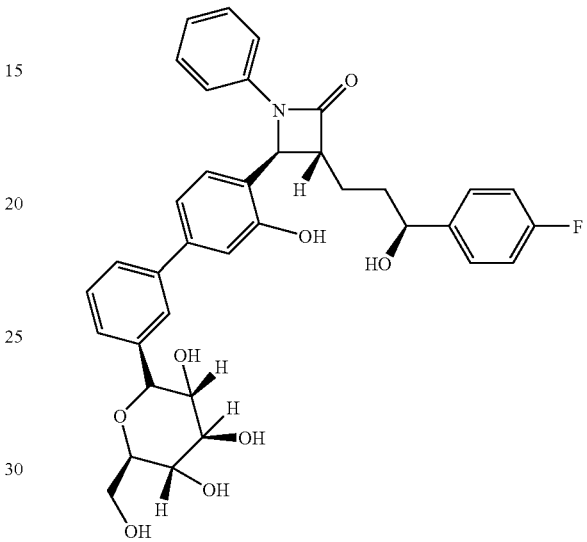

(3R,4S)-4-(4-Bromo-2-{[tert-butyl(dimethyl)silyl]oxy}phenyl)-3-[(3S)-3-{[tert-butyl(dimethyl)silyl]oxy}-3-(4-fluorophenyl)propyl]-1-phenylazetidin-2-one (0.42 g, 0.60 mmol) was dissolved in 15 mL of dioxane in a sealed tube. Bis(pinacolato)diboron (0.17 g, 0.66 mmol), potassium acetate (0.18 g, 1.83 mmol), and dichloro[1,1'-bis(diphenylphosphino)ferrocene] palladium(II) dichloromethane adduct (14.6 mg, 0.018 mmol) were added and the reaction was degassed with argon and heated to 85° C. for 24 h. The mixture was cooled to room temperature diluted with 50 mL of 1:1 ethyl acetate-hexane, washed with 100 mL of 0.1 N hydrochloric acid and 2×100 mL of brine. The organic layers were collected, partially concentrated to half the volume, filtered through 10 g of silica gel, washed with 50 mL of ethyl acetate and concentrated in vacuo.

The resulting brown oil which is (3R,4S)-3-[(3S)-3-{[tert-butyl(dimethyl)silyl]oxy}-3-(4-fluorophenyl)propyl]-4-[2-{[tert-butyl(dimethyl)silyl]oxy}-4-(4,4,5,5-tetramethyl-1,3,2-dioxaborolan-2-yl)phenyl]-1-phenylazetidin-2-one was dissolved with (1S)-2,3,4,6-tetra-O-acetyl-1,5-anhydro-1-(3-bromophenyl)-D-glucitol in 4.0 mL of toluene and 0.5 mL of ethanol. 0.150 mL of 4 N potassium carbonate was added followed by 7 mg of tetrakis(triphenylphosphine) palladium(0). The entire reaction was degassed three times with argon then heated to reflux for 1.5 h. After this time the reaction was cooled to room temperature and diluted with 25 mL of water and extracted with 1:1 hexane-ethyl acetate (3×75 mL). The organic layers were combine, dried over sodium sulfate, filtered, concentrated and purified by column chromatography (12 g silica gel, 5% to 95% ethyl acetate-hexane) to afford 41.6 mg (27%) of (1S)-2,3,4,6-tetra-O-acetyl-1,5-anhydro-1-(3'-{[tert butyl(dimethyl)silyl]oxy}-4'-{(2S,3R)-3-[(3S)-3-{[tert-butyl(dimethyl)silyl]oxy}-3-(4-fluorophenyl)propyl]-4-oxo-1-phenylazetidin-2-yl}biphenyl-3-yl)-D-glucitol as a clear oil.

This material was immediately dissolved in 0.80 mL of methanol and 0.80 mL of triethylamine followed by dropwise addition of water (2.3 mL). The yellow mixture was stirred at room temperature for 24 h, extracted with 1:1 ethyl acetate-hexane (3×100 mL), dried with sodium sulfate, and concentrated in vacuo to afford (1S)-1,5-anhydro-1-(3'-{[tert-butyl(dimethyl)silyl]oxy}-4'-{(2S,3R)-3-[(3S)-3-{[tert-butyl(dimethyl)silyl]oxy}-3-(4-fluorophenyl)propyl]-4-oxo-1-phenylazetidin-2-yl}biphenyl-3-yl)-D-glucitol.

The final deprotection was accomplished by dissolving (1S)-1,5-anhydro-1-(3'-{[tert-butyl(dimethyl)silyl]oxy}-4'-{(2S,3R)-3-[(3S)-3-{[tert-butyl(dimethyl)silyl]oxy}-3-(4-fluorophenyl)propyl]-4-oxo-1-phenylazetidin-2-yl}biphenyl-4-yl)-D-glucitol in 5 mL of acetonitrile, and adding 2.5 mL of 48% hydrofluoric acid. The mixture stirred at room temperature of 1.5 h, neutralized with 70 mL of 1 N sodium hydroxide and 50 mL of 1 M sodium phosphate buffer pH 7.4, extracted into ethyl acetate (2×100 mL), washed with saturated sodium bicarbonate (2×25 mL), dried with sodium sulfate, filtered and concentrated in vacuo. The crude sample was purified by reverse-phase HPLC (Polaris C18-A 10 μ 250×21.2 mm column, 30% to 95% acetonitrile-0.1% trifluoroacetic acid in water) to afford 7.9 mg (74%) of the desired (1S)-1,5-anhydro-1-(4'-{(2S,3R)-3-[(3S)-3-(4-fluorophenyl)-3-hydroxypropyl]-4-oxo-1-phenylazetidin-2-yl}-3'-hydroxybiphenyl-3-yl)-D-glucitol as a white solid; $^1$H NMR (300 MHz, CD$_3$OD) δ 7.49 (dd, J=6.6 Hz, 4H), 7.34-7.21 (m, 7H), 7.15 (d, J=7.8 Hz, 1H), 7.07-6.97 (m, 5H), 5.13 (d, J=2.1 Hz, 1H), 4.61 (m, 1H), 4.15 (d, J=9.3 Hz, 1H) 3.90 (d, J=12 Hz, 1H), 3.70 (m, 1H) 3.41 (m, 4H), 3.16 (m, 1H), 1.99-1.93 (m, 4H) ppm; MS [M−OH]$^+$ 612.6.

EXAMPLE 66

(1S)-1,5-Anhydro-1-(4'-{(2S,3R)-3-[(3S)-3-(4-fluorophenyl)-3-hydroxypropyl]-4-oxo-1-phenylazetidin-2-yl}-3'-hydroxybiphenyl-4-yl)-D-glucitol

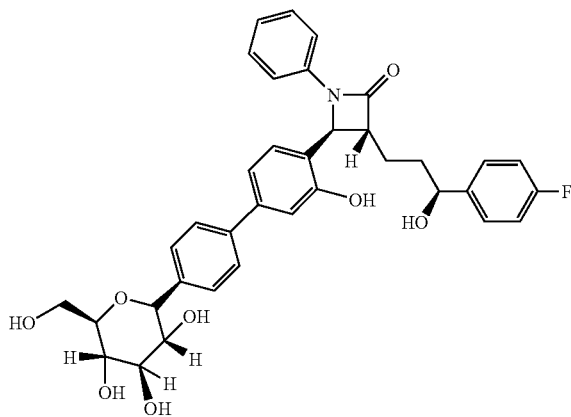

Obtained in a manner similar to Example 65, but using (1S)-2,3,4,6-tetra-O-acetyl-1,5-anhydro-1-(4-bromophenyl)-D-glucitol in place of (1S)-2,3,4,6-tetra-O-acetyl-1,5-anhydro-1-(3-bromophenyl)-D-glucitol. (1S)-1,5-Anhydro-1-(4'-{(2S,3R)-3-[(3S)-3-(4-fluorophenyl)-3-hydroxypropyl]-4-oxo-1-phenylazetidin-2-yl}-3'-hydroxybiphenyl-4-yl)-D-glucitol (20% yield, white solid). $^1$H NMR (300 MHz, CD$_3$OD) δ 7.49 (dd, J=8.1 Hz, 4H), 7.35-7.16 (m, 8H), 7.05-6.97 (m, 4H), 5.15 (d, J=1.8 Hz, 1H), 4.61 (m, 1H), 4.16 (d, J=9.6 Hz, 1H), 3.90 (d, J=11.1 Hz, 1H), 3.71 (m, 1H), 3.42 (m, 4H), 3.16 (m, 1H), 2.02-1.93 (m, 4H) ppm; MS [M−OH]$^+$ 612.6.

EXAMPLE 67

(2S/2R,3S,4S,6R,7R,8S)-3-O-tert-Butyldimethylsilyl-2,3,6,7-tetrahydroxy-6,7-O-isopropylidene-1,5-dioxa-2-(3-bromophenyl)-bicyclo [3.3.0]octane

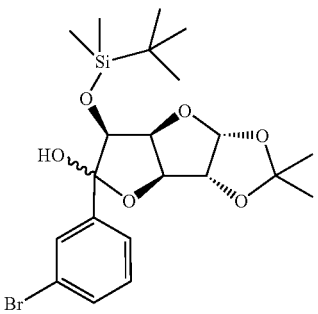

n-Butyllithium (31.5 mL, 41.0 mmol, 1.3 M hexane) was added via addition funnel to 1,3-dibromobenzene (9.64 g, 41.0 mmol, 4.94 mL) dissolved in anhydrous tetrahydrofuran (30 mL) at −78° C. over 30 min. The addition funnel was rinsed with anhydrous tetrahydrofuran (15 mL) and the reaction was allowed to stir for 30 min at −78° C. To this solution was added 5-O-tert-butyldimethylsilyl-1,2-O-isopropylidene-α-D-glucuronolactone (4.5 g, 13.6 mmol) [prepared according to *Tetrahedron Asymmetry* 7:9, 2761, (1996)] dissolved in 30 mL of anhydrous tetrahydrofuran at −78° C. and the reaction stirred for 2 h. The reaction was quenched by the addition of saturated ammonium chloride (20 mL) followed by warming to room temperature. The reaction was poured into ethyl acetate (30 mL) and water (10 mL) and the layers separated. The aqueous layer was extracted with ethyl acetate (2×20 mL). The combined organic extracts were dried over anhydrous sodium sulfate, filtered, concentrated and purified by chromatography (1:1 diethyl ether-hexane) to afford a diastereomeric mixture of (2S12R,3S,4S,6R,7R,8S)-3-O-tert-butyldimethylsilyl-2,3,6,7-tetrahydroxy-6,7-O-isopropylidene-1,5-dioxa-2-(3-bromophenyl)-bicyclo[3.3.0]octane (4.77 g, 72% yield) as a colorless viscous oil. R$_f$ 0.51 (3:1 hexane-ethyl acetate).

EXAMPLE 68

(6S)-6-C-(3-Bromophenyl)-6-O-[tert-butyl(dimethyl)silyl]-1,2-O-(1-methylethylidene)-α-D-glucofuranose

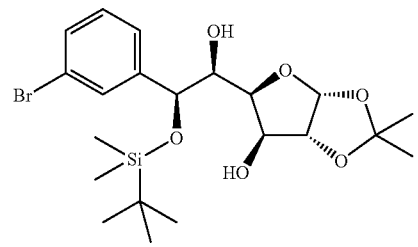

Sodium borohydride (11.1 mg, 0.29 mmol) was added to (2S/2R,3S,4S,6R,7R,8S)-3-O-tert-butyldimethylsilyl-2,3,6,7-tetrahydroxy-6,7-O-isopropylidene-1,5-dioxa-2-(3-bromophenyl)-bicyclo[3.3.0]octane dissolved in absolute ethanol (4 mL) at room temperature. The reaction was stirred at room temperature for 1 h. TLC analysis (3:1 hexane-ethyl acetate) indicated that all the starting lactol had been consumed. 1 mL of saturated ammonium chloride solution was added and the reaction was stirred until the effervescence ceased. The reaction was poured into ethyl acetate (30 mL) and water (10 mL) and the layers separated. The aqueous layer was extracted 2×20 mL with ethyl acetate. The combined organic extracts were dried over anhydrous sodium sulfate, filtered, concentrated and purified by chromatography (3:1 hexane:ethyl acetate) to afford (6S)-6-C-(3-bromophenyl)-6-O-[tert-butyl(dimethyl)silyl]-1,2-O-(1-methylethylidene)-α-D-glucofuranose (125 mg, 88% yield) as a white waxy solid. mp 76-77° C.; R$_f$ 0.24 (3:1 hexane:ethyl acetate); $^1$H NMR (300 MHz, CDCl$_3$) δ 7.51-7.17 (m, 4H), 5.95 (d, J=3.6 Hz, 1H), 4.90 (s, 1H), 4.53 (d, J=3.9 Hz, 1H), 4.32 (d, J=2.7 Hz, 1H), 4.09 (dd, J=2.7 Hz, J=8.4 Hz, 1H), 3.75 (d, J=7.2 Hz, 1H), 2.76-2.68 (br s, 2H), 1.46 (s, 3H), 1.31 (s, 3H), 0.92 (s, 9H), 0.11 (s, 3H), −0.10 (s, 3H) ppm.

EXAMPLE 69

(6R)-6-C-(3-Bromophenyl)-1,2-O-(1-methylethylidene)-α-D-glucofuranose

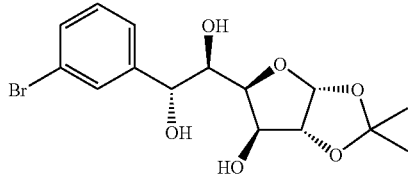

Tetrabutylammonium fluoride (1 M in tetrahydrofuran, 3.14 mL) was added dropwise to (2S/2R,3S,4S,6R,7R,8S)-3-O-tert-butyldimethylsilyl-2,3,6,7-tetrahydroxy-6,7-O-isopropylidene-1,5-dioxa-2-(3-bromophenyl)-bicyclo[3.3.0] octane (1.53 g, 3.14 mmol) and glacial acetic acid (188.4 mg, 3.14 mmol, 180 μL) in anhydrous tetrahydrofuran (30 mL) at 0° C. The reaction was stirred for 30 min at 0° C. then warmed to room temperature and stirred an additional 30 min. TLC analysis (3:1 hexane-ethyl acetate) indicated that the starting material had been completely consumed. The reaction was poured into ethyl acetate (30 mL), washed with saturated sodium bicarbonate (10 mL) and brine (2×10 mL). The aqueous layer was back extracted with ethyl acetate (2×20 mL). The combined organic extracts were dried over anhydrous sodium sulfate, filtered, concentrated and purified by chromatography (35 g, 40% ethyl acetate-hexane isocratic) to afford (2S/2R,3S,4S,6R,7R,8S)-2,3,6,7-tetrahydroxy-6,7-O-isopropylidene-1,5-oxa-2-(3-bromophenyl)-bicyclo[3.3.0]octane (1.146 g, 98% yield) as a white solid; R$_f$ 0.18 (3:1 hexane-ethyl acetate).

Sodium borohydride (116 mg, 3.1 mmol) was added to (2S/2R,3S,4S,6R,7R,8S)-2,3,6,7-tetrahydroxy-6,7-O-isopropylidene-1,5-oxa-2-(3-bromophenyl)-bicyclo[3.3.0]octane (1.15 g, 3.1 mmol) dissolved in absolute ethanol (5 mL) at room temperature. The reaction was stirred at room temperature for 1 h. TLC analysis (2:1 ethyl acetate-hexane) indicated that all the starting lactol had been consumed. 1 mL of saturated ammonium chloride solution was added and the reaction stirred until the effervescence ceased. The reaction was poured into ethyl acetate (30 mL) and water (10 mL) and the layers separated. The aqueous layer was extracted with ethyl acetate (2×20 mL). The combined organic extracts were dried over anhydrous sodium sulfate, filtered, concentrated and purified by chromatography (2:1 ethyl acetate-hexane to elute the first diastereomer then 100% ethyl acetate) to afford (6R)-6-C-(3-bromophenyl)-1,2-O-(1-methylethylidene)-α-D-glucofuranose (511 mg, 89% yield) as a white solid; mp 172-173° C.; R$_f$ 0.19 (2:1 ethyl acetate-hexane); $^1$H NMR (300 MHz, CDCl$_3$/CD$_3$OD) δ 7.62-7.61 (m, 1H), 7.42-7.38 (m, 1H), 7.21 (t, J=7.5 Hz, 1H), 5.94 (d, J=3.9 Hz, 1H), 4.86 (d, J=4.5 Hz, 1H), 4.48 (d, J=3.3 Hz, 1H), 4.24 (d, J=2.4 Hz, 1H), 4.14-4.10 (m, 1H), 3.79-3.74 (m, 1H), 1.38 (s, 3H), 1.30 (s, 3H) ppm.

EXAMPLE 70

(3R,4S)-3-[(3S)-3-(4-Fluorophenyl)-3-hydroxypropyl]-1-phenyl-4-[4-(4,4,5,5-tetramethyl-1,3,2-dioxaborolan-2-yl)phenyl]azetidin-2-one

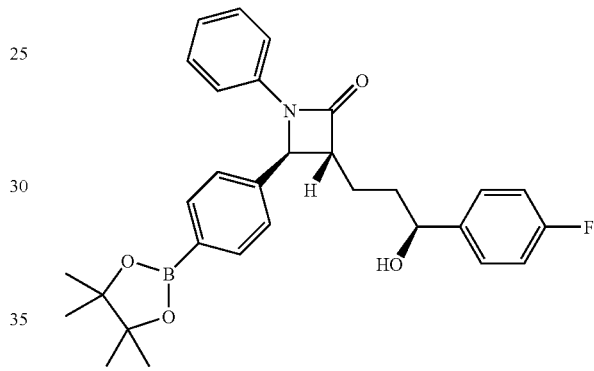

(3R,4S)-4-(4-Bromophenyl)-3-[(3S)-3-(4-fluorophenyl)-3-hydroxypropyl]-1-phenylazetidin-2-one (45.1 mg, 0.10 mmol), bis(pinacolato)diboron (27.7 mg, 0.11 mmol), dichloro[1,1'-bis(diphenylphosphino)ferrocene]palladium (II) dichloromethane adduct (2.4 mg, 0.003 mmol), and potassium acetate (29.7 mg, 0.30 mmol) were dissolved in anhydrous dimethyl sulfoxide (600 μL). The vessel was evacuated and flushed with argon three times then sealed and heated at 80° C. for 16 h. LCMS analysis indicated that some starting material remained so an additional aliquot of catalyst and bis(pinacolato)diboron were added, the solution degassed and heating continued for 2 h. The reaction was diluted into dichloromethane (30 mL) and filtered through a plug of Celite®. The filtrate was washed 2×10 mL with water. The combined aqueous washed were back extracted with 3×10 mL dichloromethane. The combined organic phase was dried over anhydrous sodium sulfate, filtered and concentrated in vacuo. The product was purified by chromatography (12 g silica gel, 20-50% ethyl acetate-hexane) to afford (3R,4S)-3-[(3S)-3-(4-fluorophenyl)-3-hydroxypropyl]-1-phenyl-4-[4-(4,4,5,5-tetramethyl-1,3,2-dioxaborolan-2-yl)phenyl]azetidin-2-one (41.9 mg, 85% yield) as a tan foam; R$^f$ (1:1 hexane-ethyl acetate); $^1$H NMR (300 MHz, CDCl$_3$) δ 7.81 (d, J=8.1 Hz, 1H), 7.35-7.18 (m, 9H), 7.04-6.97 (m, 3H), 4.70 (t, J=5.7 Hz, 1H), 4.65 (d, J=2.1 Hz, 1H), 3.08 (dt, J=7.7, 2.5, 1H), 2.02-1.87 (m, 4H), 1.33 (s, 12H) ppm.

EXAMPLE 71

(6S)-6-C-(4'-{(2S,3R)-3-[(3S)-3-(4-Fluorophenyl)-3-hydroxypropyl]-4-oxo-1-phenylazetidin-2-yl}biphenyl-3-yl)-D-glucopyranose

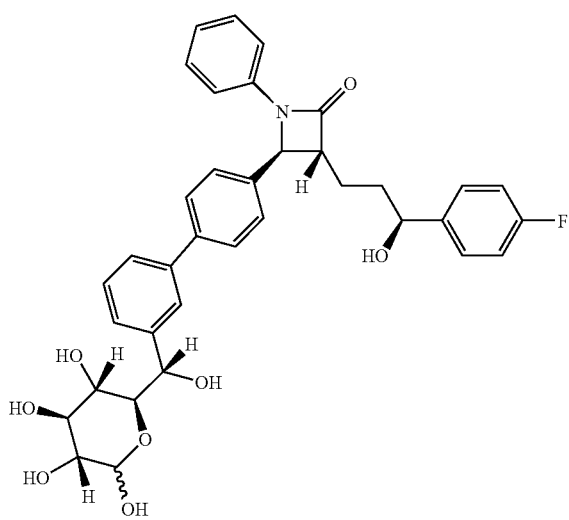

(3R,4S)-3-[(3S)-3-(4-Fluorophenyl)-3-hydroxypropyl]-1-phenyl-4-[4-(4,4,5,5-tetramethyl-1,3,2-dioxaborolan-2-yl)phenyl]azetidin-2-one (26.8 mg, 0.05 mmol), (6S)-6-C-(3-bromophenyl)-6-O-[tert-butyl(dimethyl)silyl]-1,2-O-(1-methylethylidene)-α-D-glucofuranose (18.1 mg, 0.04 mmol), and potassium carbonate (40 µL, 4 N aqueous) were dissolved in 1:1 toluene:ethanol (1 mL total volume). The solution was degassed by evacuating the vessel and flushing with argon three times.

Tetrakis(triphenylphosphine)palladium(0) (2.2 mg, 0.002 mmol) was added and the solution was degassed twice. The reaction was heated at 85° C. for 1 h. LCMS and TLC (1:1 hexane-ethyl acetate) analysis indicated consumption of the starting glycoside. The reaction was diluted into ethyl acetate (30 mL) and washed with water (2×10 mL). The combined aqueous washes were back extracted with ethyl acetate (2×10 mL). The combined organic extracts were dried over anhydrous sodium sulfate, filtered, concentrated in vacuo and purified by chromatography (12 g silica gel, 20-50% ethyl acetate-hexane) to afford (6S)-6-O-[tert-butyl(dimethyl)silyl]-6-C-(4'-{(2S,3R)-3-[(3S)-3-(4-fluorophenyl)-3-hydroxypropyl]-4-oxo-1-phenylazetidin-2-yl}biphenyl-3-yl)-1,2-O-(1-methylethylidene)-α-D-glucofuranose (13.5 mg, 45% yield) as a white foam; $R_f$ 0.23 (1:1 hexane-ethyl acetate); $^1$H NMR (300 MHz, CDCl$_3$) δ 7.58-7.22 (m, 13H), 7.07-6.98 (m, 4H), 5.97 (d, J=3.9 Hz, 1H), 4.98 (d, J=2.4 Hz, 1H), 4.73 (t, J=6.3 Hz, 1H), 4.69 (d, J=2.1 Hz, 1H), 4.54 (d, J=3.9 Hz, 1H), 4.37 (d, J=2.4 Hz, 1H), 3.87-3.86 (m, 1H), 3.13-3.09 (m, 1H), 2.04-1.86 (m, 4H), 1.43 (s, 3H), 1.31 (s, 3H), 0.94 (s, 9H), 0.12 (s, 3H), −0.09 (s, 3H) ppm.

(6S)-6-O-[tert-Butyl(dimethyl)silyl]-6-C-(4'-{(2S,3R)-3-[(3S)-3-(4-fluorophenyl)-3-hydroxypropyl]-4-oxo-1-phenylazetidin-2-yl}biphenyl-3-yl)-1,2-O-(1-methylethylidene)-α-D-glucofuranose (13.5 mg, 0.017 mmol) was dissolved in acetonitrile (5 mL) in a polypropylene centrifuge tube. 48% Hydrofluoric acid (500 µL) was added at room temperature and the reaction was stirred for 16 h monitoring by LCMS. Upon completion, 1 equivalent of solid sodium carbonate (1.27 g, 12 mmol) was added and just enough water to dissolve the solid. The reaction was diluted into ethyl acetate (20 mL) and the layers separated. The aqueous solution was extracted with ethyl acetate (3×10 mL). The combined organic extracts were washed with saturated sodium carbonate (2×10 mL), dried over anhydrous sodium sulfate, filtered, concentrated in vacuo and purified by reverse-phase HPLC (Polaris C18-A 10 µ 250×21.2 mm column, 30% to 95% acetonitrile-0.1% trifluoroacetic acid in water) to afford (6S)-6-C-(4'-{(2S,3R)-3-[(3S)-3-(4-fluorophenyl)-3-hydroxypropyl]-4-oxo-1-phenylazetidin-2-yl}biphenyl-3-yl)-D-glucopyranose (5.5 mg, 51%); $^1$H NMR (300 MHz, CDCl$_3$/CD$_3$OD) δ 7.64-7.58 (m, 2H), 7.48-7.21 (m, 12H), 7.08-6.98 (m, 3H), 5.12-5.07 (m, 1.4H), 4.73 (d, J=2.4 Hz, 1H), 4.66 (t, J=5.7 Hz, 1H), 4.39 (d, J=7.5 Hz, 0.6H), 4.00 (dd, J=1.5 Hz, J=9.6 Hz, 0.6H), 3.76-3.56 (m), 3.23-3.10 (m, 1.5H), 2.01-1.90 (m, 4H) ppm; MS [M+H]$^+$ 630.0.

EXAMPLE 72

(6R)-6-C-(4'-{(2S,3R)-3-[(3S)-3-(4-Fluorophenyl)-3-hydroxypropyl]-4-oxo-1-phenylazetidin-2-yl}biphenyl-3-yl)-D-glucopyranose

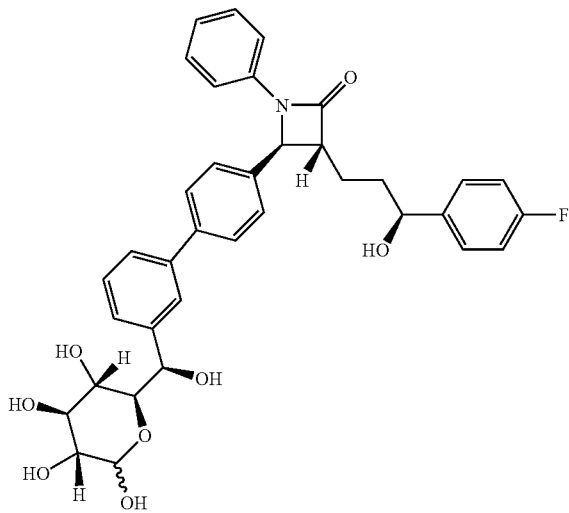

Obtained in a manner similar to Example 71 but using as starting materials the products from Examples 68 and 70. (6R)-6-C-(4'-{(2S,3R)-3-[(3S)-3-(4-Fluorophenyl)-3-hydroxypropyl]-4-oxo-1-phenylazetidin-2-yl}biphenyl-3-yl)-D-glucopyranose (2.4 mg, 53% yield); $^1$H NMR (300 MHz, CDCl$_3$/0.1% CD$_3$OD) δ 7.64-7.58 (m, 2H), 7.49-7.23 (m, 12H), 7.08-6.98 (m, 3H), 5.06 (d, J=3.6 Hz, 0.6H), 4.91 (d, J=6.0 Hz, 1H), 4.72 (d, J=4.8 Hz, 1H), 4.66 (t, J=5.4 Hz, 1H), 4.42 (d, J=7.8 Hz, 0.4H), 4.07-4.02 (m, 1H), 3.69-3.66 (m, 1H), 3.16-3.11 (m, 1H), 1.96-1.91 (m, 4H) ppm; MS [M+H]$^+$ 630.0.

EXAMPLE 73

(6S)-6-C-(4'-{(2S,3R)-3-[(3S)-3-(4-Fluorophenyl)-3-hydroxypropyl]-4-oxo-1-phenylazetidin-2-yl}-3'-hydroxybiphenyl-3-yl)-D-glucopyranose

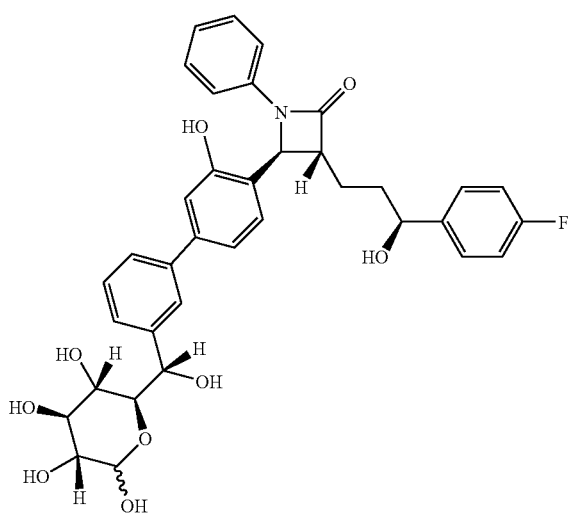

(3R,4S)-3-[(3S)-3-{[tert-Butyl(dimethyl)silyl]oxy}-3-(4-fluorophenyl)propyl]-4-[2-{[tert-butyl(dimethyl)silyl]oxy}-4-(4,4,5,5-tetramethyl-1,3,2-dioxaborolan-2-yl)phenyl]-1-phenylazetidin-2-one (53.0 mg, 0.07 mmol), (6S)-6-C-(3-bromophenyl)-6-O-[tert-butyl(dimethyl)silyl]-1,2-O-(1-methylethylidene)-α-D-glucofuranose (24.1 mg, 0.05 mmol), and potassium carbonate (50 µL, 4 N aqueous solution) were dissolved in 1:1 toluene:ethanol (1 mL total volume). The solution was degassed by evacuating the vessel and flushing with argon three times. Tetrakis(triphenylphosphine)palladium (4.0 mg, 0.003 mmol) was added and the solution degassed twice. The reaction was heated at 85° C. for 1 h. LCMS and TLC (1:1 hexane-ethyl acetate) analysis indicated consumption of the starting glycoside. The reaction was diluted into ethyl acetate (30 mL) and washed with water (2×10 mL). The combined aqueous washes were back extracted with ethyl acetate (2×10 mL). The combined organic extracts were dried over anhydrous sodium sulfate, filtered, concentrated in vacuo, and purified by chromatography (12 g silica gel, 5-50% ethyl acetate-hexane) to afford (6S)-6-O-[tert-butyl(dimethyl)silyl]-6-C-(4'-{(2S,3R)-3-[(3S)-3-{[tert-butyl(dimethyl)silyl]oxy}-3-(4-fluorophenyl)propyl]-4-oxo-1-phenylazetidin-2-yl}-3'-hydroxybiphenyl-3-yl)-1,2-O-(1-methylethylidene)-α-D-glucofuranose (10.5 mg, 20% yield) as a white foam; $^1$H NMR (300 MHz, CDCl$_3$) δ 7.44-7.18 (m, 13H), 7.05-6.93 (m, 3H), 5.97 (d, J=3.9 Hz, 1H), 5.03 (d, J=2.1 Hz, 1H), 4.95 (d, J=2.4 Hz, 1H), 4.67 (m, 1H), 4.56 (t, J=4.8 Hz, 1H), 4.38 (m, 1H), 4.10 (dd, J=7.6, 3.0 Hz, 1H), 3.87 (m, 1H), 3.12 (m, 1H), 1.94-1.89 (m, 4H), 1.44 (s, 3H), 1.31 (s, 3H), 0.93 (s, 9H), 0.86 (s, 9H), 0.11 (s, 3H), 0.01 (s, 3H), −0.11 (s, 3H), −0.16 (s, 3H) ppm.

(6S)-6-O-[tert-Butyl(dimethyl)silyl]-6-C-(4'-{(2S,3R)-3-[(3S)-3-{[tert-butyl(dimethyl)silyl]oxy}-3-(4-fluorophenyl)propyl]-4-oxo-1-phenylazetidin-2-yl}-3'-hydroxybiphenyl-3-yl)-1,2-O-(1-methylethylidene)-α-D-glucofuranose was dissolved in acetonitrile (5 mL) in a polypropylene centrifuge tube. 48% Hydrofluoric acid (750 µL) was added at room temperature and the reaction stirred for 16 h monitoring progress by LCMS. Upon completion, 1 equivalent of solid sodium carbonate (1.91 g, 18 mmol) was added and just enough water to dissolve the solid. The reaction was diluted into ethyl acetate (20 mL) and the layers separated. The aqueous solution was extracted with ethyl acetate (3×10 mL). The combined organic extracts were washed with saturated sodium carbonate (2×10 mL), dried over anhydrous sodium sulfate, filtered, concentrated in vacuo and purified by reverse-phase HPLC (Polaris C18-A 10 µ 250×21.2 mm column, 30% to 95% acetonitrile-0.1% trifluoroacetic acid in water) to afford (6S)-6-C-(4'-{(2S,3R)-3-[(3S)-3-(4-fluorophenyl)-3-hydroxypropyl]-4-oxo-1-phenylazetidin-2-yl}-3'-hydroxybiphenyl-3-yl)-D-glucopyranose (17.8 mg); $^1$H NMR (300 MHz, CDCl$_3$/CD$_3$OD) δ 7.52-6.83 (m, 16H), 5.05-5.00 (m, 2H), 4.50 (m, 1H), 4.34 (m, 1H), 3.94 (m, 1H), 3.72-3.59 (m, 2H), 2.91 (m, 1H), 1.95-1.77 (m, 4H) ppm; MS [M−OH]$^+$ 627.8.

EXAMPLE 74

(6R)-6-C-(4'-{(2S,3R)-3-[(3S)-3-(4-Fluorophenyl)-3-hydroxypropyl]-4-oxo-1-phenylazetidin-2-yl}-3'-hydroxybiphenyl-3-yl)-D-glucopyranose

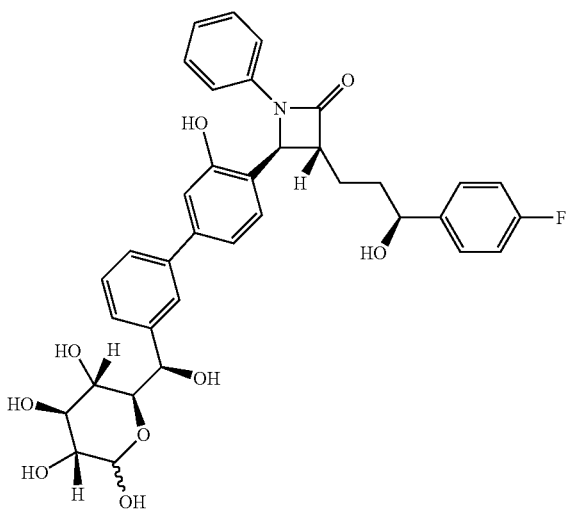

Obtained in a manner similar to Example 73. Purified by reverse-phase HPLC (Polaris C18-A 10 µ 250×21.2 mm column, 30% to 95% acetonitrile-0.1% trifluoroacetic acid in water) to afford (6R)-6-C-(4'-{(2S,3R)-3-[(3S)-3-(4-fluorophenyl)-3-hydroxypropyl]-4-oxo-1-phenylazetidin-2-yl}-3'-hydroxybiphenyl-3-yl)-D-glucopyranose (4.1 mg, 70% yield); ¹H NMR (300 MHz, CDCl₃/CD₃OD) δ 7.55-6.90 (m, 16H), 5.08-2.06 (m, 1H), 5.01-5.00 (m, 1H), 4.86 (d, J=4.5 Hz, 1H), 4.60 (t, J=5.1 Hz, 1H), 4.39 (d, J=8.1 Hz, 1H), 4.02-3.97 (m, 1H), 3.70-3.64 (m, 1H), 3.52-3.49 (m, 1H), 1.96-1.85 (m, 4H) ppm; MS [M−OH]⁺ 627.8.

EXAMPLE 75

(6S)-6-C-(4'-{(2S,3R)-3-[(3S)-3-(4-Fluorophenyl)-3-hydroxypropyl]-4-oxo-1-phenylazetidin-2-yl}-3'-hydroxybiphenyl-3-yl)-D-glucitol

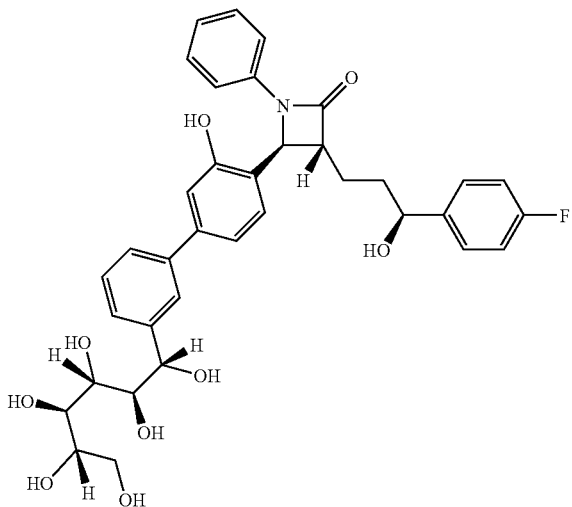

(6S)-6-C-(4'-{(2S,3R)-3-[(3S)-3-(4-Fluorophenyl)-3-hydroxypropyl]-4-oxo-1-phenylazetidin-2-yl}-3'-hydroxybiphenyl-3-yl)-D-glucopyranose (7.1 mg, 0.01 mmol) was dissolved in 80:20 acetonitrile-water (1 mL). Sodium borohydride (0.4 mg, 0.01 mmol) was added at room temperature and the reaction was stirred for 30 min monitoring by LCMS. Upon completion, the reaction was diluted with 80:20 acetonitrile:water (3 mL) then filtered through a Whatman 0.45 μM glass microfiber filter and purified by reverse-phase HPLC (Polaris C18-A 10 μ 250×21.2 mm column, 30% to 95% acetonitrile-0.1% trifluoroacetic acid in water) to afford (6S)-6-C-(4'-{(2S,3R)-3-[(3S)-3-(4-fluorophenyl)-3-hydroxypropyl]-4-oxo-1-phenylazetidin-2-yl}-3'-hydroxybiphenyl-3-yl)-D-glucitol (1.4 mg, 22% yield). ¹H NMR (300 MHz, CDCl₃/CD₃OD) δ 7.37-6.89 (m, 16H), 5.08 (d, J=2.4 Hz, 1H), 4.97-4.95 (m, 1H), 4.60 (t, J=6.0 Hz, 1H), 3.92 (m, 1H), 3.76-3.56 (m, 6H), 2.01-1.82 (m, 4H) ppm; MS [M−OH]⁺ 629.8.

EXAMPLE 76

6-O-(4'-{(2S,3R)-1-(4-Fluorophenyl)-3-[(3S)-3-(4-fluorophenyl)-3-hydroxypropyl]-4-oxoazetidin-2-yl}biphenyl-3-yl)-D-glucopyranose

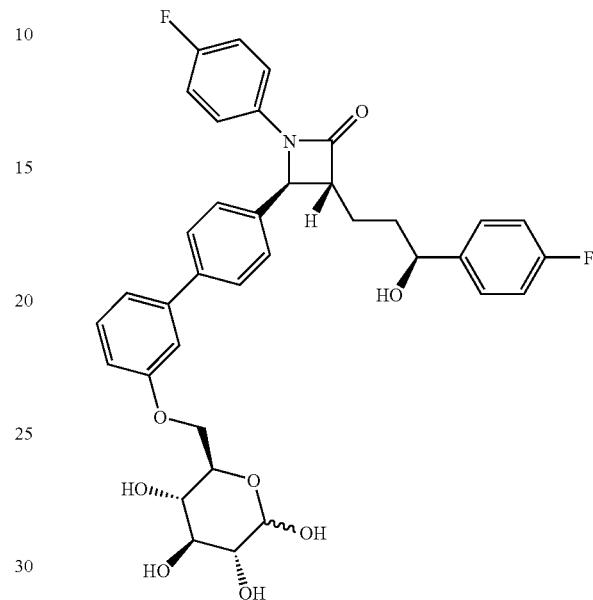

Diethylazodicarboxylate (192.4 mg, 1.11 mmol, 172 μL) was added drop-wise at 0° C. to 1,2,3,4-tetra-O-acetyl-β-D-glucopyranose (350.0 mg, 1.01 mmol), 3-bromophenyl (174.0 mg, 1.11 mmol), and triphenylphosphine (115.0 mg, 0.44 mmol) dissolved in dry tetrahydrofuran (2 mL). The reaction was stirred for 16 h warming to room temperature. The reaction was diluted into diethyl ether (30 mL) and washed with 5% sodium bisulfate (2×10 mL). The separated organic solution was dried over anhydrous sodium sulfate, filtered, concentrated in vacuo and purified by chromatography (20% ethyl acetate-dichloromethane) to afford 1,2,3,4-tetra-O-acetyl-6-O-(3-bromophenyl)-β-D-glucopyranose (357 mg, 71% yield).

Triethylamine (1 mL) was added at room temperature to 1,2,3,4-tetra-O-acetyl-6-O-(3-bromophenyl)-β-D-glucopyranose (200 mg, 0.40 mmol) dissolved in 5:1 methanol-water (6 mL). The reaction progress was monitored by LCMS and TLC (20% ethyl acetate-dichloromethane). Upon completion, the solvents were removed in vacuo to afford 6-O-(3-bromophenyl)-β-D-glucopyranose which was carried on without further purification.

tert-Butyldimethylsilyl trifluoromethanesulfonate (442 mg, 1.67 mmol, 383 μL) was added dropwise at 0° C. to 6-O-(3-bromophenyl)-β-D-glucopyranose and 4-dimethylaminopyridine (219 mg, 1.79 mmol) dissolved in dichloromethane (3 mL). The reaction was stirred for 16 h warming to room temperature. The reaction was diluted into dichloromethane (30 mL) and washed with 5% sodium bisulfate (2×10 mL). The separated organic solution was dried over anhydrous sodium sulfate, filtered, concentrated in vacuo and purified by chromatography (50% ethyl acetate:hexane) to afford a 6-O-(3-bromophenyl)-β-D-glucopyranose bis-O-[tert-butyl(dimethyl)silyl]ether (98.9 mg, 44% yield); $R_f$=0.14 (50% ethyl acetate-hexane).

(3R,4S)-1-(4-Fluorophenyl)-3-[(3S)-3-(4-fluorophenyl)-3-hydroxypropyl]-4-[4-(4,4,5,5-tetramethyl-1,3,2-dioxaborolan-2-yl)phenyl]azetidin-2-one (141.5 mg, 0.27 mmol), 6-O-(3-bromophenyl)-β-D-glucopyranose bis-O-[tert-butyl(dimethyl)silyl]ether (98.9 mg, 0.18 mmol), and potassium carbonate (175 µL, 2 M aqueous solution) were dissolved in 1:1 toluene-ethanol (1 mL total volume). The solution was degassed by evacuating the vessel and flushing with argon three times.

Tetrakis(triphenylphosphine)palladium (10.0 mg, 0.009 mmol) was added and the solution degassed twice. The reaction was heated at 85° C. for 1 h. LCMS and TLC (1:1 hexane-ethyl acetate) analysis indicated consumption of the starting glycoside. The reaction was diluted into ethyl acetate (30 mL) and washed with water (2×10 mL). The combined aqueous washes were back extracted with ethyl acetate (2×10 mL). The combined organic extracts were dried over anhydrous sodium sulfate, filtered, concentrated in vacuo and purified by chromatography (12 g silica gel, 50% ethyl acetate-hexane) to afford 6-O-(4'-{(2S,3R)-1-(4-fluorophenyl)-3-[(3S)-3-(4-fluorophenyl)-3-hydroxypropyl]-4-oxoazetidin-2-yl}biphenyl-3-yl)-β-D-glucopyranose bis-O-[tert-butyl(dimethyl)silyl]ether (113 mg, 74% yield). $^1$H NMR (300 MHz, CDCl$_3$) δ 7.56 (d, J=7.8 Hz, 2H), 7.36-7.10 (m, 8H), 7.01-6.80 (m, 6H), 4.70 (t, J=5.4 Hz, 1H), 4.64 (d, J=1.8 Hz, 1H), 4.56 (d, J=6.9 Hz, 1H), 4.35-4.32 (m, 1H), 4.16-4.07 (m, 1H), 3.68-3.58 (m, 2H), 3.51-3.46 (m, 1H), 3.38-3.32 (m, 1H), 3.11-3.09 (m, 1H), 1.98-1.88 (m, 4H), 0.91 (s, 9H), 0.91 (s, 9H), 0.14 (s, 6H), 0.13 (s, 6H) ppm.

6-O-(4'-{(2S,3R)-1-(4-Fluorophenyl)-3-[(3S)-3-(4-fluorophenyl)-3-hydroxypropyl]-4-oxoazetidin-2-yl}biphenyl-3-yl)-α-D-glucopyranose bis-O-[tert-butyl(dimethyl)silyl] ether (82.3 mg, 0.09 mmol) was dissolved in acetonitrile (10 mL) in a polypropylene centrifuge tube. 48% Hydrofluoric acid (1 mL) was added at room temperature and the reaction monitored by LCMS. Upon completion, 1 equivalent of solid sodium carbonate (2.54 g, 24 mmol) was added and just enough water to dissolve the solid. The reaction was diluted into ethyl acetate (20 mL) and the layers separated. The aqueous solution was extracted with ethyl acetate (3×10 mL). The combined organic extracts were washed with saturated sodium carbonate (2×10 mL), dried over anhydrous sodium sulfate, filtered, concentrated in vacuo and purified by reverse phase preparative HPLC (Polaris C18-A 10 µ 50×21.2 mm column, 30% to 95% acetonitrile-0.1% trifluoroacetic acid in water) to afford 6-O-(4'-{(2S,3R)-1-(4-fluorophenyl)-3-[(3S)-3-(4-fluorophenyl)-3-hydroxypropyl]-4-oxoazetidin-2-yl}biphenyl-3-yl)-α-D-glucopyranose (54.3 mg, 89% yield). $^1$H NMR (300 MHz, CDCl$_3$/1% CD$_3$OD) δ 7.58 (d, J=7.8 Hz, 2H), 7.39-7.24 (m, 7H), 7.17-7.14 (m, 2H), 7.04-6.92 (m, 5H), 5.23 (d, J=3.9 Hz, 0.6H), 4.71 (d, J=1.8 Hz, 1H), 4.66 (t, J=5.7 Hz, 1H), 4.58 (d, J=8.1 Hz, 0.4H), 4.40-4.30 (m, 1H), 4.25-4.14 (m, 1H), 3.57-3.48 (m, 2H), 3.16-3.11 (m, 1H), 2.04-1.85 (m, 4H) ppm; MS [M–OH]$^+$ 630.0.

EXAMPLE 77

Methyl 6-O-(4'-{(2S,3R)-1-(4-fluorophenyl)-3-[(3S)-3-(4-fluorophenyl)-3-hydroxypropyl]-4-oxoazetidin-2-yl}biphenyl-3-yl)-α-D-glucopyranoside

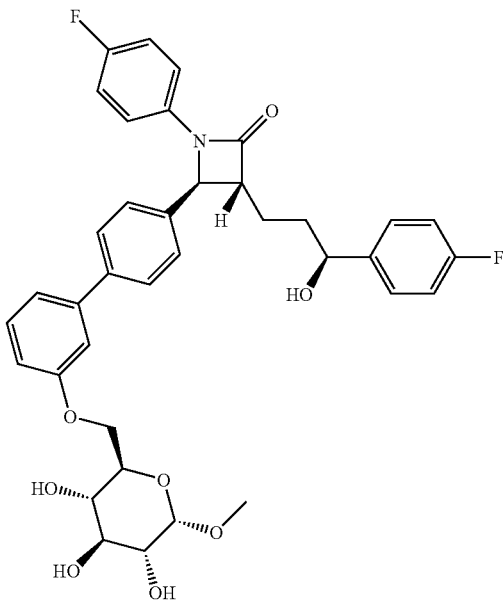

Diethylazodicarboxylate (76.2 mg, 0.44 mmol, 68 µL) was added drop-wise to methyl 2,3,4-tri-O-benzyl-α-D-glucopyranoside (184.8 mg, 0.40 mmol), 3-bromophenyl (72.3 mg, 0.42 mmol), and triphenylphosphine (115.0 mg, 0.44 mmol) dissolved in dry tetrahydrofuran (2 mL) at 0° C. The reaction was stirred for 16 h warming to room temperature. The reaction was diluted into dichloromethane (30 mL) and washed with 5% sodium bisulfate (2×10 mL). The separated organic solution was dried over anhydrous sodium sulfate, filtered, concentrated in vacuo and purified by chromatography (20% ethyl acetate-dichloromethane) to afford methyl 2,3,4-tri-O-benzyl-6-O-(3-bromophenyl)-α-D-glucopyranoside (216 mg, 87% yield).

(3R,4S)-1-(4-Fluorophenyl)-3-[(3S)-3-(4-fluorophenyl)-3-hydroxypropyl]-4-[4-(4,4,5,5-tetramethyl-1,3,2-dioxaborolan-2-yl)phenyl]azetidin-2-one (64.1 mg, 0.12 mmol), methyl 2,3,4-tri-O-benzyl-6-O-(3-bromophenyl)-D-glucopyranoside (54.6 mg, 0.09 mmol), and potassium carbonate (88 µL, 2 M aqueous solution) were dissolved in 1:1 toluen-ethanol (1 mL total volume). The solution was degassed by evacuating the vessel and flushing with argon three times. Tetrakis(triphenylphosphine)palladium (5.1 mg, 0.004 mmol) was added and the solution degassed twice. The reaction was heated at 85° C. for 1 h. LCMS and TLC (1:1 hexane-ethyl acetate) analysis indicated consumption of the starting glycoside. The reaction was diluted into ethyl acetate (30 mL) and washed with water (2×10 mL). The combined aqueous washes were back extracted with ethyl acetate (2×10 mL). The combined organic extracts were dried over anhydrous sodium sulfate, filtered, concentrated in vacuo and purified by chromatography (12 g silica gel, 20% to 50% ethyl acetate-hexane) to afford methyl 2,3,4-tri-O-benzyl-6-O-(4'-{(2S,3R)-1-(4-fluorophenyl)-3-[(3S)-

3-(4-fluorophenyl)-3-hydroxypropyl]-4-oxoazetidin-2-yl}biphenyl-3-yl)-α-D-glucopyranoside (70.0 mg, 85% yield). $^1$H NMR (300 MHz, CDCl$_3$) δ 7.55 (d, J=8.1 Hz, 2H), 7.39-6.84 (m, 29H), 5.01 (d, J=10.8 Hz, 1H), 4.89-4.80 (m, 3H), 4.73-4.64 (m, 4H), 4.52 (d, J=11.1 Hz, 1H), 4.15-4.12 (m, 2H), 4.08-4.-1 (m, 1H), 3.94-3.90 (m, 1H), 3.77-3.71 (m, 1H), 3.62 (dd, J=3.6 Hz, J=9.6 Hz, 1H), 3.39 (s, 3H), 3.13-3.10 (m, 1H), 2.03-1.89 (m, 4H) ppm.

Methyl 2,3,4-tri-O-benzyl-6-O-(4'-{(2S,3R)-1-(4-fluorophenyl)-3-[(3S)-3-(4-fluorophenyl)-3-hydroxypropyl]-4-oxoazetidin-2-yl}biphenyl-3-yl)-α-D-glucopyranoside (70 mg, 0.08 mmol) was dissolved in absolute ethanol (3 mL). 10% Pd/C (wet, 14% w/w) was added and the vessel sealed. The solution was degassed by evacuation and flushing with hydrogen gas at balloon pressure. The reaction was monitored by TLC (1:1 hexane-ethyl acetate). Upon completion, the catalyst was filtered by passing through a plug of Celite® and washing with additional ethanol. The filtrate was concentrated in vacuo and purified by preparative HPLC (Polaris C18-A 10 μ 250×21.2 mm column, 30% to 95% acetonitrile-0.1% trifluoroacetic acid in water) affording methyl 6-O-(4'-{(2S,3R)-1-(4-fluorophenyl)-3-[(3S)-3-(4-fluorophenyl)-3-hydroxypropyl]-4-oxoazetidin-2-yl}biphenyl-3-yl)-α-D-glucopyranoside (18.1 mg, 36% yield); $^1$H NMR (300 MHz, CDCl$_3$/1% CD$_3$OD) δ 7.58 (d, J=8.4 Hz, 2H), 7.38-7.23 (m, 7H), 7.17-7.14 (m, 2H), 7.04-6.92 (m, 5H), 4.80 (d, J=3.9 Hz, 1H), 4.70 (d, J=2.4 Hz, 1H), 4.67 (t, J=5.7 Hz, 1H), 4.37-4.33 (m, 1H), 4.26-4.21 (m, 1H), 3.92-3.87 (m, 1H), 3.74-3.45 (m, 3H), 3.42 (s, 3H), 3.18-3.10 (m, 1H), 2.01-1.88 (m, 4H) ppm; MS [M−OH]$^+$ 644.0.

EXAMPLE 78

6-O-(4'-{(2S,3R)-1-(4-Fluorophenyl)-3-[(3S)-3-(4-fluorophenyl)-3-hydroxypropyl]-4-oxoazetidin-2-yl}biphenyl-3-yl)-D-glucitol

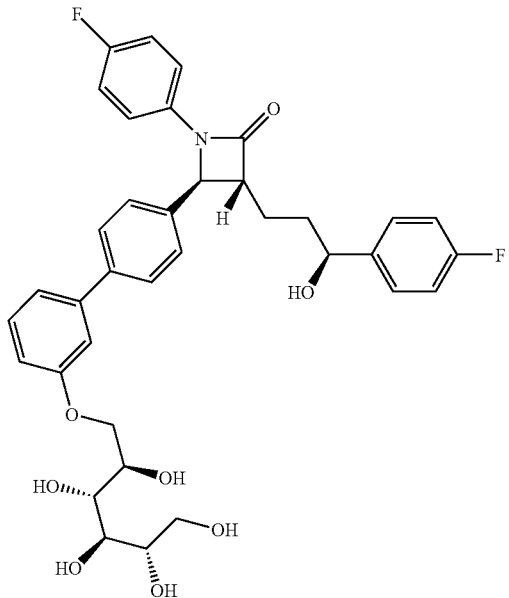

Sodium borohydride (1.6 mg, 0.04 mmol) was added to 6-O-(4'-{(2S,3R)-1-(4-fluorophenyl)-3-[(3S)-3-(4-fluorophenyl)-3-hydroxypropyl]-4-oxoazetidin-2-yl}biphenyl-3-yl)-D-glucopyranose (26.3 mg, 0.04 mmol) dissolved in 80:20 acetonitrile-water (1 mL) at room temperature. The reaction was stirred for 10 min at room temperature monitoring by LCMS. Upon completion, the reaction was diluted with 50:50 acetonitrile:water (3 mL) and filtered through a Whatman 0.45 μM glass microfiber filter then purified by preparative HPLC (Polaris C18-A 10 μ 250×21.2 mm column, 30% to 95% acetonitrile-0.1% trifluoroacetic acid in water) affording 6-O-(4'-{(2S,3R)-1-(4-fluorophenyl)-3-[(3S)-3-(4-fluorophenyl)-3-hydroxypropyl]-4-oxoazetidin-2-yl}biphenyl-3-yl)-D-glucitol (21.2 mg, 80% yield). $^1$H NMR (300 MHz, CDCl$_3$/1% CD$_3$OD) δ 7.58 (d, J=8.1 Hz, 2H), 7.39-7.24 (m, 7H), 7.17-7.15 (m, 2H), 7.04-6.92 (m, 5H), 4.71 (d, J=2.1 Hz, 1H), 4.68 (t, J=6.3 Hz, 1H), 4.31-4.27 (m, 1H), 0.19-4.14 (m, 1H), 4.08-4.02 (m, 1H), 3.97-3.95 (m, 1H), 3.86-3.65 (m, 4H), 3.14-3.12 (m, 1H), 2.01-1.88 (m, 4H) ppm; MS [M+HCO$_2$$^-$]$^-$ 694.0.

Scheme IV

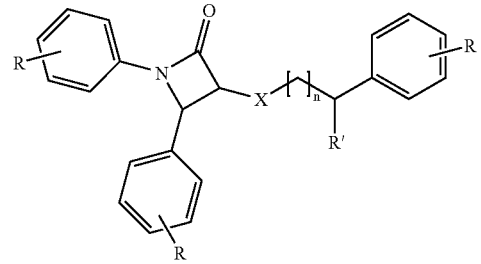

Illustrated in Scheme IV is the general method for the preparation of cholesterol absorption inhibitors of general formula IV-3. Imines IV-2 are made by refluxing anilines with the appropriate aldehydes in isopropanol. Condensation of imine IV-2 with the ester enolate of compound IV-1 affords the azetidinone IV-3. In the case where X is sulfur, one equivalent of an appropriate oxidizing agent such as MCPBA can be used to convert to the sulfoxide, two equivalents can be used to synthesize the sulfone. Where X is nitrogen, one equivalent of an appropriate oxidizing agent can be used to convert the secondary amine to a hydroxylamine (following deprotection).

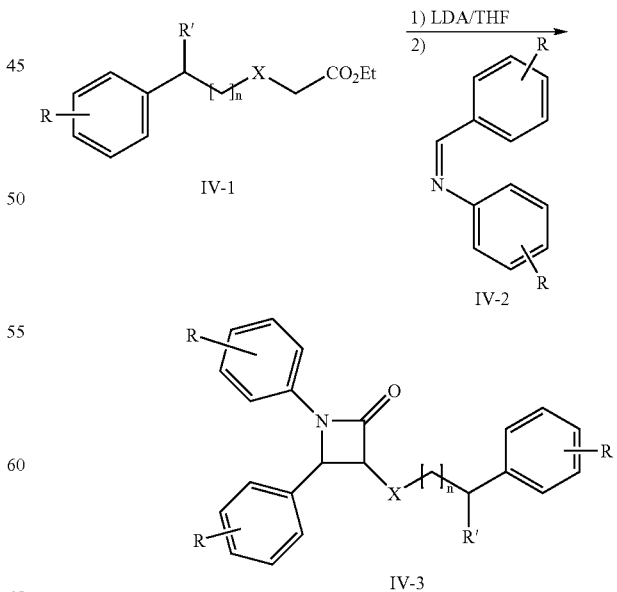

The following examples were also prepared according to the methods described above:

EXAMPLE 81

(3R,4S)-4-(3',4'-dimethoxybiphenyl-4-yl)-1-(4-fluorophenyl)-3-[(3S)-3-(4-fluorophenyl)-3-hydroxypropyl]azetidin-2-one

EXAMPLE 82

(3R,4S)-1-(4-fluorophenyl)-3-[(3S)-3-(4-fluorophenyl)-3-hydroxypropyl]-4-[3'-(methylthio)biphenyl-4-yl]azetidin-2-one

EXAMPLE 83

(3R,4S)-4-[3'-(dimethylamino)biphenyl-4-yl]-1-(4-fluorophenyl)-3-[(3S)-3-(4-fluorophenyl)-3-hydroxypropyl]azetidin-2-one

EXAMPLE 84

(3R,4S)-1-(4-fluorophenyl)-3-[(3S)-3-(4-fluorophenyl)-3-hydroxypropyl]-4-(4'-vinylbiphenyl-4-yl)azetidin-2-one

EXAMPLE 85

4'-{(2S,3R)-1-(4-fluorophenyl)-3-[(3S)-3-(4-fluorophenyl)-3-hydroxypropyl]-4-oxoazetidin-2-yl}-5-methoxybiphenyl-2-carbaldehyde

EXAMPLE 86

(3R,4S)-4-(3'-aminobiphenyl-4-yl)-1-(4-fluorophenyl)-3-[(3S)-3-(4-fluorophenyl)-3-hydroxypropyl]azetidin-2-one

EXAMPLE 87

(3R,4S)-4-[4-(2,3-dihydro-1,4-benzodioxin-6-yl)phenyl]-1-(4-fluorophenyl)-3-[(3S)-3-(4-fluorophenyl)-3-hydroxypropyl]azetidin-2-one

EXAMPLE 88

(4'-{(2S,3R)-1-(4-fluorophenyl)-3-[(3S)-3-(4-fluorophenyl)-3-hydroxypropyl]-4-oxoazetidin-2-yl}biphenyl-4-yl)acetic Acid

EXAMPLE 89 methyl 4'-{(2S,3R)-1-(4-fluorophenyl)-3-[(3S)-3-(4-fluorophenyl)-3-hydroxypropyl]-4-oxoazetidin-2-yl}biphenyl-4-carboxylate

EXAMPLE 90

(3R,4S)-4-(3',5'-dimethylbiphenyl-4-yl)-1-(4-fluorophenyl)-3-[(3S)-3-(4-fluorophenyl)-3-hydroxypropyl]azetidin-2-one

EXAMPLE 91

(3R,4S)-1-(4-fluorophenyl)-3-[(3S)-3-(4-fluorophenyl)-3-hydroxypropyl]-4-[4-(2-naphthyl)phenyl]azetidin-2-one

EXAMPLE 92

(3R,4S)-1-(4-fluorophenyl)-3-[(3S)-3-(4-fluorophenyl)-3-hydroxypropyl]-4-[3'-(trifluoromethyl)biphenyl-4-yl]azetidin-2-one

EXAMPLE 93

(3R,4S)-1-(4-fluorophenyl)-3-[(3S)-3-(4-fluorophenyl)-3-hydroxypropyl]-4-(3'-methylbiphenyl-4-yl)azetidin-2-one

EXAMPLE 94

(3R,4S)-4-(4'-fluoro-3'-methylbiphenyl-4-yl)-1-(4-fluorophenyl)-3-[(3S)-3-(4-fluorophenyl)-3-hydroxypropyl]azetidin-2-one

EXAMPLE 95

4'-{(2S,3R)-1-(4-fluorophenyl)-3-[(3S)-3-(4-fluorophenyl)-3-hydroxypropyl]-4-oxoazetidin-2-yl}biphenyl-3-yl β-L-glucopyranoside

EXAMPLE 96

(3R,4S)-1-(4-fluorophenyl)-3-[(3S)-3-(4-fluorophenyl)-3-hydroxypropyl]-4-(2',3',4'-trimethoxybiphenyl-4-yl)azetidin-2-one

EXAMPLE 97

(3R,4S)-4-(2',4'-dimethoxybiphenyl-4-yl)-1-(4-fluorophenyl)-3-[(3S)-3-(4-fluorophenyl)-3-hydroxypropyl]azetidin-2-one

EXAMPLE 98

(3R,4S)-1-(4-fluorophenyl)-3-[(3S)-3-(4-fluorophenyl)-3-hydroxypropyl]-4-(2'-methylbiphenyl-4-yl)azetidin-2-one

EXAMPLE 99

4'-{(2S,3R)-1-(4-fluorophenyl)-3-[(3S)-3-(4-fluorophenyl)-3-hydroxypropyl]-4-oxoazetidin-2-yl}biphenyl-4-carbaldehyde

EXAMPLE 100

(3R,4S)-4-(3'-ethoxybiphenyl-4-yl)-1-(4-fluorophenyl)-3-[(3S)-3-(4-fluorophenyl)-3-hydroxypropyl]azetidin-2-one

EXAMPLE 101

(3R,4S)-4-(4'-ethoxybiphenyl-4-yl)-1-(4-fluorophenyl)-3-[(3S)-3-(4-fluorophenyl)-3-hydroxypropyl]azetidin-2-one

EXAMPLE 102

(3R,4S)-1-(4-fluorophenyl)-3-[(3S)-3-(4-fluorophenyl)-3-hydroxypropyl]-4-(4'-hydroxy-3'-methoxybiphenyl-4-yl)azetidin-2-one

EXAMPLE 103

(3R,4S)-1-(4-fluorophenyl)-3-[(3S)-3-(4-fluorophenyl)-3-hydroxypropyl]-4-(3'-propoxybiphenyl-4-yl)azetidin-2-one

EXAMPLE 104

4'-{(2S,3R)-1-(4-fluorophenyl)-3-[(3S)-3-(4-fluorophenyl)-3-hydroxypropyl]-4-oxoazetidin-2-yl}-5-hydroxybiphenyl-2-carbaldehyde

EXAMPLE 105

(3R,4S)-1-(4-fluorophenyl)-3-[(3S)-3-(4-fluorophenyl)-3-hydroxypropyl]-4-(3'-isopropoxybiphenyl-4-yl)azetidin-2-one

EXAMPLE 106

4'-{(2S,3R)-1-(4-fluorophenyl)-3-[(3S)-3-(4-fluorophenyl)-3-hydroxypropyl]-4-oxoazetidin-2-yl}-4-hydroxybiphenyl-3-carboxylic Acid

EXAMPLE 107

(3R,4S)-4-(3',5'-dimethoxybiphenyl-4-yl)-1-(4-fluorophenyl)-3-[(3S)-3-(4-fluorophenyl)-3-hydroxypropyl]azetidin-2-one

EXAMPLE 108

(3R,4S)-4-(2',4'-dihydroxybiphenyl-4-yl)-1-(4-fluorophenyl)-3-[(3S)-3-(4-fluorophenyl)-3-hydroxypropyl]azetidin-2-one

EXAMPLE 109

(3R,4S)-4-(3'-butoxybiphenyl-4-yl)-1-(4-fluorophenyl)-3-[(3S)-3-(4-fluorophenyl)-3-hydroxypropyl]azetidin-2-one

EXAMPLE 110

4'-{(2S,3R)-1-(4-fluorophenyl)-3-[(3S)-3-(4-fluorophenyl)-3-hydroxypropyl]-4-oxoazetidin-2-yl}-3-hydroxybiphenyl-4-carboxylic Acid

EXAMPLE 111

(3R,4S)-4-(3'-fluoro-5'-methoxybiphenyl-4-yl)-1-(4-fluorophenyl)-3-[(3S)-3-(4-fluorophenyl)-3-hydroxypropyl]azetidin-2-one

EXAMPLE 112

(3R,4S)-4-(3'-fluoro-5'-hydroxybiphenyl-4-yl)-1-(4-fluorophenyl)-3-[(3S)-3-(4-fluorophenyl)-3-hydroxypropyl]azetidin-2-one

EXAMPLE 113

(1S)-1,5-anhydro-1-(4'-{(2S,3R)-1-(4-fluorophenyl)-3-[(3S)-3-(4-fluorophenyl)-3-hydroxypropyl]-4-oxoazetidin-2-yl}biphenyl-3-yl)-L-glucitol

EXAMPLE 114

(3R,4S)-4-(3',5'-dihydroxybiphenyl-4-yl)-1-(4-fluorophenyl)-3-[(3S)-3-(4-fluorophenyl)-3-hydroxypropyl]azetidin-2-one

EXAMPLE 115

(4'-{(2S,3R)-1-(4-fluorophenyl)-3-[(3S)-3-(4-fluorophenyl)-3-hydroxypropyl]-4-oxoazetidin-2-yl}biphenyl-3-yl)boronic Acid

EXAMPLE 116

(1R)-1,5-anhydro-1-(4'-{(2S,3R)-1-(4-fluorophenyl)-3-[(3S)-3-(4-fluorophenyl)-3-hydroxypropyl]-4-oxoazetidin-2-yl}biphenyl-4-yl)-L-glucitol

EXAMPLE 117

2,6-anhydro-1-deoxy-1-(4'-{(2S,3R)-1-(4-fluorophenyl)-3-[(3S)-3-(4-fluorophenyl)-3-hydroxypropyl]-4-oxoazetidin-2-ylbiphenyl-3-yl)-D-glycero-D-gulo-heptitol

EXAMPLE 118

4'-{(2S,3R)-1-(4-fluorophenyl)-3-[(3S)-3-(4-fluorophenyl)-3-hydroxypropyl]-4-oxoazetidin-2-yl}biphenyl-3-sulfonic Acid

EXAMPLE 119

(3R,4S)-1-(4-fluorophenyl)-3-[(3S)-3-(4-fluorophenyl)-3-hydroxypropyl]-4-(3'-mercaptobiphenyl-4-yl)azetidin-2-one

EXAMPLE 120

4'-{(2S,3R)-1-(4-fluorophenyl)-3-[(3S)-3-(4-fluorophenyl)-3-hydroxypropyl]-4-oxoazetidin-2-yl}-N,N,N-trimethylbiphenyl-3-aminium

EXAMPLE 121

(3R,4S)-4-(3,3'-dihydroxybiphenyl-4-yl)-1-(4-fluorophenyl)-3-[(3S)-3-(4-fluorophenyl)-3-hydroxypropyl]azetidin-2-one

EXAMPLE 122

(4'-{(2S,3R)-3-[(3S)-3-(4-fluorophenyl)-3-hydroxypropyl]-4-oxo-1-phenylazetidin-2-yl}biphenyl-3-yl)phosphonic Acid

EXAMPLE 123

(3R,4S)-3-[(3S)-3-(4-fluorophenyl)-3-hydroxypropyl]-4-[3-hydroxy-3'-(methylsulfonyl)biphenyl-4-yl]-1-phenylazetidin-2-one

EXAMPLE 124

(3R,4S)-1-biphenyl-4-yl-3-[(3S)-3-(4-fluorophenyl)-3-hydroxypropyl]-4-(3'-hydroxybiphenyl-4-yl)azetidin-2-one

EXAMPLE 125

(3R,4S)-4-(3,4'-dihydroxybiphenyl-4-yl)-3-[(3S)-3-(4-fluorophenyl)-3-hydroxypropyl]-1-phenylazetidin-2-one

EXAMPLE 126

Dimethyl [4-(4,4,5,5-tetramethyl-1,3,2-dioxaborolan-2-yl)phenyl]phosphonate

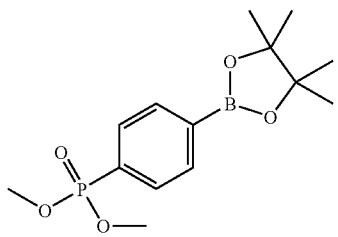

prepared in analogous manner to dimethyl [3-(4,4,5,5-tetramethyl-1,3,2-dioxaborolan-2-yl)phenyl]phosphonate (Example 60) starting with 4-chlorophenyl instead of 3-chlorophenyl. Dimethyl [4-(4,4,5,5-tetramethyl-1,3,2-dioxaborolan-2-yl)phenyl]phosphonate product was obtained as a light yellow oil (90%); $^1$H NMR (300 MHz, CDCl$_3$) δ 7.86-7.95 (m, 2H), 7.84-7.82 (m, 2H), 7.43-7.50 (m, 1H), 3.76 (s, 3H), 3.73 (s, 3H), 1.34 (s, 12H) ppm; MS [M+H] 312, [2M+H] 625.

EXAMPLE 127

(4'-{(2S,3R)-3-[(3S)-3-(4-Fluorophenyl)-3-hydroxypropyl]-4-oxo-1-phenylazetidin-2-yl}-3'-hydroxybiphenyl-4-yl)phosphonic Acid

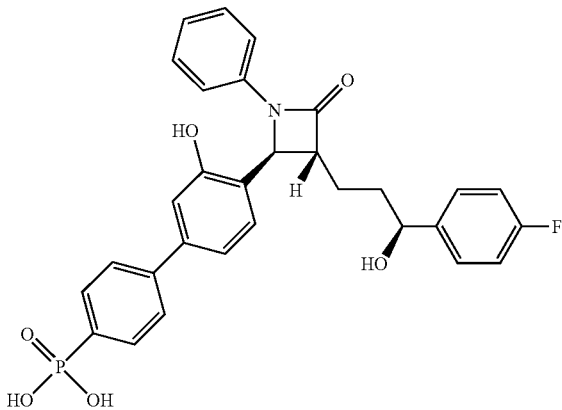

prepared in analogous manner to Example 61 using dimethyl [4-(4,4,5,5-tetramethyl-1,3,2-dioxaborolan-2-yl)phenyl]phosphonate (Example 126) in the reaction scheme instead of dimethyl [3-(4,4,5,5-tetramethyl-1,3,2-dioxaborolan-2-yl)phenyl]phosphonate (Example 60). Final purification by reverse-phase HPLC (Polaris C18-A 10±250×21.2 mm column, 30% to 59% acetonitrile-0.1% trifluoroacetic acid in water) afforded (4'-{(2S,3R)-3-[(3S)-3-(4-fluorophenyl)-3-hydroxypropyl]-4-oxo-1-phenylazetidin-2-yl}-3'-hydroxybiphenyl-4-yl)phosphonic acid as a white powder (62%); $^1$H NMR (300 MHz, CD$_3$OD) δ 7.8 (dd, J=8.0, 13.0 Hz, 1H), 7.68 (dd, J=3.2, 8.0 Hz, 1H), 6.9-7.4 (m, 14H), 5.17 (d, J=2.1 Hz, 1H), 4.60-4.66 (m, 1H), 3.13-3.22 (m, 1H), 1.8-2.1 (m, 4H) ppm; MS [M−H] 546, [2M−H] 1093.

EXAMPLE 128

Sodium 4'-{(2S,3R)-3-[(3S)-3-(4-fluorophenyl)-3-hydroxypropyl]-4-oxo-1-phenylazetidin-2-yl}-3'-hydroxybiphenyl-4-sulfonate

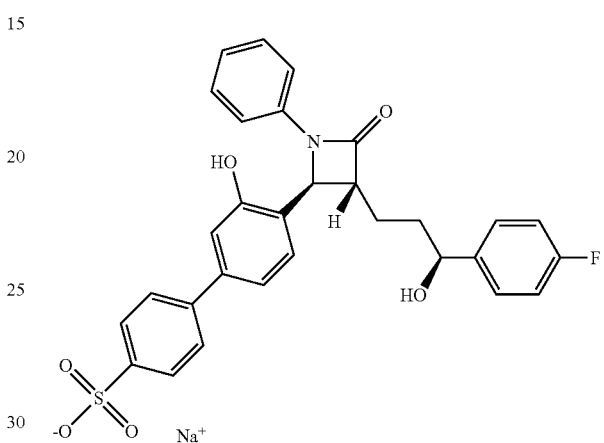

5-Bromo-2-{(2S,3R)-3-[(3S)-3-{[tert-butyl(dimethyl)silyl]oxy}-3-(4-fluorophenyl)propyl]-4-oxo-1-phenylazetidin-2-yl}phenyl acetate (850 mg, 1.36 mmol) and 4-thioanisoleboronic acid (252 mg, 1.50 mmol) were dissolved in dioxane (13.6 mL). Cesium carbonate (882 mg, 2.71 mmol) and solid bis(1-adamantylamine)palladium(0) (113 mg, 0.21 mmol) were added and the vessel was vacuum/nitrogen purged (3×). The reaction was stirred vigorously for 4 h at 80° C. under a nitrogen atmosphere and then cooled and reacted with acetic anhydride (0.70 mL, 7.3 mmol) and 4-dimethylamino-pyridine (185.6 mg, 1.52 mmol). After 15 min, the mixture was poured into 1.0 N hydrochloric acid (60 mL), extracted with 1:1 ethyl acetate-hexane (60 mL), washed with brine (60 mL), dried over sodium sulfate, filtered, concentrated and purified by chromatography (40 g silica gel, 5% to 50% ethyl acetate-hexane) to afford 4-{(2S,3R)-3-[(3S)-3-{[tert-butyl(dimethyl)silyl]oxy}-3-(4-fluorophenyl)propyl]-4-oxo-1-phenylazetidin-2-yl}-4'-(methylthio)biphenyl-3-yl acetate (478 mg, 52% yield) as a white foam; R$_f$ 0.41 (1:4 ethyl acetate-hexane).

4-{(2S,3R)-3-[(3S)-3-{[tert-butyl(dimethyl)silyl]oxy}-3-(4-fluorophenyl)propyl]-4-oxo-1-phenylazetidin-2-yl}-4'-(methylthio)biphenyl-3-yl acetate (478 mg, 0.713 mmol) was dissolved in dichloromethane (20 mL) and cooled to 0° C. 3-Chlorobenzenecarbo-peroxoic acid (134.5 mg, 0.779 mmol) was added in portions while monitoring by TLC and LCMS to make the arylsulfoxide. Once addition was complete the reaction was poured into quarter saturated sodium bicarbonate solution (60 mL), extracted with dichloromethane (60 mL) and ethyl acetate (60 mL), the combined organic layers were dried over sodium sulfate, filtered and concentrated with toluene. The residue was dissolved in dichloromethane (10 mL) and the Pummerer rearrangement was effected by the addition of trifluoroacetic anhydride (250 µL, 372 mg, 1.77 mmol). The reaction was stirred at room temperature for 8.5 h and then concentrated with toluene and diluted with a solution of degassed methanol (3.0 mL), triethylamine (3.0 mL) and water (1.0 mL). After 2.75 h the golden yellow solution was concentrated, transferred into a polypropylene Falcon® tube with acetonitrile (10.0 mL) and diluted with 48% hydrofluoric acid (1.0 mL). The reaction was stirred for 4 h at room temperature and then poured into 0.5 M potassium phosphate (50 mL), extracted with ethyl acetate (60 mL), washed with water (60 mL) and brine (60 mL), dried over sodium sulfate, filtered, concentrated and purified by chromatography (40 g silica gel, 10% to 100% ethyl acetate-hexane) to afford a mixture of compounds (some impurities and oxidized desired material). The residue was used as is in the next step.

The residue was dissolved in dichloromethane (10 mL) and added drop-wise to a solution of 3-chlorobenzenecarboperoxoic acid (489 mg, 2.83 mmol) in dichloromethane (10 mL). Dichloromethane (5 mL) was used to help transfer the material and the mixture was stirred at room temperature for 15 min. The reaction was quenched by addition of triethylamine (4 mL), concentrated, dissolved in methanol, filtered through a 0.45 µl Whatman® filter, concentrated again, purified by reverse-phase HPLC (Polaris C18-A 10 µ 250×21.2 mm column, 5% to 100% acetonitrile-0.1% triethylamine in water) and treated with Dowex® sodium ion exchange resin to afford sodium 4'-{(2S,3R)-3-[(3S)-3-(4-fluorophenyl)-3-hydroxypropyl]-4-oxo-1-phenylazetidin-2-yl}-3'-hydroxybiphenyl-4-sulfonate (249.0 mg, 57% yield) as a light pale purple solid; $^1$H NMR 300 MHz, CD$_3$OD) δ 7.88 (d, J=8.6 Hz, 2H), 7.59 (d, J=8.6 Hz, 2H), 7.35-7.19 (m, 7H), 7.14-7.11 (m, 2H), 7.03-6.97 (m, 3H), 5.14 (d, J=2.2 Hz, 1H), 4.63-4.59 (m, 1H), 3.17-3.08 (m, 1H), 2.04-1.87 (m, 4H) ppm; MS [M−Na] 546.0.

Also within the invention are compounds described by Table 3, together with Table 4 and Formula VIII which is shown below.

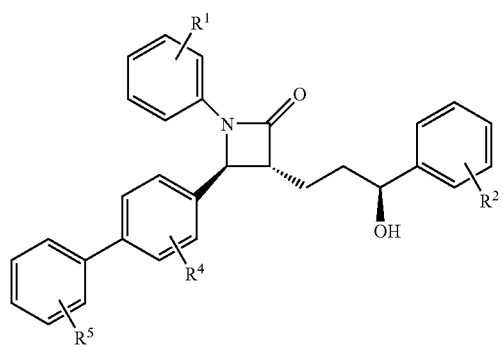

In these embodiments, $R^1$ and $R^2$ are independently chosen from H, F, CN, Cl, CH$_3$, OCH$_3$, OCF$_3$, OCF$_2$H, CF$_3$, CF$_2$H, and CH$_2$F; $R^4$ is chosen from H, Cl, CH$_3$, OCH$_3$, OH, B(OH)$_2$, and SH; $R^5$ is chosen from OH, SO$_3$H, PO$_3$H$_2$, CH$_2$OH, COOH, CHO, D-glucitol, a C-glysosyl compound and a sugar and only one R substitution is allowed on any aromatic ring. For example, where $R^5$ is —OH, all of the other substituents on the corresponding aromatic ring are H. Of course, where a given R group is H (e.g., $R^1$) all of the substituents on the corresponding aromatic ring are also H. In Table 4 when the $R^4$ substituent position is defined as 3-, the substitution occurs at the position ortho to the azetidinone ring. In Table 4 when the $R^4$ substituent position is defined as 2-, the substitution occurs at the position meta to the azetidinone ring.

Each row in Table 3 defines a unique subset of R group substituents which can be systematically substituted in an iterative fashion into Formula VIII at the positions specified by each row of Table 4 to generate specific compounds within Formula VIII. For example, in Table 3, row 1, $R^1$ is H, $R^2$ is F, $R^4$ is OH, and $R^5$ is OH. Substituting this set of R groups into Formula VIII according to the placement defined by row 1 of Table 4 (i.e., $R^1$ is ortho, $R^2$ is ortho, $R^4$ is 3- and $R^5$ is ortho) yields

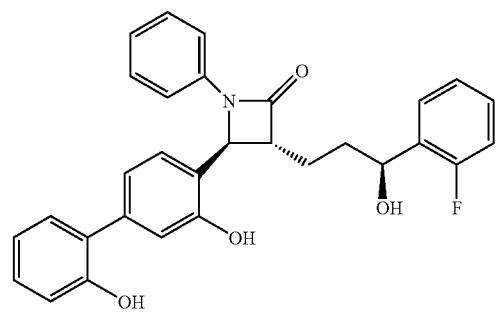

(3R,4S)-4-(2',3-dihydroxybiphenyl-4-yl)-3-[(3S)-3-(2-fluorophenyl)-3-hydroxypropyl]-1-phenylazetidin-2-one Similarly, (3R,4S)-4-(3,3'-dihydroxybiphenyl-4-yl)-3-[(3S)-3-(2-fluorophenyl)-3-hydroxypropyl]-1-phenylazetidin-2-one is disclosed by the using values in Table 3, row 1 to substitute Formula VIII according to Table 4, row 2. Tables 5-20 comprise the compounds disclosed by substituting the substituents listed in Tables 3 rows 1-16 into Formula VIII according to the placement defined by each row in Table 4. It should be understood that the compounds listed in Tables 5-20 are only a small subset of the compounds described by the systematic iterative substitution of the substituents in each row of Table 3 into generic Formula VIII according to the placement defined by each row of Table 4.

TABLE 3

| Row | R1 | R2 | R4 | R5 |
|---|---|---|---|---|
| 1 | H | F | OH | OH |
| 2 | H | F | OH | D-glucitol |
| 3 | H | F | OH | SO$_3$H |
| 4 | H | F | OH | PO$_3$H$_2$ |
| 5 | H | H | OH | OH |
| 6 | H | H | OH | D-glucitol |
| 7 | H | H | OH | SO$_3$H |
| 8 | H | H | OH | PO$_3$H$_2$ |
| 9 | H | Cl | OH | OH |
| 10 | H | Cl | OH | D-glucitol |
| 11 | H | Cl | OH | SO$_3$H |
| 12 | H | Cl | OH | PO$_3$H$_2$ |
| 13 | F | H | OH | OH |
| 14 | F | H | OH | D-glucitol |
| 15 | F | H | OH | SO$_3$H |
| 16 | F | H | OH | PO$_3$H$_2$ |
| 17 | F | F | OH | OH |
| 18 | F | F | OH | D-glucitol |
| 19 | F | F | OH | SO$_3$H |
| 20 | F | F | OH | PO$_3$H$_2$ |
| 21 | F | Cl | OH | OH |

TABLE 3-continued

| Row | R1 | R2 | R4 | R5 |
|---|---|---|---|---|
| 22 | F | Cl | OH | D-glucitol |
| 23 | F | Cl | OH | $SO_3H$ |
| 24 | F | Cl | OH | $PO_3H_2$ |
| 25 | Cl | H | OH | OH |
| 26 | Cl | H | OH | D-glucitol |
| 27 | Cl | H | OH | $SO_3H$ |
| 28 | Cl | H | OH | $PO_3H_2$ |
| 29 | Cl | F | OH | OH |
| 30 | Cl | F | OH | D-glucitol |
| 31 | Cl | F | OH | $SO_3H$ |
| 32 | Cl | F | OH | $PO_3H_2$ |
| 33 | Cl | Cl | OH | OH |
| 34 | Cl | Cl | OH | D-glucitol |
| 35 | Cl | Cl | OH | $SO_3H$ |
| 36 | Cl | Cl | OH | $PO_3H_2$ |
| 37 | H | H | H | OH |
| 38 | H | H | H | D-glucitol |
| 39 | H | H | H | $SO_3H$ |
| 40 | H | H | H | $PO_3H_2$ |
| 41 | H | H | H | CHO |
| 42 | H | H | H | COOH |
| 43 | H | H | H | $CH_2OH$ |
| 44 | H | H | H | sugar |
| 45 | H | H | H | C-glycosyl compound |
| 46 | H | H | OH | CHO |
| 47 | H | H | OH | COOH |
| 48 | H | H | OH | $CH_2OH$ |
| 49 | H | H | OH | sugar |
| 50 | H | H | OH | C-glycosyl compound |
| 51 | H | H | $CH_3$ | OH |
| 52 | H | H | $CH_3$ | D-glucitol |
| 53 | H | H | $CH_3$ | $SO_3H$ |
| 54 | H | H | $CH_3$ | $PO_3H_2$ |
| 55 | H | H | $CH_3$ | CHO |
| 56 | H | H | $CH_3$ | COOH |
| 57 | H | H | $CH_3$ | $CH_2OH$ |
| 58 | H | H | $CH_3$ | sugar |
| 59 | H | H | $CH_3$ | C-glycosyl compound |
| 60 | H | H | Cl | OH |
| 61 | H | H | Cl | D-glucitol |
| 62 | H | H | Cl | $SO_3H$ |
| 63 | H | H | Cl | $PO_3H_2$ |
| 64 | H | H | Cl | CHO |
| 65 | H | H | Cl | COOH |
| 66 | H | H | Cl | $CH_2OH$ |
| 67 | H | H | Cl | sugar |
| 68 | H | H | Cl | C-glycosyl compound |
| 69 | H | H | $B(OH)_2$ | OH |
| 70 | H | H | $B(OH)_2$ | D-glucitol |
| 71 | H | H | $B(OH)_2$ | $SO_3H$ |
| 72 | H | H | $B(OH)_2$ | $PO_3H_2$ |
| 73 | H | H | $B(OH)_2$ | CHO |
| 74 | H | H | $B(OH)_2$ | COOH |
| 75 | H | H | $B(OH)_2$ | $CH_2OH$ |
| 76 | H | H | $B(OH)_2$ | sugar |
| 77 | H | H | $B(OH)_2$ | C-glycosyl compound |
| 78 | H | H | SH | OH |
| 79 | H | H | SH | D-glucitol |
| 80 | H | H | SH | $SO_3H$ |
| 81 | H | H | SH | $PO_3H_2$ |
| 82 | H | H | SH | CHO |
| 83 | H | H | SH | COOH |
| 84 | H | H | SH | $CH_2OH$ |
| 85 | H | H | SH | sugar |
| 86 | H | H | SH | C-glycosyl compound |
| 87 | H | H | $OCH_3$ | OH |
| 88 | H | H | $OCH_3$ | D-glucitol |
| 89 | H | H | $OCH_3$ | $SO_3H$ |
| 90 | H | H | $OCH_3$ | $PO_3H_2$ |
| 91 | H | H | $OCH_3$ | CHO |
| 92 | H | H | $OCH_3$ | COOH |
| 93 | H | H | $OCH_3$ | $CH_2OH$ |
| 94 | H | H | $OCH_3$ | sugar |
| 95 | H | H | $OCH_3$ | C-glycosyl compound |
| 96 | H | F | H | OH |
| 97 | H | F | H | D-glucitol |
| 98 | H | F | H | $SO_3H$ |
| 99 | H | F | H | $PO_3H_2$ |
| 100 | H | F | H | CHO |
| 101 | H | F | H | COOH |
| 102 | H | F | H | $CH_2OH$ |
| 103 | H | F | H | sugar |
| 104 | H | F | H | C-glycosyl compound |
| 105 | H | F | OH | CHO |
| 106 | H | F | OH | COOH |
| 107 | H | F | OH | $CH_2OH$ |
| 108 | H | F | OH | sugar |
| 109 | H | F | OH | C-glycosyl compound |
| 110 | H | F | $CH_3$ | OH |
| 111 | H | F | $CH_3$ | D-glucitol |
| 112 | H | F | $CH_3$ | $SO_3H$ |
| 113 | H | F | $CH_3$ | $PO_3H_2$ |
| 114 | H | F | $CH_3$ | CHO |
| 115 | H | F | $CH_3$ | COOH |
| 116 | H | F | $CH_3$ | $CH_2OH$ |
| 117 | H | F | $CH_3$ | sugar |
| 118 | H | F | $CH_3$ | C-glycosyl compound |
| 119 | H | F | Cl | OH |
| 120 | H | F | Cl | D-glucitol |
| 121 | H | F | Cl | $SO_3H$ |
| 122 | H | F | Cl | $PO_3H_2$ |
| 123 | H | F | Cl | CHO |
| 124 | H | F | Cl | COOH |
| 125 | H | F | Cl | $CH_2OH$ |
| 126 | H | F | Cl | sugar |
| 127 | H | F | Cl | C-glycosyl compound |
| 128 | H | F | $B(OH)_2$ | OH |
| 129 | H | F | $B(OH)_2$ | D-glucitol |
| 130 | H | F | $B(OH)_2$ | $SO_3H$ |
| 131 | H | F | $B(OH)_2$ | $PO_3H_2$ |
| 132 | H | F | $B(OH)_2$ | CHO |
| 133 | H | F | $B(OH)_2$ | COOH |
| 134 | H | F | $B(OH)_2$ | $CH_2OH$ |
| 135 | H | F | $B(OH)_2$ | sugar |
| 136 | H | F | $B(OH)_2$ | C-glycosyl compound |
| 137 | H | F | SH | OH |
| 138 | H | F | SH | D-glucitol |
| 139 | H | F | SH | $SO_3H$ |
| 140 | H | F | SH | $PO_3H_2$ |
| 141 | H | F | SH | CHO |
| 142 | H | F | SH | COOH |
| 143 | H | F | SH | $CH_2OH$ |
| 144 | H | F | SH | sugar |
| 145 | H | F | SH | C-glycosyl compound |
| 146 | H | F | $OCH_3$ | OH |
| 147 | H | F | $OCH_3$ | D-glucitol |
| 148 | H | F | $OCH_3$ | $SO_3H$ |
| 149 | H | F | $OCH_3$ | $PO_3H_2$ |
| 150 | H | F | $OCH_3$ | CHO |
| 151 | H | F | $OCH_3$ | COOH |
| 152 | H | F | $OCH_3$ | $CH_2OH$ |
| 153 | H | F | $OCH_3$ | sugar |
| 154 | H | F | $OCH_3$ | C-glycosyl compound |
| 155 | H | Cl | H | OH |
| 156 | H | Cl | H | D-glucitol |
| 157 | H | Cl | H | $SO_3H$ |
| 158 | H | Cl | H | $PO_3H_2$ |
| 159 | H | Cl | H | CHO |
| 160 | H | Cl | H | COOH |
| 161 | H | Cl | H | $CH_2OH$ |
| 162 | H | Cl | H | sugar |
| 163 | H | Cl | H | C-glycosyl compound |
| 164 | H | Cl | OH | CHO |
| 165 | H | Cl | OH | COOH |
| 166 | H | Cl | OH | $CH_2OH$ |
| 167 | H | Cl | OH | sugar |
| 168 | H | Cl | OH | C-glycosyl compound |
| 169 | H | Cl | $CH_3$ | OH |
| 170 | H | Cl | $CH_3$ | D-glucitol |
| 171 | H | Cl | $CH_3$ | $SO_3H$ |
| 172 | H | Cl | $CH_3$ | $PO_3H_2$ |
| 173 | H | Cl | $CH_3$ | CHO |
| 174 | H | Cl | $CH_3$ | COOH |
| 175 | H | Cl | $CH_3$ | $CH_2OH$ |

TABLE 3-continued

| Row | R1 | R2 | R4 | R5 |
|---|---|---|---|---|
| 176 | H | Cl | CH$_3$ | sugar |
| 177 | H | Cl | CH$_3$ | C-glycosyl compound |
| 178 | H | Cl | Cl | OH |
| 179 | H | Cl | Cl | D-glucitol |
| 180 | H | Cl | Cl | SO$_3$H |
| 181 | H | Cl | Cl | PO$_3$H$_2$ |
| 182 | H | Cl | Cl | CHO |
| 183 | H | Cl | Cl | COOH |
| 184 | H | Cl | Cl | CH$_2$OH |
| 185 | H | Cl | Cl | sugar |
| 186 | H | Cl | Cl | C-glycosyl compound |
| 187 | H | Cl | B(OH)$_2$ | OH |
| 188 | H | Cl | B(OH)$_2$ | D-glucitol |
| 189 | H | Cl | B(OH)$_2$ | SO$_3$H |
| 190 | H | Cl | B(OH)$_2$ | PO$_3$H$_2$ |
| 191 | H | Cl | B(OH)$_2$ | CHO |
| 192 | H | Cl | B(OH)$_2$ | COOH |
| 193 | H | Cl | B(OH)$_2$ | CH$_2$OH |
| 194 | H | Cl | B(OH)$_2$ | sugar |
| 195 | H | Cl | B(OH)$_2$ | C-glycosyl compound |
| 196 | H | Cl | SH | OH |
| 197 | H | Cl | SH | D-glucitol |
| 198 | H | Cl | SH | SO$_3$H |
| 199 | H | Cl | SH | PO$_3$H$_2$ |
| 200 | H | Cl | SH | CHO |
| 201 | H | Cl | SH | COOH |
| 202 | H | Cl | SH | CH$_2$OH |
| 203 | H | Cl | SH | sugar |
| 204 | H | Cl | SH | C-glycosyl compound |
| 205 | H | Cl | OCH$_3$ | OH |
| 206 | H | Cl | OCH$_3$ | D-glucitol |
| 207 | H | Cl | OCH$_3$ | SO$_3$H |
| 208 | H | Cl | OCH$_3$ | PO$_3$H$_2$ |
| 209 | H | Cl | OCH$_3$ | CHO |
| 210 | H | Cl | OCH$_3$ | COOH |
| 211 | H | Cl | OCH$_3$ | CH$_2$OH |
| 212 | H | Cl | OCH$_3$ | sugar |
| 213 | H | Cl | OCH$_3$ | C-glycosyl compound |
| 214 | H | CN | H | OH |
| 215 | H | CN | H | D-glucitol |
| 216 | H | CN | H | SO$_3$H |
| 217 | H | CN | H | PO$_3$H$_2$ |
| 218 | H | CN | H | CHO |
| 219 | H | CN | H | COOH |
| 220 | H | CN | H | CH$_2$OH |
| 221 | H | CN | H | sugar |
| 222 | H | CN | H | C-glycosyl compound |
| 223 | H | CN | OH | OH |
| 224 | H | CN | OH | D-glucitol |
| 225 | H | CN | OH | SO$_3$H |
| 226 | H | CN | OH | PO$_3$H$_2$ |
| 227 | H | CN | OH | CHO |
| 228 | H | CN | OH | COOH |
| 229 | H | CN | OH | CH$_2$OH |
| 230 | H | CN | OH | sugar |
| 231 | H | CN | OH | C-glycosyl compound |
| 232 | H | CN | CH$_3$ | OH |
| 233 | H | CN | CH$_3$ | D-glucitol |
| 234 | H | CN | CH$_3$ | SO$_3$H |
| 235 | H | CN | CH$_3$ | PO$_3$H$_2$ |
| 236 | H | CN | CH$_3$ | CHO |
| 237 | H | CN | CH$_3$ | COOH |
| 238 | H | CN | CH$_3$ | CH$_2$OH |
| 239 | H | CN | CH$_3$ | sugar |
| 240 | H | CN | CH$_3$ | C-glycosyl compound |
| 241 | H | CN | Cl | OH |
| 242 | H | CN | Cl | D-glucitol |
| 243 | H | CN | Cl | SO$_3$H |
| 244 | H | CN | Cl | PO$_3$H$_2$ |
| 245 | H | CN | Cl | CHO |
| 246 | H | CN | Cl | COOH |
| 247 | H | CN | Cl | CH$_2$OH |
| 248 | H | CN | Cl | sugar |
| 249 | H | CN | Cl | C-glycosyl compound |
| 250 | H | CN | B(OH)$_2$ | OH |
| 251 | H | CN | B(OH)$_2$ | D-glucitol |
| 252 | H | CN | B(OH)$_2$ | SO$_3$H |
| 253 | H | CN | B(OH)$_2$ | PO$_3$H$_2$ |
| 254 | H | CN | B(OH)$_2$ | CHO |
| 255 | H | CN | B(OH)$_2$ | COOH |
| 256 | H | CN | B(OH)$_2$ | CH$_2$OH |
| 257 | H | CN | B(OH)$_2$ | sugar |
| 258 | H | CN | B(OH)$_2$ | C-glycosyl compound |
| 259 | H | CN | SH | OH |
| 260 | H | CN | SH | D-glucitol |
| 261 | H | CN | SH | SO$_3$H |
| 262 | H | CN | SH | PO$_3$H$_2$ |
| 263 | H | CN | SH | CHO |
| 264 | H | CN | SH | COOH |
| 265 | H | CN | SH | CH$_2$OH |
| 266 | H | CN | SH | sugar |
| 267 | H | CN | SH | C-glycosyl compound |
| 268 | H | CN | OCH$_3$ | OH |
| 269 | H | CN | OCH$_3$ | D-glucitol |
| 270 | H | CN | OCH$_3$ | SO$_3$H |
| 271 | H | CN | OCH$_3$ | PO$_3$H$_2$ |
| 272 | H | CN | OCH$_3$ | CHO |
| 273 | H | CN | OCH$_3$ | COOH |
| 274 | H | CN | OCH$_3$ | CH$_2$OH |
| 275 | H | CN | OCH$_3$ | sugar |
| 276 | H | CN | OCH$_3$ | C-glycosyl compound |
| 277 | H | CH$_3$[a] | H | OH |
| 278 | H | CH$_3$[a] | H | D-glucitol |
| 279 | H | CH$_3$[a] | H | SO$_3$H |
| 280 | H | CH$_3$[a] | H | PO$_3$H$_2$ |
| 281 | H | CH$_3$[a] | H | CHO |
| 282 | H | CH$_3$[a] | H | COOH |
| 283 | H | CH$_3$[a] | H | CH$_2$OH |
| 284 | H | CH$_3$[a] | H | sugar |
| 285 | H | CH$_3$[a] | H | C-glycosyl compound |
| 286 | H | CH$_3$[a] | OH | OH |
| 287 | H | CH$_3$[a] | OH | D-glucitol |
| 288 | H | CH$_3$[a] | OH | SO$_3$H |
| 289 | H | CH$_3$[a] | OH | PO$_3$H$_2$ |
| 290 | H | CH$_3$[a] | OH | CHO |
| 291 | H | CH$_3$[a] | OH | COOH |
| 292 | H | CH$_3$[a] | OH | CH$_2$OH |
| 293 | H | CH$_3$[a] | OH | sugar |
| 294 | H | CH$_3$[a] | OH | C-glycosyl compound |
| 295 | H | CH$_3$[a] | CH$_3$ | OH |
| 296 | H | CH$_3$[a] | CH$_3$ | D-glucitol |
| 297 | H | CH$_3$[a] | CH$_3$ | SO$_3$H |
| 298 | H | CH$_3$[a] | CH$_3$ | PO$_3$H$_2$ |
| 299 | H | CH$_3$[a] | CH$_3$ | CHO |
| 300 | H | CH$_3$[a] | CH$_3$ | COOH |
| 301 | H | CH$_3$[a] | CH$_3$ | CH$_2$OH |
| 302 | H | CH$_3$[a] | CH$_3$ | sugar |
| 303 | H | CH$_3$[a] | CH$_3$ | C-glycosyl compound |
| 304 | H | CH$_3$[a] | Cl | OH |
| 305 | H | CH$_3$[a] | Cl | D-glucitol |
| 306 | H | CH$_3$[a] | Cl | SO$_3$H |
| 307 | H | CH$_3$[a] | Cl | PO$_3$H$_2$ |
| 308 | H | CH$_3$[a] | Cl | CHO |
| 309 | H | CH$_3$[a] | Cl | COOH |
| 310 | H | CH$_3$[a] | Cl | CH$_2$OH |
| 311 | H | CH$_3$[a] | Cl | sugar |
| 312 | H | CH$_3$[a] | Cl | C-glycosyl compound |
| 313 | H | CH$_3$[a] | B(OH)$_2$ | OH |
| 314 | H | CH$_3$[a] | B(OH)$_2$ | D-glucitol |
| 315 | H | CH$_3$[a] | B(OH)$_2$ | SO$_3$H |
| 316 | H | CH$_3$[a] | B(OH)$_2$ | PO$_3$H$_2$ |
| 317 | H | CH$_3$[a] | B(OH)$_2$ | CHO |
| 318 | H | CH$_3$[a] | B(OH)$_2$ | COOH |
| 319 | H | CH$_3$[a] | B(OH)$_2$ | CH$_2$OH |
| 320 | H | CH$_3$[a] | B(OH)$_2$ | sugar |
| 321 | H | CH$_3$[a] | B(OH)$_2$ | C-glycosyl compound |
| 322 | H | CH$_3$[a] | SH | OH |
| 323 | H | CH$_3$[a] | SH | D-glucitol |
| 324 | H | CH$_3$[a] | SH | SO$_3$H |
| 325 | H | CH$_3$[a] | SH | PO$_3$H$_2$ |
| 326 | H | CH$_3$[a] | SH | CHO |
| 327 | H | CH$_3$[a] | SH | COOH |
| 328 | H | CH$_3$[a] | SH | CH$_2$OH |
| 329 | H | CH$_3$[a] | SH | sugar |

TABLE 3-continued

| Row | R1 | R2 | R4 | R5 |
|---|---|---|---|---|
| 330 | H | CH₃[a] | SH | C-glycosyl compound |
| 331 | H | CH₃[a] | OCH₃ | OH |
| 332 | H | CH₃[a] | OCH₃ | D-glucitol |
| 333 | H | CH₃[a] | OCH₃ | SO₃H |
| 334 | H | CH₃[a] | OCH₃ | PO₃H₂ |
| 335 | H | CH₃[a] | OCH₃ | CHO |
| 336 | H | CH₃[a] | OCH₃ | COOH |
| 337 | H | CH₃[a] | OCH₃ | CH₂OH |
| 338 | H | CH₃[a] | OCH₃ | sugar |
| 339 | H | CH₃[a] | OCH₃ | C-glycosyl compound |
| 340 | H | OCH3[b] | H | OH |
| 341 | H | OCH3[b] | H | D-glucitol |
| 342 | H | OCH3[b] | H | SO₃H |
| 343 | H | OCH3[b] | H | PO₃H₂ |
| 344 | H | OCH3[b] | H | CHO |
| 345 | H | OCH3[b] | H | COOH |
| 346 | H | OCH3[b] | H | CH₂OH |
| 347 | H | OCH3[b] | H | sugar |
| 348 | H | OCH3[b] | H | C-glycosyl compound |
| 349 | H | OCH3[b] | OH | OH |
| 350 | H | OCH3[b] | OH | D-glucitol |
| 351 | H | OCH3[b] | OH | SO₃H |
| 352 | H | OCH3[b] | OH | PO₃H₂ |
| 353 | H | OCH3[b] | OH | CHO |
| 354 | H | OCH3[b] | OH | COOH |
| 355 | H | OCH3[b] | OH | CH₂OH |
| 356 | H | OCH3[b] | OH | sugar |
| 357 | H | OCH3[b] | OH | C-glycosyl compound |
| 358 | H | OCH3[b] | CH₃ | OH |
| 359 | H | OCH3[b] | CH₃ | D-glucitol |
| 360 | H | OCH3[b] | CH₃ | SO₃H |
| 361 | H | OCH3[b] | CH₃ | PO₃H₂ |
| 362 | H | OCH3[b] | CH₃ | CHO |
| 363 | H | OCH3[b] | CH₃ | COOH |
| 364 | H | OCH3[b] | CH₃ | CH₂OH |
| 365 | H | OCH3[b] | CH₃ | sugar |
| 366 | H | OCH3[b] | CH₃ | C-glycosyl compound |
| 367 | H | OCH3[b] | Cl | OH |
| 368 | H | OCH3[b] | Cl | D-glucitol |
| 369 | H | OCH3[b] | Cl | SO₃H |
| 370 | H | OCH3[b] | Cl | PO₃H₂ |
| 371 | H | OCH3[b] | Cl | CHO |
| 372 | H | OCH3[b] | Cl | COOH |
| 373 | H | OCH3[b] | Cl | CH₂OH |
| 374 | H | OCH3[b] | Cl | sugar |
| 375 | H | OCH3[b] | Cl | C-glycosyl compound |
| 376 | H | OCH3[b] | B(OH)₂ | OH |
| 377 | H | OCH3[b] | B(OH)₂ | D-glucitol |
| 378 | H | OCH3[b] | B(OH)₂ | SO₃H |
| 379 | H | OCH3[b] | B(OH)₂ | PO₃H₂ |
| 380 | H | OCH3[b] | B(OH)₂ | CHO |
| 381 | H | OCH3[b] | B(OH)₂ | COOH |
| 382 | H | OCH3[b] | B(OH)₂ | CH₂OH |
| 383 | H | OCH3[b] | B(OH)₂ | sugar |
| 384 | H | OCH3[b] | B(OH)₂ | C-glycosyl compound |
| 385 | H | OCH3[b] | SH | OH |
| 386 | H | OCH3[b] | SH | D-glucitol |
| 387 | H | OCH3[b] | SH | SO₃H |
| 388 | H | OCH3[b] | SH | PO₃H₂ |
| 389 | H | OCH3[b] | SH | CHO |
| 390 | H | OCH3[b] | SH | COOH |
| 391 | H | OCH3[b] | SH | CH₂OH |
| 392 | H | OCH3[b] | SH | sugar |
| 393 | H | OCH3[b] | SH | C-glycosyl compound |
| 394 | H | OCH3[b] | OCH₃ | OH |
| 395 | H | OCH3[b] | OCH₃ | D-glucitol |
| 396 | H | OCH3[b] | OCH₃ | SO₃H |
| 397 | H | OCH3[b] | OCH₃ | PO₃H₂ |
| 398 | H | OCH3[b] | OCH₃ | CHO |
| 399 | H | OCH3[b] | OCH₃ | COOH |
| 400 | H | OCH3[b] | OCH₃ | CH₂OH |
| 401 | H | OCH3[b] | OCH₃ | sugar |
| 402 | H | OCH3[b] | OCH₃ | C-glycosyl compound |
| 403 | F | H | H | OH |
| 404 | F | H | H | D-glucitol |
| 405 | F | H | H | SO₃H |
| 406 | F | H | H | PO₃H₂ |
| 407 | F | H | H | CHO |
| 408 | F | H | H | COOH |
| 409 | F | H | H | CH₂OH |
| 410 | F | H | H | sugar |
| 411 | F | H | H | C-glycosyl compound |
| 412 | F | H | OH | CHO |
| 413 | F | H | OH | COOH |
| 414 | F | H | OH | CH₂OH |
| 415 | F | H | OH | sugar |
| 416 | F | H | OH | C-glycosyl compound |
| 417 | F | H | CH₃ | OH |
| 418 | F | H | CH₃ | D-glucitol |
| 419 | F | H | CH₃ | SO₃H |
| 420 | F | H | CH₃ | PO₃H₂ |
| 421 | F | H | CH₃ | CHO |
| 422 | F | H | CH₃ | COOH |
| 423 | F | H | CH₃ | CH₂OH |
| 424 | F | H | CH₃ | sugar |
| 425 | F | H | CH₃ | C-glycosyl compound |
| 426 | F | H | Cl | OH |
| 427 | F | H | Cl | D-glucitol |
| 428 | F | H | Cl | SO₃H |
| 429 | F | H | Cl | PO₃H₂ |
| 430 | F | H | Cl | CHO |
| 431 | F | H | Cl | COOH |
| 432 | F | H | Cl | CH₂OH |
| 433 | F | H | Cl | sugar |
| 434 | F | H | Cl | C-glycosyl compound |
| 435 | F | H | B(OH)₂ | OH |
| 436 | F | H | B(OH)₂ | D-glucitol |
| 437 | F | H | B(OH)₂ | SO₃H |
| 438 | F | H | B(OH)₂ | PO₃H₂ |
| 439 | F | H | B(OH)₂ | CHO |
| 440 | F | H | B(OH)₂ | COOH |
| 441 | F | H | B(OH)₂ | CH₂OH |
| 442 | F | H | B(OH)₂ | sugar |
| 443 | F | H | B(OH)₂ | C-glycosyl compound |
| 444 | F | H | SH | OH |
| 445 | F | H | SH | D-glucitol |
| 446 | F | H | SH | SO₃H |
| 447 | F | H | SH | PO₃H₂ |
| 448 | F | H | SH | CHO |
| 449 | F | H | SH | COOH |
| 450 | F | H | SH | CH₂OH |
| 451 | F | H | SH | sugar |
| 452 | F | H | SH | C-glycosyl compound |
| 453 | F | H | OCH₃ | OH |
| 454 | F | H | OCH₃ | D-glucitol |
| 455 | F | H | OCH₃ | SO₃H |
| 456 | F | H | OCH₃ | PO₃H₂ |
| 457 | F | H | OCH₃ | CHO |
| 458 | F | H | OCH₃ | COOH |
| 459 | F | H | OCH₃ | CH₂OH |
| 460 | F | H | OCH₃ | sugar |
| 461 | F | H | OCH₃ | C-glycosyl compound |
| 462 | F | F | H | OH |
| 463 | F | F | H | D-glucitol |
| 464 | F | F | H | SO₃H |
| 465 | F | F | H | PO₃H₂ |
| 466 | F | F | H | CHO |
| 467 | F | F | H | COOH |
| 468 | F | F | H | CH₂OH |
| 469 | F | F | H | sugar |
| 470 | F | F | H | C-glycosyl compound |
| 471 | F | F | OH | CHO |
| 472 | F | F | OH | COOH |
| 473 | F | F | OH | CH₂OH |
| 474 | F | F | OH | sugar |
| 475 | F | F | OH | C-glycosyl compound |
| 476 | F | F | CH₃ | OH |
| 477 | F | F | CH₃ | D-glucitol |
| 478 | F | F | CH₃ | SO₃H |
| 479 | F | F | CH₃ | PO₃H₂ |
| 480 | F | F | CH₃ | CHO |
| 481 | F | F | CH₃ | COOH |
| 482 | F | F | CH₃ | CH₂OH |
| 483 | F | F | CH₃ | sugar |

TABLE 3-continued

| Row | R1 | R2 | R4 | R5 |
|---|---|---|---|---|
| 484 | F | F | CH$_3$ | C-glycosyl compound |
| 485 | F | F | Cl | OH |
| 486 | F | F | Cl | D-glucitol |
| 487 | F | F | Cl | SO$_3$H |
| 488 | F | F | Cl | PO$_3$H$_2$ |
| 489 | F | F | Cl | CHO |
| 490 | F | F | Cl | COOH |
| 491 | F | F | Cl | CH$_2$OH |
| 492 | F | F | Cl | sugar |
| 493 | F | F | Cl | C-glycosyl compound |
| 494 | F | F | B(OH)$_2$ | OH |
| 495 | F | F | B(OH)$_2$ | D-glucitol |
| 496 | F | F | B(OH)$_2$ | SO$_3$H |
| 497 | F | F | B(OH)$_2$ | PO$_3$H$_2$ |
| 498 | F | F | B(OH)$_2$ | CHO |
| 499 | F | F | B(OH)$_2$ | COOH |
| 500 | F | F | B(OH)$_2$ | CH$_2$OH |
| 501 | F | F | B(OH)$_2$ | sugar |
| 502 | F | F | B(OH)$_2$ | C-glycosyl compound |
| 503 | F | F | SH | OH |
| 504 | F | F | SH | D-glucitol |
| 505 | F | F | SH | SO$_3$H |
| 506 | F | F | SH | PO$_3$H$_2$ |
| 507 | F | F | SH | CHO |
| 508 | F | F | SH | COOH |
| 509 | F | F | SH | CH$_2$OH |
| 510 | F | F | SH | sugar |
| 511 | F | F | SH | C-glycosyl compound |
| 512 | F | F | OCH$_3$ | OH |
| 513 | F | F | OCH$_3$ | D-glucitol |
| 514 | F | F | OCH$_3$ | SO$_3$H |
| 515 | F | F | OCH$_3$ | PO$_3$H$_2$ |
| 516 | F | F | OCH$_3$ | CHO |
| 517 | F | F | OCH$_3$ | COOH |
| 518 | F | F | OCH$_3$ | CH$_2$OH |
| 519 | F | F | OCH$_3$ | sugar |
| 520 | F | F | OCH$_3$ | C-glycosyl compound |
| 521 | F | Cl | H | OH |
| 522 | F | Cl | H | D-glucitol |
| 523 | F | Cl | H | SO$_3$H |
| 524 | F | Cl | H | PO$_3$H$_2$ |
| 525 | F | Cl | H | CHO |
| 526 | F | Cl | H | COOH |
| 527 | F | Cl | H | CH$_2$OH |
| 528 | F | Cl | H | sugar |
| 529 | F | Cl | H | C-glycosyl compound |
| 530 | F | Cl | OH | CHO |
| 531 | F | Cl | OH | COOH |
| 532 | F | Cl | OH | CH$_2$OH |
| 533 | F | Cl | OH | sugar |
| 534 | F | Cl | OH | C-glycosyl compound |
| 535 | F | Cl | CH$_3$ | OH |
| 536 | F | Cl | CH$_3$ | D-glucitol |
| 537 | F | Cl | CH$_3$ | SO$_3$H |
| 538 | F | Cl | CH$_3$ | PO$_3$H$_2$ |
| 539 | F | Cl | CH$_3$ | CHO |
| 540 | F | Cl | CH$_3$ | COOH |
| 541 | F | Cl | CH$_3$ | CH$_2$OH |
| 542 | F | Cl | CH$_3$ | sugar |
| 543 | F | Cl | CH$_3$ | C-glycosyl compound |
| 544 | F | Cl | Cl | OH |
| 545 | F | Cl | Cl | D-glucitol |
| 546 | F | Cl | Cl | SO$_3$H |
| 547 | F | Cl | Cl | PO$_3$H$_2$ |
| 548 | F | Cl | Cl | CHO |
| 549 | F | Cl | Cl | COOH |
| 550 | F | Cl | Cl | CH$_2$OH |
| 551 | F | Cl | Cl | sugar |
| 552 | F | Cl | Cl | C-glycosyl compound |
| 553 | F | Cl | B(OH)$_2$ | OH |
| 554 | F | Cl | B(OH)$_2$ | D-glucitol |
| 555 | F | Cl | B(OH)$_2$ | SO$_3$H |
| 556 | F | Cl | B(OH)$_2$ | PO$_3$H$_2$ |
| 557 | F | Cl | B(OH)$_2$ | CHO |
| 558 | F | Cl | B(OH)$_2$ | COOH |
| 559 | F | Cl | B(OH)$_2$ | CH$_2$OH |
| 560 | F | Cl | B(OH)$_2$ | sugar |
| 561 | F | Cl | B(OH)$_2$ | C-glycosyl compound |
| 562 | F | Cl | SH | OH |
| 563 | F | Cl | SH | D-glucitol |
| 564 | F | Cl | SH | SO$_3$H |
| 565 | F | Cl | SH | PO$_3$H$_2$ |
| 566 | F | Cl | SH | CHO |
| 567 | F | Cl | SH | COOH |
| 568 | F | Cl | SH | CH$_2$OH |
| 569 | F | Cl | SH | sugar |
| 570 | F | Cl | SH | C-glycosyl compound |
| 571 | F | Cl | OCH$_3$ | OH |
| 572 | F | Cl | OCH$_3$ | D-glucitol |
| 573 | F | Cl | OCH$_3$ | SO$_3$H |
| 574 | F | Cl | OCH$_3$ | PO$_3$H$_2$ |
| 575 | F | Cl | OCH$_3$ | CHO |
| 576 | F | Cl | OCH$_3$ | COOH |
| 577 | F | Cl | OCH$_3$ | CH$_2$OH |
| 578 | F | Cl | OCH$_3$ | sugar |
| 579 | F | Cl | OCH$_3$ | C-glycosyl compound |
| 580 | F | CN | H | OH |
| 581 | F | CN | H | D-glucitol |
| 582 | F | CN | H | SO$_3$H |
| 583 | F | CN | H | PO$_3$H$_2$ |
| 584 | F | CN | H | CHO |
| 585 | F | CN | H | COOH |
| 586 | F | CN | H | CH$_2$OH |
| 587 | F | CN | H | sugar |
| 588 | F | CN | H | C-glycosyl compound |
| 589 | F | CN | OH | OH |
| 590 | F | CN | OH | D-glucitol |
| 591 | F | CN | OH | SO$_3$H |
| 592 | F | CN | OH | PO$_3$H$_2$ |
| 593 | F | CN | OH | CHO |
| 594 | F | CN | OH | COOH |
| 595 | F | CN | OH | CH$_2$OH |
| 596 | F | CN | OH | sugar |
| 597 | F | CN | OH | C-glycosyl compound |
| 598 | F | CN | CH$_3$ | OH |
| 599 | F | CN | CH$_3$ | D-glucitol |
| 600 | F | CN | CH$_3$ | SO$_3$H |
| 601 | F | CN | CH$_3$ | PO$_3$H$_2$ |
| 602 | F | CN | CH$_3$ | CHO |
| 603 | F | CN | CH$_3$ | COOH |
| 604 | F | CN | CH$_3$ | CH$_2$OH |
| 605 | F | CN | CH$_3$ | sugar |
| 606 | F | CN | CH$_3$ | C-glycosyl compound |
| 607 | F | CN | Cl | OH |
| 608 | F | CN | Cl | D-glucitol |
| 609 | F | CN | Cl | SO$_3$H |
| 610 | F | CN | Cl | PO$_3$H$_2$ |
| 611 | F | CN | Cl | CHO |
| 612 | F | CN | Cl | COOH |
| 613 | F | CN | Cl | CH$_2$OH |
| 614 | F | CN | Cl | sugar |
| 615 | F | CN | Cl | C-glycosyl compound |
| 616 | F | CN | B(OH)$_2$ | OH |
| 617 | F | CN | B(OH)$_2$ | D-glucitol |
| 618 | F | CN | B(OH)$_2$ | SO$_3$H |
| 619 | F | CN | B(OH)$_2$ | PO$_3$H$_2$ |
| 620 | F | CN | B(OH)$_2$ | CHO |
| 621 | F | CN | B(OH)$_2$ | COOH |
| 622 | F | CN | B(OH)$_2$ | CH$_2$OH |
| 623 | F | CN | B(OH)$_2$ | sugar |
| 624 | F | CN | B(OH)$_2$ | C-glycosyl compound |
| 625 | F | CN | SH | OH |
| 626 | F | CN | SH | D-glucitol |
| 627 | F | CN | SH | SO$_3$H |
| 628 | F | CN | SH | PO$_3$H$_2$ |
| 629 | F | CN | SH | CHO |
| 630 | F | CN | SH | COOH |
| 631 | F | CN | SH | CH$_2$OH |
| 632 | F | CN | SH | sugar |
| 633 | F | CN | SH | C-glycosyl compound |
| 634 | F | CN | OCH$_3$ | OH |
| 635 | F | CN | OCH$_3$ | D-glucitol |
| 636 | F | CN | OCH$_3$ | SO$_3$H |
| 637 | F | CN | OCH$_3$ | PO$_3$H$_2$ |

TABLE 3-continued

| Row | R1 | R2 | R4 | R5 |
|-----|----|----|----|-----|
| 638 | F | CN | OCH$_3$ | CHO |
| 639 | F | CN | OCH$_3$ | COOH |
| 640 | F | CN | OCH$_3$ | CH$_2$OH |
| 641 | F | CN | OCH$_3$ | sugar |
| 642 | F | CN | OCH$_3$ | C-glycosyl compound |
| 643 | F | CH$_3$[a] | H | OH |
| 644 | F | CH$_3$[a] | H | D-glucitol |
| 645 | F | CH$_3$[a] | H | SO$_3$H |
| 646 | F | CH$_3$[a] | H | PO$_3$H$_2$ |
| 647 | F | CH$_3$[a] | H | CHO |
| 648 | F | CH$_3$[a] | H | COOH |
| 649 | F | CH$_3$[a] | H | CH$_2$OH |
| 650 | F | CH$_3$[a] | H | sugar |
| 651 | F | CH$_3$[a] | H | C-glycosyl compound |
| 652 | F | CH$_3$[a] | OH | OH |
| 653 | F | CH$_3$[a] | OH | D-glucitol |
| 654 | F | CH$_3$[a] | OH | SO$_3$H |
| 655 | F | CH$_3$[a] | OH | PO$_3$H$_2$ |
| 656 | F | CH$_3$[a] | OH | CHO |
| 657 | F | CH$_3$[a] | OH | COOH |
| 658 | F | CH$_3$[a] | OH | CH$_2$OH |
| 659 | F | CH$_3$[a] | OH | sugar |
| 660 | F | CH$_3$[a] | OH | C-glycosyl compound |
| 661 | F | CH$_3$[a] | CH$_3$ | OH |
| 662 | F | CH$_3$[a] | CH$_3$ | D-glucitol |
| 663 | F | CH$_3$[a] | CH$_3$ | SO$_3$H |
| 664 | F | CH$_3$[a] | CH$_3$ | PO$_3$H$_2$ |
| 665 | F | CH$_3$[a] | CH$_3$ | CHO |
| 666 | F | CH$_3$[a] | CH$_3$ | COOH |
| 667 | F | CH$_3$[a] | CH$_3$ | CH$_2$OH |
| 668 | F | CH$_3$[a] | CH$_3$ | sugar |
| 669 | F | CH$_3$[a] | CH$_3$ | C-glycosyl compound |
| 670 | F | CH$_3$[a] | Cl | OH |
| 671 | F | CH$_3$[a] | Cl | D-glucitol |
| 672 | F | CH$_3$[a] | Cl | SO$_3$H |
| 673 | F | CH$_3$[a] | Cl | PO$_3$H$_2$ |
| 674 | F | CH$_3$[a] | Cl | CHO |
| 675 | F | CH$_3$[a] | Cl | COOH |
| 676 | F | CH$_3$[a] | Cl | CH$_2$OH |
| 677 | F | CH$_3$[a] | Cl | sugar |
| 678 | F | CH$_3$[a] | Cl | C-glycosyl compound |
| 679 | F | CH$_3$[a] | B(OH)$_2$ | OH |
| 680 | F | CH$_3$[a] | B(OH)$_2$ | D-glucitol |
| 681 | F | CH$_3$[a] | B(OH)$_2$ | SO$_3$H |
| 682 | F | CH$_3$[a] | B(OH)$_2$ | PO$_3$H$_2$ |
| 683 | F | CH$_3$[a] | B(OH)$_2$ | CHO |
| 684 | F | CH$_3$[a] | B(OH)$_2$ | COOH |
| 685 | F | CH$_3$[a] | B(OH)$_2$ | CH$_2$OH |
| 686 | F | CH$_3$[a] | B(OH)$_2$ | sugar |
| 687 | F | CH$_3$[a] | B(OH)$_2$ | C-glycosyl compound |
| 688 | F | CH$_3$[a] | SH | OH |
| 689 | F | CH$_3$[a] | SH | D-glucitol |
| 690 | F | CH$_3$[a] | SH | SO$_3$H |
| 691 | F | CH$_3$[a] | SH | PO$_3$H$_2$ |
| 692 | F | CH$_3$[a] | SH | CHO |
| 693 | F | CH$_3$[a] | SH | COOH |
| 694 | F | CH$_3$[a] | SH | CH$_2$OH |
| 695 | F | CH$_3$[a] | SH | sugar |
| 696 | F | CH$_3$[a] | SH | C-glycosyl compound |
| 697 | F | CH$_3$[a] | OCH$_3$ | OH |
| 698 | F | CH$_3$[a] | OCH$_3$ | D-glucitol |
| 699 | F | CH$_3$[a] | OCH$_3$ | SO$_3$H |
| 700 | F | CH$_3$[a] | OCH$_3$ | PO$_3$H$_2$ |
| 701 | F | CH$_3$[a] | OCH$_3$ | CHO |
| 702 | F | CH$_3$[a] | OCH$_3$ | COOH |
| 703 | F | CH$_3$[a] | OCH$_3$ | CH$_2$OH |
| 704 | F | CH$_3$[a] | OCH$_3$ | sugar |
| 705 | F | CH$_3$[a] | OCH$_3$ | C-glycosyl compound |
| 706 | F | OCH3[b] | H | OH |
| 707 | F | OCH3[b] | H | D-glucitol |
| 708 | F | OCH3[b] | H | SO$_3$H |
| 709 | F | OCH3[b] | H | PO$_3$H$_2$ |
| 710 | F | OCH3[b] | H | CHO |
| 711 | F | OCH3[b] | H | COOH |
| 712 | F | OCH3[b] | H | CH$_2$OH |
| 713 | F | OCH3[b] | H | sugar |
| 714 | F | OCH3[b] | H | C-glycosyl compound |
| 715 | F | OCH3[b] | OH | OH |
| 716 | F | OCH3[b] | OH | D-glucitol |
| 717 | F | OCH3[b] | OH | SO$_3$H |
| 718 | F | OCH3[b] | OH | PO$_3$H$_2$ |
| 719 | F | OCH3[b] | OH | CHO |
| 720 | F | OCH3[b] | OH | COOH |
| 721 | F | OCH3[b] | OH | CH$_2$OH |
| 722 | F | OCH3[b] | OH | sugar |
| 723 | F | OCH3[b] | OH | C-glycosyl compound |
| 724 | F | OCH3[b] | CH$_3$ | OH |
| 725 | F | OCH3[b] | CH$_3$ | D-glucitol |
| 726 | F | OCH3[b] | CH$_3$ | SO$_3$H |
| 727 | F | OCH3[b] | CH$_3$ | PO$_3$H$_2$ |
| 728 | F | OCH3[b] | CH$_3$ | CHO |
| 729 | F | OCH3[b] | CH$_3$ | COOH |
| 730 | F | OCH3[b] | CH$_3$ | CH$_2$OH |
| 731 | F | OCH3[b] | CH$_3$ | sugar |
| 732 | F | OCH3[b] | CH$_3$ | C-glycosyl compound |
| 733 | F | OCH3[b] | Cl | OH |
| 734 | F | OCH3[b] | Cl | D-glucitol |
| 735 | F | OCH3[b] | Cl | SO$_3$H |
| 736 | F | OCH3[b] | Cl | PO$_3$H$_2$ |
| 737 | F | OCH3[b] | Cl | CHO |
| 738 | F | OCH3[b] | Cl | COOH |
| 739 | F | OCH3[b] | Cl | CH$_2$OH |
| 740 | F | OCH3[b] | Cl | sugar |
| 741 | F | OCH3[b] | Cl | C-glycosyl compound |
| 742 | F | OCH3[b] | B(OH)$_2$ | OH |
| 743 | F | OCH3[b] | B(OH)$_2$ | D-glucitol |
| 744 | F | OCH3[b] | B(OH)$_2$ | SO$_3$H |
| 745 | F | OCH3[b] | B(OH)$_2$ | PO$_3$H$_2$ |
| 746 | F | OCH3[b] | B(OH)$_2$ | CHO |
| 747 | F | OCH3[b] | B(OH)$_2$ | COOH |
| 748 | F | OCH3[b] | B(OH)$_2$ | CH$_2$OH |
| 749 | F | OCH3[b] | B(OH)$_2$ | sugar |
| 750 | F | OCH3[b] | B(OH)$_2$ | C-glycosyl compound |
| 751 | F | OCH3[b] | SH | OH |
| 752 | F | OCH3[b] | SH | D-glucitol |
| 753 | F | OCH3[b] | SH | SO$_3$H |
| 754 | F | OCH3[b] | SH | PO$_3$H$_2$ |
| 755 | F | OCH3[b] | SH | CHO |
| 756 | F | OCH3[b] | SH | COOH |
| 757 | F | OCH3[b] | SH | CH$_2$OH |
| 758 | F | OCH3[b] | SH | sugar |
| 759 | F | OCH3[b] | SH | C-glycosyl compound |
| 760 | F | OCH3[b] | OCH$_3$ | OH |
| 761 | F | OCH3[b] | OCH$_3$ | D-glucitol |
| 762 | F | OCH3[b] | OCH$_3$ | SO$_3$H |
| 763 | F | OCH3[b] | OCH$_3$ | PO$_3$H$_2$ |
| 764 | F | OCH3[b] | OCH$_3$ | CHO |
| 765 | F | OCH3[b] | OCH$_3$ | COOH |
| 766 | F | OCH3[b] | OCH$_3$ | CH$_2$OH |
| 767 | F | OCH3[b] | OCH$_3$ | sugar |
| 768 | F | OCH3[b] | OCH$_3$ | C-glycosyl compound |
| 769 | Cl | H | H | OH |
| 770 | Cl | H | H | D-glucitol |
| 771 | Cl | H | H | SO$_3$H |
| 772 | Cl | H | H | PO$_3$H$_2$ |
| 773 | Cl | H | H | CHO |
| 774 | Cl | H | H | COOH |
| 775 | Cl | H | H | CH$_2$OH |
| 776 | Cl | H | H | sugar |
| 777 | Cl | H | H | C-glycosyl compound |
| 778 | Cl | H | OH | CHO |
| 779 | Cl | H | OH | COOH |
| 780 | Cl | H | OH | CH$_2$OH |
| 781 | Cl | H | OH | sugar |
| 782 | Cl | H | OH | C-glycosyl compound |
| 783 | Cl | H | CH$_3$ | OH |
| 784 | Cl | H | CH$_3$ | D-glucitol |
| 785 | Cl | H | CH$_3$ | SO$_3$H |
| 786 | Cl | H | CH$_3$ | PO$_3$H$_2$ |
| 787 | Cl | H | CH$_3$ | CHO |
| 788 | Cl | H | CH$_3$ | COOH |
| 789 | Cl | H | CH$_3$ | CH$_2$OH |
| 790 | Cl | H | CH$_3$ | sugar |
| 791 | Cl | H | CH$_3$ | C-glycosyl compound |

TABLE 3-continued

| Row | R1 | R2 | R4 | R5 |
|---|---|---|---|---|
| 792 | Cl | H | Cl | OH |
| 793 | Cl | H | Cl | D-glucitol |
| 794 | Cl | H | Cl | $SO_3H$ |
| 795 | Cl | H | Cl | $PO_3H_2$ |
| 796 | Cl | H | Cl | CHO |
| 797 | Cl | H | Cl | COOH |
| 798 | Cl | H | Cl | $CH_2OH$ |
| 799 | Cl | H | Cl | sugar |
| 800 | Cl | H | Cl | C-glycosyl compound |
| 801 | Cl | H | $B(OH)_2$ | OH |
| 802 | Cl | H | $B(OH)_2$ | D-glucitol |
| 803 | Cl | H | $B(OH)_2$ | $SO_3H$ |
| 804 | Cl | H | $B(OH)_2$ | $PO_3H_2$ |
| 805 | Cl | H | $B(OH)_2$ | CHO |
| 806 | Cl | H | $B(OH)_2$ | COOH |
| 807 | Cl | H | $B(OH)_2$ | $CH_2OH$ |
| 808 | Cl | H | $B(OH)_2$ | sugar |
| 809 | Cl | H | $B(OH)_2$ | C-glycosyl compound |
| 810 | Cl | H | SH | OH |
| 811 | Cl | H | SH | D-glucitol |
| 812 | Cl | H | SH | $SO_3H$ |
| 813 | Cl | H | SH | $PO_3H_2$ |
| 814 | Cl | H | SH | CHO |
| 815 | Cl | H | SH | COOH |
| 816 | Cl | H | SH | $CH_2OH$ |
| 817 | Cl | H | SH | sugar |
| 818 | Cl | H | SH | C-glycosyl compound |
| 819 | Cl | H | $OCH_3$ | OH |
| 820 | Cl | H | $OCH_3$ | D-glucitol |
| 821 | Cl | H | $OCH_3$ | $SO_3H$ |
| 822 | Cl | H | $OCH_3$ | $PO_3H_2$ |
| 823 | Cl | H | $OCH_3$ | CHO |
| 824 | Cl | H | $OCH_3$ | COOH |
| 825 | Cl | H | $OCH_3$ | $CH_2OH$ |
| 826 | Cl | H | $OCH_3$ | sugar |
| 827 | Cl | H | $OCH_3$ | C-glycosyl compound |
| 828 | Cl | F | H | OH |
| 829 | Cl | F | H | D-glucitol |
| 830 | Cl | F | H | $SO_3H$ |
| 831 | Cl | F | H | $PO_3H_2$ |
| 832 | Cl | F | H | CHO |
| 833 | Cl | F | H | COOH |
| 834 | Cl | F | H | $CH_2OH$ |
| 835 | Cl | F | H | sugar |
| 836 | Cl | F | H | C-glycosyl compound |
| 837 | Cl | F | OH | CHO |
| 838 | Cl | F | OH | COOH |
| 839 | Cl | F | OH | $CH_2OH$ |
| 840 | Cl | F | OH | sugar |
| 841 | Cl | F | OH | C-glycosyl compound |
| 842 | Cl | F | $CH_3$ | OH |
| 843 | Cl | F | $CH_3$ | D-glucitol |
| 844 | Cl | F | $CH_3$ | $SO_3H$ |
| 845 | Cl | F | $CH_3$ | $PO_3H_2$ |
| 846 | Cl | F | $CH_3$ | CHO |
| 847 | Cl | F | $CH_3$ | COOH |
| 848 | Cl | F | $CH_3$ | $CH_2OH$ |
| 849 | Cl | F | $CH_3$ | sugar |
| 850 | Cl | F | $CH_3$ | C-glycosyl compound |
| 851 | Cl | F | Cl | OH |
| 852 | Cl | F | Cl | D-glucitol |
| 853 | Cl | F | Cl | $SO_3H$ |
| 854 | Cl | F | Cl | $PO_3H_2$ |
| 855 | Cl | F | Cl | CHO |
| 856 | Cl | F | Cl | COOH |
| 857 | Cl | F | Cl | $CH_2OH$ |
| 858 | Cl | F | Cl | sugar |
| 859 | Cl | F | Cl | C-glycosyl compound |
| 860 | Cl | F | $B(OH)_2$ | OH |
| 861 | Cl | F | $B(OH)_2$ | D-glucitol |
| 862 | Cl | F | $B(OH)_2$ | $SO_3H$ |
| 863 | Cl | F | $B(OH)_2$ | $PO_3H_2$ |
| 864 | Cl | F | $B(OH)_2$ | CHO |
| 865 | Cl | F | $B(OH)_2$ | COOH |
| 866 | Cl | F | $B(OH)_2$ | $CH_2OH$ |
| 867 | Cl | F | $B(OH)_2$ | sugar |
| 868 | Cl | F | $B(OH)_2$ | C-glycosyl compound |
| 869 | Cl | F | SH | OH |
| 870 | Cl | F | SH | D-glucitol |
| 871 | Cl | F | SH | $SO_3H$ |
| 872 | Cl | F | SH | $PO_3H_2$ |
| 873 | Cl | F | SH | CHO |
| 874 | Cl | F | SH | COOH |
| 875 | Cl | F | SH | $CH_2OH$ |
| 876 | Cl | F | SH | sugar |
| 877 | Cl | F | SH | C-glycosyl compound |
| 878 | Cl | F | $OCH_3$ | OH |
| 879 | Cl | F | $OCH_3$ | D-glucitol |
| 880 | Cl | F | $OCH_3$ | $SO_3H$ |
| 881 | Cl | F | $OCH_3$ | $PO_3H_2$ |
| 882 | Cl | F | $OCH_3$ | CHO |
| 883 | Cl | F | $OCH_3$ | COOH |
| 884 | Cl | F | $OCH_3$ | $CH_2OH$ |
| 885 | Cl | F | $OCH_3$ | sugar |
| 886 | Cl | F | $OCH_3$ | C-glycosyl compound |
| 887 | Cl | Cl | H | OH |
| 888 | Cl | Cl | H | D-glucitol |
| 889 | Cl | Cl | H | $SO_3H$ |
| 890 | Cl | Cl | H | $PO_3H_2$ |
| 891 | Cl | Cl | H | CHO |
| 892 | Cl | Cl | H | COOH |
| 893 | Cl | Cl | H | $CH_2OH$ |
| 894 | Cl | Cl | H | sugar |
| 895 | Cl | Cl | H | C-glycosyl compound |
| 896 | Cl | Cl | OH | CHO |
| 897 | Cl | Cl | OH | COOH |
| 898 | Cl | Cl | OH | $CH_2OH$ |
| 899 | Cl | Cl | OH | sugar |
| 900 | Cl | Cl | OH | C-glycosyl compound |
| 901 | Cl | Cl | $CH_3$ | OH |
| 902 | Cl | Cl | $CH_3$ | D-glucitol |
| 903 | Cl | Cl | $CH_3$ | $SO_3H$ |
| 904 | Cl | Cl | $CH_3$ | $PO_3H_2$ |
| 905 | Cl | Cl | $CH_3$ | CHO |
| 906 | Cl | Cl | $CH_3$ | COOH |
| 907 | Cl | Cl | $CH_3$ | $CH_2OH$ |
| 908 | Cl | Cl | $CH_3$ | sugar |
| 909 | Cl | Cl | $CH_3$ | C-glycosyl compound |
| 910 | Cl | Cl | Cl | OH |
| 911 | Cl | Cl | Cl | D-glucitol |
| 912 | Cl | Cl | Cl | $SO_3H$ |
| 913 | Cl | Cl | Cl | $PO_3H_2$ |
| 914 | Cl | Cl | Cl | CHO |
| 915 | Cl | Cl | Cl | COOH |
| 916 | Cl | Cl | Cl | $CH_2OH$ |
| 917 | Cl | Cl | Cl | sugar |
| 918 | Cl | Cl | Cl | C-glycosyl compound |
| 919 | Cl | Cl | $B(OH)_2$ | OH |
| 920 | Cl | Cl | $B(OH)_2$ | D-glucitol |
| 921 | Cl | Cl | $B(OH)_2$ | $SO_3H$ |
| 922 | Cl | Cl | $B(OH)_2$ | $PO_3H_2$ |
| 923 | Cl | Cl | $B(OH)_2$ | CHO |
| 924 | Cl | Cl | $B(OH)_2$ | COOH |
| 925 | Cl | Cl | $B(OH)_2$ | $CH_2OH$ |
| 926 | Cl | Cl | $B(OH)_2$ | sugar |
| 927 | Cl | Cl | $B(OH)_2$ | C-glycosyl compound |
| 928 | Cl | Cl | SH | OH |
| 929 | Cl | Cl | SH | D-glucitol |
| 930 | Cl | Cl | SH | $SO_3H$ |
| 931 | Cl | Cl | SH | $PO_3H_2$ |
| 932 | Cl | Cl | SH | CHO |
| 933 | Cl | Cl | SH | COOH |
| 934 | Cl | Cl | SH | $CH_2OH$ |
| 935 | Cl | Cl | SH | sugar |
| 936 | Cl | Cl | SH | C-glycosyl compound |
| 937 | Cl | Cl | $OCH_3$ | OH |
| 938 | Cl | Cl | $OCH_3$ | D-glucitol |
| 939 | Cl | Cl | $OCH_3$ | $SO_3H$ |
| 940 | Cl | Cl | $OCH_3$ | $PO_3H_2$ |
| 941 | Cl | Cl | $OCH_3$ | CHO |
| 942 | Cl | Cl | $OCH_3$ | COOH |
| 943 | Cl | Cl | $OCH_3$ | $CH_2OH$ |
| 944 | Cl | Cl | $OCH_3$ | sugar |
| 945 | Cl | Cl | $OCH_3$ | C-glycosyl compound |

TABLE 3-continued

| Row | R1 | R2 | R4 | R5 |
|---|---|---|---|---|
| 946 | Cl | CN | H | OH |
| 947 | Cl | CN | H | D-glucitol |
| 948 | Cl | CN | H | SO$_3$H |
| 949 | Cl | CN | H | PO$_3$H$_2$ |
| 950 | Cl | CN | H | CHO |
| 951 | Cl | CN | H | COOH |
| 952 | Cl | CN | H | CH$_2$OH |
| 953 | Cl | CN | H | sugar |
| 954 | Cl | CN | H | C-glycosyl compound |
| 955 | Cl | CN | OH | OH |
| 956 | Cl | CN | OH | D-glucitol |
| 957 | Cl | CN | OH | SO$_3$H |
| 958 | Cl | CN | OH | PO$_3$H$_2$ |
| 959 | Cl | CN | OH | CHO |
| 960 | Cl | CN | OH | COOH |
| 961 | Cl | CN | OH | CH$_2$OH |
| 962 | Cl | CN | OH | sugar |
| 963 | Cl | CN | OH | C-glycosyl compound |
| 964 | Cl | CN | CH$_3$ | OH |
| 965 | Cl | CN | CH$_3$ | D-glucitol |
| 966 | Cl | CN | CH$_3$ | SO$_3$H |
| 967 | Cl | CN | CH$_3$ | PO$_3$H$_2$ |
| 968 | Cl | CN | CH$_3$ | CHO |
| 969 | Cl | CN | CH$_3$ | COOH |
| 970 | Cl | CN | CH$_3$ | CH$_2$OH |
| 971 | Cl | CN | CH$_3$ | sugar |
| 972 | Cl | CN | CH$_3$ | C-glycosyl compound |
| 973 | Cl | CN | Cl | OH |
| 974 | Cl | CN | Cl | D-glucitol |
| 975 | Cl | CN | Cl | SO$_3$H |
| 976 | Cl | CN | Cl | PO$_3$H$_2$ |
| 977 | Cl | CN | Cl | CHO |
| 978 | Cl | CN | Cl | COOH |
| 979 | Cl | CN | Cl | CH$_2$OH |
| 980 | Cl | CN | Cl | sugar |
| 981 | Cl | CN | Cl | C-glycosyl compound |
| 982 | Cl | CN | B(OH)$_2$ | OH |
| 983 | Cl | CN | B(OH)$_2$ | D-glucitol |
| 984 | Cl | CN | B(OH)$_2$ | SO$_3$H |
| 985 | Cl | CN | B(OH)$_2$ | PO$_3$H$_2$ |
| 986 | Cl | CN | B(OH)$_2$ | CHO |
| 987 | Cl | CN | B(OH)$_2$ | COOH |
| 988 | Cl | CN | B(OH)$_2$ | CH$_2$OH |
| 989 | Cl | CN | B(OH)$_2$ | sugar |
| 990 | Cl | CN | B(OH)$_2$ | C-glycosyl compound |
| 991 | Cl | CN | SH | OH |
| 992 | Cl | CN | SH | D-glucitol |
| 993 | Cl | CN | SH | SO$_3$H |
| 994 | Cl | CN | SH | PO$_3$H$_2$ |
| 995 | Cl | CN | SH | CHO |
| 996 | Cl | CN | SH | COOH |
| 997 | Cl | CN | SH | CH$_2$OH |
| 998 | Cl | CN | SH | sugar |
| 999 | Cl | CN | SH | C-glycosyl compound |
| 1000 | Cl | CN | OCH$_3$ | OH |
| 1001 | Cl | CN | OCH$_3$ | D-glucitol |
| 1002 | Cl | CN | OCH$_3$ | SO$_3$H |
| 1003 | Cl | CN | OCH$_3$ | PO$_3$H$_2$ |
| 1004 | Cl | CN | OCH$_3$ | CHO |
| 1005 | Cl | CN | OCH$_3$ | COOH |
| 1006 | Cl | CN | OCH$_3$ | CH$_2$OH |
| 1007 | Cl | CN | OCH$_3$ | sugar |
| 1008 | Cl | CN | OCH$_3$ | C-glycosyl compound |
| 1009 | Cl | CH$_3$[a] | H | OH |
| 1010 | Cl | CH$_3$[a] | H | D-glucitol |
| 1011 | Cl | CH$_3$[a] | H | SO$_3$H |
| 1012 | Cl | CH$_3$[a] | H | PO$_3$H$_2$ |
| 1013 | Cl | CH$_3$[a] | H | CHO |
| 1014 | Cl | CH$_3$[a] | H | COOH |
| 1015 | Cl | CH$_3$[a] | H | CH$_2$OH |
| 1016 | Cl | CH$_3$[a] | H | sugar |
| 1017 | Cl | CH$_3$[a] | H | C-glycosyl compound |
| 1018 | Cl | CH$_3$[a] | OH | OH |
| 1019 | Cl | CH$_3$[a] | OH | D-glucitol |
| 1020 | Cl | CH$_3$[a] | OH | SO$_3$H |
| 1021 | Cl | CH$_3$[a] | OH | PO$_3$H$_2$ |
| 1022 | Cl | CH$_3$[a] | OH | CHO |
| 1023 | Cl | CH$_3$[a] | OH | COOH |
| 1024 | Cl | CH$_3$[a] | OH | CH$_2$OH |
| 1025 | Cl | CH$_3$[a] | OH | sugar |
| 1026 | Cl | CH$_3$[a] | OH | C-glycosyl compound |
| 1027 | Cl | CH$_3$[a] | CH$_3$ | OH |
| 1028 | Cl | CH$_3$[a] | CH$_3$ | D-glucitol |
| 1029 | Cl | CH$_3$[a] | CH$_3$ | SO$_3$H |
| 1030 | Cl | CH$_3$[a] | CH$_3$ | PO$_3$H$_2$ |
| 1031 | Cl | CH$_3$[a] | CH$_3$ | CHO |
| 1032 | Cl | CH$_3$[a] | CH$_3$ | COOH |
| 1033 | Cl | CH$_3$[a] | CH$_3$ | CH$_2$OH |
| 1034 | Cl | CH$_3$[a] | CH$_3$ | sugar |
| 1035 | Cl | CH$_3$[a] | CH$_3$ | C-glycosyl compound |
| 1036 | Cl | CH$_3$[a] | Cl | OH |
| 1037 | Cl | CH$_3$[a] | Cl | D-glucitol |
| 1038 | Cl | CH$_3$[a] | Cl | SO$_3$H |
| 1039 | Cl | CH$_3$[a] | Cl | PO$_3$H$_2$ |
| 1040 | Cl | CH$_3$[a] | Cl | CHO |
| 1041 | Cl | CH$_3$[a] | Cl | COOH |
| 1042 | Cl | CH$_3$[a] | Cl | CH$_2$OH |
| 1043 | Cl | CH$_3$[a] | Cl | sugar |
| 1044 | Cl | CH$_3$[a] | Cl | C-glycosyl compound |
| 1045 | Cl | CH$_3$[a] | B(OH)$_2$ | OH |
| 1046 | Cl | CH$_3$[a] | B(OH)$_2$ | D-glucitol |
| 1047 | Cl | CH$_3$[a] | B(OH)$_2$ | SO$_3$H |
| 1048 | Cl | CH$_3$[a] | B(OH)$_2$ | PO$_3$H$_2$ |
| 1049 | Cl | CH$_3$[a] | B(OH)$_2$ | CHO |
| 1050 | Cl | CH$_3$[a] | B(OH)$_2$ | COOH |
| 1051 | Cl | CH$_3$[a] | B(OH)$_2$ | CH$_2$OH |
| 1052 | Cl | CH$_3$[a] | B(OH)$_2$ | sugar |
| 1053 | Cl | CH$_3$[a] | B(OH)$_2$ | C-glycosyl compound |
| 1054 | Cl | CH$_3$[a] | SH | OH |
| 1055 | Cl | CH$_3$[a] | SH | D-glucitol |
| 1056 | Cl | CH$_3$[a] | SH | SO$_3$H |
| 1057 | Cl | CH$_3$[a] | SH | PO$_3$H$_2$ |
| 1058 | Cl | CH$_3$[a] | SH | CHO |
| 1059 | Cl | CH$_3$[a] | SH | COOH |
| 1060 | Cl | CH$_3$[a] | SH | CH$_2$OH |
| 1061 | Cl | CH$_3$[a] | SH | sugar |
| 1062 | Cl | CH$_3$[a] | SH | C-glycosyl compound |
| 1063 | Cl | CH$_3$[a] | OCH$_3$ | OH |
| 1064 | Cl | CH$_3$[a] | OCH$_3$ | D-glucitol |
| 1065 | Cl | CH$_3$[a] | OCH$_3$ | SO$_3$H |
| 1066 | Cl | CH$_3$[a] | OCH$_3$ | PO$_3$H$_2$ |
| 1067 | Cl | CH$_3$[a] | OCH$_3$ | CHO |
| 1068 | Cl | CH$_3$[a] | OCH$_3$ | COOH |
| 1069 | Cl | CH$_3$[a] | OCH$_3$ | CH$_2$OH |
| 1070 | Cl | CH$_3$[a] | OCH$_3$ | sugar |
| 1071 | Cl | CH$_3$[a] | OCH$_3$ | C-glycosyl compound |
| 1072 | Cl | OCH3[b] | H | OH |
| 1073 | Cl | OCH3[b] | H | D-glucitol |
| 1074 | Cl | OCH3[b] | H | SO$_3$H |
| 1075 | Cl | OCH3[b] | H | PO$_3$H$_2$ |
| 1076 | Cl | OCH3[b] | H | CHO |
| 1077 | Cl | OCH3[b] | H | COOH |
| 1078 | Cl | OCH3[b] | H | CH$_2$OH |
| 1079 | Cl | OCH3[b] | H | sugar |
| 1080 | Cl | OCH3[b] | H | C-glycosyl compound |
| 1081 | Cl | OCH3[b] | OH | OH |
| 1082 | Cl | OCH3[b] | OH | D-glucitol |
| 1083 | Cl | OCH3[b] | OH | SO$_3$H |
| 1084 | Cl | OCH3[b] | OH | PO$_3$H$_2$ |
| 1085 | Cl | OCH3[b] | OH | CHO |
| 1086 | Cl | OCH3[b] | OH | COOH |
| 1087 | Cl | OCH3[b] | OH | CH$_2$OH |
| 1088 | Cl | OCH3[b] | OH | sugar |
| 1089 | Cl | OCH3[b] | OH | C-glycosyl compound |
| 1090 | Cl | OCH3[b] | CH$_3$ | OH |
| 1091 | Cl | OCH3[b] | CH$_3$ | D-glucitol |
| 1092 | Cl | OCH3[b] | CH$_3$ | SO$_3$H |
| 1093 | Cl | OCH3[b] | CH$_3$ | PO$_3$H$_2$ |
| 1094 | Cl | OCH3[b] | CH$_3$ | CHO |
| 1095 | Cl | OCH3[b] | CH$_3$ | COOH |
| 1096 | Cl | OCH3[b] | CH$_3$ | CH$_2$OH |
| 1097 | Cl | OCH3[b] | CH$_3$ | sugar |
| 1098 | Cl | OCH3[b] | CH$_3$ | C-glycosyl compound |
| 1099 | Cl | OCH3[b] | Cl | OH |

TABLE 3-continued

| Row | R1 | R2 | R4 | R5 |
|---|---|---|---|---|
| 1100 | Cl | OCH3[b] | Cl | D-glucitol |
| 1101 | Cl | OCH3[b] | Cl | SO$_3$H |
| 1102 | Cl | OCH3[b] | Cl | PO$_3$H$_2$ |
| 1103 | Cl | OCH3[b] | Cl | CHO |
| 1104 | Cl | OCH3[b] | Cl | COOH |
| 1105 | Cl | OCH3[b] | Cl | CH$_2$OH |
| 1106 | Cl | OCH3[b] | Cl | sugar |
| 1107 | Cl | OCH3[b] | Cl | C-glycosyl compound |
| 1108 | Cl | OCH3[b] | B(OH)$_2$ | OH |
| 1109 | Cl | OCH3[b] | B(OH)$_2$ | D-glucitol |
| 1110 | Cl | OCH3[b] | B(OH)$_2$ | SO$_3$H |
| 1111 | Cl | OCH3[b] | B(OH)$_2$ | PO$_3$H$_2$ |
| 1112 | Cl | OCH3[b] | B(OH)$_2$ | CHO |
| 1113 | Cl | OCH3[b] | B(OH)$_2$ | COOH |
| 1114 | Cl | OCH3[b] | B(OH)$_2$ | CH$_2$OH |
| 1115 | Cl | OCH3[b] | B(OH)$_2$ | sugar |
| 1116 | Cl | OCH3[b] | B(OH)$_2$ | C-glycosyl compound |
| 1117 | Cl | OCH3[b] | SH | OH |
| 1118 | Cl | OCH3[b] | SH | D-glucitol |
| 1119 | Cl | OCH3[b] | SH | SO$_3$H |
| 1120 | Cl | OCH3[b] | SH | PO$_3$H$_2$ |
| 1121 | Cl | OCH3[b] | SH | CHO |
| 1122 | Cl | OCH3[b] | SH | COOH |
| 1123 | Cl | OCH3[b] | SH | CH$_2$OH |
| 1124 | Cl | OCH3[b] | SH | sugar |
| 1125 | Cl | OCH3[b] | SH | C-glycosyl compound |
| 1126 | Cl | OCH3[b] | OCH$_3$ | OH |
| 1127 | Cl | OCH3[b] | OCH$_3$ | D-glucitol |
| 1128 | Cl | OCH3[b] | OCH$_3$ | SO$_3$H |
| 1129 | Cl | OCH3[b] | OCH$_3$ | PO$_3$H$_2$ |
| 1130 | Cl | OCH3[b] | OCH$_3$ | CHO |
| 1131 | Cl | OCH3[b] | OCH$_3$ | COOH |
| 1132 | Cl | OCH3[b] | OCH$_3$ | CH$_2$OH |
| 1133 | Cl | OCH3[b] | OCH$_3$ | sugar |
| 1134 | Cl | OCH3[b] | OCH$_3$ | C-glycosyl compound |
| 1135 | CN | H | H | OH |
| 1136 | CN | H | H | D-glucitol |
| 1137 | CN | H | H | SO$_3$H |
| 1138 | CN | H | H | PO$_3$H$_2$ |
| 1139 | CN | H | H | CHO |
| 1140 | CN | H | H | COOH |
| 1141 | CN | H | H | CH$_2$OH |
| 1142 | CN | H | H | sugar |
| 1143 | CN | H | H | C-glycosyl compound |
| 1144 | CN | H | OH | OH |
| 1145 | CN | H | OH | D-glucitol |
| 1146 | CN | H | OH | SO$_3$H |
| 1147 | CN | H | OH | PO$_3$H$_2$ |
| 1148 | CN | H | OH | CHO |
| 1149 | CN | H | OH | COOH |
| 1150 | CN | H | OH | CH$_2$OH |
| 1151 | CN | H | OH | sugar |
| 1152 | CN | H | OH | C-glycosyl compound |
| 1153 | CN | H | CH$_3$ | OH |
| 1154 | CN | H | CH$_3$ | D-glucitol |
| 1155 | CN | H | CH$_3$ | SO$_3$H |
| 1156 | CN | H | CH$_3$ | PO$_3$H$_2$ |
| 1157 | CN | H | CH$_3$ | CHO |
| 1158 | CN | H | CH$_3$ | COOH |
| 1159 | CN | H | CH$_3$ | CH$_2$OH |
| 1160 | CN | H | CH$_3$ | sugar |
| 1161 | CN | H | CH$_3$ | C-glycosyl compound |
| 1162 | CN | H | Cl | OH |
| 1163 | CN | H | Cl | D-glucitol |
| 1164 | CN | H | Cl | SO$_3$H |
| 1165 | CN | H | Cl | PO$_3$H$_2$ |
| 1166 | CN | H | Cl | CHO |
| 1167 | CN | H | Cl | COOH |
| 1168 | CN | H | Cl | CH$_2$OH |
| 1169 | CN | H | Cl | sugar |
| 1170 | CN | H | Cl | C-glycosyl compound |
| 1171 | CN | H | B(OH)$_2$ | OH |
| 1172 | CN | H | B(OH)$_2$ | D-glucitol |
| 1173 | CN | H | B(OH)$_2$ | SO$_3$H |
| 1174 | CN | H | B(OH)$_2$ | PO$_3$H$_2$ |
| 1175 | CN | H | B(OH)$_2$ | CHO |
| 1176 | CN | H | B(OH)$_2$ | COOH |
| 1177 | CN | H | B(OH)$_2$ | CH$_2$OH |
| 1178 | CN | H | B(OH)$_2$ | sugar |
| 1179 | CN | H | B(OH)$_2$ | C-glycosyl compound |
| 1180 | CN | H | SH | OH |
| 1181 | CN | H | SH | D-glucitol |
| 1182 | CN | H | SH | SO$_3$H |
| 1183 | CN | H | SH | PO$_3$H$_2$ |
| 1184 | CN | H | SH | CHO |
| 1185 | CN | H | SH | COOH |
| 1186 | CN | H | SH | CH$_2$OH |
| 1187 | CN | H | SH | sugar |
| 1188 | CN | H | SH | C-glycosyl compound |
| 1189 | CN | H | OCH$_3$ | OH |
| 1190 | CN | H | OCH$_3$ | D-glucitol |
| 1191 | CN | H | OCH$_3$ | SO$_3$H |
| 1192 | CN | H | OCH$_3$ | PO$_3$H$_2$ |
| 1193 | CN | H | OCH$_3$ | CHO |
| 1194 | CN | H | OCH$_3$ | COOH |
| 1195 | CN | H | OCH$_3$ | CH$_2$OH |
| 1196 | CN | H | OCH$_3$ | sugar |
| 1197 | CN | H | OCH$_3$ | C-glycosyl compound |
| 1198 | CN | F | H | OH |
| 1199 | CN | F | H | D-glucitol |
| 1200 | CN | F | H | SO$_3$H |
| 1201 | CN | F | H | PO$_3$H$_2$ |
| 1202 | CN | F | H | CHO |
| 1203 | CN | F | H | COOH |
| 1204 | CN | F | H | CH$_2$OH |
| 1205 | CN | F | H | sugar |
| 1206 | CN | F | H | C-glycosyl compound |
| 1207 | CN | F | OH | OH |
| 1208 | CN | F | OH | D-glucitol |
| 1209 | CN | F | OH | SO$_3$H |
| 1210 | CN | F | OH | PO$_3$H$_2$ |
| 1211 | CN | F | OH | CHO |
| 1212 | CN | F | OH | COOH |
| 1213 | CN | F | OH | CH$_2$OH |
| 1214 | CN | F | OH | sugar |
| 1215 | CN | F | OH | C-glycosyl compound |
| 1216 | CN | F | CH$_3$ | OH |
| 1217 | CN | F | CH$_3$ | D-glucitol |
| 1218 | CN | F | CH$_3$ | SO$_3$H |
| 1219 | CN | F | CH$_3$ | PO$_3$H$_2$ |
| 1220 | CN | F | CH$_3$ | CHO |
| 1221 | CN | F | CH$_3$ | COOH |
| 1222 | CN | F | CH$_3$ | CH$_2$OH |
| 1223 | CN | F | CH$_3$ | sugar |
| 1224 | CN | F | CH$_3$ | C-glycosyl compound |
| 1225 | CN | F | Cl | OH |
| 1226 | CN | F | Cl | D-glucitol |
| 1227 | CN | F | Cl | SO$_3$H |
| 1228 | CN | F | Cl | PO$_3$H$_2$ |
| 1229 | CN | F | Cl | CHO |
| 1230 | CN | F | Cl | COOH |
| 1231 | CN | F | Cl | CH$_2$OH |
| 1232 | CN | F | Cl | sugar |
| 1233 | CN | F | Cl | C-glycosyl compound |
| 1234 | CN | F | B(OH)$_2$ | OH |
| 1235 | CN | F | B(OH)$_2$ | D-glucitol |
| 1236 | CN | F | B(OH)$_2$ | SO$_3$H |
| 1237 | CN | F | B(OH)$_2$ | PO$_3$H$_2$ |
| 1238 | CN | F | B(OH)$_2$ | CHO |
| 1239 | CN | F | B(OH)$_2$ | COOH |
| 1240 | CN | F | B(OH)$_2$ | CH$_2$OH |
| 1241 | CN | F | B(OH)$_2$ | sugar |
| 1242 | CN | F | B(OH)$_2$ | C-glycosyl compound |
| 1243 | CN | F | SH | OH |
| 1244 | CN | F | SH | D-glucitol |
| 1245 | CN | F | SH | SO$_3$H |
| 1246 | CN | F | SH | PO$_3$H$_2$ |
| 1247 | CN | F | SH | CHO |
| 1248 | CN | F | SH | COOH |
| 1249 | CN | F | SH | CH$_2$OH |
| 1250 | CN | F | SH | sugar |
| 1251 | CN | F | SH | C-glycosyl compound |
| 1252 | CN | F | OCH$_3$ | OH |
| 1253 | CN | F | OCH$_3$ | D-glucitol |

TABLE 3-continued

| Row | R1 | R2 | R4 | R5 |
|---|---|---|---|---|
| 1254 | CN | F | OCH$_3$ | SO$_3$H |
| 1255 | CN | F | OCH$_3$ | PO$_3$H$_2$ |
| 1256 | CN | F | OCH$_3$ | CHO |
| 1257 | CN | F | OCH$_3$ | COOH |
| 1258 | CN | F | OCH$_3$ | CH$_2$OH |
| 1259 | CN | F | OCH$_3$ | sugar |
| 1260 | CN | F | OCH$_3$ | C-glycosyl compound |
| 1261 | CN | Cl | H | OH |
| 1262 | CN | Cl | H | D-glucitol |
| 1263 | CN | Cl | H | SO$_3$H |
| 1264 | CN | Cl | H | PO$_3$H$_2$ |
| 1265 | CN | Cl | H | CHO |
| 1266 | CN | Cl | H | COOH |
| 1267 | CN | Cl | H | CH$_2$OH |
| 1268 | CN | Cl | H | sugar |
| 1269 | CN | Cl | H | C-glycosyl compound |
| 1270 | CN | Cl | OH | OH |
| 1271 | CN | Cl | OH | D-glucitol |
| 1272 | CN | Cl | OH | SO$_3$H |
| 1273 | CN | Cl | OH | PO$_3$H$_2$ |
| 1274 | CN | Cl | OH | CHO |
| 1275 | CN | Cl | OH | COOH |
| 1276 | CN | Cl | OH | CH$_2$OH |
| 1277 | CN | Cl | OH | sugar |
| 1278 | CN | Cl | OH | C-glycosyl compound |
| 1279 | CN | Cl | CH$_3$ | OH |
| 1280 | CN | Cl | CH$_3$ | D-glucitol |
| 1281 | CN | Cl | CH$_3$ | SO$_3$H |
| 1282 | CN | Cl | CH$_3$ | PO$_3$H$_2$ |
| 1283 | CN | Cl | CH$_3$ | CHO |
| 1284 | CN | Cl | CH$_3$ | COOH |
| 1285 | CN | Cl | CH$_3$ | CH$_2$OH |
| 1286 | CN | Cl | CH$_3$ | sugar |
| 1287 | CN | Cl | CH$_3$ | C-glycosyl compound |
| 1288 | CN | Cl | Cl | OH |
| 1289 | CN | Cl | Cl | D-glucitol |
| 1290 | CN | Cl | Cl | SO$_3$H |
| 1291 | CN | Cl | Cl | PO$_3$H$_2$ |
| 1292 | CN | Cl | Cl | CHO |
| 1293 | CN | Cl | Cl | COOH |
| 1294 | CN | Cl | Cl | CH$_2$OH |
| 1295 | CN | Cl | Cl | sugar |
| 1296 | CN | Cl | Cl | C-glycosyl compound |
| 1297 | CN | Cl | B(OH)$_2$ | OH |
| 1298 | CN | Cl | B(OH)$_2$ | D-glucitol |
| 1299 | CN | Cl | B(OH)$_2$ | SO$_3$H |
| 1300 | CN | Cl | B(OH)$_2$ | PO$_3$H$_2$ |
| 1301 | CN | Cl | B(OH)$_2$ | CHO |
| 1302 | CN | Cl | B(OH)$_2$ | COOH |
| 1303 | CN | Cl | B(OH)$_2$ | CH$_2$OH |
| 1304 | CN | Cl | B(OH)$_2$ | sugar |
| 1305 | CN | Cl | B(OH)$_2$ | C-glycosyl compound |
| 1306 | CN | Cl | SH | OH |
| 1307 | CN | Cl | SH | D-glucitol |
| 1308 | CN | Cl | SH | SO$_3$H |
| 1309 | CN | Cl | SH | PO$_3$H$_2$ |
| 1310 | CN | Cl | SH | CHO |
| 1311 | CN | Cl | SH | COOH |
| 1312 | CN | Cl | SH | CH$_2$OH |
| 1313 | CN | Cl | SH | sugar |
| 1314 | CN | Cl | SH | C-glycosyl compound |
| 1315 | CN | Cl | OCH$_3$ | OH |
| 1316 | CN | Cl | OCH$_3$ | D-glucitol |
| 1317 | CN | Cl | OCH$_3$ | SO$_3$H |
| 1318 | CN | Cl | OCH$_3$ | PO$_3$H$_2$ |
| 1319 | CN | Cl | OCH$_3$ | CHO |
| 1320 | CN | Cl | OCH$_3$ | COOH |
| 1321 | CN | Cl | OCH$_3$ | CH$_2$OH |
| 1322 | CN | Cl | OCH$_3$ | sugar |
| 1323 | CN | Cl | OCH$_3$ | C-glycosyl compound |
| 1324 | CN | CN | H | OH |
| 1325 | CN | CN | H | D-glucitol |
| 1326 | CN | CN | H | SO$_3$H |
| 1327 | CN | CN | H | PO$_3$H$_2$ |
| 1328 | CN | CN | H | CHO |
| 1329 | CN | CN | H | COOH |
| 1330 | CN | CN | H | CH$_2$OH |
| 1331 | CN | CN | H | sugar |
| 1332 | CN | CN | H | C-glycosyl compound |
| 1333 | CN | CN | OH | OH |
| 1334 | CN | CN | OH | D-glucitol |
| 1335 | CN | CN | OH | SO$_3$H |
| 1336 | CN | CN | OH | PO$_3$H$_2$ |
| 1337 | CN | CN | OH | CHO |
| 1338 | CN | CN | OH | COOH |
| 1339 | CN | CN | OH | CH$_2$OH |
| 1340 | CN | CN | OH | sugar |
| 1341 | CN | CN | OH | C-glycosyl compound |
| 1342 | CN | CN | CH$_3$ | OH |
| 1343 | CN | CN | CH$_3$ | D-glucitol |
| 1344 | CN | CN | CH$_3$ | SO$_3$H |
| 1345 | CN | CN | CH$_3$ | PO$_3$H$_2$ |
| 1346 | CN | CN | CH$_3$ | CHO |
| 1347 | CN | CN | CH$_3$ | COOH |
| 1348 | CN | CN | CH$_3$ | CH$_2$OH |
| 1349 | CN | CN | CH$_3$ | sugar |
| 1350 | CN | CN | CH$_3$ | C-glycosyl compound |
| 1351 | CN | CN | Cl | OH |
| 1352 | CN | CN | Cl | D-glucitol |
| 1353 | CN | CN | Cl | SO$_3$H |
| 1354 | CN | CN | Cl | PO$_3$H$_2$ |
| 1355 | CN | CN | Cl | CHO |
| 1356 | CN | CN | Cl | COOH |
| 1357 | CN | CN | Cl | CH$_2$OH |
| 1358 | CN | CN | Cl | sugar |
| 1359 | CN | CN | Cl | C-glycosyl compound |
| 1360 | CN | CN | B(OH)$_2$ | OH |
| 1361 | CN | CN | B(OH)$_2$ | D-glucitol |
| 1362 | CN | CN | B(OH)$_2$ | SO$_3$H |
| 1363 | CN | CN | B(OH)$_2$ | PO$_3$H$_2$ |
| 1364 | CN | CN | B(OH)$_2$ | CHO |
| 1365 | CN | CN | B(OH)$_2$ | COOH |
| 1366 | CN | CN | B(OH)$_2$ | CH$_2$OH |
| 1367 | CN | CN | B(OH)$_2$ | sugar |
| 1368 | CN | CN | B(OH)$_2$ | C-glycosyl compound |
| 1369 | CN | CN | SH | OH |
| 1370 | CN | CN | SH | D-glucitol |
| 1371 | CN | CN | SH | SO$_3$H |
| 1372 | CN | CN | SH | PO$_3$H$_2$ |
| 1373 | CN | CN | SH | CHO |
| 1374 | CN | CN | SH | COOH |
| 1375 | CN | CN | SH | CH$_2$OH |
| 1376 | CN | CN | SH | sugar |
| 1377 | CN | CN | SH | C-glycosyl compound |
| 1378 | CN | CN | OCH$_3$ | OH |
| 1379 | CN | CN | OCH$_3$ | D-glucitol |
| 1380 | CN | CN | OCH$_3$ | SO$_3$H |
| 1381 | CN | CN | OCH$_3$ | PO$_3$H$_2$ |
| 1382 | CN | CN | OCH$_3$ | CHO |
| 1383 | CN | CN | OCH$_3$ | COOH |
| 1384 | CN | CN | OCH$_3$ | CH$_2$OH |
| 1385 | CN | CN | OCH$_3$ | sugar |
| 1386 | CN | CN | OCH$_3$ | C-glycosyl compound |
| 1387 | CN | CH$_3$[a] | H | OH |
| 1388 | CN | CH$_3$[a] | H | D-glucitol |
| 1389 | CN | CH$_3$[a] | H | SO$_3$H |
| 1390 | CN | CH$_3$[a] | H | PO$_3$H$_2$ |
| 1391 | CN | CH$_3$[a] | H | CHO |
| 1392 | CN | CH$_3$[a] | H | COOH |
| 1393 | CN | CH$_3$[a] | H | CH$_2$OH |
| 1394 | CN | CH$_3$[a] | H | sugar |
| 1395 | CN | CH$_3$[a] | H | C-glycosyl compound |
| 1396 | CN | CH$_3$[a] | OH | OH |
| 1397 | CN | CH$_3$[a] | OH | D-glucitol |
| 1398 | CN | CH$_3$[a] | OH | SO$_3$H |
| 1399 | CN | CH$_3$[a] | OH | PO$_3$H$_2$ |
| 1400 | CN | CH$_3$[a] | OH | CHO |
| 1401 | CN | CH$_3$[a] | OH | COOH |
| 1402 | CN | CH$_3$[a] | OH | CH$_2$OH |
| 1403 | CN | CH$_3$[a] | OH | sugar |
| 1404 | CN | CH$_3$[a] | OH | C-glycosyl compound |
| 1405 | CN | CH$_3$[a] | CH$_3$ | OH |
| 1406 | CN | CH$_3$[a] | CH$_3$ | D-glucitol |
| 1407 | CN | CH$_3$[a] | CH$_3$ | SO$_3$H |

TABLE 3-continued

| Row | R1 | R2 | R4 | R5 |
|---|---|---|---|---|
| 1408 | CN | $CH_3^a$ | $CH_3$ | $PO_3H_2$ |
| 1409 | CN | $CH_3^a$ | $CH_3$ | CHO |
| 1410 | CN | $CH_3^a$ | $CH_3$ | COOH |
| 1411 | CN | $CH_3^a$ | $CH_3$ | $CH_2OH$ |
| 1412 | CN | $CH_3^a$ | $CH_3$ | sugar |
| 1413 | CN | $CH_3^a$ | $CH_3$ | C-glycosyl compound |
| 1414 | CN | $CH_3^a$ | Cl | OH |
| 1415 | CN | $CH_3^a$ | Cl | D-glucitol |
| 1416 | CN | $CH_3^a$ | Cl | $SO_3H$ |
| 1417 | CN | $CH_3^a$ | Cl | $PO_3H_2$ |
| 1418 | CN | $CH_3^a$ | Cl | CHO |
| 1419 | CN | $CH_3^a$ | Cl | COOH |
| 1420 | CN | $CH_3^a$ | Cl | $CH_2OH$ |
| 1421 | CN | $CH_3^a$ | Cl | sugar |
| 1422 | CN | $CH_3^a$ | Cl | C-glycosyl compound |
| 1423 | CN | $CH_3^a$ | $B(OH)_2$ | OH |
| 1424 | CN | $CH_3^a$ | $B(OH)_2$ | D-glucitol |
| 1425 | CN | $CH_3^a$ | $B(OH)_2$ | $SO_3H$ |
| 1426 | CN | $CH_3^a$ | $B(OH)_2$ | $PO_3H_2$ |
| 1427 | CN | $CH_3^a$ | $B(OH)_2$ | CHO |
| 1428 | CN | $CH_3^a$ | $B(OH)_2$ | COOH |
| 1429 | CN | $CH_3^a$ | $B(OH)_2$ | $CH_2OH$ |
| 1430 | CN | $CH_3^a$ | $B(OH)_2$ | sugar |
| 1431 | CN | $CH_3^a$ | $B(OH)_2$ | C-glycosyl compound |
| 1432 | CN | $CH_3^a$ | SH | OH |
| 1433 | CN | $CH_3^a$ | SH | D-glucitol |
| 1434 | CN | $CH_3^a$ | SH | $SO_3H$ |
| 1435 | CN | $CH_3^a$ | SH | $PO_3H_2$ |
| 1436 | CN | $CH_3^a$ | SH | CHO |
| 1437 | CN | $CH_3^a$ | SH | COOH |
| 1438 | CN | $CH_3^a$ | SH | $CH_2OH$ |
| 1439 | CN | $CH_3^a$ | SH | sugar |
| 1440 | CN | $CH_3^a$ | SH | C-glycosyl compound |
| 1441 | CN | $CH_3^a$ | $OCH_3$ | OH |
| 1442 | CN | $CH_3^a$ | $OCH_3$ | D-glucitol |
| 1443 | CN | $CH_3^a$ | $OCH_3$ | $SO_3H$ |
| 1444 | CN | $CH_3^a$ | $OCH_3$ | $PO_3H_2$ |
| 1445 | CN | $CH_3^a$ | $OCH_3$ | CHO |
| 1446 | CN | $CH_3^a$ | $OCH_3$ | COOH |
| 1447 | CN | $CH_3^a$ | $OCH_3$ | $CH_2OH$ |
| 1448 | CN | $CH_3^a$ | $OCH_3$ | sugar |
| 1449 | CN | $CH_3^a$ | $OCH_3$ | C-glycosyl compound |
| 1450 | CN | $OCH3^b$ | H | OH |
| 1451 | CN | $OCH3^b$ | H | D-glucitol |
| 1452 | CN | $OCH3^b$ | H | $SO_3H$ |
| 1453 | CN | $OCH3^b$ | H | $PO_3H_2$ |
| 1454 | CN | $OCH3^b$ | H | CHO |
| 1455 | CN | $OCH3^b$ | H | COOH |
| 1456 | CN | $OCH3^b$ | H | $CH_2OH$ |
| 1457 | CN | $OCH3^b$ | H | sugar |
| 1458 | CN | $OCH3^b$ | H | C-glycosyl compound |
| 1459 | CN | $OCH3^b$ | OH | OH |
| 1460 | CN | $OCH3^b$ | OH | D-glucitol |
| 1461 | CN | $OCH3^b$ | OH | $SO_3H$ |
| 1462 | CN | $OCH3^b$ | OH | $PO_3H_2$ |
| 1463 | CN | $OCH3^b$ | OH | CHO |
| 1464 | CN | $OCH3^b$ | OH | COOH |
| 1465 | CN | $OCH3^b$ | OH | $CH_2OH$ |
| 1466 | CN | $OCH3^b$ | OH | sugar |
| 1467 | CN | $OCH3^b$ | OH | C-glycosyl compound |
| 1468 | CN | $OCH3^b$ | $CH_3$ | OH |
| 1469 | CN | $OCH3^b$ | $CH_3$ | D-glucitol |
| 1470 | CN | $OCH3^b$ | $CH_3$ | $SO_3H$ |
| 1471 | CN | $OCH3^b$ | $CH_3$ | $PO_3H_2$ |
| 1472 | CN | $OCH3^b$ | $CH_3$ | CHO |
| 1473 | CN | $OCH3^b$ | $CH_3$ | COOH |
| 1474 | CN | $OCH3^b$ | $CH_3$ | $CH_2OH$ |
| 1475 | CN | $OCH3^b$ | $CH_3$ | sugar |
| 1476 | CN | $OCH3^b$ | $CH_3$ | C-glycosyl compound |
| 1477 | CN | $OCH3^b$ | Cl | OH |
| 1478 | CN | $OCH3^b$ | Cl | D-glucitol |
| 1479 | CN | $OCH3^b$ | Cl | $SO_3H$ |
| 1480 | CN | $OCH3^b$ | Cl | $PO_3H_2$ |
| 1481 | CN | $OCH3^b$ | Cl | CHO |
| 1482 | CN | $OCH3^b$ | Cl | COOH |
| 1483 | CN | $OCH3^b$ | Cl | $CH_2OH$ |
| 1484 | CN | $OCH3^b$ | Cl | sugar |
| 1485 | CN | $OCH3^b$ | Cl | C-glycosyl compound |
| 1486 | CN | $OCH3^b$ | $B(OH)_2$ | OH |
| 1487 | CN | $OCH3^b$ | $B(OH)_2$ | D-glucitol |
| 1488 | CN | $OCH3^b$ | $B(OH)_2$ | $SO_3H$ |
| 1489 | CN | $OCH3^b$ | $B(OH)_2$ | $PO_3H_2$ |
| 1490 | CN | $OCH3^b$ | $B(OH)_2$ | CHO |
| 1491 | CN | $OCH3^b$ | $B(OH)_2$ | COOH |
| 1492 | CN | $OCH3^b$ | $B(OH)_2$ | $CH_2OH$ |
| 1493 | CN | $OCH3^b$ | $B(OH)_2$ | sugar |
| 1494 | CN | $OCH3^b$ | $B(OH)_2$ | C-glycosyl compound |
| 1495 | CN | $OCH3^b$ | SH | OH |
| 1496 | CN | $OCH3^b$ | SH | D-glucitol |
| 1497 | CN | $OCH3^b$ | SH | $SO_3H$ |
| 1498 | CN | $OCH3^b$ | SH | $PO_3H_2$ |
| 1499 | CN | $OCH3^b$ | SH | CHO |
| 1500 | CN | $OCH3^b$ | SH | COOH |
| 1501 | CN | $OCH3^b$ | SH | $CH_2OH$ |
| 1502 | CN | $OCH3^b$ | SH | sugar |
| 1503 | CN | $OCH3^b$ | SH | C-glycosyl compound |
| 1504 | CN | $OCH3^b$ | $OCH_3$ | OH |
| 1505 | CN | $OCH3^b$ | $OCH_3$ | D-glucitol |
| 1506 | CN | $OCH3^b$ | $OCH_3$ | $SO_3H$ |
| 1507 | CN | $OCH3^b$ | $OCH_3$ | $PO_3H_2$ |
| 1508 | CN | $OCH3^b$ | $OCH_3$ | CHO |
| 1509 | CN | $OCH3^b$ | $OCH_3$ | COOH |
| 1510 | CN | $OCH3^b$ | $OCH_3$ | $CH_2OH$ |
| 1511 | CN | $OCH3^b$ | $OCH_3$ | sugar |
| 1512 | CN | $OCH3^b$ | $OCH_3$ | C-glycosyl compound |
| 1513 | $CH_3^a$ | H | H | OH |
| 1514 | $CH_3^a$ | H | H | D-glucitol |
| 1515 | $CH_3^a$ | H | H | $SO_3H$ |
| 1516 | $CH_3^a$ | H | H | $PO_3H_2$ |
| 1517 | $CH_3^a$ | H | H | CHO |
| 1518 | $CH_3^a$ | H | H | COOH |
| 1519 | $CH_3^a$ | H | H | $CH_2OH$ |
| 1520 | $CH_3^a$ | H | H | sugar |
| 1521 | $CH_3^a$ | H | H | C-glycosyl compound |
| 1522 | $CH_3^a$ | H | OH | OH |
| 1523 | $CH_3^a$ | H | OH | D-glucitol |
| 1524 | $CH_3^a$ | H | OH | $SO_3H$ |
| 1525 | $CH_3^a$ | H | OH | $PO_3H_2$ |
| 1526 | $CH_3^a$ | H | OH | CHO |
| 1527 | $CH_3^a$ | H | OH | COOH |
| 1528 | $CH_3^a$ | H | OH | $CH_2OH$ |
| 1529 | $CH_3^a$ | H | OH | sugar |
| 1530 | $CH_3^a$ | H | OH | C-glycosyl compound |
| 1531 | $CH_3^a$ | H | $CH_3$ | OH |
| 1532 | $CH_3^a$ | H | $CH_3$ | D-glucitol |
| 1533 | $CH_3^a$ | H | $CH_3$ | $SO_3H$ |
| 1534 | $CH_3^a$ | H | $CH_3$ | $PO_3H_2$ |
| 1535 | $CH_3^a$ | H | $CH_3$ | CHO |
| 1536 | $CH_3^a$ | H | $CH_3$ | COOH |
| 1537 | $CH_3^a$ | H | $CH_3$ | $CH_2OH$ |
| 1538 | $CH_3^a$ | H | $CH_3$ | sugar |
| 1539 | $CH_3^a$ | H | $CH_3$ | C-glycosyl compound |
| 1540 | $CH_3^a$ | H | Cl | OH |
| 1541 | $CH_3^a$ | H | Cl | D-glucitol |
| 1542 | $CH_3^a$ | H | Cl | $SO_3H$ |
| 1543 | $CH_3^a$ | H | Cl | $PO_3H_2$ |
| 1544 | $CH_3^a$ | H | Cl | CHO |
| 1545 | $CH_3^a$ | H | Cl | COOH |
| 1546 | $CH_3^a$ | H | Cl | $CH_2OH$ |
| 1547 | $CH_3^a$ | H | Cl | sugar |
| 1548 | $CH_3^a$ | H | Cl | C-glycosyl compound |
| 1549 | $CH_3^a$ | H | $B(OH)_2$ | OH |
| 1550 | $CH_3^a$ | H | $B(OH)_2$ | D-glucitol |
| 1551 | $CH_3^a$ | H | $B(OH)_2$ | $SO_3H$ |
| 1552 | $CH_3^a$ | H | $B(OH)_2$ | $PO_3H_2$ |
| 1553 | $CH_3^a$ | H | $B(OH)_2$ | CHO |
| 1554 | $CH_3^a$ | H | $B(OH)_2$ | COOH |
| 1555 | $CH_3^a$ | H | $B(OH)_2$ | $CH_2OH$ |
| 1556 | $CH_3^a$ | H | $B(OH)_2$ | sugar |
| 1557 | $CH_3^a$ | H | $B(OH)_2$ | C-glycosyl compound |
| 1558 | $CH_3^a$ | H | SH | OH |
| 1559 | $CH_3^a$ | H | SH | D-glucitol |
| 1560 | $CH_3^a$ | H | SH | $SO_3H$ |
| 1561 | $CH_3^a$ | H | SH | $PO_3H_2$ |

TABLE 3-continued

| Row | R1 | R2 | R4 | R5 |
|---|---|---|---|---|
| 1562 | CH$_3$[a] | H | SH | CHO |
| 1563 | CH$_3$[a] | H | SH | COOH |
| 1564 | CH$_3$[a] | H | SH | CH$_2$OH |
| 1565 | CH$_3$[a] | H | SH | sugar |
| 1566 | CH$_3$[a] | H | SH | C-glycosyl compound |
| 1567 | CH$_3$[a] | H | OCH$_3$ | OH |
| 1568 | CH$_3$[a] | H | OCH$_3$ | D-glucitol |
| 1569 | CH$_3$[a] | H | OCH$_3$ | SO$_3$H |
| 1570 | CH$_3$[a] | H | OCH$_3$ | PO$_3$H$_2$ |
| 1571 | CH$_3$[a] | H | OCH$_3$ | CHO |
| 1572 | CH$_3$[a] | H | OCH$_3$ | COOH |
| 1573 | CH$_3$[a] | H | OCH$_3$ | CH$_2$OH |
| 1574 | CH$_3$[a] | H | OCH$_3$ | sugar |
| 1575 | CH$_3$[a] | H | OCH$_3$ | C-glycosyl compound |
| 1576 | CH$_3$[a] | F | H | OH |
| 1577 | CH$_3$[a] | F | H | D-glucitol |
| 1578 | CH$_3$[a] | F | H | SO$_3$H |
| 1579 | CH$_3$[a] | F | H | PO$_3$H$_2$ |
| 1580 | CH$_3$[a] | F | H | CHO |
| 1581 | CH$_3$[a] | F | H | COOH |
| 1582 | CH$_3$[a] | F | H | CH$_2$OH |
| 1583 | CH$_3$[a] | F | H | sugar |
| 1584 | CH$_3$[a] | F | H | C-glycosyl compound |
| 1585 | CH$_3$[a] | F | OH | OH |
| 1586 | CH$_3$[a] | F | OH | D-glucitol |
| 1587 | CH$_3$[a] | F | OH | SO$_3$H |
| 1588 | CH$_3$[a] | F | OH | PO$_3$H$_2$ |
| 1589 | CH$_3$[a] | F | OH | CHO |
| 1590 | CH$_3$[a] | F | OH | COOH |
| 1591 | CH$_3$[a] | F | OH | CH$_2$OH |
| 1592 | CH$_3$[a] | F | OH | sugar |
| 1593 | CH$_3$[a] | F | OH | C-glycosyl compound |
| 1594 | CH$_3$[a] | F | CH$_3$ | OH |
| 1595 | CH$_3$[a] | F | CH$_3$ | D-glucitol |
| 1596 | CH$_3$[a] | F | CH$_3$ | SO$_3$H |
| 1597 | CH$_3$[a] | F | CH$_3$ | PO$_3$H$_2$ |
| 1598 | CH$_3$[a] | F | CH$_3$ | CHO |
| 1599 | CH$_3$[a] | F | CH$_3$ | COOH |
| 1600 | CH$_3$[a] | F | CH$_3$ | CH$_2$OH |
| 1601 | CH$_3$[a] | F | CH$_3$ | sugar |
| 1602 | CH$_3$[a] | F | CH$_3$ | C-glycosyl compound |
| 1603 | CH$_3$[a] | F | Cl | OH |
| 1604 | CH$_3$[a] | F | Cl | D-glucitol |
| 1605 | CH$_3$[a] | F | Cl | SO$_3$H |
| 1606 | CH$_3$[a] | F | Cl | PO$_3$H$_2$ |
| 1607 | CH$_3$[a] | F | Cl | CHO |
| 1608 | CH$_3$[a] | F | Cl | COOH |
| 1609 | CH$_3$[a] | F | Cl | CH$_2$OH |
| 1610 | CH$_3$[a] | F | Cl | sugar |
| 1611 | CH$_3$[a] | F | Cl | C-glycosyl compound |
| 1612 | CH$_3$[a] | F | B(OH)$_2$ | OH |
| 1613 | CH$_3$[a] | F | B(OH)$_2$ | D-glucitol |
| 1614 | CH$_3$[a] | F | B(OH)$_2$ | SO$_3$H |
| 1615 | CH$_3$[a] | F | B(OH)$_2$ | PO$_3$H$_2$ |
| 1616 | CH$_3$[a] | F | B(OH)$_2$ | CHO |
| 1617 | CH$_3$[a] | F | B(OH)$_2$ | COOH |
| 1618 | CH$_3$[a] | F | B(OH)$_2$ | CH$_2$OH |
| 1619 | CH$_3$[a] | F | B(OH)$_2$ | sugar |
| 1620 | CH$_3$[a] | F | B(OH)$_2$ | C-glycosyl compound |
| 1621 | CH$_3$[a] | F | SH | OH |
| 1622 | CH$_3$[a] | F | SH | D-glucitol |
| 1623 | CH$_3$[a] | F | SH | SO$_3$H |
| 1624 | CH$_3$[a] | F | SH | PO$_3$H$_2$ |
| 1625 | CH$_3$[a] | F | SH | CHO |
| 1626 | CH$_3$[a] | F | SH | COOH |
| 1627 | CH$_3$[a] | F | SH | CH$_2$OH |
| 1628 | CH$_3$[a] | F | SH | sugar |
| 1629 | CH$_3$[a] | F | SH | C-glycosyl compound |
| 1630 | CH$_3$[a] | F | OCH$_3$ | OH |
| 1631 | CH$_3$[a] | F | OCH$_3$ | D-glucitol |
| 1632 | CH$_3$[a] | F | OCH$_3$ | SO$_3$H |
| 1633 | CH$_3$[a] | F | OCH$_3$ | PO$_3$H$_2$ |
| 1634 | CH$_3$[a] | F | OCH$_3$ | CHO |
| 1635 | CH$_3$[a] | F | OCH$_3$ | COOH |
| 1636 | CH$_3$[a] | F | OCH$_3$ | CH$_2$OH |
| 1637 | CH$_3$[a] | F | OCH$_3$ | sugar |
| 1638 | CH$_3$[a] | F | OCH$_3$ | C-glycosyl compound |
| 1639 | CH$_3$[a] | Cl | H | OH |
| 1640 | CH$_3$[a] | Cl | H | D-glucitol |
| 1641 | CH$_3$[a] | Cl | H | SO$_3$H |
| 1642 | CH$_3$[a] | Cl | H | PO$_3$H$_2$ |
| 1643 | CH$_3$[a] | Cl | H | CHO |
| 1644 | CH$_3$[a] | Cl | H | COOH |
| 1645 | CH$_3$[a] | Cl | H | CH$_2$OH |
| 1646 | CH$_3$[a] | Cl | H | sugar |
| 1647 | CH$_3$[a] | Cl | H | C-glycosyl compound |
| 1648 | CH$_3$[a] | Cl | OH | OH |
| 1649 | CH$_3$[a] | Cl | OH | D-glucitol |
| 1650 | CH$_3$[a] | Cl | OH | SO$_3$H |
| 1651 | CH$_3$[a] | Cl | OH | PO$_3$H$_2$ |
| 1652 | CH$_3$[a] | Cl | OH | CHO |
| 1653 | CH$_3$[a] | Cl | OH | COOH |
| 1654 | CH$_3$[a] | Cl | OH | CH$_2$OH |
| 1655 | CH$_3$[a] | Cl | OH | sugar |
| 1656 | CH$_3$[a] | Cl | OH | C-glycosyl compound |
| 1657 | CH$_3$[a] | Cl | CH$_3$ | OH |
| 1658 | CH$_3$[a] | Cl | CH$_3$ | D-glucitol |
| 1659 | CH$_3$[a] | Cl | CH$_3$ | SO$_3$H |
| 1660 | CH$_3$[a] | Cl | CH$_3$ | PO$_3$H$_2$ |
| 1661 | CH$_3$[a] | Cl | CH$_3$ | CHO |
| 1662 | CH$_3$[a] | Cl | CH$_3$ | COOH |
| 1663 | CH$_3$[a] | Cl | CH$_3$ | CH$_2$OH |
| 1664 | CH$_3$[a] | Cl | CH$_3$ | sugar |
| 1665 | CH$_3$[a] | Cl | CH$_3$ | C-glycosyl compound |
| 1666 | CH$_3$[a] | Cl | Cl | OH |
| 1667 | CH$_3$[a] | Cl | Cl | D-glucitol |
| 1668 | CH$_3$[a] | Cl | Cl | SO$_3$H |
| 1669 | CH$_3$[a] | Cl | Cl | PO$_3$H$_2$ |
| 1670 | CH$_3$[a] | Cl | Cl | CHO |
| 1671 | CH$_3$[a] | Cl | Cl | COOH |
| 1672 | CH$_3$[a] | Cl | Cl | CH$_2$OH |
| 1673 | CH$_3$[a] | Cl | Cl | sugar |
| 1674 | CH$_3$[a] | Cl | Cl | C-glycosyl compound |
| 1675 | CH$_3$[a] | Cl | B(OH)$_2$ | OH |
| 1676 | CH$_3$[a] | Cl | B(OH)$_2$ | D-glucitol |
| 1677 | CH$_3$[a] | Cl | B(OH)$_2$ | SO$_3$H |
| 1678 | CH$_3$[a] | Cl | B(OH)$_2$ | PO$_3$H$_2$ |
| 1679 | CH$_3$[a] | Cl | B(OH)$_2$ | CHO |
| 1680 | CH$_3$[a] | Cl | B(OH)$_2$ | COOH |
| 1681 | CH$_3$[a] | Cl | B(OH)$_2$ | CH$_2$OH |
| 1682 | CH$_3$[a] | Cl | B(OH)$_2$ | sugar |
| 1683 | CH$_3$[a] | Cl | B(OH)$_2$ | C-glycosyl compound |
| 1684 | CH$_3$[a] | Cl | SH | OH |
| 1685 | CH$_3$[a] | Cl | SH | D-glucitol |
| 1686 | CH$_3$[a] | Cl | SH | SO$_3$H |
| 1687 | CH$_3$[a] | Cl | SH | PO$_3$H$_2$ |
| 1688 | CH$_3$[a] | Cl | SH | CHO |
| 1689 | CH$_3$[a] | Cl | SH | COOH |
| 1690 | CH$_3$[a] | Cl | SH | CH$_2$OH |
| 1691 | CH$_3$[a] | Cl | SH | sugar |
| 1692 | CH$_3$[a] | Cl | SH | C-glycosyl compound |
| 1693 | CH$_3$[a] | Cl | OCH$_3$ | OH |
| 1694 | CH$_3$[a] | Cl | OCH$_3$ | D-glucitol |
| 1695 | CH$_3$[a] | Cl | OCH$_3$ | SO$_3$H |
| 1696 | CH$_3$[a] | Cl | OCH$_3$ | PO$_3$H$_2$ |
| 1697 | CH$_3$[a] | Cl | OCH$_3$ | CHO |
| 1698 | CH$_3$[a] | Cl | OCH$_3$ | COOH |
| 1699 | CH$_3$[a] | Cl | OCH$_3$ | CH$_2$OH |
| 1700 | CH$_3$[a] | Cl | OCH$_3$ | sugar |
| 1701 | CH$_3$[a] | Cl | OCH$_3$ | C-glycosyl compound |
| 1702 | CH$_3$[a] | CN | H | OH |
| 1703 | CH$_3$[a] | CN | H | D-glucitol |
| 1704 | CH$_3$[a] | CN | H | SO$_3$H |
| 1705 | CH$_3$[a] | CN | H | PO$_3$H$_2$ |
| 1706 | CH$_3$[a] | CN | H | CHO |
| 1707 | CH$_3$[a] | CN | H | COOH |
| 1708 | CH$_3$[a] | CN | H | CH$_2$OH |
| 1709 | CH$_3$[a] | CN | H | Sugar |
| 1710 | CH$_3$[a] | CN | H | C-glycosyl compound |
| 1711 | CH$_3$[a] | CN | OH | OH |
| 1712 | CH$_3$[a] | CN | OH | D-glucitol |
| 1713 | CH$_3$[a] | CN | OH | SO$_3$H |
| 1714 | CH$_3$[a] | CN | OH | PO$_3$H$_2$ |
| 1715 | CH$_3$[a] | CN | OH | CHO |

TABLE 3-continued

| Row | R1 | R2 | R4 | R5 |
|---|---|---|---|---|
| 1716 | CH$_3$[a] | CN | OH | COOH |
| 1717 | CH$_3$[a] | CN | OH | CH$_2$OH |
| 1718 | CH$_3$[a] | CN | OH | sugar |
| 1719 | CH$_3$[a] | CN | OH | C-glycosyl compound |
| 1720 | CH$_3$[a] | CN | CH$_3$ | OH |
| 1721 | CH$_3$[a] | CN | CH$_3$ | D-glucitol |
| 1722 | CH$_3$[a] | CN | CH$_3$ | SO$_3$H |
| 1723 | CH$_3$[a] | CN | CH$_3$ | PO$_3$H$_2$ |
| 1724 | CH$_3$[a] | CN | CH$_3$ | CHO |
| 1725 | CH$_3$[a] | CN | CH$_3$ | COOH |
| 1726 | CH$_3$[a] | CN | CH$_3$ | CH$_2$OH |
| 1727 | CH$_3$[a] | CN | CH$_3$ | sugar |
| 1728 | CH$_3$[a] | CN | CH$_3$ | C-glycosyl compound |
| 1729 | CH$_3$[a] | CN | Cl | OH |
| 1730 | CH$_3$[a] | CN | Cl | D-glucitol |
| 1731 | CH$_3$[a] | CN | Cl | SO$_3$H |
| 1732 | CH$_3$[a] | CN | Cl | PO$_3$H$_2$ |
| 1733 | CH$_3$[a] | CN | Cl | CHO |
| 1734 | CH$_3$[a] | CN | Cl | COOH |
| 1735 | CH$_3$[a] | CN | Cl | CH$_2$OH |
| 1736 | CH$_3$[a] | CN | Cl | sugar |
| 1737 | CH$_3$[a] | CN | Cl | C-glycosyl compound |
| 1738 | CH$_3$[a] | CN | B(OH)$_2$ | OH |
| 1739 | CH$_3$[a] | CN | B(OH)$_2$ | D-glucitol |
| 1740 | CH$_3$[a] | CN | B(OH)$_2$ | SO$_3$H |
| 1741 | CH$_3$[a] | CN | B(OH)$_2$ | PO$_3$H$_2$ |
| 1742 | CH$_3$[a] | CN | B(OH)$_2$ | CHO |
| 1743 | CH$_3$[a] | CN | B(OH)$_2$ | COOH |
| 1744 | CH$_3$[a] | CN | B(OH)$_2$ | CH$_2$OH |
| 1745 | CH$_3$[a] | CN | B(OH)$_2$ | sugar |
| 1746 | CH$_3$[a] | CN | B(OH)$_2$ | C-glycosyl compound |
| 1747 | CH$_3$[a] | CN | SH | OH |
| 1748 | CH$_3$[a] | CN | SH | D-glucitol |
| 1749 | CH$_3$[a] | CN | SH | SO$_3$H |
| 1750 | CH$_3$[a] | CN | SH | PO$_3$H$_2$ |
| 1751 | CH$_3$[a] | CN | SH | CHO |
| 1752 | CH$_3$[a] | CN | SH | COOH |
| 1753 | CH$_3$[a] | CN | SH | CH$_2$OH |
| 1754 | CH$_3$[a] | CN | SH | sugar |
| 1755 | CH$_3$[a] | CN | SH | C-glycosyl compound |
| 1756 | CH$_3$[a] | CN | OCH$_3$ | OH |
| 1757 | CH$_3$[a] | CN | OCH$_3$ | D-glucitol |
| 1758 | CH$_3$[a] | CN | OCH$_3$ | SO$_3$H |
| 1759 | CH$_3$[a] | CN | OCH$_3$ | PO$_3$H$_2$ |
| 1760 | CH$_3$[a] | CN | OCH$_3$ | CHO |
| 1761 | CH$_3$[a] | CN | OCH$_3$ | COOH |
| 1762 | CH$_3$[a] | CN | OCH$_3$ | CH$_2$OH |
| 1763 | CH$_3$[a] | CN | OCH$_3$ | sugar |
| 1764 | CH$_3$[a] | CN | OCH$_3$ | C-glycosyl compound |
| 1765 | CH$_3$[a] | CH$_3$[a] | H | OH |
| 1766 | CH$_3$[a] | CH$_3$[a] | H | D-glucitol |
| 1767 | CH$_3$[a] | CH$_3$[a] | H | SO$_3$H |
| 1768 | CH$_3$[a] | CH$_3$[a] | H | PO$_3$H$_2$ |
| 1769 | CH$_3$[a] | CH$_3$[a] | H | CHO |
| 1770 | CH$_3$[a] | CH$_3$[a] | H | COOH |
| 1771 | CH$_3$[a] | CH$_3$[a] | H | CH$_2$OH |
| 1772 | CH$_3$[a] | CH$_3$[a] | H | sugar |
| 1773 | CH$_3$[a] | CH$_3$[a] | H | C-glycosyl compound |
| 1774 | CH$_3$[a] | CH$_3$[a] | OH | OH |
| 1775 | CH$_3$[a] | CH$_3$[a] | OH | D-glucitol |
| 1776 | CH$_3$[a] | CH$_3$[a] | OH | SO$_3$H |
| 1777 | CH$_3$[a] | CH$_3$[a] | OH | PO$_3$H$_2$ |
| 1778 | CH$_3$[a] | CH$_3$[a] | OH | CHO |
| 1779 | CH$_3$[a] | CH$_3$[a] | OH | COOH |
| 1780 | CH$_3$[a] | CH$_3$[a] | OH | CH$_2$OH |
| 1781 | CH$_3$[a] | CH$_3$[a] | OH | sugar |
| 1782 | CH$_3$[a] | CH$_3$[a] | OH | C-glycosyl compound |
| 1783 | CH$_3$[a] | CH$_3$[a] | CH$_3$ | OH |
| 1784 | CH$_3$[a] | CH$_3$[a] | CH$_3$ | D-glucitol |
| 1785 | CH$_3$[a] | CH$_3$[a] | CH$_3$ | SO$_3$H |
| 1786 | CH$_3$[a] | CH$_3$[a] | CH$_3$ | PO$_3$H$_2$ |
| 1787 | CH$_3$[a] | CH$_3$[a] | CH$_3$ | CHO |
| 1788 | CH$_3$[a] | CH$_3$[a] | CH$_3$ | COOH |
| 1789 | CH$_3$[a] | CH$_3$[a] | CH$_3$ | CH$_2$OH |
| 1790 | CH$_3$[a] | CH$_3$[a] | CH$_3$ | sugar |
| 1791 | CH$_3$[a] | CH$_3$[a] | CH$_3$ | C-glycosyl compound |
| 1792 | CH$_3$[a] | CH$_3$[a] | Cl | OH |
| 1793 | CH$_3$[a] | CH$_3$[a] | Cl | D-glucitol |
| 1794 | CH$_3$[a] | CH$_3$[a] | Cl | SO$_3$H |
| 1795 | CH$_3$[a] | CH$_3$[a] | Cl | PO$_3$H$_2$ |
| 1796 | CH$_3$[a] | CH$_3$[a] | Cl | CHO |
| 1797 | CH$_3$[a] | CH$_3$[a] | Cl | COOH |
| 1798 | CH$_3$[a] | CH$_3$[a] | Cl | CH$_2$OH |
| 1799 | CH$_3$[a] | CH$_3$[a] | Cl | sugar |
| 1800 | CH$_3$[a] | CH$_3$[a] | Cl | C-glycosyl compound |
| 1801 | CH$_3$[a] | CH$_3$[a] | B(OH)$_2$ | OH |
| 1802 | CH$_3$[a] | CH$_3$[a] | B(OH)$_2$ | D-glucitol |
| 1803 | CH$_3$[a] | CH$_3$[a] | B(OH)$_2$ | SO$_3$H |
| 1804 | CH$_3$[a] | CH$_3$[a] | B(OH)$_2$ | PO$_3$H$_2$ |
| 1805 | CH$_3$[a] | CH$_3$[a] | B(OH)$_2$ | CHO |
| 1806 | CH$_3$[a] | CH$_3$[a] | B(OH)$_2$ | COOH |
| 1807 | CH$_3$[a] | CH$_3$[a] | B(OH)$_2$ | CH$_2$OH |
| 1808 | CH$_3$[a] | CH$_3$[a] | B(OH)$_2$ | sugar |
| 1809 | CH$_3$[a] | CH$_3$[a] | B(OH)$_2$ | C-glycosyl compound |
| 1810 | CH$_3$[a] | CH$_3$[a] | SH | OH |
| 1811 | CH$_3$[a] | CH$_3$[a] | SH | D-glucitol |
| 1812 | CH$_3$[a] | CH$_3$[a] | SH | SO$_3$H |
| 1813 | CH$_3$[a] | CH$_3$[a] | SH | PO$_3$H$_2$ |
| 1814 | CH$_3$[a] | CH$_3$[a] | SH | CHO |
| 1815 | CH$_3$[a] | CH$_3$[a] | SH | COOH |
| 1816 | CH$_3$[a] | CH$_3$[a] | SH | CH$_2$OH |
| 1817 | CH$_3$[a] | CH$_3$[a] | SH | sugar |
| 1818 | CH$_3$[a] | CH$_3$[a] | SH | C-glycosyl compound |
| 1819 | CH$_3$[a] | CH$_3$[a] | OCH$_3$ | OH |
| 1820 | CH$_3$[a] | CH$_3$[a] | OCH$_3$ | D-glucitol |
| 1821 | CH$_3$[a] | CH$_3$[a] | OCH$_3$ | SO$_3$H |
| 1822 | CH$_3$[a] | CH$_3$[a] | OCH$_3$ | PO$_3$H$_2$ |
| 1823 | CH$_3$[a] | CH$_3$[a] | OCH$_3$ | CHO |
| 1824 | CH$_3$[a] | CH$_3$[a] | OCH$_3$ | COOH |
| 1825 | CH$_3$[a] | CH$_3$[a] | OCH$_3$ | CH$_2$OH |
| 1826 | CH$_3$[a] | CH$_3$[a] | OCH$_3$ | sugar |
| 1827 | CH$_3$[a] | CH$_3$[a] | OCH$_3$ | C-glycosyl compound |
| 1828 | CH$_3$[a] | OCH3[b] | H | OH |
| 1829 | CH$_3$[a] | OCH3[b] | H | D-glucitol |
| 1830 | CH$_3$[a] | OCH3[b] | H | SO$_3$H |
| 1831 | CH$_3$[a] | OCH3[b] | H | PO$_3$H$_2$ |
| 1832 | CH$_3$[a] | OCH3[b] | H | CHO |
| 1833 | CH$_3$[a] | OCH3[b] | H | COOH |
| 1834 | CH$_3$[a] | OCH3[b] | H | CH$_2$OH |
| 1835 | CH$_3$[a] | OCH3[b] | H | sugar |
| 1836 | CH$_3$[a] | OCH3[b] | H | C-glycosyl compound |
| 1837 | CH$_3$[a] | OCH3[b] | OH | OH |
| 1838 | CH$_3$[a] | OCH3[b] | OH | D-glucitol |
| 1839 | CH$_3$[a] | OCH3[b] | OH | SO$_3$H |
| 1840 | CH$_3$[a] | OCH3[b] | OH | PO$_3$H$_2$ |
| 1841 | CH$_3$[a] | OCH3[b] | OH | CHO |
| 1842 | CH$_3$[a] | OCH3[b] | OH | COOH |
| 1843 | CH$_3$[a] | OCH3[b] | OH | CH$_2$OH |
| 1844 | CH$_3$[a] | OCH3[b] | OH | sugar |
| 1845 | CH$_3$[a] | OCH3[b] | OH | C-glycosyl compound |
| 1846 | CH$_3$[a] | OCH3[b] | CH$_3$ | OH |
| 1847 | CH$_3$[a] | OCH3[b] | CH$_3$ | D-glucitol |
| 1848 | CH$_3$[a] | OCH3[b] | CH$_3$ | SO$_3$H |
| 1849 | CH$_3$[a] | OCH3[b] | CH$_3$ | PO$_3$H$_2$ |
| 1850 | CH$_3$[a] | OCH3[b] | CH$_3$ | CHO |
| 1851 | CH$_3$[a] | OCH3[b] | CH$_3$ | COOH |
| 1852 | CH$_3$[a] | OCH3[b] | CH$_3$ | CH$_2$OH |
| 1853 | CH$_3$[a] | OCH3[b] | CH$_3$ | sugar |
| 1854 | CH$_3$[a] | OCH3[b] | CH$_3$ | C-glycosyl compound |
| 1855 | CH$_3$[a] | OCH3[b] | Cl | OH |
| 1856 | CH$_3$[a] | OCH3[b] | Cl | D-glucitol |
| 1857 | CH$_3$[a] | OCH3[b] | Cl | SO$_3$H |
| 1858 | CH$_3$[a] | OCH3[b] | Cl | PO$_3$H$_2$ |
| 1859 | CH$_3$[a] | OCH3[b] | Cl | CHO |
| 1860 | CH$_3$[a] | OCH3[b] | Cl | COOH |
| 1861 | CH$_3$[a] | OCH3[b] | Cl | CH$_2$OH |
| 1862 | CH$_3$[a] | OCH3[b] | Cl | sugar |
| 1863 | CH$_3$[a] | OCH3[b] | Cl | C-glycosyl compound |
| 1864 | CH$_3$[a] | OCH3[b] | B(OH)$_2$ | OH |
| 1865 | CH$_3$[a] | OCH3[b] | B(OH)$_2$ | D-glucitol |
| 1866 | CH$_3$[a] | OCH3[b] | B(OH)$_2$ | SO$_3$H |
| 1867 | CH$_3$[a] | OCH3[b] | B(OH)$_2$ | PO$_3$H$_2$ |
| 1868 | CH$_3$[a] | OCH3[b] | B(OH)$_2$ | CHO |
| 1869 | CH$_3$[a] | OCH3[b] | B(OH)$_2$ | COOH |

TABLE 3-continued

| Row | R1 | R2 | R4 | R5 |
|---|---|---|---|---|
| 1870 | CH$_3$[a] | OCH3[b] | B(OH)$_2$ | CH$_2$OH |
| 1871 | CH$_3$[a] | OCH3[b] | B(OH)$_2$ | sugar |
| 1872 | CH$_3$[a] | OCH3[b] | B(OH)$_2$ | C-glycosyl compound |
| 1873 | CH$_3$[a] | OCH3[b] | SH | OH |
| 1874 | CH$_3$[a] | OCH3[b] | SH | D-glucitol |
| 1875 | CH$_3$[a] | OCH3[b] | SH | SO$_3$H |
| 1876 | CH$_3$[a] | OCH3[b] | SH | PO$_3$H$_2$ |
| 1877 | CH$_3$[a] | OCH3[b] | SH | CHO |
| 1878 | CH$_3$[a] | OCH3[b] | SH | COOH |
| 1879 | CH$_3$[a] | OCH3[b] | SH | CH$_2$OH |
| 1880 | CH$_3$[a] | OCH3[b] | SH | sugar |
| 1881 | CH$_3$[a] | OCH3[b] | SH | C-glycosyl compound |
| 1882 | CH$_3$[a] | OCH3[b] | OCH$_3$ | OH |
| 1883 | CH$_3$[a] | OCH3[b] | OCH$_3$ | D-glucitol |
| 1884 | CH$_3$[a] | OCH3[b] | OCH$_3$ | SO$_3$H |
| 1885 | CH$_3$[a] | OCH3[b] | OCH$_3$ | PO$_3$H$_2$ |
| 1886 | CH$_3$[a] | OCH3[b] | OCH$_3$ | CHO |
| 1887 | CH$_3$[a] | OCH3[b] | OCH$_3$ | COOH |
| 1888 | CH$_3$[a] | OCH3[b] | OCH$_3$ | CH$_2$OH |
| 1889 | CH$_3$[a] | OCH3[b] | OCH$_3$ | sugar |
| 1890 | CH$_3$[a] | OCH3[b] | OCH$_3$ | C-glycosyl compound |
| 1891 | OCH3[b] | H | H | OH |
| 1892 | OCH3[b] | H | H | D-glucitol |
| 1893 | OCH3[b] | H | H | SO$_3$H |
| 1894 | OCH3[b] | H | H | PO$_3$H$_2$ |
| 1895 | OCH3[b] | H | H | CHO |
| 1896 | OCH3[b] | H | H | COOH |
| 1897 | OCH3[b] | H | H | CH$_2$OH |
| 1898 | OCH3[b] | H | H | sugar |
| 1899 | OCH3[b] | H | H | C-glycosyl compound |
| 1900 | OCH3[b] | H | OH | OH |
| 1901 | OCH3[b] | H | OH | D-glucitol |
| 1902 | OCH3[b] | H | OH | SO$_3$H |
| 1903 | OCH3[b] | H | OH | PO$_3$H$_2$ |
| 1904 | OCH3[b] | H | OH | CHO |
| 1905 | OCH3[b] | H | OH | COOH |
| 1906 | OCH3[b] | H | OH | CH$_2$OH |
| 1907 | OCH3[b] | H | OH | sugar |
| 1908 | OCH3[b] | H | OH | C-glycosyl compound |
| 1909 | OCH3[b] | H | CH3 | OH |
| 1910 | OCH3[b] | H | CH3 | D-glucitol |
| 1911 | OCH3[b] | H | CH3 | SO$_3$H |
| 1912 | OCH3[b] | H | CH3 | PO$_3$H$_2$ |
| 1913 | OCH3[b] | H | CH3 | CHO |
| 1914 | OCH3[b] | H | CH3 | COOH |
| 1915 | OCH3[b] | H | CH3 | CH$_2$OH |
| 1916 | OCH3[b] | H | CH3 | sugar |
| 1917 | OCH3[b] | H | CH3 | C-glycosyl compound |
| 1918 | OCH3[b] | H | Cl | OH |
| 1919 | OCH3[b] | H | Cl | D-glucitol |
| 1920 | OCH3[b] | H | Cl | SO$_3$H |
| 1921 | OCH3[b] | H | Cl | PO$_3$H$_2$ |
| 1922 | OCH3[b] | H | Cl | CHO |
| 1923 | OCH3[b] | H | Cl | COOH |
| 1924 | OCH3[b] | H | Cl | CH$_2$OH |
| 1925 | OCH3[b] | H | Cl | sugar |
| 1926 | OCH3[b] | H | Cl | C-glycosyl compound |
| 1927 | OCH3[b] | H | B(OH)$_2$ | OH |
| 1928 | OCH3[b] | H | B(OH)$_2$ | D-glucitol |
| 1929 | OCH3[b] | H | B(OH)$_2$ | SO$_3$H |
| 1930 | OCH3[b] | H | B(OH)$_2$ | PO$_3$H$_2$ |
| 1931 | OCH3[b] | H | B(OH)$_2$ | CHO |
| 1932 | OCH3[b] | H | B(OH)$_2$ | COOH |
| 1933 | OCH3[b] | H | B(OH)$_2$ | CH$_2$OH |
| 1934 | OCH3[b] | H | B(OH)$_2$ | sugar |
| 1935 | OCH3[b] | H | B(OH)$_2$ | C-glycosyl compound |
| 1936 | OCH3[b] | H | SH | OH |
| 1937 | OCH3[b] | H | SH | D-glucitol |
| 1938 | OCH3[b] | H | SH | SO$_3$H |
| 1939 | OCH3[b] | H | SH | PO$_3$H$_2$ |
| 1940 | OCH3[b] | H | SH | CHO |
| 1941 | OCH3[b] | H | SH | COOH |
| 1942 | OCH3[b] | H | SH | CH$_2$OH |
| 1943 | OCH3[b] | H | SH | sugar |
| 1944 | OCH3[b] | H | SH | C-glycosyl compound |
| 1945 | OCH3[b] | H | OCH3 | OH |
| 1946 | OCH3[b] | H | OCH3 | D-glucitol |
| 1947 | OCH3[b] | H | OCH3 | SO$_3$H |
| 1948 | OCH3[b] | H | OCH3 | PO$_3$H$_2$ |
| 1949 | OCH3[b] | H | OCH3 | CHO |
| 1950 | OCH3[b] | H | OCH3 | COOH |
| 1951 | OCH3[b] | H | OCH3 | CH$_2$OH |
| 1952 | OCH3[b] | H | OCH3 | sugar |
| 1953 | OCH3[b] | H | OCH3 | C-glycosyl compound |
| 1954 | OCH3[b] | F | H | OH |
| 1955 | OCH3[b] | F | H | D-glucitol |
| 1956 | OCH3[b] | F | H | SO$_3$H |
| 1957 | OCH3[b] | F | H | PO$_3$H$_2$ |
| 1958 | OCH3[b] | F | H | CHO |
| 1959 | OCH3[b] | F | H | COOH |
| 1960 | OCH3[b] | F | H | CH$_2$OH |
| 1961 | OCH3[b] | F | H | sugar |
| 1962 | OCH3[b] | F | H | C-glycosyl compound |
| 1963 | OCH3[b] | F | OH | OH |
| 1964 | OCH3[b] | F | OH | D-glucitol |
| 1965 | OCH3[b] | F | OH | SO$_3$H |
| 1966 | OCH3[b] | F | OH | PO$_3$H$_2$ |
| 1967 | OCH3[b] | F | OH | CHO |
| 1968 | OCH3[b] | F | OH | COOH |
| 1969 | OCH3[b] | F | OH | CH$_2$OH |
| 1970 | OCH3[b] | F | OH | sugar |
| 1971 | OCH3[b] | F | OH | C-glycosyl compound |
| 1972 | OCH3[b] | F | CH3 | OH |
| 1973 | OCH3[b] | F | CH3 | D-glucitol |
| 1974 | OCH3[b] | F | CH3 | SO$_3$H |
| 1975 | OCH3[b] | F | CH3 | PO$_3$H$_2$ |
| 1976 | OCH3[b] | F | CH3 | CHO |
| 1977 | OCH3[b] | F | CH3 | COOH |
| 1978 | OCH3[b] | F | CH3 | CH$_2$OH |
| 1979 | OCH3[b] | F | CH3 | sugar |
| 1980 | OCH3[b] | F | CH3 | C-glycosyl compound |
| 1981 | OCH3[b] | F | Cl | OH |
| 1982 | OCH3[b] | F | Cl | D-glucitol |
| 1983 | OCH3[b] | F | Cl | SO$_3$H |
| 1984 | OCH3[b] | F | Cl | PO$_3$H$_2$ |
| 1985 | OCH3[b] | F | Cl | CHO |
| 1986 | OCH3[b] | F | Cl | COOH |
| 1987 | OCH3[b] | F | Cl | CH$_2$OH |
| 1988 | OCH3[b] | F | Cl | sugar |
| 1989 | OCH3[b] | F | Cl | C-glycosyl compound |
| 1990 | OCH3[b] | F | B(OH)$_2$ | OH |
| 1991 | OCH3[b] | F | B(OH)$_2$ | D-glucitol |
| 1992 | OCH3[b] | F | B(OH)$_2$ | SO$_3$H |
| 1993 | OCH3[b] | F | B(OH)$_2$ | PO$_3$H$_2$ |
| 1994 | OCH3[b] | F | B(OH)$_2$ | CHO |
| 1995 | OCH3[b] | F | B(OH)$_2$ | COOH |
| 1996 | OCH3[b] | F | B(OH)$_2$ | CH$_2$OH |
| 1997 | OCH3[b] | F | B(OH)$_2$ | sugar |
| 1998 | OCH3[b] | F | B(OH)$_2$ | C-glycosyl compound |
| 1999 | OCH3[b] | F | SH | OH |
| 2000 | OCH3[b] | F | SH | D-glucitol |
| 2001 | OCH3[b] | F | SH | SO$_3$H |
| 2002 | OCH3[b] | F | SH | PO$_3$H$_2$ |
| 2003 | OCH3[b] | F | SH | CHO |
| 2004 | OCH3[b] | F | SH | COOH |
| 2005 | OCH3[b] | F | SH | CH$_2$OH |
| 2006 | OCH3[b] | F | SH | sugar |
| 2007 | OCH3[b] | F | SH | C-glycosyl compound |
| 2008 | OCH3[b] | F | OCH3 | OH |
| 2009 | OCH3[b] | F | OCH3 | D-glucitol |
| 2010 | OCH3[b] | F | OCH3 | SO$_3$H |
| 2011 | OCH3[b] | F | OCH3 | PO$_3$H$_2$ |
| 2012 | OCH3[b] | F | OCH3 | CHO |
| 2013 | OCH3[b] | F | OCH3 | COOH |
| 2014 | OCH3[b] | F | OCH3 | CH$_2$OH |
| 2015 | OCH3[b] | F | OCH3 | sugar |
| 2016 | OCH3[b] | F | OCH3 | C-glycosyl compound |
| 2017 | OCH3[b] | Cl | H | OH |
| 2018 | OCH3[b] | Cl | H | D-glucitol |
| 2019 | OCH3[b] | Cl | H | SO$_3$H |
| 2020 | OCH3[b] | Cl | H | PO$_3$H$_2$ |
| 2021 | OCH3[b] | Cl | H | CHO |
| 2022 | OCH3[b] | Cl | H | COOH |
| 2023 | OCH3[b] | Cl | H | CH$_2$OH |

TABLE 3-continued

| Row | R1 | R2 | R4 | R5 |
|---|---|---|---|---|
| 2024 | OCH3[b] | Cl | H | sugar |
| 2025 | OCH3[b] | Cl | H | C-glycosyl compound |
| 2026 | OCH3[b] | Cl | OH | OH |
| 2027 | OCH3[b] | Cl | OH | D-glucitol |
| 2028 | OCH3[b] | Cl | OH | SO3H |
| 2029 | OCH3[b] | Cl | OH | PO3H2 |
| 2030 | OCH3[b] | Cl | OH | CHO |
| 2031 | OCH3[b] | Cl | OH | COOH |
| 2032 | OCH3[b] | Cl | OH | CH2OH |
| 2033 | OCH3[b] | Cl | OH | sugar |
| 2034 | OCH3[b] | Cl | OH | C-glycosyl compound |
| 2035 | OCH3[b] | Cl | CH3 | OH |
| 2036 | OCH3[b] | Cl | CH3 | D-glucitol |
| 2037 | OCH3[b] | Cl | CH3 | SO3H |
| 2038 | OCH3[b] | Cl | CH3 | PO3H2 |
| 2039 | OCH3[b] | Cl | CH3 | CHO |
| 2040 | OCH3[b] | Cl | CH3 | COOH |
| 2041 | OCH3[b] | Cl | CH3 | CH2OH |
| 2042 | OCH3[b] | Cl | CH3 | sugar |
| 2043 | OCH3[b] | Cl | CH3 | C-glycosyl compound |
| 2044 | OCH3[b] | Cl | Cl | OH |
| 2045 | OCH3[b] | Cl | Cl | D-glucitol |
| 2046 | OCH3[b] | Cl | Cl | SO3H |
| 2047 | OCH3[b] | Cl | Cl | PO3H2 |
| 2048 | OCH3[b] | Cl | Cl | CHO |
| 2049 | OCH3[b] | Cl | Cl | COOH |
| 2050 | OCH3[b] | Cl | Cl | CH2OH |
| 2051 | OCH3[b] | Cl | Cl | sugar |
| 2052 | OCH3[b] | Cl | Cl | C-glycosyl compound |
| 2053 | OCH3[b] | Cl | B(OH)2 | OH |
| 2054 | OCH3[b] | Cl | B(OH)2 | D-glucitol |
| 2055 | OCH3[b] | Cl | B(OH)2 | SO3H |
| 2056 | OCH3[b] | Cl | B(OH)2 | PO3H2 |
| 2057 | OCH3[b] | Cl | B(OH)2 | CHO |
| 2058 | OCH3[b] | Cl | B(OH)2 | COOH |
| 2059 | OCH3[b] | Cl | B(OH)2 | CH2OH |
| 2060 | OCH3[b] | Cl | B(OH)2 | sugar |
| 2061 | OCH3[b] | Cl | B(OH)2 | C-glycosyl compound |
| 2062 | OCH3[b] | Cl | SH | OH |
| 2063 | OCH3[b] | Cl | SH | D-glucitol |
| 2064 | OCH3[b] | Cl | SH | SO3H |
| 2065 | OCH3[b] | Cl | SH | PO3H2 |
| 2066 | OCH3[b] | Cl | SH | CHO |
| 2067 | OCH3[b] | Cl | SH | COOH |
| 2068 | OCH3[b] | Cl | SH | CH2OH |
| 2069 | OCH3[b] | Cl | SH | sugar |
| 2070 | OCH3[b] | Cl | SH | C-glycosyl compound |
| 2071 | OCH3[b] | Cl | OCH3 | OH |
| 2072 | OCH3[b] | Cl | OCH3 | D-glucitol |
| 2073 | OCH3[b] | Cl | OCH3 | SO3H |
| 2074 | OCH3[b] | Cl | OCH3 | PO3H2 |
| 2075 | OCH3[b] | Cl | OCH3 | CHO |
| 2076 | OCH3[b] | Cl | OCH3 | COOH |
| 2077 | OCH3[b] | Cl | OCH3 | CH2OH |
| 2078 | OCH3[b] | Cl | OCH3 | sugar |
| 2079 | OCH3[b] | Cl | OCH3 | C-glycosyl compound |
| 2080 | OCH3[b] | CN | H | OH |
| 2081 | OCH3[b] | CN | H | D-glucitol |
| 2082 | OCH3[b] | CN | H | SO3H |
| 2083 | OCH3[b] | CN | H | PO3H2 |
| 2084 | OCH3[b] | CN | H | CHO |
| 2085 | OCH3[b] | CN | H | COOH |
| 2086 | OCH3[b] | CN | H | CH2OH |
| 2087 | OCH3[b] | CN | H | sugar |
| 2088 | OCH3[b] | CN | H | C-glycosyl compound |
| 2089 | OCH3[b] | CN | OH | OH |
| 2090 | OCH3[b] | CN | OH | D-glucitol |
| 2091 | OCH3[b] | CN | OH | SO3H |
| 2092 | OCH3[b] | CN | OH | PO3H2 |
| 2093 | OCH3[b] | CN | OH | CHO |
| 2094 | OCH3[b] | CN | OH | COOH |
| 2095 | OCH3[b] | CN | OH | CH2OH |
| 2096 | OCH3[b] | CN | OH | sugar |
| 2097 | OCH3[b] | CN | OH | C-glycosyl compound |
| 2098 | OCH3[b] | CN | CH3 | OH |
| 2099 | OCH3[b] | CN | CH3 | D-glucitol |
| 2100 | OCH3[b] | CN | CH3 | SO3H |
| 2101 | OCH3[b] | CN | CH3 | PO3H2 |
| 2102 | OCH3[b] | CN | CH3 | CHO |
| 2103 | OCH3[b] | CN | CH3 | COOH |
| 2104 | OCH3[b] | CN | CH3 | CH2OH |
| 2105 | OCH3[b] | CN | CH3 | sugar |
| 2106 | OCH3[b] | CN | CH3 | C-glycosyl compound |
| 2107 | OCH3[b] | CN | Cl | OH |
| 2108 | OCH3[b] | CN | Cl | D-glucitol |
| 2109 | OCH3[b] | CN | Cl | SO3H |
| 2110 | OCH3[b] | CN | Cl | PO3H2 |
| 2111 | OCH3[b] | CN | Cl | CHO |
| 2112 | OCH3[b] | CN | Cl | COOH |
| 2113 | OCH3[b] | CN | Cl | CH2OH |
| 2114 | OCH3[b] | CN | Cl | sugar |
| 2115 | OCH3[b] | CN | Cl | C-glycosyl compound |
| 2116 | OCH3[b] | CN | B(OH)2 | OH |
| 2117 | OCH3[b] | CN | B(OH)2 | D-glucitol |
| 2118 | OCH3[b] | CN | B(OH)2 | SO3H |
| 2119 | OCH3[b] | CN | B(OH)2 | PO3H2 |
| 2120 | OCH3[b] | CN | B(OH)2 | CHO |
| 2121 | OCH3[b] | CN | B(OH)2 | COOH |
| 2122 | OCH3[b] | CN | B(OH)2 | CH2OH |
| 2123 | OCH3[b] | CN | B(OH)2 | sugar |
| 2124 | OCH3[b] | CN | B(OH)2 | C-glycosyl compound |
| 2125 | OCH3[b] | CN | SH | OH |
| 2126 | OCH3[b] | CN | SH | D-glucitol |
| 2127 | OCH3[b] | CN | SH | SO3H |
| 2128 | OCH3[b] | CN | SH | PO3H2 |
| 2129 | OCH3[b] | CN | SH | CHO |
| 2130 | OCH3[b] | CN | SH | COOH |
| 2131 | OCH3[b] | CN | SH | CH2OH |
| 2132 | OCH3[b] | CN | SH | sugar |
| 2133 | OCH3[b] | CN | SH | C-glycosyl compound |
| 2134 | OCH3[b] | CN | OCH3 | OH |
| 2135 | OCH3[b] | CN | OCH3 | D-glucitol |
| 2136 | OCH3[b] | CN | OCH3 | SO3H |
| 2137 | OCH3[b] | CN | OCH3 | PO3H2 |
| 2138 | OCH3[b] | CN | OCH3 | CHO |
| 2139 | OCH3[b] | CN | OCH3 | COOH |
| 2140 | OCH3[b] | CN | OCH3 | CH2OH |
| 2141 | OCH3[b] | CN | OCH3 | sugar |
| 2142 | OCH3[b] | CN | OCH3 | C-glycosyl compound |
| 2143 | OCH3[b] | CH3[a] | H | OH |
| 2144 | OCH3[b] | CH3[a] | H | D-glucitol |
| 2145 | OCH3[b] | CH3[a] | H | SO3H |
| 2146 | OCH3[b] | CH3[a] | H | PO3H2 |
| 2147 | OCH3[b] | CH3[a] | H | CHO |
| 2148 | OCH3[b] | CH3[a] | H | COOH |
| 2149 | OCH3[b] | CH3[a] | H | CH2OH |
| 2150 | OCH3[b] | CH3[a] | H | sugar |
| 2151 | OCH3[b] | CH3[a] | H | C-glycosyl compound |
| 2152 | OCH3[b] | CH3[a] | OH | OH |
| 2153 | OCH3[b] | CH3[a] | OH | D-glucitol |
| 2154 | OCH3[b] | CH3[a] | OH | SO3H |
| 2155 | OCH3[b] | CH3[a] | OH | PO3H2 |
| 2156 | OCH3[b] | CH3[a] | OH | CHO |
| 2157 | OCH3[b] | CH3[a] | OH | COOH |
| 2158 | OCH3[b] | CH3[a] | OH | CH2OH |
| 2159 | OCH3[b] | CH3[a] | OH | sugar |
| 2160 | OCH3[b] | CH3[a] | OH | C-glycosyl compound |
| 2161 | OCH3[b] | CH3[a] | CH3 | OH |
| 2162 | OCH3[b] | CH3[a] | CH3 | D-glucitol |
| 2163 | OCH3[b] | CH3[a] | CH3 | SO3H |
| 2164 | OCH3[b] | CH3[a] | CH3 | PO3H2 |
| 2165 | OCH3[b] | CH3[a] | CH3 | CHO |
| 2166 | OCH3[b] | CH3[a] | CH3 | COOH |
| 2167 | OCH3[b] | CH3[a] | CH3 | CH2OH |
| 2168 | OCH3[b] | CH3[a] | CH3 | sugar |
| 2169 | OCH3[b] | CH3[a] | CH3 | C-glycosyl compound |
| 2170 | OCH3[b] | CH3[a] | Cl | OH |
| 2171 | OCH3[b] | CH3[a] | Cl | D-glucitol |
| 2172 | OCH3[b] | CH3[a] | Cl | SO3H |
| 2173 | OCH3[b] | CH3[a] | Cl | PO3H2 |
| 2174 | OCH3[b] | CH3[a] | Cl | CHO |
| 2175 | OCH3[b] | CH3[a] | Cl | COOH |
| 2176 | OCH3[b] | CH3[a] | Cl | CH2OH |
| 2177 | OCH3[b] | CH3[a] | Cl | sugar |

TABLE 3-continued

| Row | R1 | R2 | R4 | R5 |
|---|---|---|---|---|
| 2178 | OCH3[b] | CH3[a] | Cl | C-glycosyl compound |
| 2179 | OCH3[b] | CH3[a] | B(OH)2 | OH |
| 2180 | OCH3[b] | CH3[a] | B(OH)2 | D-glucitol |
| 2181 | OCH3[b] | CH3[a] | B(OH)2 | SO3H |
| 2182 | OCH3[b] | CH3[a] | B(OH)2 | PO3H2 |
| 2183 | OCH3[b] | CH3[a] | B(OH)2 | CHO |
| 2184 | OCH3[b] | CH3[a] | B(OH)2 | COOH |
| 2185 | OCH3[b] | CH3[a] | B(OH)2 | CH2OH |
| 2186 | OCH3[b] | CH3[a] | B(OH)2 | sugar |
| 2187 | OCH3[b] | CH3[a] | B(OH)2 | C-glycosyl compound |
| 2188 | OCH3[b] | CH3[a] | SH | OH |
| 2189 | OCH3[b] | CH3[a] | SH | D-glucitol |
| 2190 | OCH3[b] | CH3[a] | SH | SO3H |
| 2191 | OCH3[b] | CH3[a] | SH | PO3H2 |
| 2192 | OCH3[b] | CH3[a] | SH | CHO |
| 2193 | OCH3[b] | CH3[a] | SH | COOH |
| 2194 | OCH3[b] | CH3[a] | SH | CH2OH |
| 2195 | OCH3[b] | CH3[a] | SH | sugar |
| 2196 | OCH3[b] | CH3[a] | SH | C-glycosyl compound |
| 2197 | OCH3[b] | CH3[a] | OCH3 | OH |
| 2198 | OCH3[b] | CH3[a] | OCH3 | D-glucitol |
| 2199 | OCH3[b] | CH3[a] | OCH3 | SO3H |
| 2200 | OCH3[b] | CH3[a] | OCH3 | PO3H2 |
| 2201 | OCH3[b] | CH3[a] | OCH3 | CHO |
| 2202 | OCH3[b] | CH3[a] | OCH3 | COOH |
| 2203 | OCH3[b] | CH3[a] | OCH3 | CH2OH |
| 2204 | OCH3[b] | CH3[a] | OCH3 | sugar |
| 2205 | OCH3[b] | CH3[a] | OCH3 | C-glycosyl compound |
| 2206 | OCH3[b] | OCH3[b] | H | OH |
| 2207 | OCH3[b] | OCH3[b] | H | D-glucitol |
| 2208 | OCH3[b] | OCH3[b] | H | SO3H |
| 2209 | OCH3[b] | OCH3[b] | H | PO3H2 |
| 2210 | OCH3[b] | OCH3[b] | H | CHO |
| 2211 | OCH3[b] | OCH3[b] | H | COOH |
| 2212 | OCH3[b] | OCH3[b] | H | CH2OH |
| 2213 | OCH3[b] | OCH3[b] | H | sugar |
| 2214 | OCH3[b] | OCH3[b] | H | C-glycosyl compound |
| 2215 | OCH3[b] | OCH3[b] | OH | OH |
| 2216 | OCH3[b] | OCH3[b] | OH | D-glucitol |
| 2217 | OCH3[b] | OCH3[b] | OH | SO3H |
| 2218 | OCH3[b] | OCH3[b] | OH | PO3H2 |
| 2219 | OCH3[b] | OCH3[b] | OH | CHO |
| 2220 | OCH3[b] | OCH3[b] | OH | COOH |
| 2221 | OCH3[b] | OCH3[b] | OH | CH2OH |
| 2222 | OCH3[b] | OCH3[b] | OH | sugar |
| 2223 | OCH3[b] | OCH3[b] | OH | C-glycosyl compound |
| 2224 | OCH3[b] | OCH3[b] | CH3 | OH |
| 2225 | OCH3[b] | OCH3[b] | CH3 | D-glucitol |
| 2226 | OCH3[b] | OCH3[b] | CH3 | SO3H |
| 2227 | OCH3[b] | OCH3[b] | CH3 | PO3H2 |
| 2228 | OCH3[b] | OCH3[b] | CH3 | CHO |
| 2229 | OCH3[b] | OCH3[b] | CH3 | COOH |
| 2230 | OCH3[b] | OCH3[b] | CH3 | CH2OH |
| 2231 | OCH3[b] | OCH3[b] | CH3 | sugar |
| 2232 | OCH3[b] | OCH3[b] | CH3 | C-glycosyl compound |
| 2233 | OCH3[b] | OCH3[b] | Cl | OH |
| 2234 | OCH3[b] | OCH3[b] | Cl | D-glucitol |
| 2235 | OCH3[b] | OCH3[b] | Cl | SO3H |
| 2236 | OCH3[b] | OCH3[b] | Cl | PO3H2 |
| 2237 | OCH3[b] | OCH3[b] | Cl | CHO |
| 2238 | OCH3[b] | OCH3[b] | Cl | COOH |
| 2239 | OCH3[b] | OCH3[b] | Cl | CH2OH |
| 2240 | OCH3[b] | OCH3[b] | Cl | sugar |
| 2241 | OCH3[b] | OCH3[b] | Cl | C-glycosyl compound |
| 2242 | OCH3[b] | OCH3[b] | B(OH)2 | OH |
| 2243 | OCH3[b] | OCH3[b] | B(OH)2 | D-glucitol |
| 2244 | OCH3[b] | OCH3[b] | B(OH)2 | SO3H |
| 2245 | OCH3[b] | OCH3[b] | B(OH)2 | PO3H2 |
| 2246 | OCH3[b] | OCH3[b] | B(OH)2 | CHO |
| 2247 | OCH3[b] | OCH3[b] | B(OH)2 | COOH |
| 2248 | OCH3[b] | OCH3[b] | B(OH)2 | CH2OH |
| 2249 | OCH3[b] | OCH3[b] | B(OH)2 | sugar |
| 2250 | OCH3[b] | OCH3[b] | B(OH)2 | C-glycosyl compound |
| 2251 | OCH3[b] | OCH3[b] | SH | OH |
| 2252 | OCH3[b] | OCH3[b] | SH | D-glucitol |
| 2253 | OCH3[b] | OCH3[b] | SH | SO3H |
| 2254 | OCH3[b] | OCH3[b] | SH | PO3H2 |
| 2255 | OCH3[b] | OCH3[b] | SH | CHO |
| 2256 | OCH3[b] | OCH3[b] | SH | COOH |
| 2257 | OCH3[b] | OCH3[b] | SH | CH2OH |
| 2258 | OCH3[b] | OCH3[b] | SH | sugar |
| 2259 | OCH3[b] | OCH3[b] | SH | C-glycosyl compound |
| 2260 | OCH3[b] | OCH3[b] | OCH3 | OH |
| 2261 | OCH3[b] | OCH3[b] | OCH3 | D-glucitol |
| 2262 | OCH3[b] | OCH3[b] | OCH3 | SO3H |
| 2263 | OCH3[b] | OCH3[b] | OCH3 | PO3H2 |
| 2264 | OCH3[b] | OCH3[b] | OCH3 | CHO |
| 2265 | OCH3[b] | OCH3[b] | OCH3 | COOH |
| 2266 | OCH3[b] | OCH3[b] | OCH3 | CH2OH |
| 2267 | OCH3[b] | OCH3[b] | OCH3 | sugar |
| 2268 | OCH3[b] | OCH3[b] | OCH3 | C-glycosyl compound |

[a] optionally substituted with one, two or three F
[b] optionally substituted with two or three F

TABLE 4

| row number | R1 | R2 | R4 | R5 |
|---|---|---|---|---|
| 1 | ortho | ortho | 3- | ortho |
| 2 | ortho | ortho | 3- | meta |
| 3 | ortho | ortho | 3- | para |
| 4 | ortho | ortho | 2- | ortho |
| 5 | ortho | ortho | 2- | meta |
| 6 | ortho | ortho | 2- | para |
| 7 | ortho | meta | 3- | ortho |
| 8 | ortho | meta | 3- | meta |
| 9 | ortho | meta | 3- | para |
| 10 | ortho | meta | 2- | ortho |
| 11 | ortho | meta | 2- | meta |
| 12 | ortho | meta | 2- | para |
| 13 | ortho | para | 3- | ortho |
| 14 | ortho | para | 3- | meta |
| 15 | ortho | para | 3- | para |
| 16 | ortho | para | 2- | ortho |
| 17 | ortho | para | 2- | meta |
| 18 | ortho | para | 2- | para |
| 19 | meta | ortho | 3- | ortho |
| 20 | meta | ortho | 3- | meta |
| 21 | meta | ortho | 3- | para |
| 22 | meta | ortho | 2- | ortho |
| 23 | meta | ortho | 2- | meta |
| 24 | meta | ortho | 2- | para |
| 25 | meta | meta | 3- | ortho |
| 26 | meta | meta | 3- | meta |
| 27 | meta | meta | 3- | para |
| 28 | meta | meta | 2- | ortho |
| 29 | meta | meta | 2- | meta |
| 30 | meta | meta | 2- | para |
| 31 | meta | para | 3- | ortho |
| 32 | meta | para | 3- | meta |
| 33 | meta | para | 3- | para |
| 34 | meta | para | 2- | ortho |
| 35 | meta | para | 2- | meta |
| 36 | meta | para | 2- | para |
| 37 | para | ortho | 3- | ortho |
| 38 | para | ortho | 3- | meta |
| 39 | para | ortho | 3- | para |
| 40 | para | ortho | 2- | ortho |
| 41 | para | ortho | 2- | meta |
| 42 | para | ortho | 2- | para |
| 43 | para | meta | 3- | ortho |
| 44 | para | meta | 3- | meta |
| 45 | para | meta | 3- | para |
| 46 | para | meta | 2- | ortho |
| 47 | para | meta | 2- | meta |
| 48 | para | meta | 2- | para |
| 49 | para | para | 3- | ortho |
| 50 | para | para | 3- | meta |
| 51 | para | para | 3- | para |

TABLE 4-continued

| row number | R1 | R2 | R4 | R5 |
|---|---|---|---|---|
| 52 | para | para | 2- | ortho |
| 53 | para | para | 2- | meta |
| 54 | para | para | 2- | para |

Table 5 lists the compounds disclosed by substitution of Formula VIII wherein $R^1$ is H, $R^2$ is F, $R^4$ is OH and $R^5$ is OH (i.e. Table 3, row 1) according to the positions defined by all rows of Table 4.

| | |
|---|---|
| 1 | (3R,4S)-4-(2',3-dihydroxybiphenyl-4-yl)-3-[(3S)-3-(2-fluorophenyl)-3-hydroxypropyl]-1-phenylazetidin-2-one |
| 2 | (3R,4S)-4-(3,3'-dihydroxybiphenyl-4-yl)-3-[(3S)-3-(2-fluorophenyl)-3-hydroxypropyl]-1-phenylazetidin-2-one |
| 3 | (3R,4S)-4-(3,4'-dihydroxybiphenyl-4-yl)-3-[(3S)-3-(2-fluorophenyl)-3-hydroxypropyl]-1-phenylazetidin-2-one |
| 4 | (3R,4S)-4-(2,2'-dihydroxybiphenyl-4-yl)-3-[(3S)-3-(2-fluorophenyl)-3-hydroxypropyl]-1-phenylazetidin-2-one |
| 5 | (3R,4S)-4-(2,3'-dihydroxybiphenyl-4-yl)-3-[(3S)-3-(2-fluorophenyl)-3-hydroxypropyl]-1-phenylazetidin-2-one |
| 6 | (3R,4S)-4-(2,4'-dihydroxybiphenyl-4-yl)-3-[(3S)-3-(2-fluorophenyl)-3-hydroxypropyl]-1-phenylazetidin-2-one |
| 7 | (3R,4S)-4-(2',3-dihydroxybiphenyl-4-yl)-3-[(3S)-3-(3-fluorophenyl)-3-hydroxypropyl]-1-phenylazetidin-2-one |
| 8 | (3R,4S)-4-(3,3'-dihydroxybiphenyl-4-yl)-3-[(3S)-3-(3-fluorophenyl)-3-hydroxypropyl]-1-phenylazetidin-2-one |
| 9 | (3R,4S)-4-(3,4'-dihydroxybiphenyl-4-yl)-3-[(3S)-3-(3-fluorophenyl)-3-hydroxypropyl]-1-phenylazetidin-2-one |
| 10 | (3R,4S)-4-(2,2'-dihydroxybiphenyl-4-yl)-3-[(3S)-3-(3-fluorophenyl)-3-hydroxypropyl]-1-phenylazetidin-2-one |
| 11 | (3R,4S)-4-(2,3'-dihydroxybiphenyl-4-yl)-3-[(3S)-3-(3-fluorophenyl)-3-hydroxypropyl]-1-phenylazetidin-2-one |
| 12 | (3R,4S)-4-(2,4'-dihydroxybiphenyl-4-yl)-3-[(3S)-3-(3-fluorophenyl)-3-hydroxypropyl]-1-phenylazetidin-2-one |
| 13 | (3R,4S)-4-(2',3-dihydroxybiphenyl-4-yl)-3-[(3S)-3-(4-fluorophenyl)-3-hydroxypropyl]-1-phenylazetidin-2-one |
| 14 | (3R,4S)-4-(3,3'-dihydroxybiphenyl-4-yl)-3-[(3S)-3-(4-fluorophenyl)-3-hydroxypropyl]-1-phenylazetidin-2-one |
| 15 | (3R,4S)-4-(3,4'-dihydroxybiphenyl-4-yl)-3-[(3S)-3-(4-fluorophenyl)-3-hydroxypropyl]-1-phenylazetidin-2-one |
| 16 | (3R,4S)-4-(2,2'-dihydroxybiphenyl-4-yl)-3-[(3S)-3-(4-fluorophenyl)-3-hydroxypropyl]-1-phenylazetidin-2-one |
| 17 | (3R,4S)-4-(2,3'-dihydroxybiphenyl-4-yl)-3-[(3S)-3-(4-fluorophenyl)-3-hydroxypropyl]-1-phenylazetidin-2-one |
| 18 | (3R,4S)-4-(2,4'-dihydroxybiphenyl-4-yl)-3-[(3S)-3-(4-fluorophenyl)-3-hydroxypropyl]-1-phenylazetidin-2-one |

Table 6 lists the compounds disclosed by substitution of Formula VIII wherein $R^1$ is H, $R^2$ is F, $R^4$ is OH and $R^5$ is D-glucitol (i.e. Table 3, row 2) according to the positions defined by all rows of Table 4.

| | |
|---|---|
| 1 | (1S)-1,5-anhydro-1-(4'-{(2S,3R)-3-[(3S)-3-(2-fluorophenyl)-3-hydroxypropyl]-4-oxo-1-phenylazetidin-2-yl}-3'-hydroxybiphenyl-2-yl)-D-glucitol |
| 2 | (1S)-1,5-anhydro-1-(4'-{(2S,3R)-3-[(3S)-3-(2-fluorophenyl)-3-hydroxypropyl]-4-oxo-1-phenylazetidin-2-yl}-3'-hydroxybiphenyl-3-yl)-D-glucitol |
| 3 | (1S)-1,5-anhydro-1-(4'-{(2S,3R)-3-[(3S)-3-(2-fluorophenyl)-3-hydroxypropyl]-4-oxo-1-phenylazetidin-2-yl}-3'-hydroxybiphenyl-4-yl)-D-glucitol |
| 4 | (1S)-1,5-anhydro-1-(4'-{(2S,3R)-3-[(3S)-3-(2-fluorophenyl)-3-hydroxypropyl]-4-oxo-1-phenylazetidin-2-yl}-2'-hydroxybiphenyl-2-yl)-D-glucitol |
| 5 | (1S)-1,5-anhydro-1-(4'-{(2S,3R)-3-[(3S)-3-(2-fluorophenyl)-3-hydroxypropyl]-4-oxo-1-phenylazetidin-2-yl}-2'-hydroxybiphenyl-3-yl)-D-glucitol |
| 6 | (1S)-1,5-anhydro-1-(4'-{(2S,3R)-3-[(3S)-3-(2-fluorophenyl)-3-hydroxypropyl]-4-oxo-1-phenylazetidin-2-yl}-2'-hydroxybiphenyl-4-yl)-D-glucitol |
| 7 | (1S)-1,5-anhydro-1-(4'-{(2S,3R)-3-[(3S)-3-(3-fluorophenyl)-3-hydroxypropyl]-4-oxo-1-phenylazetidin-2-yl}-3'-hydroxybiphenyl-2-yl)-D-glucitol |
| 8 | (1S)-1,5-anhydro-1-(4'-{(2S,3R)-3-[(3S)-3-(3-fluorophenyl)-3-hydroxypropyl]-4-oxo-1-phenylazetidin-2-yl}-3'-hydroxybiphenyl-3-yl)-D-glucitol |
| 9 | (1S)-1,5-anhydro-1-(4'-{(2S,3R)-3-[(3S)-3-(3-fluorophenyl)-3-hydroxypropyl]-4-oxo-1-phenylazetidin-2-yl}-3'-hydroxybiphenyl-4-yl)-D-glucitol |
| 10 | (1S)-1,5-anhydro-1-(4'-{(2S,3R)-3-[(3S)-3-(3-fluorophenyl)-3-hydroxypropyl]-4-oxo-1-phenylazetidin-2-yl}-2'-hydroxybiphenyl-2-yl)-D-glucitol |
| 11 | (1S)-1,5-anhydro-1-(4'-{(2S,3R)-3-[(3S)-3-(3-fluorophenyl)-3-hydroxypropyl]-4-oxo-1-phenylazetidin-2-yl}-2'-hydroxybiphenyl-3-yl)-D-glucitol |
| 12 | (1S)-1,5-anhydro-1-(4'-{(2S,3R)-3-[(3S)-3-(3-fluorophenyl)-3-hydroxypropyl]-4-oxo-1-phenylazetidin-2-yl}-2'-hydroxybiphenyl-4-yl)-D-glucitol |
| 13 | (1S)-1,5-anhydro-1-(4'-{(2S,3R)-3-[(3S)-3-(4-fluorophenyl)-3-hydroxypropyl]-4-oxo-1-phenylazetidin-2-yl}-3'-hydroxybiphenyl-2-yl)-D-glucitol |
| 14 | (1S)-1,5-anhydro-1-(4'-{(2S,3R)-3-[(3S)-3-(4-fluorophenyl)-3-hydroxypropyl]-4-oxo-1-phenylazetidin-2-yl}-3'-hydroxybiphenyl-3-yl)-D-glucitol |
| 15 | (1S)-1,5-anhydro-1-(4'-{(2S,3R)-3-[(3S)-3-(4-fluorophenyl)-3-hydroxypropyl]-4-oxo-1-phenylazetidin-2-yl}-3'-hydroxybiphenyl-4-yl)-D-glucitol |
| 16 | (1S)-1,5-anhydro-1-(4'-{(2S,3R)-3-[(3S)-3-(4-fluorophenyl)-3-hydroxypropyl]-4-oxo-1-phenylazetidin-2-yl}-2'-hydroxybiphenyl-2-yl)-D-glucitol |
| 17 | (1S)-1,5-anhydro-1-(4'-{(2S,3R)-3-[(3S)-3-(4-fluorophenyl)-3-hydroxypropyl]-4-oxo-1-phenylazetidin-2-yl}-2'-hydroxybiphenyl-3-yl)-D-glucitol |
| 18 | (1S)-1,5-anhydro-1-(4'-{(2S,3R)-3-[(3S)-3-(4-fluorophenyl)-3-hydroxypropyl]-4-oxo-1-phenylazetidin-2-yl}-2'-hydroxybiphenyl-4-yl)-D-glucitol |

Table 7 lists the compounds disclosed by substitution of Formula VIII wherein $R^1$ is H, $R^2$ is F, $R^4$ is OH and $R^5$ is $SO_3H$ (i.e. Table 3, row 3) according to the positions defined by all rows of Table 4.

| | |
|---|---|
| 1 | 4'-{(2S,3R)-3-[(3S)-3-(2-fluorophenyl)-3-hydroxypropyl]-4-oxo-1-phenylazetidin-2-yl}-3'-hydroxybiphenyl-2-sulfonic acid |
| 2 | 4'-{(2S,3R)-3-[(3S)-3-(2-fluorophenyl)-3-hydroxypropyl]-4-oxo-1-phenylazetidin-2-yl}-3'-hydroxybiphenyl-3-sulfonic acid |
| 3 | 4'-{(2S,3R)-3-[(3S)-3-(2-fluorophenyl)-3-hydroxypropyl]-4-oxo-1-phenylazetidin-2-yl}-3'-hydroxybiphenyl-4-sulfonic acid |
| 4 | 4'-{(2S,3R)-3-[(3S)-3-(2-fluorophenyl)-3-hydroxypropyl]-4-oxo-1-phenylazetidin-2-yl}-2'-hydroxybiphenyl-2-sulfonic acid |
| 5 | 4'-{(2S,3R)-3-[(3S)-3-(2-fluorophenyl)-3-hydroxypropyl]-4-oxo-1-phenylazetidin-2-yl}-2'-hydroxybiphenyl-3-sulfonic acid |

| | |
|---|---|
| 6 | 4'-{(2S,3R)-3-[(3S)-3-(2-fluorophenyl)-3-hydroxypropyl]-4-oxo-1-phenylazetidin-2-yl}-2'-hydroxybiphenyl-4-sulfonic acid |
| 7 | 4'-{(2S,3R)-3-[(3S)-3-(3-fluorophenyl)-3-hydroxypropyl]-4-oxo-1-phenylazetidin-2-yl}-3'-hydroxybiphenyl-2-sulfonic acid |
| 8 | 4'-{(2S,3R)-3-[(3S)-3-(3-fluorophenyl)-3-hydroxypropyl]-4-oxo-1-phenylazetidin-2-yl}-3'-hydroxybiphenyl-3-sulfonic acid |
| 9 | 4'-{(2S,3R)-3-[(3S)-3-(3-fluorophenyl)-3-hydroxypropyl]-4-oxo-1-phenylazetidin-2-yl}-3'-hydroxybiphenyl-4-sulfonic acid |
| 10 | 4'-{(2S,3R)-3-[(3S)-3-(3-fluorophenyl)-3-hydroxypropyl]-4-oxo-1-phenylazetidin-2-yl}-2'-hydroxybiphenyl-2-sulfonic acid |
| 11 | 4'-{(2S,3R)-3-[(3S)-3-(3-fluorophenyl)-3-hydroxypropyl]-4-oxo-1-phenylazetidin-2-yl}-2'-hydroxybiphenyl-3-sulfonic acid |
| 12 | 4'-{(2S,3R)-3-[(3S)-3-(3-fluorophenyl)-3-hydroxypropyl]-4-oxo-1-phenylazetidin-2-yl}-2'-hydroxybiphenyl-4-sulfonic acid |
| 13 | 4'-{(2S,3R)-3-[(3S)-3-(4-fluorophenyl)-3-hydroxypropyl]-4-oxo-1-phenylazetidin-2-yl}-3'-hydroxybiphenyl-2-sulfonic acid |
| 14 | 4'-{(2S,3R)-3-[(3S)-3-(4-fluorophenyl)-3-hydroxypropyl]-4-oxo-1-phenylazetidin-2-yl}-3'-hydroxybiphenyl-3-sulfonic acid |
| 15 | 4'-{(2S,3R)-3-[(3S)-3-(4-fluorophenyl)-3-hydroxypropyl]-4-oxo-1-phenylazetidin-2-yl}-3'-hydroxybiphenyl-4-sulfonic acid |
| 16 | 4'-{(2S,3R)-3-[(3S)-3-(4-fluorophenyl)-3-hydroxypropyl]-4-oxo-1-phenylazetidin-2-yl}-2'-hydroxybiphenyl-2-sulfonic acid |
| 17 | 4'-{(2S,3R)-3-[(3S)-3-(4-fluorophenyl)-3-hydroxypropyl]-4-oxo-1-phenylazetidin-2-yl}-2'-hydroxybiphenyl-3-sulfonic acid |
| 18 | 4'-{(2S,3R)-3-[(3S)-3-(4-fluorophenyl)-3-hydroxypropyl]-4-oxo-1-phenylazetidin-2-yl}-2'-hydroxybiphenyl-4-sulfonic acid |

Table 8 lists the compounds disclosed by substitution of Formula VIII wherein $R^1$ is H, $R^2$ is F, $R^4$ is OH and $R^5$ is $PO_3H_2$ (i.e. Table 3, row 4) according to the positions defined by all rows of Table 4.

| | |
|---|---|
| 1 | (4'-{(2S,3R)-3-[(3S)-3-(2-fluorophenyl)-3-hydroxypropyl]-4-oxo-1-phenylazetidin-2-yl}-3'-hydroxybiphenyl-2-yl)phosphonic acid |
| 2 | (4'-{(2S,3R)-3-[(3S)-3-(2-fluorophenyl)-3-hydroxypropyl]-4-oxo-1-phenylazetidin-2-yl}-3'-hydroxybiphenyl-3-yl)phosphonic acid |
| 3 | (4'-{(2S,3R)-3-[(3S)-3-(2-fluorophenyl)-3-hydroxypropyl]-4-oxo-1-phenylazetidin-2-yl}-3'-hydroxybiphenyl-4-yl)phosphonic acid |
| 4 | (4'-{(2S,3R)-3-[(3S)-3-(2-fluorophenyl)-3-hydroxypropyl]-4-oxo-1-phenylazetidin-2-yl}-2'-hydroxybiphenyl-2-yl)phosphonic acid |
| 5 | (4'-{(2S,3R)-3-[(3S)-3-(2-fluorophenyl)-3-hydroxypropyl]-4-oxo-1-phenylazetidin-2-yl}-2'-hydroxybiphenyl-3-yl)phosphonic acid |
| 6 | (4'-{(2S,3R)-3-[(3S)-3-(2-fluorophenyl)-3-hydroxypropyl]-4-oxo-1-phenylazetidin-2-yl}-2'-hydroxybiphenyl-4-yl)phosphonic acid |
| 7 | (4'-{(2S,3R)-3-[(3S)-3-(3-fluorophenyl)-3-hydroxypropyl]-4-oxo-1-phenylazetidin-2-yl}-3'-hydroxybiphenyl-2-yl)phosphonic acid |
| 8 | (4'-{(2S,3R)-3-[(3S)-3-(3-fluorophenyl)-3-hydroxypropyl]-4-oxo-1-phenylazetidin-2-yl}-3'-hydroxybiphenyl-3-yl)phosphonic acid |
| 9 | (4'-{(2S,3R)-3-[(3S)-3-(3-fluorophenyl)-3-hydroxypropyl]-4-oxo-1-phenylazetidin-2-yl}-3'-hydroxybiphenyl-4-yl)phosphonic acid |
| 10 | (4'-{(2S,3R)-3-[(3S)-3-(3-fluorophenyl)-3-hydroxypropyl]-4-oxo-1-phenylazetidin-2-yl}-2'-hydroxybiphenyl-2-yl)phosphonic acid |
| 11 | (4'-{(2S,3R)-3-[(3S)-3-(3-fluorophenyl)-3-hydroxypropyl]-4-oxo-1-phenylazetidin-2-yl}-2'-hydroxybiphenyl-3-yl)phosphonic acid |
| 12 | (4'-{(2S,3R)-3-[(3S)-3-(3-fluorophenyl)-3-hydroxypropyl]-4-oxo-1-phenylazetidin-2-yl}-2'-hydroxybiphenyl-4-yl)phosphonic acid |
| 13 | (4'-{(2S,3R)-3-[(3S)-3-(4-fluorophenyl)-3-hydroxypropyl]-4-oxo-1-phenylazetidin-2-yl}-3'-hydroxybiphenyl-2-yl)phosphonic acid |
| 14 | (4'-{(2S,3R)-3-[(3S)-3-(4-fluorophenyl)-3-hydroxypropyl]-4-oxo-1-phenylazetidin-2-yl}-3'-hydroxybiphenyl-3-yl)phosphonic acid |
| 15 | (4'-{(2S,3R)-3-[(3S)-3-(4-fluorophenyl)-3-hydroxypropyl]-4-oxo-1-phenylazetidin-2-yl}-3'-hydroxybiphenyl-4-yl)phosphonic acid |
| 16 | (4'-{(2S,3R)-3-[(3S)-3-(4-fluorophenyl)-3-hydroxypropyl]-4-oxo-1-phenylazetidin-2-yl}-2'-hydroxybiphenyl-2-yl)phosphonic acid |
| 17 | (4'-{(2S,3R)-3-[(3S)-3-(4-fluorophenyl)-3-hydroxypropyl]-4-oxo-1-phenylazetidin-2-yl}-2'-hydroxybiphenyl-3-yl)phosphonic acid |
| 18 | (4'-{(2S,3R)-3-[(3S)-3-(4-fluorophenyl)-3-hydroxypropyl]-4-oxo-1-phenylazetidin-2-yl}-2'-hydroxybiphenyl-4-yl)phosphonic acid |

Table 9 lists the compounds disclosed by substitution of Formula VIII wherein $R^1$ is H, $R^2$ is H, $R^4$ is OH and $R^5$ is OH (i.e. Table 3, row 5) according to the positions defined by all rows of Table 4.

| | |
|---|---|
| 1 | (3R,4S)-4-(2',3-dihydroxybiphenyl-4-yl)-3-[(3S)-3-hydroxy-3-phenylpropyl]-1-phenylazetidin-2-one |
| 2 | (3R,4S)-4-(3,3'-dihydroxybiphenyl-4-yl)-3-[(3S)-3-hydroxy-3-phenylpropyl]-1-phenylazetidin-2-one |
| 3 | (3R,4S)-4-(3,4'-dihydroxybiphenyl-4-yl)-3-[(3S)-3-hydroxy-3-phenylpropyl]-1-phenylazetidin-2-one |
| 4 | (3R,4S)-4-(2,2'-dihydroxybiphenyl-4-yl)-3-[(3S)-3-hydroxy-3-phenylpropyl]-1-phenylazetidin-2-one |
| 5 | (3R,4S)-4-(2,3'-dihydroxybiphenyl-4-yl)-3-[(3S)-3-hydroxy-3-phenylpropyl]-1-phenylazetidin-2-one |
| 6 | (3R,4S)-4-(2,4'-dihydroxybiphenyl-4-yl)-3-[(3S)-3-hydroxy-3-phenylpropyl]-1-phenylazetidin-2-one |

Table 10 lists the compounds disclosed by substitution of Formula VIII wherein $R^1$ is H, $R^2$ is H, $R^4$ is OH and $R^5$ is D-glucitol (i.e. Table 3, row 6) according to the positions defined by all rows of Table 4.

| | |
|---|---|
| 1 | (1S)-1,5-anhydro-1-(3'-hydroxy-4'-{(2S,3R)-3-[(3S)-3-hydroxy-3-phenylpropyl]-4-oxo-1-phenylazetidin-2-yl}biphenyl-2-yl)-D-glucitol |
| 2 | (1S)-1,5-anhydro-1-(3'-hydroxy-4'-{(2S,3R)-3-[(3S)-3-hydroxy-3-phenylpropyl]-4-oxo-1-phenylazetidin-2-yl}biphenyl-3-yl)-D-glucitol |
| 3 | (1S)-1,5-anhydro-1-(3'-hydroxy-4'-{(2S,3R)-3-[(3S)-3-hydroxy-3-phenylpropyl]-4-oxo-1-phenylazetidin-2-yl}biphenyl-4-yl)-D-glucitol |
| 4 | (1S)-1,5-anhydro-1-(2'-hydroxy-4'-{(2S,3R)-3-[(3S)-3-hydroxy-3-phenylpropyl]-4-oxo-1-phenylazetidin-2-yl}biphenyl-2-yl)-D-glucitol |
| 5 | (1S)-1,5-anhydro-1-(2'-hydroxy-4'-{(2S,3R)-3-[(3S)-3-hydroxy-3-phenylpropyl]-4-oxo-1-phenylazetidin-2-yl}biphenyl-3-yl)-D-glucitol |
| 6 | (1S)-1,5-anhydro-1-(2'-hydroxy-4'-{(2S,3R)-3-[(3S)-3-hydroxy-3-phenylpropyl]-4-oxo-1-phenylazetidin-2-yl}biphenyl-4-yl)-D-glucitol |

Table 11 lists the compounds disclosed by substitution of Formula VIII wherein $R^1$ is H, $R^2$ is H, $R^4$ is OH and $R^5$ is $SO_3H$ (i.e. Table 3, row 7) according to the positions defined by all rows of Table 4.

| | |
|---|---|
| 1 | 3'-hydroxy-4'-{(2S,3R)-3-[(3S)-3-hydroxy-3-phenylpropyl]-4-oxo-1-phenylazetidin-2-yl}biphenyl-2-sulfonic acid |
| 2 | 3'-hydroxy-4'-{(2S,3R)-3-[(3S)-3-hydroxy-3-phenylpropyl]-4-oxo-1-phenylazetidin-2-yl}biphenyl-3-sulfonic acid |
| 3 | 3'-hydroxy-4'-{(2S,3R)-3-[(3S)-3-hydroxy-3-phenylpropyl]-4-oxo-1-phenylazetidin-2-yl}biphenyl-4-sulfonic acid |
| 4 | 2'-hydroxy-4'-{(2S,3R)-3-[(3S)-3-hydroxy-3-phenylpropyl]-4-oxo-1-phenylazetidin-2-yl}biphenyl-2-sulfonic acid |
| 5 | 2'-hydroxy-4'-{(2S,3R)-3-[(3S)-3-hydroxy-3-phenylpropyl]-4-oxo-1-phenylazetidin-2-yl}biphenyl-3-sulfonic acid |
| 6 | 2'-hydroxy-4'-{(2S,3R)-3-[(3S)-3-hydroxy-3-phenylpropyl]-4-oxo-1-phenylazetidin-2-yl}biphenyl-4-sulfonic acid |

Table 12 lists the compounds disclosed by substitution of Formula VIII wherein $R^1$ is H, $R^2$ is H, $R^4$ is OH and $R^5$ is $PO_3H_2$ (i.e. Table 3, row 8) according to the positions defined by all rows of Table 4.

| | |
|---|---|
| 1 | (3'-hydroxy-4'-{(2S,3R)-3-[(3S)-3-hydroxy-3-phenylpropyl]-4-oxo-1-phenylazetidin-2-yl}biphenyl-2-yl)phosphonic acid |
| 2 | (3'-hydroxy-4'-{(2S,3R)-3-[(3S)-3-hydroxy-3-phenylpropyl]-4-oxo-1-phenylazetidin-2-yl}biphenyl-3-yl)phosphonic acid |
| 3 | (3'-hydroxy-4'-{(2S,3R)-3-[(3S)-3-hydroxy-3-phenylpropyl]-4-oxo-1-phenylazetidin-2-yl}biphenyl-4-yl)phosphonic acid |
| 4 | (2'-hydroxy-4'-{(2S,3R)-3-[(3S)-3-hydroxy-3-phenylpropyl]-4-oxo-1-phenylazetidin-2-yl}biphenyl-2-yl)phosphonic acid |
| 5 | (2'-hydroxy-4'-{(2S,3R)-3-[(3S)-3-hydroxy-3-phenylpropyl]-4-oxo-1-phenylazetidin-2-yl}biphenyl-3-yl)phosphonic acid |
| 6 | (2'-hydroxy-4'-{(2S,3R)-3-[(3S)-3-hydroxy-3-phenylpropyl]-4-oxo-1-phenylazetidin-2-yl}biphenyl-4-yl)phosphonic acid |

Table 13 lists the compounds disclosed by substitution of Formula VIII wherein $R^1$ is H, $R^2$ is Cl, $R^4$ is OH and $R^5$ is OH (i.e. Table 3, row 9) according to the positions defined by all rows of Table 4.

| | |
|---|---|
| 1 | (3R,4S)-4-(2',3-dihydroxybiphenyl-4-yl)-3-[(3S)-3-(2-chlorophenyl)-3-hydroxypropyl]-1-phenylazetidin-2-one |
| 2 | (3R,4S)-4-(3,3'-dihydroxybiphenyl-4-yl)-3-[(3S)-3-(2-chlorophenyl)-3-hydroxypropyl]-1-phenylazetidin-2-one |
| 3 | (3R,4S)-4-(3,4'-dihydroxybiphenyl-4-yl)-3-[(3S)-3-(2-chlorophenyl)-3-hydroxypropyl]-1-phenylazetidin-2-one |
| 4 | (3R,4S)-4-(2,2'-dihydroxybiphenyl-4-yl)-3-[(3S)-3-(2-chlorophenyl)-3-hydroxypropyl]-1-phenylazetidin-2-one |
| 5 | (3R,4S)-4-(2,3-dihydroxybiphenyl-4-yl)-3-[(3S)-3-(2-chlorophenyl)-3-hydroxypropyl]-1-phenylazetidin-2-one |
| 6 | (3R,4S)-4-(2,4'-dihydroxybiphenyl-4-yl)-3-[(3S)-3-(2-chlorophenyl)-3-hydroxypropyl]-1-phenylazetidin-2-one |
| 7 | (3R,4S)-4-(2',3-dihydroxybiphenyl-4-yl)-3-[(3S)-3-(3-chlorophenyl)-3-hydroxypropyl]-1-phenylazetidin-2-one |
| 8 | (3R,4S)-4-(3,3'-dihydroxybiphenyl-4-yl)-3-[(3S)-3-(3-chlorophenyl)-3-hydroxypropyl]-1-phenylazetidin-2-one |
| 9 | (3R,4S)-4-(3,4'-dihydroxybiphenyl-4-yl)-3-[(3S)-3-(3-chlorophenyl)-3-hydroxypropyl]-1-phenylazetidin-2-one |
| 10 | (3R,4S)-4-(2,2'-dihydroxybiphenyl-4-yl)-3-[(3S)-3-(3-chlorophenyl)-3-hydroxypropyl]-1-phenylazetidin-2-one |
| 11 | (3R,4S)-4-(2,3-dihydroxybiphenyl-4-yl)-3-[(3S)-3-(3-cjlorophenyl)-3-hydroxypropyl]-1-phenylazetidin-2-one |
| 12 | (3R,4S)-4-(2,4'-dihydroxybiphenyl-4-yl)-3-[(3S)-3-(3-chlorophenyl)-3-hydroxypropyl]-1-phenylazetidin-2-one |
| 13 | (3R,4S)-4-(2',3-dihydroxybiphenyl-4-yl)-3-[(3S)-3-(4-chlorophenyl)-3-hydroxypropyl]-1-phenylazetidin-2-one |
| 14 | (3R,4S)-4-(3,3'-dihydroxybiphenyl-4-yl)-3-[(3S)-3-(4-chlorophenyl)-3-hydroxypropyl]-1-phenylazetidin-2-one |
| 15 | (3R,4S)-4-(3,4'-dihydroxybiphenyl-4-yl)-3-[(3S)-3-(4-chlorophenyl)-3-hydroxypropyl]-1-phenylazetidin-2-one |
| 16 | (3R,4S)-4-(2,2'-dihydroxybiphenyl-4-yl)-3-[(3S)-3-(4-chlorophenyl)-3-hydroxypropyl]-1-phenylazetidin-2-one |
| 17 | (3R,4S)-4-(2,3'-dihydroxybiphenyl-4-yl)-3-[(3S)-3-(4-chlorophenyl)-3-hydroxypropyl]-1-phenylazetidin-2-one |
| 18 | (3R,4S)-4-(2,4'-dihydroxybiphenyl-4-yl)-3-[(3S)-3-(4chlorophenyl)-3-hydroxypropyl]-1-phenylazetidin-2-one |

Table 14 lists the compounds disclosed by substitution of Formula VIII wherein $R^1$ is H, $R^2$ is Cl, $R^4$ is OH and $R^5$ is D-glucitol (i.e. Table 3, row 10) according to the positions defined by all rows of Table 4.

| | |
|---|---|
| 1 | (1S)-1,5-anhydro-1-(4'-{(2S,3R)-3-[(3S)-3-(2-chlorophenyl)-3-hydroxypropyl]-4-oxo-1-phenylazetidin-2-yl}-3'-hydroxybiphenyl-2-yl)-D-glucitol |
| 2 | (1S)-1,5-anhydro-1-(4'-{(2S,3R)-3-[(3S)-3-(2-chlorophenyl)-3-hydroxypropyl]-4-oxo-1-phenylazetidin-2-yl}-3'-hydroxybiphenyl-3-yl)-D-glucitol |
| 3 | (1S)-1,5-anhydro-1-(4'-{(2S,3R)-3-[(3S)-3-(2-chlorophenyl)-3-hydroxypropyl]-4-oxo-1-phenylazetidin-2-yl}-3'-hydroxybiphenyl-4-yl)-D-glucitol |
| 4 | (1S)-1,5-anhydro-1-(4'-{(2S,3R)-3-[(3S)-3-(2-chlorophenyl)-3-hydroxypropyl]-4-oxo-1-phenylazetidin-2-yl}-2'-hydroxybiphenyl-2-yl)-D-glucitol |
| 5 | (1S)-1,5-anhydro-1-(4'-{(2S,3R)-3-[(3S)-3-(2-chlorophenyl)-3-hydroxypropyl]-4-oxo-1-phenylazetidin-2-yl}-2'-hydroxybiphenyl-3-yl)-D-glucitol |
| 6 | (1S)-1,5-anhydro-1-(4'-{(2S,3R)-3-[(3S)-3-(2-chlorophenyl)-3-hydroxypropyl]-4-oxo-1-phenylazetidin-2-yl}-2'-hydroxybiphenyl-4-yl)-D-glucitol |
| 7 | (1S)-1,5-anhydro-1-(4'-{(2S,3R)-3-[(3S)-3-(3-chlorophenyl)-3-hydroxypropyl]-4-oxo-1-phenylazetidin-2-yl}-3'-hydroxybiphenyl-2-yl)-D-glucitol |
| 8 | (1S)-1,5-anhydro-1-(4'-{(2S,3R)-3-[(3S)-3-(3-chlorophenyl)-3-hydroxypropyl]-4-oxo-1-phenylazetidin-2-yl}-3'-hydroxybiphenyl-3-yl)-D-glucitol |
| 9 | (1S)-1,5-anhydro-1-(4'-{(2S,3R)-3-[(3S)-3-(3-chlorophenyl)-3-hydroxypropyl]-4-oxo-1-phenylazetidin-2-yl}-3'-hydroxybiphenyl-4-yl)-D-glucitol |
| 10 | (1S)-1,5-anhydro-1-(4'-{(2S,3R)-3-[(3S)-3-(3-chlorophenyl)-3-hydroxypropyl]-4-oxo-1-phenylazetidin-2-yl}-2'-hydroxybiphenyl-2-yl)-D-glucitol |
| 11 | (1S)-1,5-anhydro-1-(4'-{(2S,3R)-3-[(3S)-3-(3-chlorophenyl)-3-hydroxypropyl]-4-oxo-1-phenylazetidin-2-yl}-2'-hydroxybiphenyl-3-yl)-D-glucitol |
| 12 | (1S)-1,5-anhydro-1-(4'-{(2S,3R)-3-[(3S)-3-(3-chlorophenyl)-3-hydroxypropyl]-4-oxo-1-phenylazetidin-2-yl}-2'-hydroxybiphenyl-4-yl)-D-glucitol |
| 13 | (1S)-1,5-anhydro-1-(4'-{(2S,3R)-3-[(3S)-3-(4-chlorophenyl)-3-hydroxypropyl]-4-oxo-1-phenylazetidin-2-yl}-3'-hydroxybiphenyl-2-yl)-D-glucitol |
| 14 | (1S)-1,5-anhydro-1-(4'-{(2S,3R)-3-[(3S)-3-(4-chlorophenyl)-3-hydroxypropyl]-4-oxo-1-phenylazetidin-2-yl}-3'-hydroxybiphenyl-3-yl)-D-glucitol |
| 15 | (1S)-1,5-anhydro-1-(4'-{(2S,3R)-3-[(3S)-3-(4-chlorophenyl)-3-hydroxypropyl]-4-oxo-1-phenylazetidin-2-yl}-3'-hydroxybiphenyl-4-yl)-D-glucitol |
| 16 | (1S)-1,5-anhydro-1-(4'-{(2S,3R)-3-[(3S)-3-(4-chlorophenyl)-3-hydroxypropyl]-4-oxo-1-phenylazetidin-2-yl}-2'-hydroxybiphenyl-2-yl)-D-glucitol |

-continued

| | |
|---|---|
| 17 | (1S)-1,5-anhydro-1-(4'-{(2S,3R)-3-[(3S)-3-(4-chlorophenyl)-3-hydroxypropyl]-4-oxo-1-phenylazetidin-2-yl}-2'-hydroxybiphenyl-3-yl)-D-glucitol |
| 18 | (1S)-1,5-anhydro-1-(4'-{(2S,3R)-3-[(3S)-3-(4-chlorophenyl)-3-hydroxypropyl]-4-oxo-1-phenylazetidin-2-yl}-2'-hydroxybiphenyl-4-yl)-D-glucitol |

Table 15 lists the compounds disclosed by substitution of Formula VIII wherein $R^1$ is H, $R^2$ is Cl, $R^4$ is OH and $R^5$ is $SO_3H$ (i.e. Table 3, row 11) according to the positions defined by all rows of Table 4.

| | |
|---|---|
| 1 | 4'-{(2S,3R)-3-[(3S)-3-(2-chlorophenyl)-3-hydroxypropyl]-4-oxo-1-phenylazetidin-2-yl}-3'-hydroxybiphenyl-2-sulfonic acid |
| 2 | 4'-{(2S,3R)-3-[(3S)-3-(2-chlorophenyl)-3-hydroxypropyl]-4-oxo-1-phenylazetidin-2-yl}-3'-hydroxybiphenyl-3-sulfonic acid |
| 3 | 4'-{(2S,3R)-3-[(3S)-3-(2-chlorophenyl)-3-hydroxypropyl]-4-oxo-1-phenylazetidin-2-yl}-3'-hydroxybiphenyl-4-sulfonic acid |
| 4 | 4'-{(2S,3R)-3-[(3S)-3-(2-chlorophenyl)-3-hydroxypropyl]-4-oxo-1-phenylazetidin-2-yl}-2'-hydroxybiphenyl-2-sulfonic acid |
| 5 | 4'-{(2S,3R)-3-[(3S)-3-(2-chlorophenyl)-3-hydroxypropyl]-4-oxo-1-phenylazetidin-2-yl}-2'-hydroxybiphenyl-3-sulfonic acid |
| 6 | 4'-{(2S,3R)-3-[(3S)-3-(2-chlorophenyl)-3-hydroxypropyl]-4-oxo-1-phenylazetidin-2-yl}-2'-hydroxybiphenyl-4-sulfonic acid |
| 7 | 4'-{(2S,3R)-3-[(3S)-3-(3-chlorophenyl)-3-hydroxypropyl]-4-oxo-1-phenylazetidin-2-yl}-3'-hydroxybiphenyl-2-sulfonic acid |
| 8 | 4'-{(2S,3R)-3-[(3S)-3-(3-chlorophenyl)-3-hydroxypropyl]-4-oxo-1-phenylazetidin-2-yl}-3'-hydroxybiphenyl-3-sulfonic acid |
| 9 | 4'-{(2S,3R)-3-[(3S)-3-(3-chlorophenyl)-3-hydroxypropyl]-4-oxo-1-phenylazetidin-2-yl}-3'-hydroxybiphenyl-4-sulfonic acid |
| 10 | 4'-{(2S,3R)-3-[(3S)-3-(3-chlorophenyl)-3-hydroxypropyl]-4-oxo-1-phenylazetidin-2-yl}-2'-hydroxybiphenyl-2-sulfonic acid |
| 11 | 4'-{(2S,3R)-3-[(3S)-3-(3-chlorophenyl)-3-hydroxypropyl]-4-oxo-1-phenylazetidin-2-yl}-2'-hydroxybiphenyl-3-sulfonic acid |
| 12 | 4'-{(2S,3R)-3-[(3S)-3-(3-chlorophenyl)-3-hydroxypropyl]-4-oxo-1-phenylazetidin-2-yl}-2'-hydroxybiphenyl-4-sulfonic acid |
| 13 | 4'-{(2S,3R)-3-[(3S)-3-(4-chlorophenyl)-3-hydroxypropyl]-4-oxo-1-phenylazetidin-2-yl}-3'-hydroxybiphenyl-2-sulfonic acid |
| 14 | 4'-{(2S,3R)-3-[(3S)-3-(4-chlorophenyl)-3-hydroxypropyl]-4-oxo-1-phenylazetidin-2-yl}-3'-hydroxybiphenyl-3-sulfonic acid |
| 15 | 4'-{(2S,3R)-3-[(3S)-3-(4-chlorophenyl)-3-hydroxypropyl]-4-oxo-1-phenylazetidin-2-yl}-3'-hydroxybiphenyl-4-sulfonic acid |
| 16 | 4'-{(2S,3R)-3-[(3S)-3-(4-chlorophenyl)-3-hydroxypropyl]-4-oxo-1-phenylazetidin-2-yl}-2'-hydroxybiphenyl-2-sulfonic acid |
| 17 | 4'-{(2S,3R)-3-[(3S)-3-(4-chlorophenyl)-3-hydroxypropyl]-4-oxo-1-phenlyazetidin-2-yl}-2'-hydroxybiphenyl-3-sulfonic acid |
| 18 | 4'-{(2S,3R)-3-[(3S)-3-(4-chlorophenyl)-3-hydroxypropyl]-4-oxo-1-phenylazetidin-2-yl}-2'-hydroxybiphenyl-4-sulfonic acid |

Table 16 lists the compounds disclosed by substitution of Formula VIII wherein $R^1$ is H, $R^2$ is Cl, $R^4$ is OH and $R^5$ is $PO_3H_2$ (i.e. Table 3, row 12) according to the positions defined by all rows of Table 4.

| | |
|---|---|
| 1 | (4'-{(2S,3R)-3-[(3S)-3-(2-chlorophenyl)-3-hydroxypropyl]-4-oxo-1-phenylazetidin-2-yl}-3'-hydroxybiphenyl-2-yl)phosphonic acid |
| 2 | (4'-{(2S,3R)-3-[(3S)-3-(2-chlorophenyl)-3-hydroxypropyl]-4-oxo-1-phenylazetidin-2-yl}-3'-hydroxybiphenyl-3-yl)phosphonic acid |
| 3 | (4'-{(2S,3R)-3-[(3S)-3-(2-chlorophenyl)-3-hydroxypropyl]-4-oxo-1-phenylazetidin-2-yl}-3'-hydroxybiphenyl-4-yl)phosphonic acid |
| 4 | (4'-{(2S,3R)-3-[(3S)-3-(2-chlorophenyl)-3-hydroxypropyl]-4-oxo-1-phenylazetidin-2-yl}-2'-hydroxybiphenyl-2-yl)phosphonic acid |
| 5 | (4'-{(2S,3R)-3-[(3S)-3-(2-chlorophenyl)-3-hydroxypropyl]-4-oxo-1-phenylazetidin-2-yl}-2'-hydroxybiphenyl-3-yl)phosphonic acid |
| 6 | (4'-{(2S,3R)-3-[(3S)-3-(2-chlorophenyl)-3-hydroxypropyl]-4-oxo-1-phenylazetidin-2-yl}-2'-hydroxybiphenyl-4-yl)phosphonic acid |
| 7 | (4'-{(2S,3R)-3-[(3S)-3-(3-chlorophenyl)-3-hydroxypropyl]-4-oxo-1-phenylazetidin-2-yl}-3'-hydroxybiphenyl-2-yl)phosphonic acid |
| 8 | (4'-{(2S,3R)-3-[(3S)-3-(3-chlorophenyl)-3-hydroxypropyl]-4-oxo-1-phenylazetidin-2-yl}-3'-hydroxybiphenyl-3-yl)phosphonic acid |
| 9 | (4'-{(2S,3R)-3-[(3S)-3-(3-chlorophenyl)-3-hydroxypropyl]-4-oxo-1-phenylazetidin-2-yl}-3'-hydroxybiphenyl-4-yl)phosphonic acid |
| 10 | (4'-{(2S,3R)-3-[(3S)-3-(3-chlorophenyl)-3-hydroxypropyl]-4-oxo-1-phenylazetidin-2-yl}-2'-hydroxybiphenyl-2-yl)phosphonic acid |
| 11 | (4'-{(2S,3R)-3-[(3S)-3-(3-chlorophenyl)-3-hydroxypropyl]-4-oxo-1-phenylazetidin-2-yl}-2'-hydroxybiphenyl-3-yl)phosphonic acid |
| 12 | (4'-{(2S,3R)-3-[(3S)-3-(3-chlorophenyl)-3-hydroxypropyl]-4-oxo-1-phenylazetidin-2-yl}-2'-hydroxybiphenyl-4-yl)phosphonic acid |
| 13 | (4'-{(2S,3R)-3-[(3S)-3-(4-chlorophenyl)-3-hydroxypropyl]-4-oxo-1-phenylazetidin-2-yl}-3'-hydroxybiphenyl-2-yl)phosphonic acid |
| 14 | (4'-{(2S,3R)-3-[(3S)-3-(4-chlorophenyl)-3-hydroxypropyl]-4-oxo-1-phenylazetidin-2-yl}-3'-hydroxybiphenyl-3-yl)phosphonic acid |
| 15 | (4'-{(2S,3R)-3-[(3S)-3-(4-chlorophenyl)-3-hydroxypropyl]-4-oxo-1-phenylazetidin-2-yl}-3'-hydroxybiphenyl-4-yl)phosphonic acid |
| 16 | (4'-{(2S,3R)-3-[(3S)-3-(4-chlorophenyl)-3-hydroxypropyl]-4-oxo-1-phenylazetidin-2-yl}-2'-hydroxybiphenyl-2-yl)phosphonic acid |
| 17 | (4'-{(2S,3R)-3-[(3S)-3-(4-chlorophenyl)-3-hydroxypropyl]-4-oxo-1-phenylazetidin-2-yl}-2'-hydroxybiphenyl-3-yl)phosphonic acid |
| 18 | (4'-{(2S,3R)-3-[(3S)-3-(4-chlorophenyl)-3-hydroxypropyl]-4-oxo-1-phenylazetidin-2-yl}-2'-hydroxybiphenyl-4-yl)phosphonic acid |

Table 17 lists the compounds disclosed by substitution of Formula VIII wherein $R^1$ is F, $R^2$ is H, $R^4$ is OH and $R^5$ is OH (i.e. Table 3, row 13) according to the positions defined by all rows of Table 4.

| | |
|---|---|
| 1 | (3R,4S)-4-(2',3-dihydroxybiphenyl-4-yl)-1-(2-fluorophenyl)-3-[(3S)-3-hydroxy-3-phenylpropyl]azetidin-2-one |
| 2 | (3R,4S)-4-(3,3'-dihydroxybiphenyl-4-yl)-1-(2-fluorophenyl)-3-[(3S)-3-hydroxy-3-phenylpropyl]azetidin-2-one |
| 3 | (3R,4S)-4-(3,4'-dihydroxybiphenyl-4-yl)-1-(2-fluorophenyl)-3-[(3S)-3-hydroxy-3-phenylpropyl]azetidin-2-one |
| 4 | (3R,4S)-4-(2,2'-dihydroxybiphenyl-4-yl)-1-(2-fluorophenyl)-3-[(3S)-3-hydroxy-3-phenylpropyl]azetidin-2-one |
| 5 | (3R,4S)-4-(2,3'-dihydroxybiphenyl-4-yl)-1-(2-fluorophenyl)-3-[(3S)-3-hydroxy-3-phenylpropyl]azetidin-2-one |
| 6 | (3R,4S)-4-(2,4'-dihydroxybiphenyl-4-yl)-1-(2-fluorophenyl)-3-[(3S)-3-hydroxy-3-phenylpropyl]azetidin-2-one |
| 7 | (3R,4S)-4-(2',3-dihydroxybiphenyl-4-yl)-1-(3-fluorophenyl)-3-[(3S)-3-hydroxy-3-phenylpropyl]azetidin-2-one |
| 8 | (3R,4S)-4-(3,3'-dihydroxybiphenyl-4-yl)-1-(3-fluorophenyl)-3-[(3S)-3-hydroxy-3-phenylpropyl]azetidin-2-one |
| 9 | (3R,4S)-4-(3,4'-dihydroxybiphenyl-4-yl)-1-(3-fluorophenyl)-3-[(3S)-3-hydroxy-3-phenylpropyl]azetidin-2-one |
| 10 | (3R,4S)-4-(2,2'-dihydroxybiphenyl-4-yl)-1-(3-fluorophenyl)-3-[(3S)-3-hydroxy-3-phenylpropyl]azetidin-2-one |
| 11 | (3R,4S)-4-(2,3'-dihydroxybiphenyl-4-yl)-1-(3-fluorophenyl)-3-[(3S)-3-hydroxy-3-phenylpropyl]azetidin-2-one |
| 12 | (3R,4S)-4-(2,4'-dihydroxybiphenyl-4-yl)-1-(3-fluorophenyl)-3-[(3S)-3-hydroxy-3-phenylpropyl]azetidin-2-one |
| 13 | (3R,4S)-4-(2',3-dihydroxybiphenyl-4-yl)-1-(4-fluorophenyl)-3-[(3S)-3-hydroxy-3-phenylpropyl]azetidin-2-one |
| 14 | (3R,4S)-4-(3,3'-dihydroxybiphenyl-4-yl)-1-(4-fluorophenyl)-3-[(3S)-3-hydroxy-3-phenylpropyl]azetidin-2-one |
| 15 | (3R,4S)-4-(3,4'-dihydroxybiphenyl-4-yl)-1-(4-fluorophenyl)-3-[(3S)-3-hydroxy-3-phenylpropyl]azetidin-2-one |
| 16 | (3R,4S)-4-(2,2'-dihydroxybiphenyl-4-yl)-1-(4-fluorophenyl)-3-[(3S)-3-hydroxy-3-phenylpropyl]azetidin-2-one |
| 17 | (3R,4S)-4-(2,3'-dihydroxybiphenyl-4-yl)-1-(4-fluorophenyl)-3-[(3S)-3-hydroxy-3-phenylpropyl]azetidin-2-one |
| 18 | (3R,4S)-4-(2,4'-dihydroxybiphenyl-4-yl)-1-(4-fluorophenyl)-3-[(3S)-3-hydroxy-3-phenylpropyl]azetidin-2-one |

Table 18 lists the compounds disclosed by substitution of Formula VIII wherein $R^1$ is F, $R^2$ is H, $R^4$ is OH and $R^5$ is D-glucitol (i.e. Table 3, row 14) according to the positions defined by all rows of Table 4.

| # | Compound |
|---|---|
| 1 | (1S)-1,5-anhydro-1-(4'-{(2S,3R)-1-(2-fluorophenyl)-3-[(3S)-3-hydroxy-3-phenylpropyl]-4-oxoazetidin-2-yl}-3'-hydroxybiphenyl-2-yl)-D-glucitol |
| 2 | (1S)-1,5-anhydro-1-(4'-{(2S,3R)-1-(2-fluorophenyl)-3-[(3S)-3-hydroxy-3-phenylpropyl]-4-oxoazetidin-2-yl}-3'-hydroxybiphenyl-3-yl)-D-glucitol |
| 3 | (1S)-1,5-anhydro-1-(4'-{(2S,3R)-1-(2-fluorophenyl)-3-[(3S)-3-hydroxy-3-phenylpropyl]-4-oxoazetidin-2-yl}-3'-hydroxybiphenyl-4-yl)-D-glucitol |
| 4 | (1S)-1,5-anhydro-1-(4'-{(2S,3R)-1-(2-fluorophenyl)-3-[(3S)-3-hydroxy-3-phenylpropyl]-4-oxoazetidin-2-yl}-2'-hydroxybiphenyl-2-yl)-D-glucitol |
| 5 | (1S)-1,5-anhydro-1-(4'-{(2S,3R)-1-(2-fluorophenyl)-3-[(3S)-3-hydroxy-3-phenylpropyl]-4-oxoazetidin-2-yl}-2'-hydroxybiphenyl-3-yl)-D-glucitol |
| 6 | (1S)-1,5-anhydro-1-(4'-{(2S,3R)-1-(2-fluorophenyl)-3-[(3S)-3-hydroxy-3-phenylpropyl]-4-oxoazetidin-2-yl}-2'-hydroxybiphenyl-4-yl)-D-glucitol |
| 7 | (1S)-1,5-anhydro-1-(4'-{(2S,3R)-1-(3-fluorophenyl)-3-[(3S)-3-hydroxy-3-phenylpropyl]-4-oxoazetidin-2-yl}-3'-hydroxybiphenyl-2-yl)-D-glucitol |
| 8 | (1S)-1,5-anhydro-1-(4'-{(2S,3R)-1-(3-fluorophenyl)-3-[(3S)-3-hydroxy-3-phenylpropyl]-4-oxoazetidin-2-yl}-3'-hydroxybiphenyl-3-yl)-D-glucitol |
| 9 | (1S)-1,5-anhydro-1-(4'-{(2S,3R)-1-(3-fluorophenyl)-3-[(3S)-3-hydroxy-3-phenylpropyl]-4-oxoazetidin-2-yl}-3'-hydroxybiphenyl-4-yl)-D-glucitol |
| 10 | (1S)-1,5-anhydro-1-(4'-{(2S,3R)-1-(3-fluorophenyl)-3-[(3S)-3-hydroxy-3-phenylpropyl]-4-oxoazetidin-2-yl}-2'-hydroxybiphenyl-2-yl)-D-glucitol |
| 11 | (1S)-1,5-anhydro-1-(4'-{(2S,3R)-1-(3-fluorophenyl)-3-[(3S)-3-hydroxy-3-phenylpropyl]-4-oxoazetidin-2-yl}-2'-hydroxybiphenyl-3-yl)-D-glucitol |
| 12 | (1S)-1,5-anhydro-1-(4'-{(2S,3R)-1-(3-fluorophenyl)-3-[(3S)-3-hydroxy-3-phenylpropyl]-4-oxoazetidin-2-yl}-2'-hydroxybiphenyl-4-yl)-D-glucitol |
| 13 | (1S)-1,5-anhydro-1-(4'-{(2S,3R)-1-(4-fluorophenyl)-3-[(3S)-3-hydroxy-3-phenylpropyl]-4-oxoazetidin-2-yl}-3'-hydroxybiphenyl-2-yl)-D-glucitol |
| 14 | (1S)-1,5-anhydro-1-(4'-{(2S,3R)-1-(4-fluorophenyl)-3-[(3S)-3-hydroxy-3-phenylpropyl]-4-oxoazetidin-2-yl}-3'-hydroxybiphenyl-3-yl)-D-glucitol |
| 15 | (1S)-1,5-anhydro-1-(4'-{(2S,3R)-1-(4-fluorophenyl)-3-[(3S)-3-hydroxy-3-phenylpropyl]-4-oxoazetidin-2-yl}-3'-hydroxybiphenyl-4-yl)-D-glucitol |
| 16 | (1S)-1,5-anhydro-1-(4'-{(2S,3R)-1-(4-fluorophenyl)-3-[(3S)-3-hydroxy-3-phenylpropyl]-4-oxoazetidin-2-yl}-2'-hydroxybiphenyl-2-yl)-D-glucitol |
| 17 | (1S)-1,5-anhydro-1-(4'-{(2S,3R)-1-(4-fluorophenyl)-3-[(3S)-3-hydroxy-3-phenylpropyl]-4-oxoazetidin-2-yl}-2'-hydroxybiphenyl-3-yl)-D-glucitol |
| 18 | (1S)-1,5-anhydro-1-(4'-{(2S,3R)-1-(4-fluorophenyl)-3-[(3S)-3-hydroxy-3-phenylpropyl]-4-oxoazetidin-2-yl}-2'-hydroxybiphenyl-4-yl)-D-glucitol |

Table 19 lists the compounds disclosed by substitution of Formula VIII wherein $R^1$ is F, $R^2$ is H, $R^4$ is OH and $R^5$ is $SO_3H$ (i.e. Table 3, row 15) according to the positions defined by all rows of Table 4.

| # | Compound |
|---|---|
| 1 | 4'-{(2S,3R)-1-(2-fluorophenyl)-3-[(3S)-3-hydroxy-3-phenylpropyl]-4-oxoazetidin-2-yl}-3'-hydroxybiphenyl-2-sulfonic acid |
| 2 | 4'-{(2S,3R)-1-(2-fluorophenyl)-3-[(3S)-3-hydroxy-3-phenylpropyl]-4-oxoazetidin-2-yl}-3'-hydroxybiphenyl-3-sulfonic acid |
| 3 | 4'-{(2S,3R)-1-(2-fluorophenyl)-3-[(3S)-3-hydroxy-3-phenylpropyl]-4-oxoazetidin-2-yl}-3'-hydroxybiphenyl-4-sulfonic acid |
| 4 | 4'-{(2S,3R)-1-(2-fluorophenyl)-3-[(3S)-3-hydroxy-3-phenylpropyl]-4-oxoazetidin-2-yl}-2'-hydroxybiphenyl-2-sulfonic acid |
| 5 | 4'-{(2S,3R)-1-(2-fluorophenyl)-3-[(3S)-3-hydroxy-3-phenylpropyl]-4-oxoazetidin-2-yl}-2'-hydroxybiphenyl-3-sulfonic acid |
| 6 | 4'-{(2S,3R)-1-(2-fluorophenyl)-3-[(3S)-3-hydroxy-3-phenylpropyl]-4-oxoazetidin-2-yl}-2'-hydroxybiphenyl-4-sulfonic acid |
| 7 | 4'-{(2S,3R)-1-(3-fluorophenyl)-3-[(3S)-3-hydroxy-3-phenylpropyl]-4-oxoazetidin-2-yl}-3'-hydroxybiphenyl-2-sulfonic acid |
| 8 | 4'-{(2S,3R)-1-(3-fluorophenyl)-3-[(3S)-3-hydroxy-3-phenylpropyl]-4-oxoazetidin-2-yl}-3'-hydroxybiphenyl-3-sulfonic acid |
| 9 | 4'-{(2S,3R)-1-(3-fluorophenyl)-3-[(3S)-3-hydroxy-3-phenylpropyl]-4-oxoazetidin-2-yl}-3'-hydroxybiphenyl-4-sulfonic acid |
| 10 | 4'-{(2S,3R)-1-(3-fluorophenyl)-3-[(3S)-3-hydroxy-3-phenylpropyl]-4-oxoazetidin-2-yl}-2'-hydroxybiphenyl-2-sulfonic acid |
| 11 | 4'-{(2S,3R)-1-(3-fluorophenyl)-3-[(3S)-3-hydroxy-3-phenylpropyl]-4-oxoazetidin-2-yl}-2'-hydroxybiphenyl-3-sulfonic acid |
| 12 | 4'-{(2S,3R)-1-(3-fluorophenyl)-3-[(3S)-3-hydroxy-3-phenylpropyl]-4-oxoazetidin-2-yl}-2'-hydroxybiphenyl-4-sulfonic acid |
| 13 | 4'-{(2S,3R)-1-(4-fluorophenyl)-3-[(3S)-3-hydroxy-3-phenylpropyl]-4-oxoazetidin-2-yl}-3'-hydroxybiphenyl-2-sulfonic acid |
| 14 | 4'-{(2S,3R)-1-(4-fluorophenyl)-3-[(3S)-3-hydroxy-3-phenylpropyl]-4-oxoazetidin-2-yl}-3'-hydroxybiphenyl-3-sulfonic acid |
| 15 | 4'-{(2S,3R)-1-(4-fluorophenyl)-3-[(3S)-3-hydroxy-3-phenylpropyl]-4-oxoazetidin-2-yl}-3'-hydroxybiphenyl-4-sulfonic acid |
| 16 | 4'-{(2S,3R)-1-(4-fluorophenyl)-3-[(3S)-3-hydroxy-3-phenylpropyl]-4-oxoazetidin-2-yl}-2'-hydroxybiphenyl-2-sulfonic acid |
| 17 | 4'-{(2S,3R)-1-(4-fluorophenyl)-3-[(3S)-3-hydroxy-3-phenylpropyl]-4-oxoazetidin-2-yl}-2'-hydroxybiphenyl-3-sulfonic acid |
| 18 | 4'-{(2S,3R)-1-(4-fluorophenyl)-3-[(3S)-3-hydroxy-3-phenylpropyl]-4-oxoazetidin-2-yl}-2'-hydroxybiphenyl-4-sulfonic acid |

Table 20 lists the compounds disclosed by substitution of Formula VIII wherein $R^1$ is F, $R^2$ is H, $R^4$ is OH and $R^5$ is $PO_3H_2$ (i.e. Table 3, row 16) according to the positions defined by all rows of Table 4.

| # | Compound |
|---|---|
| 1 | (4'-{(2S,3R)-1-(2-fluorophenyl)-3-[(3S)-3-hydroxy-3-phenylpropyl]-4-oxoazetidin-2-yl}-3'-hydroxybiphenyl-2-yl)phosphonic acid |
| 2 | (4'-{(2S,3R)-1-(2-fluorophenyl)-3-[(3S)-3-hydroxy-3-phenylpropyl]-4-oxoazetidin-2-yl}-3'-hydroxybiphenyl-3-yl)phosphonic acid |
| 3 | (4'-{(2S,3R)-1-(2-fluorophenyl)-3-[(3S)-3-hydroxy-3-phenylpropyl]-4-oxoazetidin-2-yl}-3'-hydroxybiphenyl-4-yl)phosphonic acid |
| 4 | (4'-{(2S,3R)-1-(2-fluorophenyl)-3-[(3S)-3-hydroxy-3-phenylpropyl]-4-oxoazetidin-2-yl}-2'-hydroxybiphenyl-2-yl)phosphonic acid |
| 5 | (4'-{(2S,3R)-1-(2-fluorophenyl)-3-[(3S)-3-hydroxy-3-phenylpropyl]-4-oxoazetidin-2-yl}-2'-hydroxybiphenyl-3-yl)phosphonic acid |
| 6 | (4'-{(2S,3R)-1-(2-fluorophenyl)-3-[(3S)-3-hydroxy-3-phenylpropyl]-4-oxoazetidin-2-yl}-2'-hydroxybiphenyl-4-yl)phosphonic acid |
| 7 | (4'-{(2S,3R)-1-(3-fluorophenyl)-3-[(3S)-3-hydroxy-3-phenylpropyl]-4-oxoazetidin-2-yl}-3'-hydroxybiphenyl-2-yl)phosphonic acid |
| 8 | (4'-{(2S,3R)-1-(3-fluorophenyl)-3-[(3S)-3-hydroxy-3-phenylpropyl]-4-oxoazetidin-2-yl}-3'-hydroxybiphenyl-3-yl)phosphonic acid |
| 9 | (4'-{(2S,3R)-1-(3-fluorophenyl)-3-[(3S)-3-hydroxy-3-phenylpropyl]-4-oxoazetidin-2-yl}-3'-hydroxybiphenyl-4-yl)phosphonic acid |
| 10 | (4'-{(2S,3R)-1-(3-fluorophenyl)-3-[(3S)-3-hydroxy-3-phenylpropyl]-4-oxoazetidin-2-yl}-2'-hydroxybiphenyl-2-yl)phosphonic acid |
| 11 | (4'-{(2S,3R)-1-(3-fluorophenyl)-3-[(3S)-3-hydroxy-3-phenylpropyl]-4-oxoazetidin-2-yl}-2'-hydroxybiphenyl-3-yl)phosphonic acid |
| 12 | (4'-{(2S,3R)-1-(3-fluorophenyl)-3-[(3S)-3-hydroxy-3-phenylpropyl]-4-oxoazetidin-2-yl}-2'-hydroxybiphenyl-4-yl)phosphonic acid |
| 13 | (4'-{(2S,3R)-1-(4-fluorophenyl)-3-[(3S)-3-hydroxy-3-phenylpropyl]-4-oxoazetidin-2-yl}-3'-hydroxybiphenyl-2-yl)phosphonic acid |
| 14 | (4'-{(2S,3R)-1-(4-fluorophenyl)-3-[(3S)-3-hydroxy-3-phenylpropyl]-4-oxoazetidin-2-yl}-3'-hydroxybiphenyl-3-yl)phosphonic acid |
| 15 | (4'-{(2S,3R)-1-(4-fluorophenyl)-3-[(3S)-3-hydroxy-3-phenylpropyl]-4-oxoazetidin-2-yl}-3'-hydroxybiphenyl-4-yl)phosphonic acid |
| 16 | (4'-{(2S,3R)-1-(4-fluorophenyl)-3-[(3S)-3-hydroxy-3-phenylpropyl]-4-oxoazetidin-2-yl}-2'-hydroxybiphenyl-2-yl)phosphonic acid |
| 17 | (4'-{(2S,3R)-1-(4-fluorophenyl)-3-[(3S)-3-hydroxy-3-phenylpropyl]-4-oxoazetidin-2-yl}-2'-hydroxybiphenyl-3-yl)phosphonic acid |
| 18 | (4'-{(2S,3R)-1-(4-fluorophenyl)-3-[(3S)-3-hydroxy-3-phenylpropyl]-4-oxoazetidin-2-yl}-2'-hydroxybiphenyl-4-yl)phosphonic acid |

The invention claimed is:
1. A compound of formula:

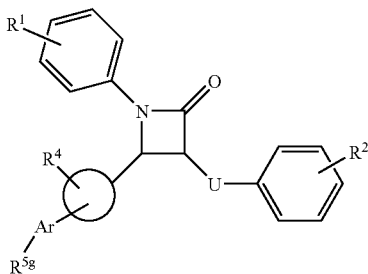

wherein

represents an aryl or heteroaryl residue;
Ar represents an aryl residue;
$R^1$ represents one, two, three, four or five residues chosen independently from H, halogen, —OH, loweralkyl, $OCF_2H$, $OCF_3$, $CF_2H$, $CH_2F$, —O-loweralkyl, methylenedioxy, ethylenedioxy, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, phenyl, benzyl, phenoxy, benzyloxy, —$PO_3H_2$, —$SO_3H$, and —$B(OH)_2$,
$R^2$ represents one, two, three, four or five residues chosen independently from H, halogen, —OH, loweralkyl, $OCF_2H$, $OCF_3$, $CF_2H$, $CH_2F$, —O-loweralkyl, methylenedioxy, ethylenedioxy, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, —$PO_3H_2$, —$SO_3H$, and —$B(OH)_2$,;
$R^4$ represents one, two, three or four residues chosen independently from H, halogen, —OH, loweralkyl, —O-loweralkyl, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, —$PO_3H_2$, —$SO_3H$, and —$B(OH)_2$,
$R^{5g}$ represents one, two, three, four or five residues on Ar chosen independently from halogen, —OH, loweralkyl, —O-loweralkyl, methylenedioxy, ethylenedioxy, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, —$PO_3H_2$, —$SO_3H$, and —$B(OH)_2$;
U is $(C_2-C_6)$-alkylene in which one or more individual —$CH_2$— may be replaced by a radical chosen from —S—, —S(O)—, —$SO_2$—, —O—, —C(=O)—, —CHOH—, —NH—, CHF, $CF_2$, —CH(O-loweralkyl)-, —CH(O-loweracyl)-, —CH($OSO_3H$)—, —CH($OPO_3H_2$)—, —CH($OB(OH)_2$)—, or —NOH—;
with the provisos that
$R^{5g}$ cannot be —CN; 2,5-dimethoxy; 2,6-dimethoxy or halogen when neither of $R^4$ and $R^{5g}$ includes an —OH, amino, loweralkyl, O-loweralkyl, alkoxycarbonyl, —$B(OH)_2$, —$PO_3H_2$ or —$SO_3H$ group;
$R^{5g}$ cannot be 2-hydroxy when

represents a 2,5-thienyl residue;
adjacent —$CH_2$— residues in U cannot be replaced by —S—, —S(O)—, —$SO_2$— or —O—; and
—S—, —S(O)—, —$SO_2$—, —O— and —NH— residues in U cannot be separated only by a single carbon.

2. A compound of formula:

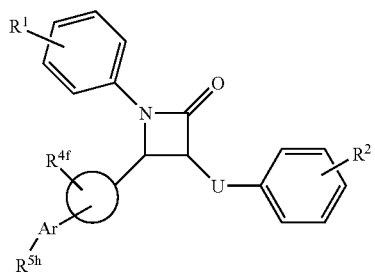

wherein

represents an aryl or heteroaryl residue;
Ar represents an aryl residue;
$R^1$ represents one, two, three, four or five residues chosen independently from H, halogen, —OH, loweralkyl, $OCF_2H$, $OCF_3$, $CF_2H$, $CH_2F$, —O-loweralkyl, methylenedioxy, ethylenedioxy, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, phenyl, benzyl, phenoxy, benzyloxy, —$PO_3H_2$, —$SO_3H$, and —$B(OH)_2$,
$R^2$ represents one, two, three, four or five residues chosen independently from H, halogen, —OH, loweralkyl, $OCF_2H$, $OCF_3$, $CF_2H$, $CH_2F$, —O-loweralkyl, methylenedioxy, ethylenedioxy, hydroxyloweralkyl, —CN, $CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, —$PO_3H_2$, —$SO_3H$, and —$B(OH)_2$,
$R^{4f}$ is —OH, —SH or —$B(OH)_2$;
$R^{5h}$ represents one, two, three, four or five residues on Ar chosen independently from hydrogen, halogen, —OH, loweralkyl, —O-loweralkyl, methylenedioxy, ethylenedioxy, hydroxyloweralkyl, —CN, —$CF_3$, nitro, —SH, —S-loweralkyl, amino, alkylamino, dialkylamino, aminosulfonyl, alkylaminosulfonyl, dialkylaminosulfonyl, alkylsulfonyl, arylsulfonyl, acyl, carboxy, alkoxycarbonyl, carboxyalkyl, carboxamido, alkylsulfoxide, acylamino, amidino, —PO$_3$H$_2$, —SO$_3$H, and —B(OH)$_2$, U is (C$_2$-C$_6$)-alkylene in which one or more —CH$_2$— may be replaced by a radical chosen from —S—, —S(O)—, —SO$_2$—, —O—, —C(=O)—, —CHOH—, —NH—, CHF, CF$_2$, —CH(O-loweralkyl)-, —CH(O-loweracyl)-, —CH(OSO$_3$H)—, —CH(OPO$_3$H$_2$)—, —CH(OB(OH)$_2$)—, or —NOH—, with the provisos that:

adjacent —CH$_2$— residues in U cannot be replaced by —S—, —S(O)—, —SO$_2$— or —O—; and —S—, —S(O)—, —SO$_2$—, —O— and —NH— residues in U cannot be separated only by a single carbon.

3. A compound according to claim 1 wherein U is chosen from —CH$_2$CH$_2$CH(OH)—, —SCH$_2$CH$_2$—, —S(O)CH$_2$CH$_2$—, —S(O)CH$_2$CH(OH)—, —SCH$_2$C(=O)—, —SCH$_2$CH(OH)—, —CH(OH)CH$_2$CH$_2$—, —CH(OH)CH$_2$CH(OH)—, —(CH$_2$)$_3$CH(OH)— and —(CH$_2$)$_4$—, wherein the left end of the string is the point of attachment to the azetidinone ring and the right end of the string is the point of attachment to the phenyl ring.

4. A compound according to claim 3 wherein U is —CH$_2$CH$_2$CH(OH)—.

5. A compound of formula:

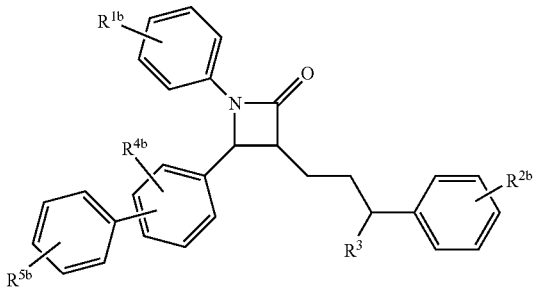

wherein

R$^{2b}$ represents one or two residues chosen independently from H, halogen, —OH, loweralkyl, OCF$_2$H, OCF$_3$, CF$_2$H, CH$_2$F, —O-loweralkyl, methylenedioxy, hydroxyloweralkyl, —CN, CF$_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, benzyloxy;

R$^3$ is chosen from H, —OH, fluoro, —O-loweralkyl and —O-acyl;

one of R$^{1b}$, R$^{4b}$ and R$^{5b}$ is R$^{12}$ and the other two of R$^{1b}$, R$^{4b}$ and R$^{5b}$ are chosen independently from hydrogen, halogen, —OH, loweralkyl, —O-loweralkyl, methylenedioxy, hydroxyloweralkyl, —CN, CF$_3$, nitro, —S-loweralkyl, amino, alkylamino, dialkylamino, aminosulfonyl, alkylaminosulfonyl, dialkylaminosulfonyl, alkylsulfonyl, arylsulfonyl, acyl, carboxy, carboalkoxy, carboxamido, alkylsulfoxide, acylamino, amidino, phenyl, benzyl, phenoxy, and benzyloxy;

R$^{6a}$ is C$_1$ to C$_{20}$ hydrocarbon;

R$^{7a}$ is alkyl;

R$^{8a}$ is alkyl;

R$^{12}$ is (C$_0$ to C$_{30}$)alkylene-G$_n$ in which one or more —CH$_2$— residues in said alkylene may be replaced by —S—, —SO—, —SO$_2$—, —O—, —NH—, —N(alkyl)-, —N(phenyl)-, —N(alkylphenyl)-, —C(=O)—, —C(=S), CH=CH—, —C≡C—, phenylene or —N[(C=O)alkyleneCOOH]—;

G is chosen from —SO$_3$H, —PO$_3$H$_2$, —O—PO$_3$H$_2$, —COOH, —C(N=H)NH$_2$, —N$^+$R$^{6a}$R$^{7a}$R$^{8a}$X$^-$;

n is 1, 2, 3, 4 or 5 and

X is an anion.

6. A compound according to claim 1 wherein R$^1$, R$^2$ and R$^4$ are chosen from H, halogen, —OH, and methoxy.

7. A compound according to claim 1 wherein at least one of R$^1$, R$^2$, R$^4$ and R$^{5g}$ is chosen from SO$_3$H and PO$_3$H$_2$.

8. A compound according to claim 5 wherein R$^3$ is chosen from hydrogen and hydroxy.

9. A compound according to claim 1 wherein R$^4$ is hydrogen.

10. A compound according to claim 1 wherein R$^4$ is OH.

11. A compound according to claim 1 of formula

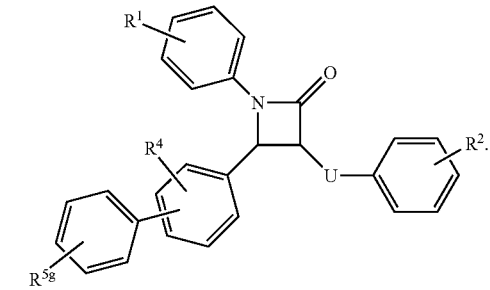

12. A compound according to claim 11 of formula

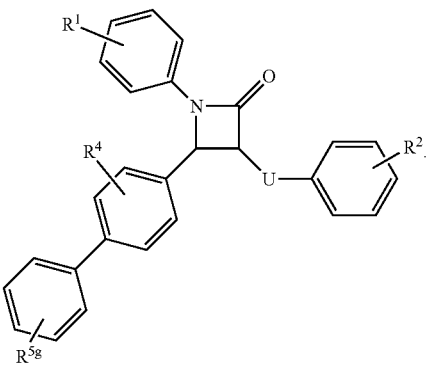

13. A compound according to claim 12 of formula

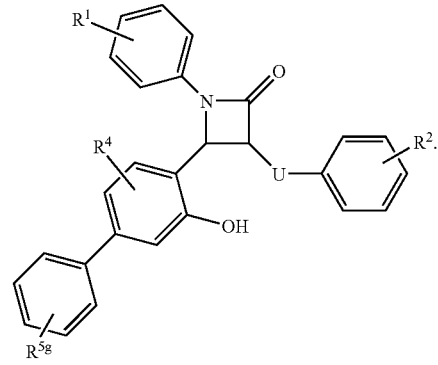

14. A compound according to claim 12 of formula

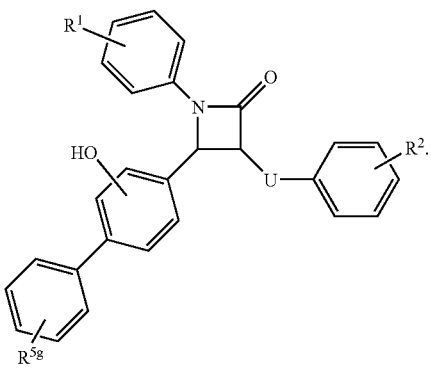

15. A compound according to claim 14 of formula

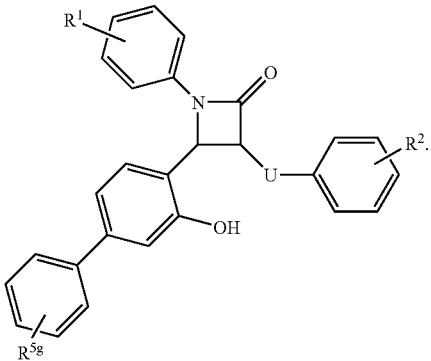

16. A compound according to claim 15 wherein $R^1$ is H.

17. A compound according to claim 1 of formula

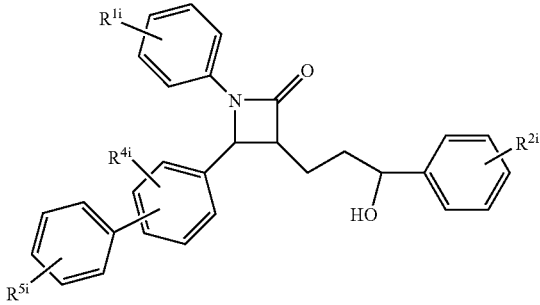

wherein $R^{1i}$ and $R^{2i}$ are independently chosen from H, F, Cl, $CH_3$, CN, $OCH_3$, $OCF_3$, $OCF_2H$, $CF_3$, $CF_2H$, and $CH_2F$;

$R^{4i}$ is chosen from H, F, Cl, $CH_3$, $OCH_3$, OH, $B(OH)_2$, and SH; and $R^{5i}$ is chosen from OH, $SO_3H$, $PO_3H_2$, $CH_2OH$, COOH, and CHO.

18. A compound according to claim 17 wherein $R^{5i}$ is —OH of formula

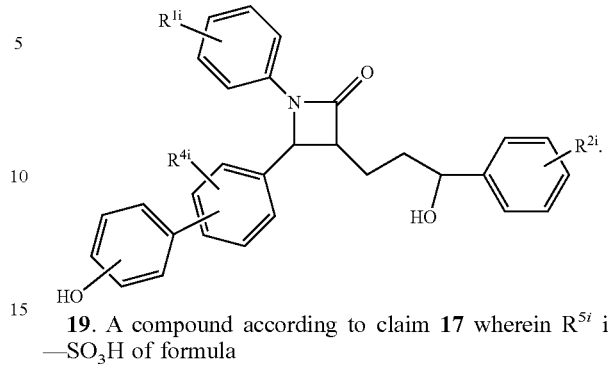

19. A compound according to claim 17 wherein $R^{5i}$ is —$SO_3H$ of formula

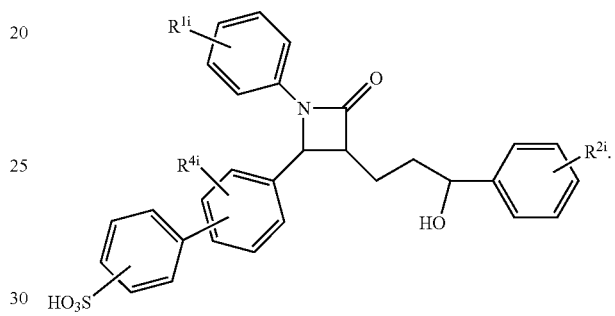

20. A compound according to claim 17 wherein $R^{5i}$ is —$PO_3H_2$ of formula

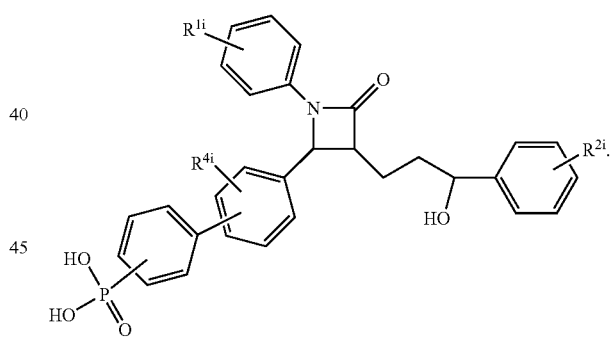

21. A compound according to claim 18 wherein $R^{5i}$ is —OH of formula

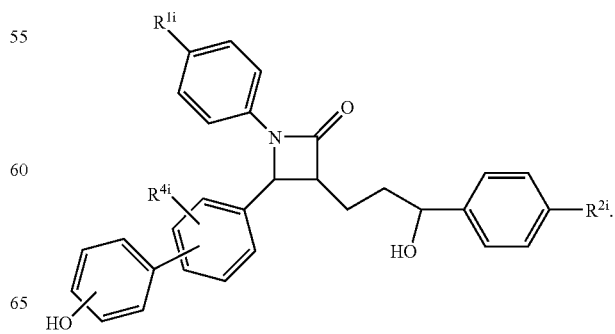

22. A compound according to claim 19 wherein $R^{5i}$ is —SO$_3$H of formula

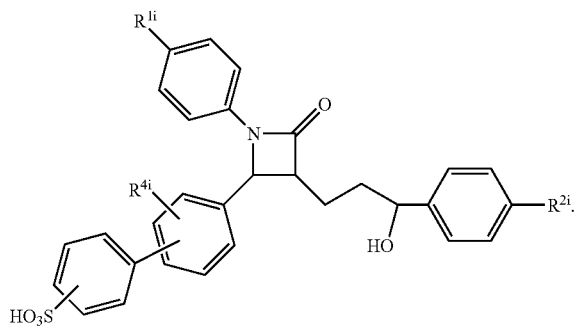

23. A compound according to claim 20 wherein $R^{5i}$ is —PO$_3$H$_2$ of formula

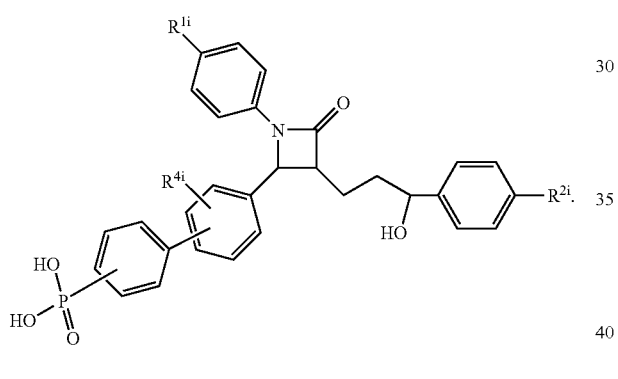

24. A compound according to claim 21 wherein $R^{5i}$ is —OH of formula

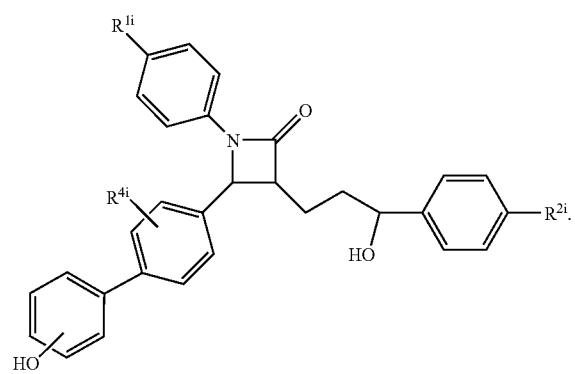

25. A compound according to claim 21 wherein $R^{5i}$ is —OH of formula

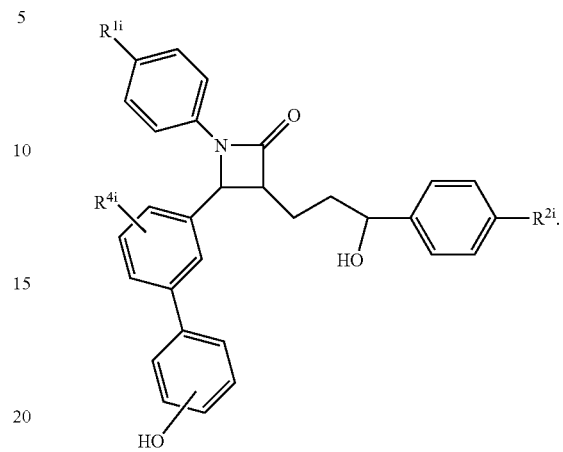

26. A compound according to claim 22 wherein $R^{5i}$ is —SO$_3$H of formula

27. A compound according to claim 22 wherein $R^{5i}$ is —SO$_3$H of formula

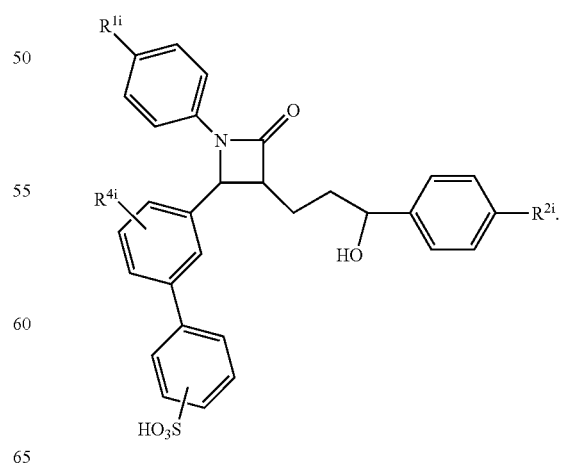

28. A compound according to claim 23 wherein $R^{5i}$ is —$PO_3H_2$ of formula

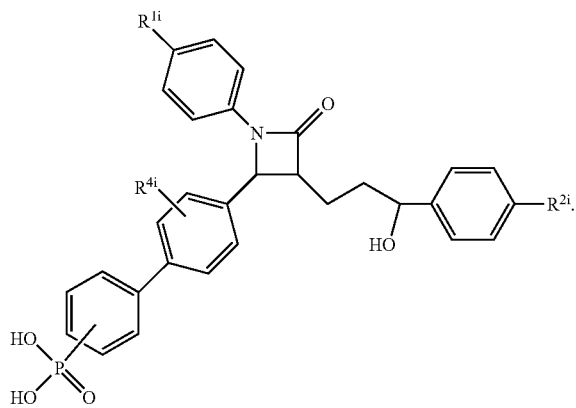

29. A compound according to claim 23 wherein $R^{5i}$ is —$PO_3H_2$ of formula

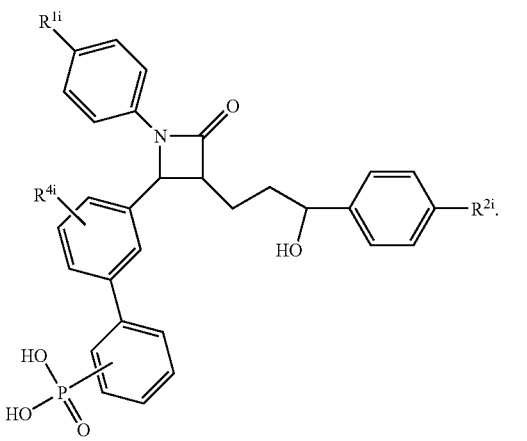

30. A compound according to claim 17 wherein $R^{4i}$ is OH.
31. A compound according to claim 30 wherein $R^{4i}$ is ortho to the azetidine ring.
32. A compound according to claim 17 wherein $R^{5i}$ is an ortho substituent.
33. A compound according to claim 17 wherein $R^{5i}$ is a meta substituent.
34. A compound according to claim 17 wherein $R^{5i}$ is a para substituent.
35. A compound according to claim 17 wherein $R^{1i}$ and $R^{2i}$ are chosen from H, Cl and F.
36. A compound according to claim 35 wherein $R^{1i}$ is H.
37. A compound according to claim 1 of formula

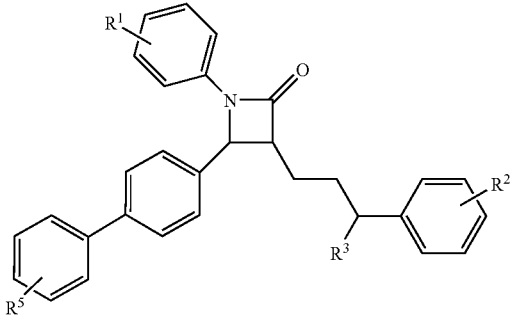

wherein
$R^1$ and $R^2$ are chosen from H, halogen, —OH, and methoxy;

$R^3$ is chosen from hydrogen and hydroxy; and
$R^5$ is chosen from halogen, hydroxy, loweralkyl, —O-loweralkyl, $CF_3$, alkylsulfonyl and arylsulfonyl.

38. A compound according to claim 37 of formula

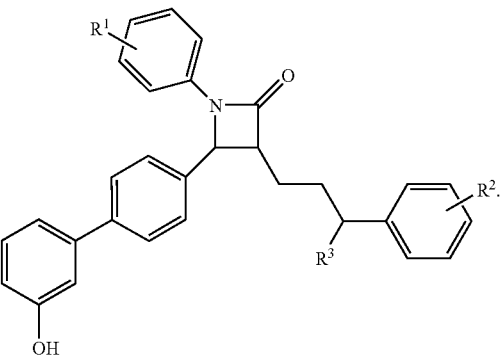

39. A compound according to claim 38 of formula

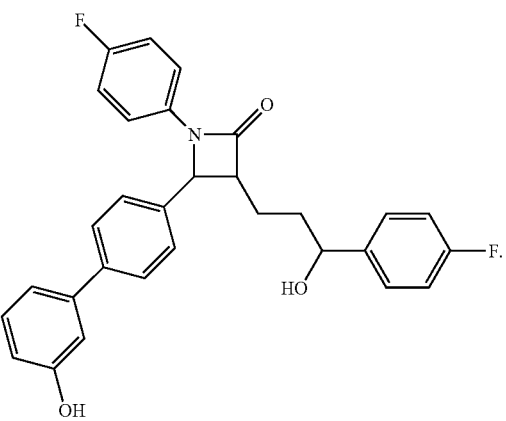

40. A compound according to claim 5 wherein
$R^{1b}$ is $R^{12}$;
$R^{2b}$ and $R^{4b}$ are chosen from H, halogen, —OH, and methoxy;
$R^{12}$ is ($C_6$ to $C_{20}$)alkylene-G in which one or more —$CH_2$— residues in said alkylene may be replaced by —O—, —NH—, —N(alkyl)-, —C(=O)— or —CH=CH—; and
G is chosen from —$SO_3H$, and —$PO_3H_2$.

41. A compound according to claim 1 wherein the substituents at positions 3 and 4 of the azetidin-2-one are in a cis relative configuration.
42. A compound according to claim 1 wherein the substituents at positions 3 and 4 of the azetidin-2-one are in a trans relative configuration.
43. A compound according to claim 42 wherein the substituent at position 3 of the azetidin-2-one is of the R absolute configuration and the substituent at position 4 of the azetidin-2-one is of the S absolute configuration.
44. A compound according to claim 1 wherein U is ($C_2$-$C_6$)-alkylene in which at least one —$CH_2$— is replaced by —CHOH—.
45. A compound chosen from the group consisting of:
(6) (3R,4S)-1-(4-fluorophenyl)-3-[(3S)-3-(4-fluorophenyl)-3-hydroxypropyl]-4-(2',3',4'-trimethoxybiphenyl-4-yl)azetidin-2-one, (7) (3R,4S)-1-(4-fluorophenyl)-3-[(3S)-3-(4-fluorophenyl)-3-hydroxypropyl]-4-(3'-hydroxybiphenyl-4-yl)azetidin-2-one,
(8) (3R,4S)-1-(4-fluorophenyl)-3-[(3S)-3-(4-fluorophenyl)-3-hydroxypropyl]-4-(3'-mercaptobiphenyl-4-yl)azetidin-2-one,
(9) (3R,4S)-1-(4-fluorophenyl)-3-[(3S)-3-(4-fluorophenyl)-3-hydroxypropyl]-4-(3'-methoxybiphenyl-4-yl)azetidin-2-one,
(10) (3R,4S)-1-(4-fluorophenyl)-3-[(3S)-3-(4-fluorophenyl)-3-hydroxypropyl]-4-(3'-nitrobiphenyl-4-yl)azetidin-2-one,
(11) (3R,4S)-1-(4-fluorophenyl)-3-[(3S)-3-(4-fluorophenyl)-3-hydroxypropyl]-4-(4'-hydroxy-3'-methoxybiphenyl-4-yl)azetidin-2-one,
(12) (3R,4S)-1-(4-fluorophenyl)-3-[(3S)-3-(4-fluorophenyl)-3-hydroxypropyl]-4-(4'-vinylbiphenyl-4-yl)azetidin-2-one,
(13) (3R,4S)-1-(4-fluorophenyl)-3-[(3S)-3-(4-fluorophenyl)-3-hydroxypropyl]-4-[3'-(hydroxymethyl)biphenyl-4-yl]azetidin-2-one,
(14) (3R,4S)-1-(4-fluorophenyl)-3-[(3S)-3-(4-fluorophenyl)-3-hydroxypropyl]-4-[3'-(methylsulfonyl)biphenyl-4-yl]azetidin-2-one,
(15) (3R,4S)-1-(4-fluorophenyl)-3-[(3S)-3-(4-fluorophenyl)-3-hydroxypropyl]-4-[4-(2-naphthyl)phenyl]azetidin-2-one,
(16) (3R,4S)-1-(4-fluorophenyl)-3-[(3S)-3-(4-fluorophenyl)-3-hydroxypropyl]-4-[4'-(hydroxymethyl)biphenyl-4-yl]azetidin-2-one,
(17) (3R,4S)-1-(4-fluorophenyl)-3-[(3S)-3-(4-fluorophenyl)-3-hydroxypropyl]-4-[4'-(methylsulfonyl)biphenyl-4-yl]azetidin-2-one,
(18) (3R,4S)-1-biphenyl-4-yl-3-[(3S)-3-(4-fluorophenyl)-3-hydroxypropyl]-4-(3'-hydroxybiphenyl-4-yl)azetidin-2-one,
(19) (3R,4S)-3-[(3S)-3-(4-fluorophenyl)-3-hydroxypropyl]-4-(3'-hydroxybiphenyl-4-yl)-1-phenylazetidin-2-one,
(20) (3R,4S)-3-[(3S)-3-(4-fluorophenyl)-3-hydroxypropyl]-4-[3-hydroxy-3'-(methylsulfonyl)biphenyl-4-yl]-1-phenylazetidin-2-one,
(21) (3R,4S)-4-(2',3'-difluorobiphenyl-4-yl)-1-(4-fluorophenyl)-3-[(3S)-3-(4-fluorophenyl)-3-hydroxypropyl]azetidin-2-one,
(22) (3R,4S)-4-(2',4'-dihydroxybiphenyl-4-yl)-1-(4-fluorophenyl)-3-[(3S)-3-(4-fluorophenyl)-3-hydroxypropyl]azetidin-2-one,
(23) (3R,4S)-4-(2'-bromo-5'-hydroxybiphenyl-4-yl)-1-(4-fluorophenyl)-3-[(3S)-3-(4-fluorophenyl)-3-hydroxypropyl]azetidin-2-one,
(24) (3R,4S)-4-(3,3'-dihydroxybiphenyl-4-yl)-1-(4-fluorophenyl)-3-[(3S)-3-(4-fluorophenyl)-3-hydroxypropyl]azetidin-2-one,
(26) (3R,4S)-4-(3,4'-dihydroxybiphenyl-4-yl)-3-[(3S)-3-(4-fluorophenyl)-3-hydroxypropyl]-1-phenylazetidin-2-one,
(27) (3R,4S)-4-(3',5'-dihydroxybiphenyl-4-yl)-1-(4-fluorophenyl)-3-[(3S)-3-(4-fluorophenyl)-3-hydroxypropyl]azetidin-2-one,
(28) (3R,4S)-4-(3',5'-dimethoxybiphenyl-4-yl)-1-(4-fluorophenyl)-3-[(3S)-3-(4-fluorophenyl)-3-hydroxypropyl]azetidin-2-one,
(29) (3R,4S)-4-(3'-butoxybiphenyl-4-yl)-1-(4-fluorophenyl)-3-[(3S)-3-(4-fluorophenyl)-3-hydroxypropyl]azetidin-2-one,
(30) (3R,4S)-4-(3'-ethoxybiphenyl-4-yl)-1-(4-fluorophenyl)-3-[(3S)-3-(4-fluorophenyl)-3-hydroxypropyl]azetidin-2-one,
(31) (3R,4S)-4-(3'-fluoro-5'-hydroxybiphenyl-4-yl)-1-(4-fluorophenyl)-3[(3S)-3-(4-fluorophenyl)-3-hydroxypropyl]azetidin-2-one,
(32) (3R,4S)-4-(3'-fluoro-5'-methoxybiphenyl-4-yl)-1-(4-fluorophenyl)-3-[(3S)-3-(4-fluorophenyl)-3-hydroxypropyl]azetidin-2-one,
(33) (3R,4S)-4-(4'-aminobiphenyl-4-yl)-1-(4-fluorophenyl)-3-[(3S)-3-(4-fluorophenyl)-3-hydroxypropyl]azetidin-2-one,
(34) (3R,4S)-4-(4'-ethoxybiphenyl-4-yl)-1-(4-fluorophenyl)-3-[(3S)-3-(4-fluorophenyl)-3-hydroxypropyl]azetidin-2-one,
(35) (3R,4S)-4-[4-(2,3-dihydro-1,4-benzodioxin-6-yl)phenyl]-1-(4-fluorophenyl)-3-[(3S)-3-(4-fluorophenyl)-3-hydroxypropyl]azetidin-2-one,
(36) (3R,4S)-4-[4'-(dimethylamino)biphenyl-4-yl]-1-(4-fluorophenyl)-3-[(3S)-3-(4-fluorophenyl)-3-hydroxypropyl]azetidin-2-one,
(37) (4'-{(2S,3R)-1-(4-fluorophenyl)-3-[(3S)-3-(4-fluorophenyl)-3-hydroxypropyl]-4-oxoazetidin-2-yl}biphenyl-3-yl)boronic acid,
(38) (4'-{(2S,3R)-1-(4-fluorophenyl)-3-[(3S)-3-(4-fluorophenyl)-3-hydroxypropyl]-4-oxoazetidin-2-yl}biphenyl-3-yl)phosphonic acid,
(39) (4'-{(2S,3R)-3-[(3S)-3-(4-fluorophenyl)-3-hydroxypropyl]-4-oxo-1-phenylazetidin-2-yl}-3'-hydroxybiphenyl-3-yl)phosphonic acid,
(40) (4'-{(2S,3R)-3-[(3S)-3-(4-fluorophenyl)-3-hydroxypropyl]-4-oxo-1-phenylazetidin-2-yl}biphenyl-3-yl)boronic acid,
(41) (4'-{(2S,3R)-3-[(3S)-3-(4-fluorophenyl)-3-hydroxypropyl]-4-oxo-1-phenylazetidin-2-yl}biphenyl-3-yl)phosphonic acid,
(47) 4'-{(2S,3R)-1-(4-fluorophenyl)-3-[(3S)-3-(4-fluorophenyl)-3-hydroxypropyl]-4-oxoazetidin-2-yl}-3-hydroxybiphenyl-4-carboxylic acid,
(48) 4'-{(2S,3R)-1-(4-fluorophenyl)-3-[(3S)-3-(4-fluorophenyl)-3-hydroxypropyl]-4-oxoazetidin-2-yl}-4-hydroxybiphenyl-3-carboxylic acid,
(49) 4'-{(2S,3R)-1-(4-fluorophenyl)-3-[(3S)-3-(4-fluorophenyl)-3-hydroxypropyl]-4-oxoazetidin-2-yl}-5-hydroxybiphenyl-2-carbaldehyde,
(50) 4'-{(2S,3R)-1-(4-fluorophenyl)-3-[(3S)-3-(4-fluorophenyl)-3-hydroxypropyl]-4-oxoazetidin-2-yl}biphenyl-3-carbaldehyde,
(51) 4'-{(2S,3R)-1-(4-fluorophenyl)-3-[(3S)-3-(4-fluorophenyl)-3-hydroxypropyl]-4-oxoazetidin-2-yl}biphenyl-3-carboxylic acid,
(55) 4'-{(2S,3R)-1-(4-fluorophenyl)-3-[(3S)-3-(4-fluorophenyl)-3-hydroxypropyl]-4-oxoazetidin-2-yl}biphenyl-4-carboxylic acid,
(59) methyl 4'-{(2S,3R)-1-(4-fluorophenyl)-3-[(3S)-3-(4-fluorophenyl)-3-hydroxypropyl]-4-oxoazetidin-2-yl}biphenyl-4-carboxylate,
(61) N-(4'-{(2S,3R)-1-(4-fluorophenyl)-3-[(3S)-3-(4-fluorophenyl)-3-hydroxypropyl]-4-oxoazetidin-2-yl}biphenyl-3-yl)acetamide, and
(62) (4'-{(2S,3R)-3-[(3S)-3-(4-Fluorophenyl)-3-hydroxypropyl]-4-oxo-1-phenylazetidin-2-yl}-3'-hydroxybiphenyl-4-yl)phosphonic acid.

46. A compound according to claim 5 wherein X is a pharmaceutically acceptable anion.

47. A pharmaceutical formulation comprising a compound according to claim 1 and a pharmaceutically acceptable carrier.

48. A pharmaceutical formulation according to claim 47 additionally comprising an inhibitor of cholesterol biosynthesis.

49. A pharmaceutical formulation according to claim 48 wherein said inhibitor of cholesterol biosynthesis is an HMG-CoA reductase inhibitor.

50. A pharmaceutical formulation according to claim 49 wherein said HMG-CoA reductase inhibitor is chosen from the group consisting of lovastatin, simvastatin, pravastatin, rosuvastatin, mevastatin, atorvastatin, cerivastatin, pitavastatin, fluvastatin, bervastatin, crilvastatin, carvastatin, rivastatin, sirrivastatin, glenvastatin and dalvastatin.

51. A pharmaceutical formulation according to claim 47 additionally comprising at least one bile acid sequestrant.

52. A pharmaceutical formulation according to claim 51 wherein the at least one bile acid sequestrant is selected from the group consisting of cholestyramine, colestipol, colesevelam hydrochloride and mixtures thereof.

53. A pharmaceutical formulation according to claim 47 additionally comprising at least one nicotinic acid or derivative thereof selected from the group consisting of nicotinic acid, niceritrol, nicofuranose, acipimox and mixtures thereof.

54. A pharmaceutical formulation according to claim 47 additionally comprising at least one peroxisome proliferator-activated receptor alpha activator.

55. A pharmaceutical formulation according to claim 54 wherein said peroxisome proliferator-activated receptor alpha activator is a fibric acid derivative.

56. A pharmaceutical formulation according to claim 55 wherein said fibric acid derivative is selected from the group consisting of fenofibrate, clofibrate, gemfibrozil, ciprofibrate, bezafibrate, clinofibrate, binifibrate, lifibrol and mixtures thereof.

57. A pharmaceutical formulation according to claim 47 additionally comprising at least one cholesterol ester transfer protein (CETP) inhibitor.

58. An article of manufacture comprising a container, instructions, and a pharmaceutical formulation according to claim 47, wherein the instructions are for the administration of the pharmaceutical formulation for a purpose chosen from: the prevention or treatment of a disorder of lipid metabolism; reducing the plasma or tissue concentration of at least one 5α-cholestanol or cholest-5-enol other than (3β)-cholest-5ene-3-ol; reducing the blood plasma or serum concentrations of LDL cholesterol; reducing the concentrations of cholesterol and cholesterol ester in the blood plasma or serum; increasing the fecal excretion of cholesterol; reducing the incidence of coronary heart disease-related events; reducing blood plasma or serum concentrations of C-reactive protein (CRP); treating or preventing vascular inflammation; reducing blood plasma or serum concentrations of triglycerides; increasing blood plasma or serum concentrations of HDL cholesterol; reducing blood plasma or serum concentrations of apolipoprotein B.

59. A method for treating a disorder of lipid metabolism comprising administering to a mammal a therapeutically effective amount of a compound having the formula show in claim 1, wherein said disorder is chosen from hypercholesterolemia, hyperlipidemia, arteriosclerosis, and sitosterolemia.

60. A method according to claim 59, wherein said disorder of lipid metabolism is hyperlipidemia.

61. A method according to claim 59, wherein said disorder of lipid metabolism is arteriosclerosis.

62. A method according to claim 59, wherein said disorder of lipid metabolism is sitosterolemia.

63. A method for inhibiting the absorption of cholesterol from the intestine of a mammal, which comprises administering an effective cholesterol-absorption-inhibiting amount of a compound according to claim 1 to the mammal.

64. A method of reducing plasma or tissue concentration of at least one non-cholesterol sterol or 5α-stanol comprising administering to a mammal in need of such treatment an effective amount of a compound according to any of claims claim 1.

65. A method for reducing the blood plasma or serum concentrations of LDL cholesterol in a mammal, which comprises administering an effective cholesterol reducing amount of a compound according to claim 1 to the mammal.

66. A method for reducing the concentrations of cholesterol and cholesterol ester in the blood plasma or serum of a mammal, which comprises administering an effective cholesterol and cholesterol ester reducing amount of a compound according to claim 1 to the mammal.

67. A method for increasing the fecal excretion of cholesterol in a mammal, which comprises administering an effective cholesterol fecal excretion increasing amount of a compound according to claim 1 to the mammal.

68. A compound of formula

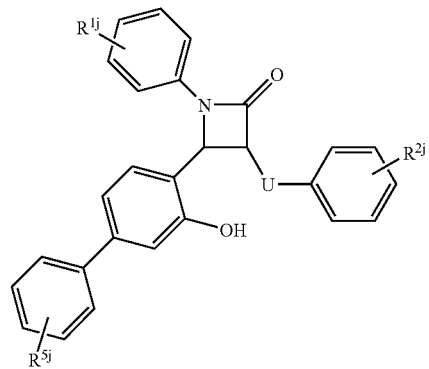

wherein
U is $(C_2-C_6)$-alkylene in which one or more —$CH_2$— may be replaced by a radical chosen from —S—, —S(O)—, —$SO_2$—, —O—, —C(=O)—, —CHOH—, —NH—, CHF, $CF_2$, —CH(O-loweralkyl)-, —CH(O-loweracyl)-, —CH($OSO_3H$)—, —CH($OPO_3H_2$)—, —CH(OB(OH)$_2$)—, or —NOH—;

$R^{1j}$ and $R^{2j}$ are independently chosen from H, F and Cl; and $R^{5j}$ is chosen from $SO_3H$, and $PO_3H_2$.

69. A compound according to claim 68 wherein $R^{1j}$ is H.

70. A compound according to claim 68 wherein $R^{2j}$ is F.

71. A method according to claim 59, wherein said diaorder of lipid metabolism is hypercholestetolemia.

* * * * *

UNITED STATES PATENT AND TRADEMARK OFFICE
CERTIFICATE OF CORRECTION

PATENT NO. : 7,320,972 B2 Page 1 of 1
APPLICATION NO. : 10/986570
DATED : January 22, 2008
INVENTOR(S) : Martinez et al.

It is certified that error appears in the above-identified patent and that said Letters Patent is hereby corrected as shown below:

In The Claims:

Claim 64, Col. 160, Line 14: delete "any of claims"

Signed and Sealed this

Thirteenth Day of May, 2008

JON W. DUDAS
*Director of the United States Patent and Trademark Office*